(12) United States Patent
Breitfelder et al.

(10) Patent No.: US 8,232,286 B2
(45) Date of Patent: *Jul. 31, 2012

(54) INHIBITORS OF PI3-KINASES

(75) Inventors: Steffen Breitfelder, Attenweiler (DE); Udo Maier, Senden (DE); Trixi Brandl, Basel (CH); Christoph Hoenke, Ingelheim (DE); Matthias Grauert, Biberach (DE); Alexander Pautsch, Ulm (DE); Matthias Hoffmann, Mittelbiberach (DE); Frank Kalkbrenner, Attenweiler (DE); Anne T. Joergensen, Kobenhavn (DK); Gerhard Schaenze, Biberach (DE); Stefan Peters, Biberach (DE); Frank Buettner, Attenweiler (DE); Eckhart Bauer, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 599 days.

This patent is subject to a terminal disclaimer.

(21) Appl. No.: 12/366,248

(22) Filed: Feb. 5, 2009

(65) Prior Publication Data
US 2009/0156554 A1 Jun. 18, 2009

Related U.S. Application Data

(63) Continuation of application No. 11/244,299, filed on Oct. 5, 2005, now abandoned.

(30) Foreign Application Priority Data

Oct. 7, 2004 (DE) .......................... 10 2004 048 877
Feb. 9, 2005 (DE) .......................... 10 2005 005 813

(51) Int. Cl.
*C07D 487/04* (2006.01)
*A61K 31/519* (2006.01)
*A61P 11/06* (2006.01)
*A61P 19/02* (2006.01)
*A61P 17/06* (2006.01)

(52) U.S. Cl. ........................................ 514/267; 544/234

(58) Field of Classification Search .................. 544/234; 514/267

See application file for complete search history.

(56) References Cited

U.S. PATENT DOCUMENTS

| 5,182,290 A | 1/1993 | Albaugh |
| 5,358,949 A | 10/1994 | Tabusa et al. |
| 2002/0151544 A1 | 10/2002 | Hayakawa et al. |

FOREIGN PATENT DOCUMENTS

| WO | 01/57008 A1 | 8/2001 |
| WO | 03/035618 A2 | 5/2003 |
| WO | 03/072557 A1 | 9/2003 |
| WO | 2004/007491 A1 | 1/2004 |
| WO | 2004/029055 A1 | 4/2004 |
| WO | 2004/052373 A1 | 6/2004 |
| WO | 2004/056820 A1 | 7/2004 |
| WO | 2005/005438 A1 | 1/2005 |

OTHER PUBLICATIONS

International Search Report for PCT/US02/34086 mailed Apr. 22, 2003.
S. Alazawe, et al; Preparation of Substituted 2-Aminothiazoles; Database Capllus Online; Chemical Abstracts Service, Columbus, Ohio, US; Bulletin of the College of Science; (1973) vol. 12-13, pp. 91-97.
M.D. Chordia, et al; 2-Aminothiazoles: A New Class of Agonist Allosteric Enhancers of A1 Adnosine Receptors; Bioorganis & Medicinal Chemistry Letters; (2002) pp. 1563-1566.
Bart Vanhaesebroeck, et al; Signaling by Distinct Classes of Phosphoinositide 3-Kinases; Experimental Cell Research (1999) vol. 253, pp. 239-254.
Bart Vanhaesebroeck, et al; Synthesis and Function of 3-Phosphorylated Inositol Lipids; Annual Review Biochemical (2001) vol. 70, pp. 535-602.
Edward H. Walker, et al; Structural Insights Into Phosphoinositide 3-Kinase Catalysis and Signalling; Nature (1999) vol. 402, pp. 313-320.
Matthias P. Wymann, et al; Phosphoinositide 3-Kinase Signalling which Way to Target? Trends in Pharmacological Sciences (2003) vol. 24, No. 7, pp. 366-376.
P. Workman, et al; Inbiting the Phosphoinositide 3-Kinase Pathway for Cancer Treatment; Biochemical Society (2004) vol. 32 pp. 393-396.
Yardena Samuels, et al; High Frequency of Mutations of the PIK3CA Gene in Human Cancers; Science (2004) vol. 304 p. 554.
Klaus Okkenhaug, et al; Impaired B and T Cell Antigen Receptor Signaling in p. 110δPI 3-Kinase Mutant Mice; Science (2002) vol. 297 pp. 1031-1034.

(Continued)

*Primary Examiner* — Susanna Moore
(74) *Attorney, Agent, or Firm* — Michael P. Morris; Edward S. Lazer

(57) ABSTRACT

New compounds of formula 1 are provided which by virtue of their pharmaceutical activity as PI3-kinase modulators may be used in the therapeutic field for the treatment of inflammatory or allergic diseases.

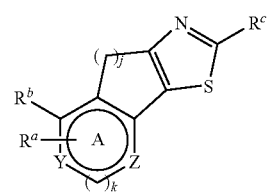

Examples of these include inflammatory and allergic respiratory complaints, inflammatory diseases of the gastro-intestinal tract and motor apparatus, inflammatory and allergic skin diseases, inflammatory eye diseases, diseases of the nasal mucosa, inflammatory or allergic conditions involving autoimmune reactions or inflammations of the kidney.

13 Claims, No Drawings

OTHER PUBLICATIONS

Emilio Hirsch, et al; Central Role for G Protein-Coupled Phosphoinositide 3 Kinase γ in Inflammation; Science (2000) vol. 287 pp. 1049-1053.

Muriel Laffargue, et al; Phosphoinositide 3-Kinase γ Is an Essential Amplifier of Mast Cell Function; Immunity (2002) vol. 16 pp. 441-451.

Stephen G. Ward, et al; Isoform-Specific Phosphoinositide 3-Kinase Inhibitors as Therapeutic Agents; Current Opinion in Pharmacology (2003) vol. 3 pp. 426-434.

Michael A Crackower, et al; Regulation of Myocardial Contractility and Cell Size by Distinct PI3K-PTEN Signaling Pathways; Cell (2002) vol. 110 pp. 737-749.

Gavin Y. Oudit, et al; Phosphoinositide 3-Kinase γ-Deficient Mice Are Protected From Isoproterenol-Induced Heart Failure; Circulation (2003) vol. 108 No. 17 pp. 2147-2152.

S. Shuetz, et al; Basically Alkylated Imides of Naphthalene-1,4,5,8-Tetracarboxylic Acid and Their Chemotherapeutic Properties; Arzneimittel-Forschung Drug Research (1971) vol. 21, No. 6 pp. 739-763.

V. M. Belikov, et al; The Kinetics and Mechanism of Mannich Base Dissociation in Aqueous Buffers; Tetrahedron (1970) vol. 26 pp. 1199-1216.

George B. Butler, et al; Some Sulfanilamide Derivates of Substituted Ethylenediamines; Journal America Chemical Society (1950) vol. 72 p. 2978.

David E. Nichols, et al; Synthesis and evaluation of N , N—Di-n—propyltetrahydrobenz[f]indol-7-amine and Related Congeners as Dopaminergic Agonists; Journal Med. Chem. (1989) vol. 32 pp. 2128-2134.

Udo Maier, et al; Roles on Non-Catalytic Subunits in Gβγ-Induced Activation of Class I Phosphoinositide 3-Kinase Isoforms β and γ; The Journal of Biological Chemistry (1999) vol. 274 No. 41 pp. 29311-29317.

Arnaldo Fravolino, et al; New Heterocyclic Ring Systems From Hydroxymethylene-Ketones; Gazzetta Chimica italiana (1973) vol. 103 pp. 755-770.

M. Vandewalle, et al; Halogen Derivatives of 2-Acylcyclopentane-1,3-Diones; Bull. Soc. Chim. Belges (1966) vol. 75 pp. 648-654.

INHIBITORS OF PI3-KINASES

RELATED APPLICATION

This application is a Continuation of U.S. application Ser. No. 11/244,299 filed Oct. 5, 2005, which claims priority benefits of German Application No. 10 2004 048 877 filed Oct. 7, 2004 and German Application No. 10 2005 005 813 filed Feb. 9, 2005, respectively, all of which are incorporated by reference herein.

TECHNICAL FIELD

Phosphatidylinositol-3-kinases (PI3-kinases) are a subfamily of the lipid kinases which catalyse the transfer of a phosphate group to the 3'-position of the inositol ring of phosphoinositides (Vanhaesebroeck and Waterfield, Exp Cell Res. 1999 Nov. 25; 253(1):239-54).

They have an important role in numerous cell processes such as e.g. cell growth and differentiation processes, the control of cytoskeletal changes and the regulation of intracellular transport processes (Vanhaesebroeck et al., Annu Rev Biochem. 2001; 70:535-602). In view of their in vitro specificity for particular phosphoinositide substrates the PI3-kinases may be divided into various classes. The members of the receptor-regulated class I are heterodimeric enzymes which are made up of a catalytic subunit (p110) weighing 110-120 kDa and a non-catalytic subunit (p50, p55, p85, p101) weighing 50-101 kDa. The most highly conserved region in all the PI3-kinases is the C-terminally situated kinase domain. It has structural features which can also be found in the majority of known protein kinases. These also include e.g. highly conserved amino acids which are responsible for the coordination of the ATP molecule (Walker et al., Nature. 1999 Nov. 18; 402(6759):313-20).

Three of the four members of the class I PI3-kinases associate constitutively with an adaptor subunit weighing 50-85 kDa, of which p85 is the prototype. The interaction takes place via the so-called p85 binding domain which can be found on the catalytic subunits of the PI3-kinase α, β and δ. The three forms are grouped in class IA on account of this structural feature. The catalytic subunit γ of the PI3-kinase, p110γ, associates instead with a regulatory protein weighing 101 kDa, which is known as p101. It constitutes Class IB of the PI3-kinases—of which it is currently the sole member. This structural division into class IA and IB also shows parallels in the functional properties of the corresponding PI3-kinase isoforms (Vanhaesebroeck and Waterfield, Exp Cell Res. 1999 Nov. 25; 253(1):239-54)

Thus, the PI3-kinase α, β and δ are activated predominantly by receptor-tyrosine-kinases (RTKs) or soluble tyrosine kinases. The p85-subunit serves as an adaptor, as it is able to recognise and bind the phosphorylated tyrosine groups of specific amino acid sequences (YxxM) with its SH2 domains. The PI3Kγ on the other hand is activated mainly by Gβγ-subunits which are released from heterotrimeric G-proteins after activation of heptahelical receptors. This differing coupling to cell surface receptors combined with a more or less restrictive expression necessarily results in very different tasks and functions for the 4 class I PI3-kinases in the intact organism (Wymann et al., Trends Pharmacol Sci. 2003 July; 24(7):366-76).

A number of independent findings would appear to indicate that class IA PI3-kinases are involved in uncontrolled cell growth and differentiation processes. Thus, the first detected PI3-kinase activity was associated with the transforming activity of viral oncogenes, such as e.g. the middle T antigen of polyomaviruses, Src tyrosine kinases or activated growth factors (Workman, Biochem Soc Trans. April; 32(Pt 2):393-6). In many tumours, such as e.g. breast cancer, ovarian or pancreatic carcinoma, there is found to be an overactivity of Akt/PKB, which is activated directly by the lipid products of class I PI3-kinases and thus transmits the signals on into the cell. Moreover, it was found just recently that the PIK3CA-gene which codes for p110α has a high mutation frequency in various types of tumour, such as colon, breast or lung carcinomas, some examples of which were able to be characterised as activating mutations (Samuels et al., Science. 2004 Apr. 23; 304(5670):554).

The most recent member of the class IA PI3-kinases, PI3Kδ, is expressed more restrictively than PI3Kα and β. In so-called "knock-in" mice in which the catalytic subunit of PI3Kδ, p110δ, had been replaced by an inactive mutant, it was demonstrated that this PI3K-isoenzyme plays a specific part in the signal transmission of B- and T-lymphocytes after antigen receptor stimulation (Okkenhaug et al., Science. 2002 August; 297(5583):1031-4). These are mechanisms which play a part especially in autoimmune diseases such as e.g. Crohn's disease or rheumatoid arthritis.

The PI3Kγ is activated almost exclusively by $G_i$-coupling heptahelical receptors. Thus, in neutrophils in mice which express no PI3Kγ, no $PI3,4,5-P_3$ formation was observed if they were stimulated with IL-8, fMLP, $LTB_4$ or C5a (Hirsch et al., Science. 2000 Feb. 11; 287(5455):1049-53). This shows that at least in this type of cell PI3Kγ is the only PI3-kinase isoform which binds to these heptahelical receptors. Moreover, isolated neutrophils and macrophages from the PI3Kγ-deficient mice exhibited a sharply reduced chemotactic activity or production of oxygen radicals compared with a whole series of chemokines and chemoattractors. Also reduced was the IgE-mediated activation of mast cells which had been isolated from p110γ-deficient mice. There has been some discussion that the mechanism responsible might be a positive feedback mechanism in which the PI3Kγ is activated by $G_i$-coupling adenosine $A_3$ receptors (Laffargue et al., Immunity. 2002 March; 16(3):441-51).

In spite of this decreased ability to react to inflammation mediators, the p110γ-deficient mice have normal viability and reproductive powers and have the same life expectancy as wild-type comparison animals reared identically. From this it can be concluded that the class IB PI3Kγ plays a central role in the activation of various inflammatory cells, and therefore isoform-specific inhibitors represent an attractive possibility for anti-inflammatory therapy with comparatively minor side effects (Ward and Finan, Curr Opin Pharmacol. 2003 August; 3(4):426-34). Apart from its function in leukocytes PI3Kγ also appears to be involved in the cardiovascular system, despite its low expression in cardiomyocytes. Thus, p110γ-deficient mice exhibited an increase in cardiac muscle contractility which may presumably be explained by an overproduction of cAMP (Crackower et al., Cell. 2002 Sep. 20; 110(6):737-49). It has only recently been possible to demonstrate that PI3Kγ is also involved in the development of cardiac hypertrophy. Thus, p110γ-deficient mice exhibited significantly reduced hypertrophy and fibrosis compared with wild-type animals in an isoproterenol-induced cardiac insufficiency model (Oudit et al., Circulation. 2003 Oct. 28; 108 (17):2147-52).

The problem of the present invention was to provide new compounds which by virtue of their pharmaceutical efficacy as PI3-kinase modulators may be used in the therapeutic field for the treatment of inflammatory or allergic diseases. Examples which may be mentioned here include inflammatory and allergic respiratory complaints, inflammatory diseases of the gastrointestinal tract, rheumatoid arthritis, inflammatory and allergic skin diseases, inflammatory eye diseases, diseases of the nasal mucosa, inflammatory or allergic conditions involving autoimmune reactions, or inflammation of the kidneys.

PRIOR ART

PI3-kinase inhibitors for the treatment of inflammatory diseases are known in the literature. Thus, WO 03/072557 discloses 5-phenylthiazole derivatives, WO 04/029055 discloses annelated azolopyrimidines and WO 04/007491 discloses azolidinone-vinyl linked benzene derivatives. Moreover, the two specifications WO 04/052373 and WO 04/056820 disclose benzoxazine into benzoxazin-3-one derivatives.

DETAILED DESCRIPTION OF THE INVENTION

Surprisingly it has been found that the above-mentioned problems are solved by compounds of formula 1. Accordingly, the present invention relates to compounds of formula 1,

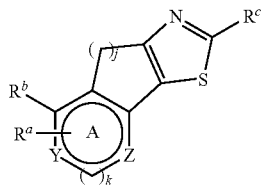

with the proviso that the circular line designated A denotes an aromatic system; wherein Y denotes carbon, nitrogen atom, sulphur; preferably carbon, nitrogen;

Z denotes carbon, nitrogen atom, sulphur; preferably carbon, nitrogen;

j denotes 1, 2 or 3;

k denotes 0 or 1;

$R^a$ denotes H, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, or a group selected from among $C_{1-6}$-alkyl, $C_{2-6}$-alkenyl, $C_{3-8}$-cycloalkyl, $C_{3-8}$-cycloalkenyl, $C_{1-6}$-Haloalkyl, aryl, $C_{7-11}$-aralkyl, Spiro, het, heteroaryl and $CH_2$—O-aryl, which may optionally be substituted;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$, $CONR^{12}$ or $C_{1-6}$-alkyl, optionally substituted by one or more COOH, $N(C_{1-6}$-alkyl$)_2$ or het, optionally substituted by one or more $C_{1-6}$-alkyl; or $R^9$ denotes het, optionally substituted by one or more $C_{1-4}$-alkyl;

$R^{10}$ denotes H, $C_{1-6}$-alkyl, CO—$C_{1-6}$-alkyl or $C_{2-6}$-alkynyl;

$R^{11}$ denotes $C_{1-6}$-alkyl, optionally substituted by one or more $N(C_{1-4}$-alkyl$)_2$;

$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4$, $NR^5CONR^4R^5$, $NR^5SOR^4$ or $NR^5SO_2R^4$;

$R^4$, $R^5$ denote H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by $Si(C_{1-4}$-alkyl$)_3$, or $R^4$ denotes a group selected from among aryl, het, hetaryl and optionally substituted by $C_{1-4}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

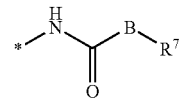

wherein

B denotes a bond, $C_{1-6}$-alkyl, $C_{2-6}$-alkenyl or $C_{2-6}$-alkynyl;

$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;

$R^{6.1}$ denotes halogen, $CF_3$, OH, CN, OMe, $SO_2(C_{1-4}$-alkyl);

$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;

$R^{7.1}$ denotes H, $C_{1-6}$-alkyl, $(CH_2)_{2-4}R^{7.1.1}$ or COObutyl;

$R^{7.2}$ denotes H, $C_{1-6}$-alkyl, optionally substituted by one or more OH;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes a group selected from among aryl, $C_{7-11}$-aralkyl and heteroaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl, $R^{1.1}$ denotes OH, $C_{1-6}$-alkyl, $C_{2-6}$-alkenyl $C_{2-6}$-alkynyl, $NR^{1.1.1}R^{1.1.2}$ $R^{1.1.1}$ denotes H, $C_{1-6}$-alkyl, optionally substituted by a group selected from among $NH_2$, NHMe, $NMe_2$;

$R^{1.1.2}$ denotes H, $C_{1-6}$-alkyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

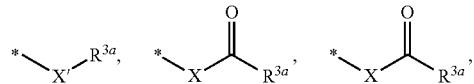

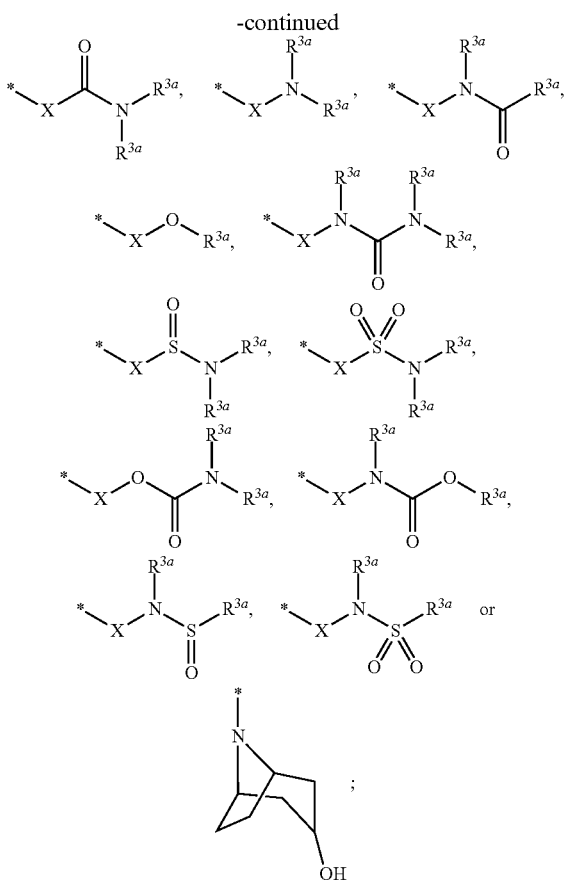

wherein

X denotes a bond or $C_{1-4}$-alkylene;

X' denotes $C_{1-4}$-alkylene, $C_{2-4}$-alkenylene or $C_{1-4}$-alkynylene $R^{3a}$ denotes a group, which may be identical or different, selected from among $R^{3.1}$, $R^{3.2}$ and $R^{3.3}$ $R^{3.1}$ denotes spiro or het, while het may optionally be substituted by one or more $R^{3.1.1}$;

$R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, $NHCOR^{3.1.1.1}$ $R^{3.1.1.1}$ denotes a group selected from among H, $C_{1-4}$-alkyl, aryl and $C_{7-11}$-aralkyl; optionally substituted by a group selected from among halogen, OH and CN;

$R^{3.1.1.2}$ denotes H, $C_{1-4}$-alkyl;

$R^{3.2}$ denotes a group selected from among $C_{3-6}$-cycloalkyl, het, hetaryl and spiro which is optionally substituted by one or more $R^{3.2.1}$ $R^{3.2.1}$ denotes $C_{1-6}$-alkyl, $C_{3-6}$-cycloalkyl, OH, $NR^{3.2.1.1}R^{3.2.1.2}$, $NHCOR^{3.2.1.3}$ or het, optionally substituted by one or more groups selected from among $C_{1-4}$-alkyl, $SO_2R^{3.2.1.1}$, $CH_2$—$C_{3-6}$-cycloalkyl and aryl;

$R^{3.2.1.1}$ denotes H, $C_{1-4}$-alkyl or $C_{7-11}$-aralkyl;
$R^{3.2.1.2}$ denotes H, $C_{1-4}$-alkyl or $C_{7-11}$-aralkyl;
$R^{3.2.1.3}$ denotes aryl, $C_{7-11}$-aralkyl; or $C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH, imidazolidinone;

$R^{3.2.2.1}$ denotes H or $C_{1-6}$-alkyl, aryl, $C_{7-11}$-aralkyl
$R^{3.2.2.2}$ denotes H or $C_{1-6}$-alkyl; or aryl, which is optionally substituted by one or two $R^{3.2.3}$ $R^{3.2.3}$ denotes a group selected from among NH—$C_{1-6}$-alkyl-N($C_{1-6}$-alkyl)$_2$ or het, while het may optionally be substituted by a $C_{1-6}$-alkyl group;

$R^{3.3}$ denotes H or a group selected from among $C_{1-6}$-alkyl, $C_{2-6}$-alkenyl, $C_{2-6}$-alkynyl, $C_{1-6}$-haloalkyl and aryl, which may optionally be substituted by one or more groups $R^{3.3.1}$;

$R^{3.3.1}$ denotes $C_{3-6}$-cycloalkyl, $C_{3-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2H$, $SO_2$—$C_{1-4}$-alkyl, $SO_2C_{7-11}$-aralkyl, $CH_2$—$C_{3-6}$-cycloalkyl and aryl;

$R^{3.3.1.1}$, $R^{3.3.1.2}$ and $R^{3.3.1.3}$ denote a group selected from among $C_{1-6}$-alkyl, $C_{2-6}$-alkenyl, $C_{2-6}$-alkynyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $COC_{1-4}$-alkyl-hetaryl, $COC_{2-4}$-alkenyl-hetaryl, $COC_{2-4}$-alkynyl-hetaryl; or two of the groups $R^{3.3.1.1}$, $R^{3.3.1.2}$ and $R^{3.3.1.3}$ together form a ring, consisting of carbon atoms and optionally a heteroatom selected from among oxygen, nitrogen and sulphur;

$R^a$ denotes H, $C_{1-6}$-alkyl, $C_{2-6}$-alkenyl, $C_{3-8}$-cycloalkyl, $C_{3-8}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$, $CONR^{12}$ or $C_{1-6}$-alkyl, optionally substituted by one or more COOH, N($C_{1-6}$-alkyl)$_2$ or het, optionally substituted by one or more $C_{1-6}$-alkyl; or $R^9$ denotes het, optionally substituted by one or more $C_{1-4}$-alkyl;

$R^{10}$ denotes H, $C_{1-6}$-alkyl, CO—$C_{1-6}$-alkyl or $C_{2-6}$-alkynyl;
$R^{11}$ denotes $C_{1-6}$-alkyl, optionally substituted by one or more N($C_{1-4}$-alkyl)$_2$;
$R^{12}$ denotes H, $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes a group selected from among aryl, $C_{7-11}$-aralkyl and hetaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, COR$^{1.1}$, O—C$_{1-4}$-haloalkyl, NO$_2$ or SR$^{1.1}$, SOR$^{1.1}$, SO$_2$R$^{1.1}$, het or hetaryl, R$^{1.1}$ denotes OH, C$_{1-6}$-alkyl, C$_{2-6}$-alkenyl C$_{2-6}$-alkynyl, NR$^{1.1.1}$R$^{1.1.2}$ R$^{1.1.1}$ denotes H, C$_{1-6}$-alkyl, optionally substituted by a group selected from among NH$_2$, NHMe, NMe$_2$;

R$^{1.1.2}$ denotes H, C$_{1-6}$-alkyl;

or R$^{1.1.1}$ and R$^{1.1.2}$ together form a five- or six-membered heterocyclic ring, which may optionally be substituted by a group selected from among methyl, ethyl, propyl;

R$^3$ denotes a group selected from among

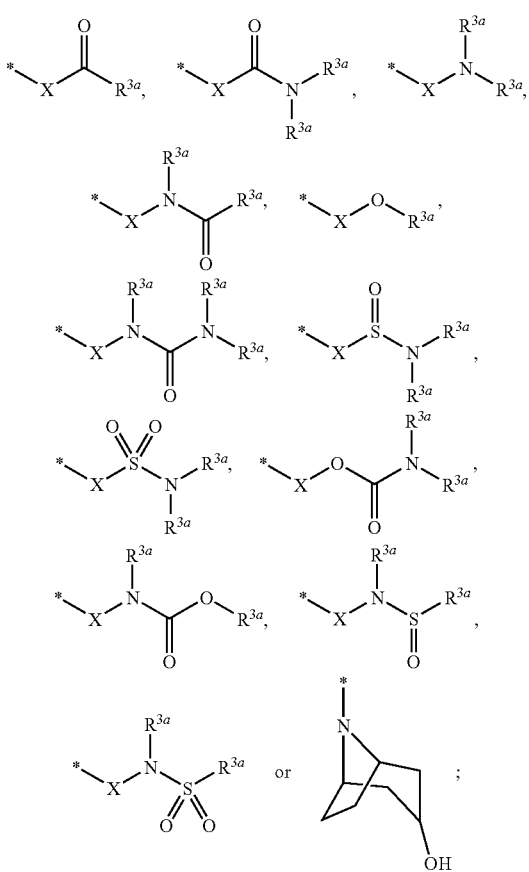

wherein

X denotes a bond or C$_{1-4}$-alkylene;

R$^{3a}$ denotes a group, which may be identical or different, selected from among R$^{3.1}$, R$^{3.2}$ and R$^{3.3}$ R$^{3.1}$ denotes spiro or het, while het may optionally be substituted by one or more R$^{3.11}$ R$^{3.1.1}$ denotes C$_{1-6}$-alkyl, C$_{2-6}$-alkenyl, OH, C$_{1-4}$-alkylene-OH, C$_{1-4}$-alkylene-NR$^{3.1.1.1}$R$^{3.1.1.2}$, COR$^{3.1.11}$, COOR$^{3.1.1.1}$, CONR$^{3.1.1.1}$R$^{3.1.1.2}$, NR$^{3.1.1.1}$R$^{3.1.1.2}$, het, hetaryl, NHCOR$^{3.1.1.1}$ R$^{3.1.1.1}$ denotes a group selected from among H, C$_{1-4}$-alkyl, aryl and C$_{7-11}$-aralkyl; optionally substituted by a group selected from among halogen, OH and CN;

R$^{3.1.1.2}$ denotes H, C$_{1-4}$-alkyl;

R$^{3.2}$ denotes a group selected from among C$_{3-6}$-cycloalkyl, het, hetaryl and spiro which is optionally substituted by one or more R$^{3.2.1}$ R$^{3.2.1}$ denotes C$_{1-6}$-alkyl, C$_{3-6}$-cycloalkyl, OH, NR$^{3.2.1.1}$R$^{3.2.1.2}$, NHCOR$^{3.2.1.3}$ or het, optionally substituted by one or more groups selected from among C$_{1-4}$-alkyl, SO$_2$R$^{3.2.1.1}$, CH$_2$—C$_{3-6}$-cycloalkyl and aryl;

R$^{3.2.1.1}$ denotes H, C$_{1-4}$-alkyl or C$_{7-11}$-aralkyl;

R$^{3.2.1.2}$ denotes H, C$_{1-4}$-alkyl or C$_{7-11}$-aralkyl;

R$^{3.2.1.3}$ denotes aryl, C$_{7-11}$-aralkyl; or

C$_{1-6}$-alkyl, which is optionally substituted by one or two R$^{3.2.2}$;

R$^{3.2.2}$ denotes C$_{1-6}$-alkyl, C$_{2-6}$-alkenyl, C$_{2-6}$-alkynyl, COOR$^{3.2.2.1}$ CONR$^{3.2.2.1}$R$^{3.2.2.2}$, NR$^{3.2.2.1}$R$^{3.2.2.2}$, NHCOR$^{3.2.2.1}$, C$_{1-6}$-haloalkyl, CN, OR$^{3.2.2.1}$, SO$_2$R$^{3.2.2.1}$, C$_{3-6}$-cycloalkyl, CO-het, C$_{2-4}$-alkynyl-hetaryl, guanidine or a group selected from among het, hetaryl and aryl, which is optionally substituted by one or more groups selected from among halogen, C$_{1-6}$-alkyl, CONR$^{3.2.2.1}$R$^{3.2.2.2}$, OH, imidazolidinone;

R$^{3.2.2.1}$ denotes H or C$_{1-6}$-alkyl, aryl, C$_{7-11}$-aralkyl

R$^{3.2.2.2}$ denotes H or C$_{1-6}$-alkyl; or aryl, which is optionally substituted by one or two R$^{3.2.3}$ R$^{3.2.3}$ denotes a group selected from among NH—C$_{1-6}$-alkyl-N(C$_{1-6}$-alkyl)$_2$ or het, while het may optionally be substituted by a C$_{1-6}$-alkyl group;

R$^{3.3}$ denotes H or a group selected from among C$_{1-6}$-alkyl, C$_{2-6}$-alkenyl, C$_{2-6}$-alkynyl, C$_{1-6}$-haloalkyl and aryl, which may optionally be substituted by one or more groups R$^{3.3.1}$;

R$^{3.3.1}$ denotes C$_{3-6}$-cycloalkyl, C$_{3-6}$-cycloalkenyl, OR$^{3.3.1.1}$, NR$^{3.3.1.1}$R$^{3.3.1.2}$, CONR$^{3.3.1.1}$R$^{3.3.1.2}$, COOR$^{3.3.1.1}$, NR$^{3.3.1.1}$COR$^{3.3.1.2}$, SOR$^{3.3.1.1}$, SO$_2$R$^{3.3.1.1}$, C(NR$^{3.3.1.1}$R$^{3.3.1.2}$)NR$^{3.3.1.3}$, NR$^{3.3.1.1}$CONR$^{3.3.1.2}$R$^{3.3.1.3}$, OH, CN, halogen or het, optionally substituted by one or more groups selected from among C$_{1-4}$-alkyl, SO$_2$H, SO$_2$—C$_{1-4}$-alkyl, SO$_2$C$_{7-11}$-aralkyl, CH$_2$—C$_{3-6}$-cycloalkyl and aryl;

R$^{3.3.1.1}$, R$^{3.3.1.2}$ and R$^{3.3.1.3}$ denote a group selected from among C$_{1-6}$-alkyl, C$_{2-6}$-alkenyl, C$_{2-6}$-alkynyl, C$_{7-11}$-aralkyl, C$_{2-4}$-alkenyl-aryl, C$_{2-4}$-alkynyl-aryl, C$_{1-4}$-alkyl-hetaryl, C$_{2-4}$-alkenyl-hetaryl, C$_{2-4}$-alkynyl-hetaryl, COC$_{1-4}$-alkyl-hetaryl, COC$_{2-4}$-alkenyl-hetaryl, COC$_{2-4}$-alkynyl-hetaryl, or two of the groups R$^{3.3.1.1}$, R$^{3.3.1.2}$ and R$^{3.3.1.3}$ together form a ring, consisting of carbon atoms and optionally a heteroatom selected from among oxygen, nitrogen and sulphur;

R$^a$ denotes H, C$_{1-6}$-alkyl, C$_{2-6}$-alkenyl, C$_{3-8}$-cycloalkyl, C$_{3-8}$-cycloalkenyl, C$_{1-6}$-haloalkyl, COR$^8$, NR$^9$R$^{10}$, NO$_2$, OR$^8$, SR$^{11}$, SOR$^{11}$, SO$_2$R$^{11}$, NHCO—C$_{1-6}$-alkyl-NH$_2$, spiro or a group selected from among C$_{7-11}$-aralkyl, CH$_2$—O-aryl and het which may optionally be substituted by one or more halogens, C$_{1-6}$-alkyl, CO—C$_{1-4}$-haloalkyl, C$_{1-4}$-alkyl-NH$_2$ or CH$_2$NHCOOR$^{12}$;

R$^8$ denotes C$_{1-6}$-alkyl, C$_{3-6}$-cycloalkyl, NH$_2$, hetaryl or aryl, optionally substituted by one or more halogens or C$_{1-4}$-alkyl;

R$^9$ denotes H, COOR$^{12}$, CONR$^{12}$ or C$_{1-6}$-alkyl, optionally substituted by one or more COOH, N(C$_{1-6}$-alkyl)$_2$ or het, optionally substituted by one or more C$_{1-6}$-alkyl; or R$^9$ denotes het, optionally substituted by one or more C$_{1-4}$-alkyl;

R$^{10}$ denotes H, C$_{1-6}$-alkyl, CO—C$_{1-6}$-alkyl or C$_{2-6}$-alkynyl;

R$^{11}$ denotes C$_{1-6}$-alkyl, optionally substituted by one or more N(C$_{1-4}$-alkyl)$_2$;

R$^{12}$ denotes H, C$_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes a group selected from among aryl, $C_{7-11}$-aralkyl and hetaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl, $R^{1.1}$ denotes OH, $C_{1-6}$-alkyl, $C_{2-6}$-alkenyl $C_{2-6}$-alkynyl, $NR^{1.1.1}R^{1.1.2}$ $R^{1.1.1}$ denotes H, $C_{1-6}$-alkyl, optionally substituted by a group selected from among $NH_2$, NHMe, $NMe_2$;

$R^{1.1.2}$ denotes H, $C_{1-6}$-alkyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

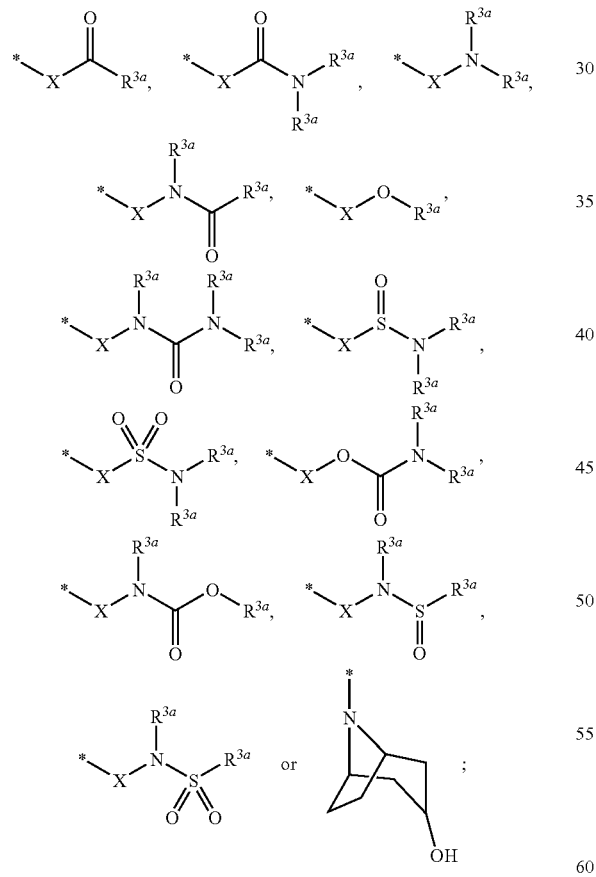

wherein

X denotes a bond or $C_{1-4}$-alkylene;

$R^{3a}$ denotes a group, which may be identical or different, selected from among $R^{3.1}$, $R^{3.2}$ and $R^{3.3}$;

$R^{3.1}$ denotes spiro or het, while het may optionally be substituted by one or more $R^{3.1.1}$;

$R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, $NHCOR^{3.1.1.1}$ $R^{3.1.1.1}$ denotes a group selected from among H, $C_{1-4}$-alkyl, aryl and $C_{7-11}$-aralkyl; optionally substituted by a group selected from among halogen, OH and CN;

$R^{3.1.1.2}$ denotes H, $C_{1-4}$-alkyl;

$R^{3.2}$ denotes a group selected from among $C_{3-6}$-cycloalkyl, het, hetaryl and spiro which is optionally substituted by one or more $R^{3.2.1}$ $R^{3.2.1}$ denotes $C_{1-6}$-alkyl, $C_{3-6}$-cycloalkyl, OH, —$NR^{3.2.1.1}R^{3.2.1.2}$ $NHCOR^{3.2.1.3}$ or het, optionally substituted by one or more groups selected from among $C_{1-4}$-alkyl, $SO_2R^{3.2.1.1}$, $CH_2$—$C_{3-6}$-cycloalkyl and aryl;

$R^{3.2.1.1}$ denotes H, $C_{1-4}$-alkyl or $C_{7-11}$-aralkyl;

$R^{3.2.1.2}$ denotes H, $C_{1-4}$-alkyl or $C_{7-11}$-aralkyl;

$R^{3.2.1.3}$ denotes aryl, $C_{7-11}$-aralkyl; or

—$C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH, imidazolidinone;

$R^{3.2.2.1}$ denotes H or $C_{1-6}$-alkyl, aryl, $C_{7-11}$-aralkyl $R^{3.2.2.2}$ denotes H or $C_{1-6}$-alkyl; or aryl, which is optionally substituted by one or two $R^{3.2.3}$ $R^{3.2.3}$ denotes a group selected from among NH—$C_{1-6}$-alkyl-N($C_{1-6}$-alkyl)$_2$ or het, while het may optionally be substituted by a $C_{1-6}$-alkyl group;

$R^{3.3}$ denotes H or a group selected from among $C_{1-6}$-alkyl, $C_{2-4}$-alkenyl, $C_{2-4}$-alkynyl, $C_{1-4}$-haloalkyl and aryl, which may optionally be substituted by one or more groups $R^{3.3.1}$;

$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2H$, $SO_2$—$C_{1-4}$-alkyl, $SO_2C_{7-11}$-aralkyl, $CH_2$—$C_{3-6}$-cycloalkyl and aryl;

$R^{3.3.1.1}$, $R^{3.3.1.2}$ and $R^{3.3.1.3}$ denote a group selected from among $C_{1-4}$-alkyl, $C_{2-4}$-alkenyl, $C_{2-4}$-alkynyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $COC_{1-4}$-alkyl-hetaryl, $COC_{2-4}$-alkenyl-hetaryl, $COC_{2-4}$-alkynyl-hetaryl; or two of the groups $R^{3.3.1.1}$, $R^{3.3.1.2}$ and $R^{3.3.1.3}$ together form a five-, six- or seven-membered ring, consisting of carbon atoms and optionally a heteroatom selected from among oxygen, nitrogen and sulphur;

$R^a$ denotes H, $C_{1-6}$-alkyl, $C_{2-6}$-alkenyl, $C_{3-8}$-cycloalkyl, $C_{3-8}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$ or $C_{1-4}$-alkyl, optionally substituted by one or more COOH, $N(C_{1-4}$-alkyl$)_2$ or het, optionally substituted by one or more $C_{1-4}$-alkyl; or $R^9$ denotes het, optionally substituted by one or more $C_{1-4}$-alkyl;

$R^{10}$ denotes H, $C_{1-6}$-alkyl, CO—$C_{1-4}$-alkyl or $C_{2-6}$-alkynyl;

$R^{11}$ denotes $C_{1-6}$-alkyl, optionally substituted by one or more $N(C_{1-4}$-alkyl$)_2$;

$R^{12}$ denotes $C_{1-6}$-alkyl;

$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4$, $NR^5CONR^4R^5$, $NR^5SOR^4$ or $NR^5SO_2R^4$;

$R^4$ denotes H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by $Si(C_{1-4}$-alkyl$)_3$, or $R^4$ denotes a group selected from among aryl, het, hetaryl and optionally substituted by $C_{1-4}$-alkyl;

$R^5$ denotes H or $C_{1-6}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

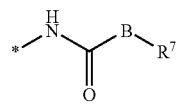

wherein

B denotes a bond, $C_{1-4}$-alkyl or $C_{2-4}$-alkynyl;

$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;

$R^{6.1}$ denotes halogen, $CF_3$, OH, CN, OMe, $SO_2(C_{1-4}$-alkyl);

$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;

$R^{7.1}$ denotes H, $C_{1-4}$-alkyl, $(CH_2)_{2-4}R^{7.1.1}$ or COObutyl;

$R^{7.2}$ denotes H, $C_{1-6}$-alkyl, optionally substituted by one or more OH;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes a group selected from among aryl, $C_{7-11}$-aralkyl and hetaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl, $R^{1.1}$ denotes OH, $C_{1-6}$-alkyl, $C_{2-6}$-alkenyl $C_{2-6}$-alkynyl, $NR^{1.1.1}R^{1.1.2}$ $R^{1.1.1}$ denotes H, $C_{1-6}$-alkyl, optionally substituted by a group selected from among $NH_2$, NHMe, $NMe_2$;

$R^{1.1.2}$ denotes H, $C_{1-6}$-alkyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

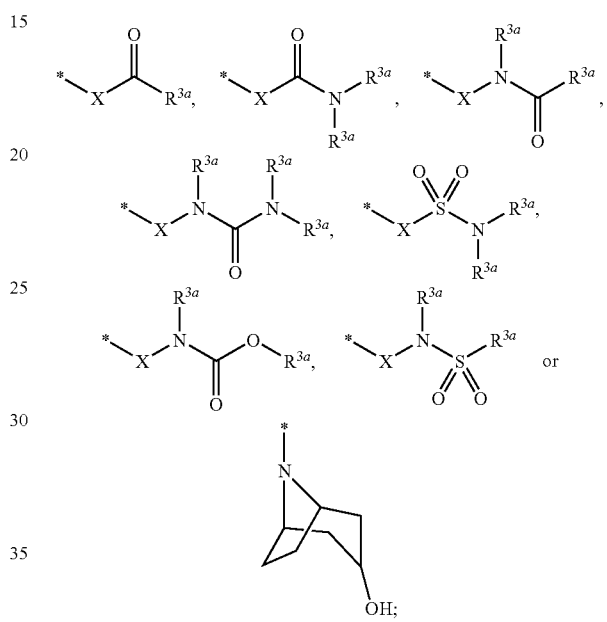

wherein

X denotes a bond or $C_{1-4}$-alkylene;

$R^{3a}$ denotes a group, which may be identical or different, selected from among $R^{3.1}$, $R^{3.2}$ and $R^{3.3}$;

$R^{3.1}$ denotes spiro or het, while het may optionally be substituted by one or more $R^{3.1.1}$ $R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, $NHCOR^{3.1.1.1}$, $R^{3.1.1.1}$ denotes a group selected from among H, $C_{1-4}$-alkyl, aryl and $C_{7-11}$-aralkyl; optionally substituted by a group selected from among halogen, OH and CN;

$R^{3.1.1.2}$ denotes H, $C_{1-4}$-alkyl;

$R^{3.2}$ denotes a group selected from among $C_{3-6}$-cycloalkyl, het, hetaryl and spiro which is optionally substituted by one or more $R^{3.2.1}$ $R^{3.2.1}$ denotes $C_{1-6}$-alkyl, $C_{3-6}$-cycloalkyl, OH, —$NR^{3.2.1.1}R^{3.2.1.2}$, $NHCOR^{3.2.1.3}$ or het, optionally substituted by one or more groups selected from among $C_{1-4}$-alkyl, $SO_2R^{3.2.1.1}$, $CH_2$—$C_{3-6}$-cycloalkyl and aryl;

$R^{3.2.1.1}$ denotes H, $C_{1-4}$-alkyl or $C_{7-11}$-aralkyl;

$R^{3.2.1.2}$ denotes H, $C_{1-4}$-alkyl or $C_{7-11}$-aralkyl;

$R^{3.2.1.3}$ denotes aryl, $C_{7-11}$-aralkyl; or

—$C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$ $CONR^{3.2.2.1}R^{3.2.2.2}$, $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH, imidazolidinone;

$R^{3.2.2.1}$ denotes H or $C_{1-6}$-alkyl, aryl, $C_{7-11}$-aralkyl
$R^{3.2.2.2}$ denotes H or $C_{1-6}$-alkyl; or aryl, which is optionally substituted by one or two $R^{3.2.3}$
$R^{3.2.3}$ denotes a group selected from among NH—$C_{1-6}$-alkyl-N($C_{1-6}$-alkyl)$_2$ or het, while het may optionally be substituted by a $C_{1-6}$-alkyl group;

$R^{3.3}$ denotes H or a group selected from among $C_{1-6}$-alkyl, $C_{2-4}$-alkenyl, $C_{2-4}$-alkynyl and aryl, which may optionally be substituted by one or more groups $R^{3.3.1}$;

$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2H$, $SO_2$—$C_{1-4}$-alkyl, $SO_2C_{7-11}$-aralkyl, $CH_2$—$C_{3-6}$-cycloalkyl and aryl;

$R^{3.3.1.1}$, $R^{3.3.1.2}$ and $R^{3.3.1.3}$ denote a group selected from among $C_{1-4}$-alkyl, $C_{7-11}$-aralkyl, $C_{1-4}$-alkyl-hetaryl, $COC_{1-4}$-alkyl-hetaryl; or two of the groups $R^{3.3.1.1}$, $R^{3.3.1.2}$ and $R^{3.3.1.3}$ together form a five-, six- or seven-membered ring, consisting of carbon atoms and optionally a heteroatom selected from among oxygen, nitrogen and sulphur;

$R^a$ denotes H, $C_{1-6}$-alkyl, $C_{2-6}$-alkenyl, $C_{3-6}$-cycloalkyl, $C_{3-6}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$ or $C_{1-4}$-alkyl, optionally substituted by one or more COOH, N($C_{1-4}$-alkyl)$_2$ or het, optionally substituted by one or more $C_{1-4}$-alkyl; or $R^9$ denotes het, optionally substituted by one or more $C_{1-4}$-alkyl;

$R^{10}$ denotes H, $C_{1-6}$-alkyl, CO—$C_{1-4}$-alkyl or $C_{2-6}$-alkynyl;
$R^{11}$ denotes $C_{1-6}$-alkyl, optionally substituted by one or more N($C_{1-4}$-alkyl)$_2$;
$R^{12}$ denotes $C_{1-6}$-alkyl;
$R^b$ denotes $R^4$, $OR^4$, —$CH_2OR^4$, $COR^4$, $COOR^4$, $CONR^4R^5$, $NH_2$, $NR^5COOR^4$, $NR^5CONR^4R^5$ or $NR^5SOR^4$;
$R^4$ denotes H, $C_{1-6}$-alkyl, $C_{1-6}$-haloalkyl, $C_{1-6}$-alkylene-OH, $C_{2-6}$-alkenyl, $C_{7-11}$-aralkyl, $C_{1-4}$-alkyl-hetaryl, $C_{2-6}$-alkynyl, optionally substituted by Si($C_{1-4}$-alkyl)$_3$, or $R^4$ denotes a group selected from among aryl, het, hetaryl and optionally substituted by $C_{1-4}$-alkyl;
$R^5$ denotes H or $C_{1-6}$-alkyl;
or $R^4$ and $R^5$ together form a five-, six- or seven-membered ring consisting of carbon atoms and optionally a heteroatom selected from among oxygen, nitrogen and sulphur;
$R^c$ denotes $NHR^6$ or a group selected from among

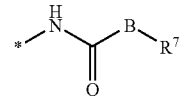

wherein
B denotes a bond, $C_{1-4}$-alkyl or $C_{2-4}$-alkynyl;
$R^6$ denotes H or a group selected from among $C_{1-4}$-alkyl, $C_{3-6}$-cycloalkyl, het, aryl, hetaryl optionally substituted by one or more groups $R^{6.1}$;
$R^{6.1}$ denotes halogen, $CF_3$, OH, CN, OMe, $SO_2(C_{1-4}$-alkyl);
$R^7$ denotes H, $C_{1-4}$-alkyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;
$R^{7.1}$ denotes H, $C_{1-4}$-alkyl, $(CH_2)_{2-4}R^{7.1.1}$ or COObutyl;
$R^{7.2}$ denotes H, $C_{1-6}$-alkyl, optionally substituted by one or more OH;
$R^{7.1.1}$ denotes $NR^{7.1.1.1}R^{7.1.1.2}$, het or 1-imidazolyl, 2-(N-ethylpyrrolidine);
$R^{7.1.1.1}$ denotes H or $C_{1-6}$-alkyl;
$R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein
$R^a$ denotes a group selected from among aryl and $C_{7-11}$-aralkyl, which may optionally be substituted by one or more groups selected from among $R^1$, $R^2$ and $R^3$; or hetaryl optionally substituted by one or more $C_{1-4}$-alkyl;
$R^1$ denotes $C_{1-4}$-alkyl, $C_{1-4}$-haloalkyl, $C_{1-4}$-alkylene-COOH, $C_{1-4}$-alkoxy, halogen, OH, CN, $COR^{1.1}$, O—$C_{1-4}$-haloalkyl, $NO_2$ or $SO_2R^{1.1}$;
$R^{1.1}$ denotes OH, methyl, $NH_2$, NHMe, $NMe_2$,

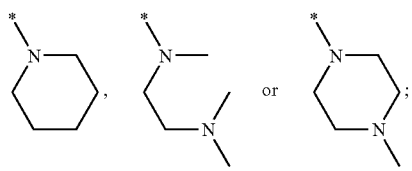

$R^2$ denotes $C_{1-4}$-alkyl, $C_{1-4}$-alkoxy or halogen;
$R^3$ denotes a group selected from among

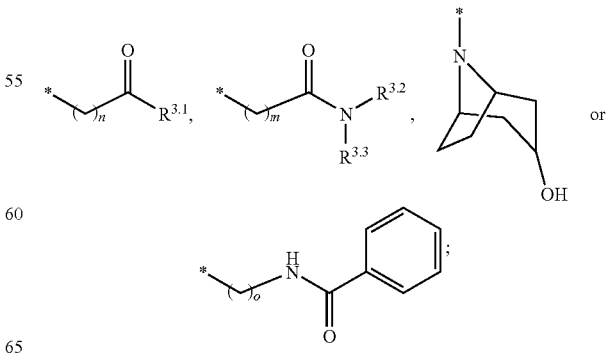

wherein n denotes 0 or 1;
m denotes 0 or 1;
o denotes 2;
$R^{3.1}$ denotes spiro or het, while het may optionally be substituted by one or more $R^{3.1.1}$;
$R^{3.1.1}$ denotes $C_{1-4}$-alkyl, $C_{2-4}$-alkenyl, OH, $C_{1-4}$-alkylene-OH, $CH_2NEt_2$, COMe, COOH, $CONH_2$, $NH_2$, het, hetaryl,

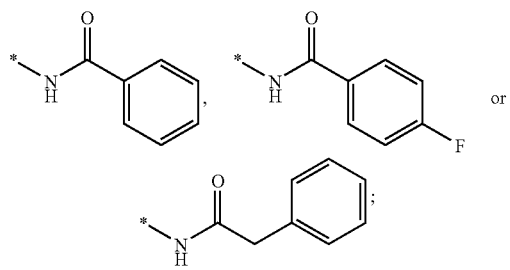

$R^{3.2}$ denotes a group selected from among $C_{3-6}$-cycloalkyl, het, hetaryl and spiro which is optionally substituted by one or two $R^{3.2.1}$
$R^{3.2.1}$ denotes $C_{1-4}$-alkyl, cyclopentyl, OH, $-NR^{3.2.1.1}R^{3.2.1.2}$ or

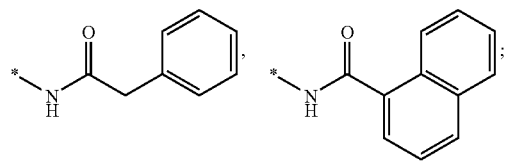

or het, is optionally substituted by one or more groups selected from among methyl, $SO_2R^{3.2.1.1}$,

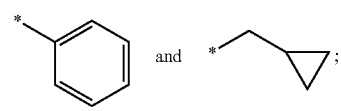

$R^{3.2.1.1}$ denotes H, methyl or benzyl;
$R^{3.2.1.2}$ denotes H, methyl or benzyl; or
$-C_{1-6}$-alkyl, which is optionally substituted by one or two $R^{3.2.2}$;
$R^{3.2.2}$ denotes $C_{2-4}$-alkenyl, $C_{2-4}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-4}$-haloalkyl, CN, OH, $SO_2R^{3.2.2.1}$, $C_{3-6}$-cycloalkyl or a group selected from among

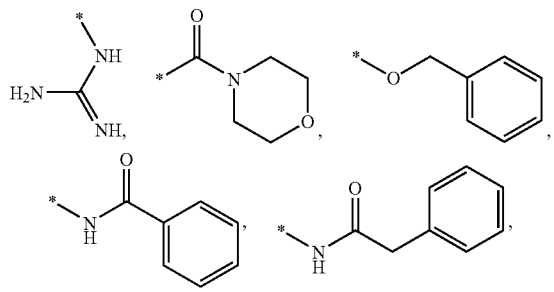

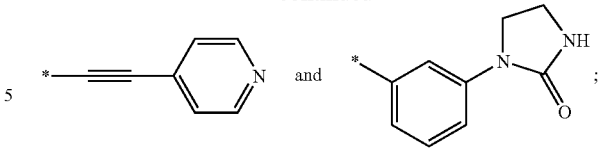

or a group selected from among het, hetaryl and aryl, which is optionally substituted by one or more groups selected from among Cl, methyl, $CONR^{3.2.2.1}R^{3.2.2.2}$, OH;
$R^{3.2.2.1}$ denotes H or methyl;
$R^{3.2.2.2}$ denotes H or methyl; or
aryl, which is optionally substituted by one or two $R^{3.2.3}$
$R^{3.2.3}$ denotes a group selected from among

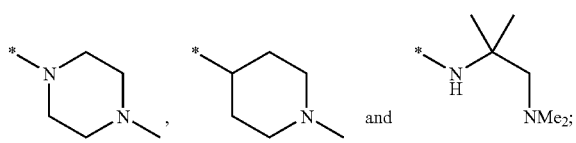

$R^{3.3}$ denotes H or a group selected from among $C_{1-6}$-alkyl and aryl, which may optionally be substituted by one or more groups $R^{3.3.1}$;
$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, is optionally substituted by one or more groups selected from among methyl, $SO_2H$, $SO_2-C_{1-4}$-alkyl, $SO_2C_{7-11}$-aralkyl,

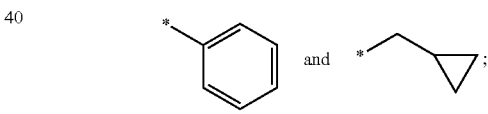

$R^{3.3.1.1}$, $R^{3.3.1.2}$ and $R^{3.3.1.3}$ denote a group selected from among $C_{1-4}$-alkyl, $C_{7-11}$-aralkyl, $C_{1-4}$-alkyl-hetaryl, $COC_{1-4}$-alkyl-hetaryl;
$R^a$ denotes H, $C_{1-6}$-alkyl, $C_{2-6}$-alkenyl, $C_{3-6}$-cycloalkyl, $CF_3$, $COR^8$, $NR^9R^{10}$, $NO_2$, $S(O)_nR^{11}$, or a group selected from among

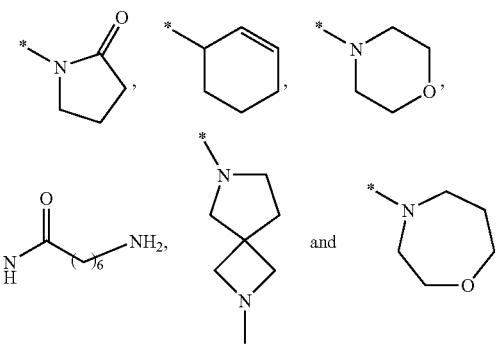

or a group selected from among

*-CH2-C6H5 , *-CH2CH2-C6H5 and

*-CH2-O-C6H5 which may optionally be substituted by one or more Cl;
or a group selected from among

*-(4-piperidinyl)NH and *-N-(1-piperidinyl)

which may optionally be substituted by one or more $CH_3$, $COCF_3$, $CH_2NH_2$ or $CH_2NHCOOR^{12}$;

$R^8$ denotes $C_{1-4}$-alkyl, $C_{3-6}$-cycloalkyl, $NH_2$, furanyl or phenyl, optionally substituted by one or more chlorine;

$R^9$ denotes H, $COOR^{12}$ or piperidino, optionally substituted by one or more $CH_3$, or a group selected from among $C_{1-4}$-alkyl, which may optionally be substituted by one or more COOH, $NMe_2$ or 4-methylpiperazine;

$R^{10}$ denotes H, $C_{1-4}$-alkyl, $C_{2-4}$-alkynyl or $COCH_3$;

$R^{11}$ denotes $C_{1-4}$-alkyl, optionally substituted by one or more $NMe_2$, $R^{12}$ denotes $C_{1-4}$-alkyl;

$R^b$ denotes $R^4$, $CH_2OR^4$, $COR^4$, $COOR^4$, $CONR^4R^5$, $NH_2$, $NHCOOR^4$, $NHCONR^4R^5$ or OH;

$R^4$ denotes H, $C_{1-4}$-alkyl, $C_{1-4}$-alkylene-OH, $C_{2-4}$-alkynyl, $C_{1-6}$-haloalkyl, aryl, het, hetaryl,

*-(1-methylimidazol-4-yl) or *-C≡C-SiMe3

$R^5$ denotes H or $C_{1-4}$-alkyl;

$R^c$ denotes $NHR^6$ or a group selected from among

*-NH-C(O)-B-$R^7$ wherein
B denotes a bond, $C_{1-4}$-alkyl or $C_{2-4}$-alkynyl;

$R^6$ denotes H, $C_{1-4}$-alkyl, $C_{3-6}$-cycloalkyl, $C_{7-11}$-aralkyl, aryl, optionally substituted by $SO_2CH_3$;

$R^7$ denotes H, $NR^{7.1}R^{7.2}$, $OR^{7.2}$, $SR^{7.2}$, hetaryl, het, optionally substituted by $C_{1-4}$-alkyl or $CONH_2$, or a group selected from among

*-CH2-(N-ethylpyrrolidin-2-yl) and *-CH2-NH-CH(OH)-CH(OH)-CH(OH)-CH(OH)-CH2OH;

$R^{7.1}$ denotes H, $C_{1-4}$-alkyl, $(CH_2)_2R^{7.1.1}$ or COObutyl;

$R^{7.2}$ denotes H, $C_{1-4}$-alkyl;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes phenyl or benzyl, in each case optionally substituted by one or more groups selected from among $R^1$, $R^2$ and $R^3$; or

*-(1-pyrazolyl), *-(2-pyridyl), *-(4-pyridyl), *-(2-pyrimidyl),

*-(1-naphthyl), *-(2-naphthyl),

*-(2,6-dimethoxypyrimidin-4-yl), *-(1H-indazol-6-yl) or

*-(benzothiazol-6-yl);

$R^1$ denotes methyl, ethyl, propyl, butyl, $CF_3$, $CH_2COOH$, methoxy, F, Cl, Br, OH, CN, $COR^{1.1}$, $OCF_3$, $NO_2$ or $SO_2R^{1.1}$;

$R^{1.1}$ denotes OH, methyl, $NH_2$, NHMe, $NMe_2$,

*-(1-piperidinyl), *-N(Me)-CH2CH2-NMe2 or *-(4-methylpiperazin-1-yl);

$R^2$ denotes methyl, methoxy, F, Cl or Br;

$R^3$ denotes a group selected from among

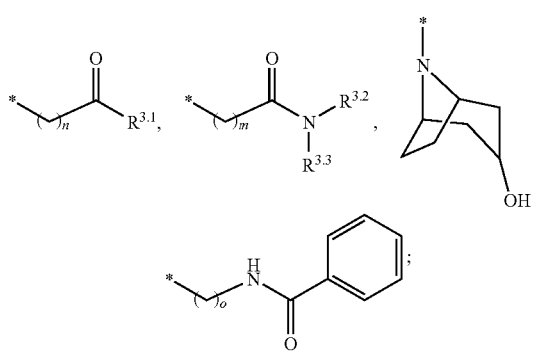

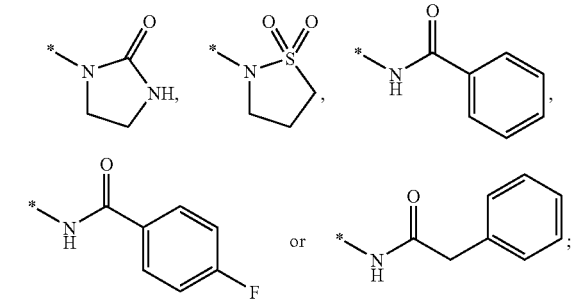

wherein n denotes 0 or 1;
m denotes 0 or 1;
o denotes 2;
$R^{3.1}$ denotes a group selected from among

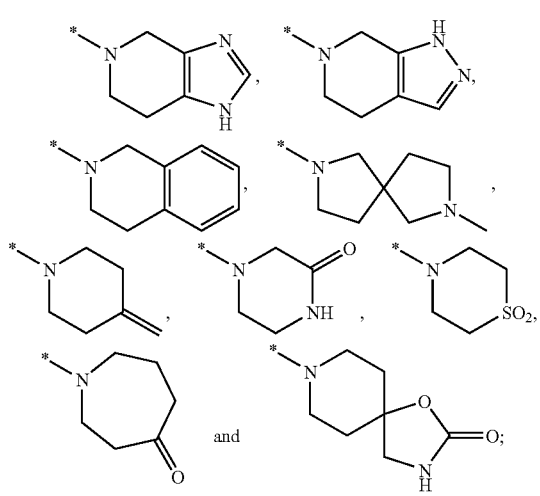

or a group selected from among

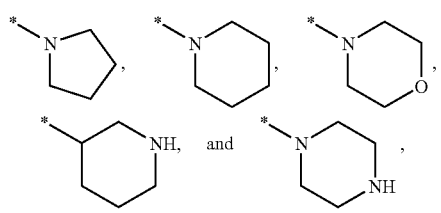

which may optionally be substituted by one or more $R^{3.1.1}$;

$R^{3.1.1}$ denotes methyl, ethyl, OH, $CH_2OH$, $CH_2CH_2OH$, $CH_2NEt_2$, COMe, COOH, $CONH_2$, $NH_2$,

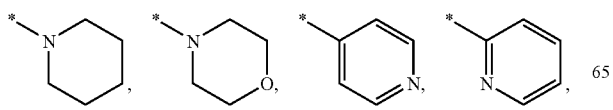

$R^{3.2}$ denotes a group selected from among

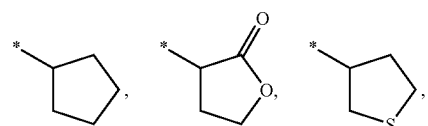

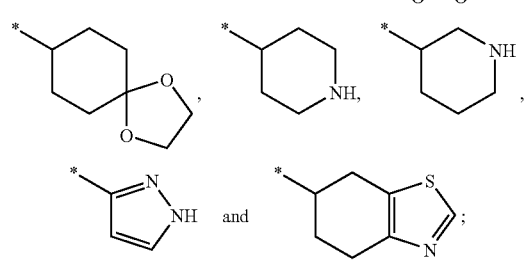

which is optionally substituted by one or more groups selected from among methyl, ethyl, cyclopentyl, OH, $NH_2$; or cyclohexyl, which is optionally substituted by one or two $R^{3.2.1}$ $R^{3.2.1}$—$NR^{3.2.1.1}R^{3.2.1.2}$ or a group selected from among

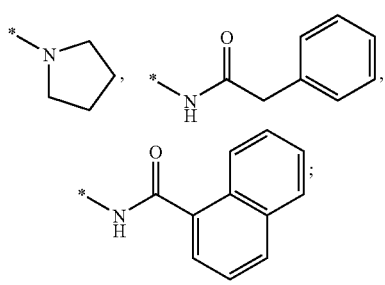

or a group selected from among

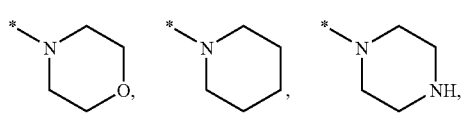

which is optionally substituted by one or more groups selected from among methyl, $SO_2R^{3.2.1.1}$,

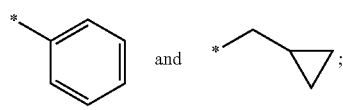 and 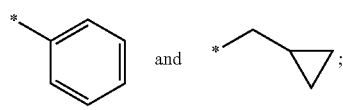;

$R^{3.2.1.1}$ denotes H, methyl or benzyl;
$R^{3.2.1.2}$ denotes H, methyl or benzyl; or
—$C_{1-6}$-alkyl, straight-chain or branched, which is optionally substituted by one or two $R^{3.2.2}$;
$R^{3.2.2}$ denotes C=$CH_2$, C≡CH, $COOR^{3.2.2.1}$, $CONR^{3.2.2.1}R^{3.2.2.2}$, $NR^{3.2.2.1}R^{3.2.2.2}$, $NHCOR^{3.2.2.1}$, $CF_3$, CN, OH, $SO_2R^{3.2.2.1}$ or a group selected from among

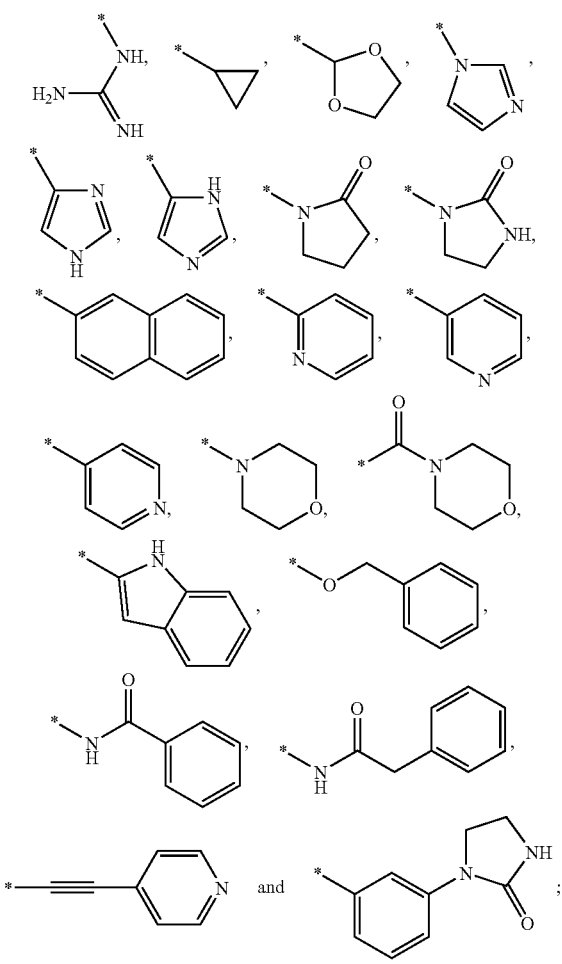

or a group selected from among

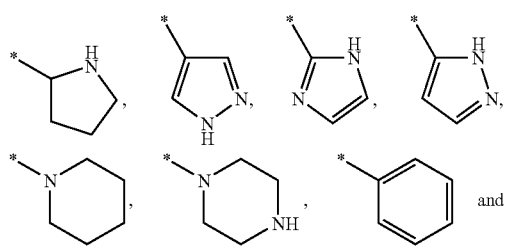

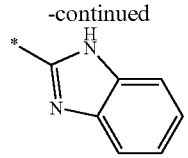

which is optionally substituted by one or more groups selected from among Cl, methyl, $CONR^{3.2.2.1}R^{3.2.2.2}$, OH;
$R^{3.2.2.1}$ denotes H or methyl;
$R^{3.2.2.2}$ denotes H or methyl; or
phenyl, which is optionally substituted by one or two $R^{3.2.3}$
$R^{3.2.3}$ denotes a group selected from among

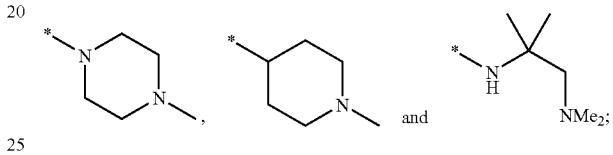

$R^{3.3}$ denotes H, $C_{1-6}$-alkyl, optionally substituted by one or more $R^{3.3.1.1}$,
$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het which is optionally substituted by one or more groups selected from among methyl, $SO_2H$, $SO_2Me$, $SO_2CH_2$phenyl;

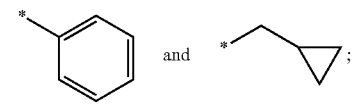

$R^{3.3.1.1}$, $R^{3.3.1.2}$ and $R^{3.3.1.3}$ denote a group selected from among $C_{1-4}$-alkyl, $C_{7-11}$-aralkyl, $C_{1-4}$-alkyl-hetaryl, $COC_{1-4}$-alkyl-hetaryl;
$R^a$ denotes H, methyl, ethyl, propyl, butyl, 3-methyl-butyl, propenyl, cyclopropyl, cyclohexyl, $CF_3$, $COR^8$, $NR^9R^{10}$, $NO_2$, $OR^8$, $SR^{11}$, $SOR^{11}$, $SO_2R^{11}$ or a group selected from among

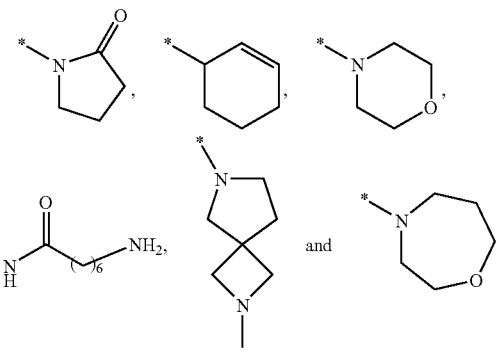

or a group selected from among

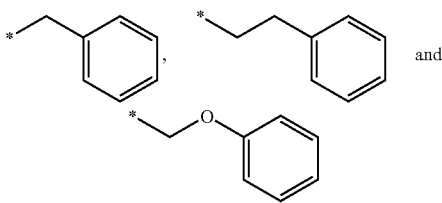

which may optionally be substituted by one or more Cl, or a group selected from among

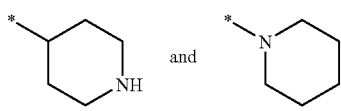

which may optionally be substituted by one or more $CH_3$, $COCF_3$, $CH_2NH_2$ or $CH_2NHCOOR^{12}$;

$R^8$ denotes methyl, propyl, cyclopropyl, $NH_2$, furanyl or phenyl, optionally substituted by one or more chlorine;

$R^9$ denotes H, $COOR^{12}$ or piperidino, optionally substituted by one or more $CH_3$, or a group selected from among methyl, ethyl and propyl, which may optionally be substituted by one or more COOH, $NMe_2$ or 4-methylpiperazine;

$R^{10}$ denotes H, methyl, $COCH_3$, C≡CH or $CH_2C$≡CH;

$R^{11}$ denotes ethyl or propyl, optionally substituted by one or more $NMe_2$, $R^{12}$ denotes butyl $R^b$ denotes $R^4$, $CH_2OR^4$, $COR^4$, $COOR^4$, $CONR^4R^5$, $NH_2$, $NHCOOR^4$, $NHCONR^4R^5$ or OH;

$R^4$ denotes H, methyl, ethyl, 2-hydroxyethyl, propyl, C≡CH, $CF_3$, phenyl,

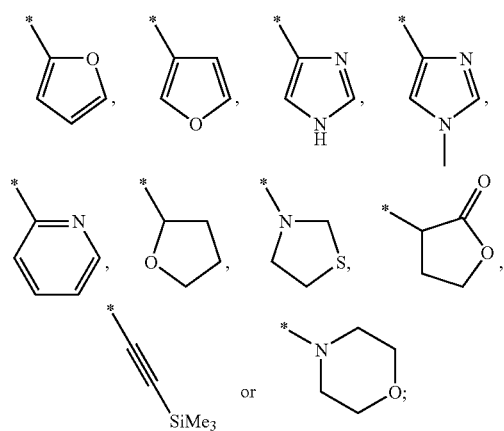

$R^5$ denotes H, methyl or ethyl;
$R^c$ denotes $NHR^6$ or a group selected from among

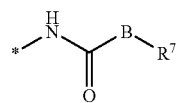

wherein
B denotes a bond, methylene, ethylene, propylene or butynylene;
$R^6$ denotes H, $C_{1-4}$-alkyl, aryl, optionally substituted by $SO_2CH_3$;
$R^7$ denotes H, $NR^{7.1}R^{7.2}$, $OR^{7.2}$, $SR^{7.2}$ or a group selected from among

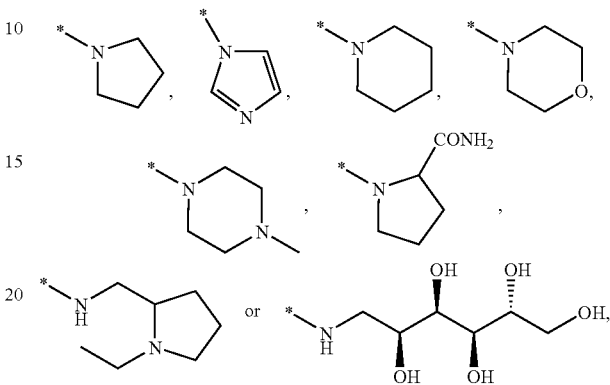

$R^{7.1}$ denotes H, methyl, ethyl, $(CH_2)_2R^{7.1.1}$ or COObutyl;
$R^{7.2}$ denotes H, methyl or ethyl;
$R^{7.1.1}$ denotes $NR^{7.1.1.1}R^{7.1.1.2}$, het or 1-imidazolyl, 2-(N-ethylpyrrolidine);
$R^{7.1.1.1}$ denotes H or $C_{1-6}$-alkyl;
$R^{7.1.1.2}$ denotes H or $C_{1-6}$-alkyl;
and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein
$R^a$ denotes a group selected from among aryl, $C_{7-11}$-aralkyl and hetaryl, which may optionally be substituted by one or more groups selected from among $R^1$, $R^2$ and $R^3$;
$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl,
$R^{1.1}$ denotes OH, $C_{1-6}$-alkyl, $C_{2-6}$-alkenyl $C_{2-6}$-alkynyl, $NR^{1.1.1}R^{1.1.2}$
$R^{1.1.1}$ denotes H, $C_{1-6}$-alkyl, optionally substituted by a group selected from among $NH_2$, NHMe, $NMe_2$;
$R^{1.1.2}$ denotes H, $C_{1-6}$-alkyl;
or $R^{1.1.1}$ and $R^{1.1.2}$ together form a five- or six-membered heterocyclic ring, which may optionally be substituted by a group selected from among methyl, ethyl, propyl;
$R^3$ denotes a group selected from among

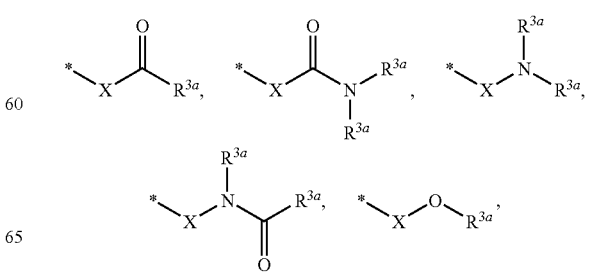

-continued

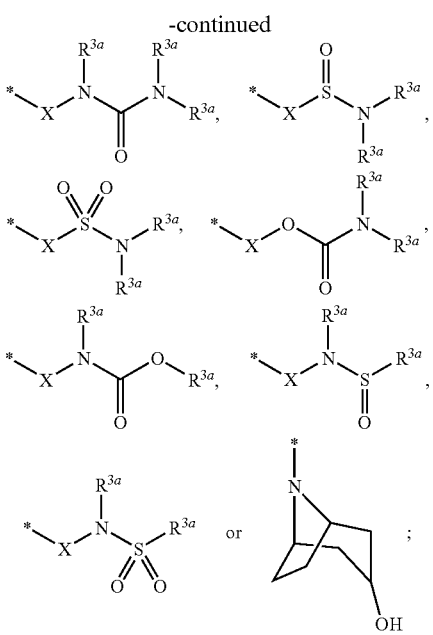

wherein

X denotes a bond or $C_{1-4}$-alkylene;

$R^{3a}$ denotes a group, which may be identical or different, selected from among $R^{3.1}$, $R^{3.2}$ and $R^{3.3}$;

$R^{3.1}$ denotes spiro or het, while het may optionally be substituted by one or more $R^{3.1.1}$;

$R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, $NHCOR^{3.1.1.1}$ $R^{3.1.1.1}$ denotes a group selected from among H, $C_{1-4}$-alkyl, aryl and $C_{7-11}$-aralkyl; optionally substituted by a group selected from among halogen, OH and CN;

$R^{3.1.1.2}$ denotes H, $C_{1-4}$-alkyl;

$R^{3.2}$ denotes a group selected from among $C_{3-6}$-cycloalkyl, het, hetaryl and spiro which is optionally substituted by one or more $R^{3.2.1}$ $R^{3.2.1}$ denotes $C_{1-6}$-alkyl, $C_{3-6}$-cycloalkyl, OH, $NR^{3.2.1.1}R^{3.2.1.2}$, $NHCOR^{3.2.1.3}$ or het, optionally substituted by one or more groups selected from among $C_{1-4}$-alkyl, $SO_2R^{3.2.1.1}$, $CH_2$—$C_{3-6}$-cycloalkyl and aryl;

$R^{3.2.1.1}$ denotes H, $C_{1-4}$-alkyl or $C_{7-11}$-aralkyl;

$R^{3.2.1.2}$ denotes H, $C_{1-4}$-alkyl or $C_{7-11}$-aralkyl;

$R^{3.2.1.3}$ denotes aryl, $C_{7-11}$-aralkyl; or $C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH, imidazolidinone;

$R^{3.2.2.1}$ denotes H or $C_{1-6}$-alkyl, aryl, $C_{7-11}$-aralkyl $R^{3.2.2.2}$ denotes H or $C_{1-6}$-alkyl; or aryl, which is optionally substituted by one or two $R^{3.2.3}$ $R^{3.2.3}$ denotes a group selected from among NH—$C_{1-6}$-alkyl-$N(C_{1-6}$-alkyl$)_2$ or het, while het may optionally be substituted by a $C_{1-6}$-alkyl group;

$R^{3.3}$ denotes H or a group selected from among $C_{1-6}$-alkyl, $C_{2-6}$-alkenyl, $C_{2-6}$-alkynyl, $C_{1-6}$-haloalkyl and aryl, which may optionally be substituted by one or more groups $R^{3.3.1}$;

$R^{3.3.1}$ denotes $C_{3-6}$-cycloalkyl, $C_{3-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2R^{3.2.1.1}$, $SO_2$ $C_{1-4}$-alkyl, $SO_2C_{7-11}$-aralkyl, $CH_2$—$C_{3-6}$-cycloalkyl and aryl;

$R^{3.3.1.1}$, $R^{3.3.1.2}$ and $R^{3.3.1.3}$ denote a group selected from among $C_{1-6}$-alkyl, $C_{2-6}$-alkenyl, $C_{2-6}$-alkynyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $COC_{1-4}$-alkyl-hetaryl, $COC_{2-4}$-alkenyl-hetaryl, $COC_{2-4}$-alkynyl-hetaryl; or two of the groups $R^{3.3.1.1}$, $R^{3.3.1.2}$ and $R^{3.3.1.3}$ together form a ring, consisting of carbon atoms and optionally a heteroatom selected from among oxygen, nitrogen and sulphur;

$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4$, $NR^5CONR^4R^5$, $NR^5SOR^4$ or $NR^5SO_2R^4$;

$R^4$, $R^5$ denote H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by $Si(C_{1-4}$-alkyl$)_3$, or $R^4$ denotes a group selected from among aryl, het, hetaryl and optionally substituted by $C_{1-4}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

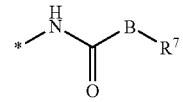

wherein

B denotes a bond, $C_{1-6}$-alkyl, $C_{2-6}$-alkenyl or $C_{2-6}$-alkynyl;

$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;

$R^{6.1}$ denotes halogen, $CF_3$, OH, CN, OMe, $SO_2(C_{1-4}$-alkyl);

$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;

$R^{7.1}$ denotes H, $C_{1-6}$-alkyl, $(CH_2)_{2-4}R^{7.1.1}$ or COObutyl;

$R^{7.2}$ denotes H, $C_{1-6}$-alkyl, optionally substituted by one or more OH;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof.

Preferred compounds of formula 1 mentioned above are those wherein $R^a$ denotes a group selected from among aryl, $C_{7-11}$-aralkyl and hetaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl, $R^{1.1}$ denotes OH, $C_{1-6}$-alkyl, $C_{2-6}$-alkenyl $C_{2-6}$-alkynyl, $NR^{1.1.1}R^{1.1.2}$ $R^{1.1.1}$ denotes H, $C_{1-6}$-alkyl, optionally substituted by a group selected from among $NH_2$, NHMe, $NMe_2$;

$R^{1.1.2}$ denotes H, $C_{1-6}$-alkyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

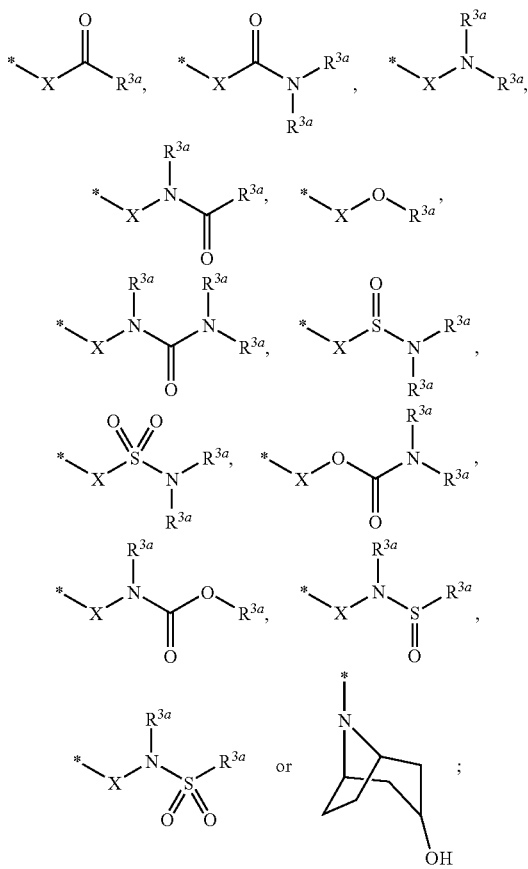

wherein

X denotes a bond or $C_{1-4}$-alkylene;

$R^{3a}$ denotes a group, which may be identical or different, selected from among $R^{3.1}$, $R^{3.2}$ and $R^{3.3}$ $R^{3.1}$ denotes spiro or het, while het may optionally be substituted by one or more $R^{3.1.1}$;

$R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, $NHCOR^{3.1.1.1}$ $R^{3.1.1.1}$ denotes a group selected from among H, $C_{1-4}$-alkyl, aryl and $C_{7-11}$-aralkyl; optionally substituted by a group selected from among halogen, OH and CN;

$R^{3.1.1.2}$ denotes H, $C_{1-4}$-alkyl;

$R^{3.2}$ denotes a group selected from among $C_{3-6}$-cycloalkyl, het, hetaryl and spiro which is optionally substituted by one or more $R^{3.2.1}$ $R^{3.2.1}$ denotes $C_{1-6}$-alkyl, $C_{3-6}$-cycloalkyl, OH, —$NR^{3.2.1.1}R^{3.2.1.2}$, $NHCOR^{3.2.1.3}$ or het, optionally substituted by one or more groups selected from among $C_{1-4}$-alkyl, $SO_2R^{3.2.1.1}$, $CH_2$—$C_{3-6}$-cycloalkyl and aryl;

$R^{3.2.1.1}$ denotes H, $C_{1-4}$-alkyl or $C_{7-11}$-aralkyl;

$R^{3.2.1.2}$ denotes H, $C_{1-4}$-alkyl or $C_{7-11}$-aralkyl;

$R^{3.2.1.3}$ denotes aryl, $C_{7-11}$-aralkyl; or

—$C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH, imidazolidinone;

$R^{3.2.2.1}$ denotes H or $C_{1-6}$-alkyl, aryl, $C_{7-11}$-aralkyl $R^{3.2.2.2}$ denotes H or $C_{1-6}$-alkyl; or aryl, which is optionally substituted by one or two $R^{3.2.3}$ $R^{3.2.3}$ denotes a group selected from among NH—$C_{1-6}$-alkyl-$N(C_{1-6}$-alkyl$)_2$ or het, while het may optionally be substituted by a $C_{1-6}$-alkyl group;

$R^{3.3}$ denotes H or a group selected from among $C_{1-6}$-alkyl, $C_{2-4}$-alkenyl, $C_{2-4}$-alkynyl, $C_{1-4}$-haloalkyl and aryl, which may optionally be substituted by one or more groups $R^{3.3.1}$;

$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2R^{3.2.1.1}$, $SO_2$ $C_{1-4}$-alkyl, $SO_2C_{7-11}$-aralkyl, $CH_2$—$C_{3-6}$-cycloalkyl and aryl;

$R^{3.3.1.1}$, $R^{3.3.1.2}$ and $R^{3.3.1.3}$ denote a group selected from among $C_{1-4}$-alkyl, $C_{2-4}$-alkenyl, $C_{2-4}$-alkynyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $COC_{1-4}$-alkyl-hetaryl, $COC_{2-4}$-alkenyl-hetaryl, $COC_{2-4}$-alkynyl-hetaryl; or two of the groups $R^{3.3.1.1}$, $R^{3.3.1.2}$ and $R^{3.3.1.3}$ together form a five-, six- or seven-membered ring, consisting of carbon atoms and optionally a heteroatom selected from among oxygen, nitrogen and sulphur;

$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4$, $NR^5CONR^4R^5$, $NR^5SOR^4$ or $NR^5SO_2R^4$;

$R^4$ denotes H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by Si($C_{1-4}$-alkyl)$_3$, or $R^4$ denotes a group selected from among aryl, het, hetaryl and optionally substituted by $C_{1-4}$-alkyl;

$R^5$ denotes H or $C_{1-6}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

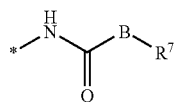

wherein

B denotes a bond, $C_{1-4}$-alkyl or $C_{2-4}$-alkynyl;

$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;

$R^{6.1}$ denotes halogen, $CF_3$, OH, CN, OMe, $SO_2(C_{1-4}$-alkyl);

$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;

$R^{7.1}$ denotes H, $C_{1-4}$-alkyl, $(CH_2)_{2-4}R^{7.1.1}$ or COObutyl;

$R^{7.2}$ denotes H, $C_{1-6}$-alkyl, optionally substituted by one or more OH;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof.

Preferred compounds of formula 1 mentioned above are those wherein $R^a$ denotes a group selected from among aryl, $C_{7-11}$-aralkyl and hetaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl, $R^{1.1}$ denotes OH, $C_{1-6}$-alkyl, $C_{2-6}$-alkenyl $C_{2-6}$-alkynyl, $NR^{1.1.1}R^{1.1.2}$ $R^{1.1.1}$ denotes H, $C_{1-6}$-alkyl, optionally substituted by a group selected from among $NH_2$, NHMe, $NMe_2$;

$R^{1.1.2}$ denotes H, $C_{1-6}$-alkyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

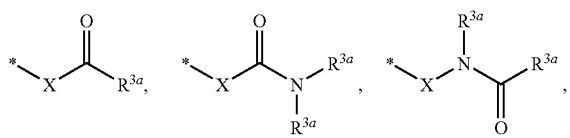

-continued

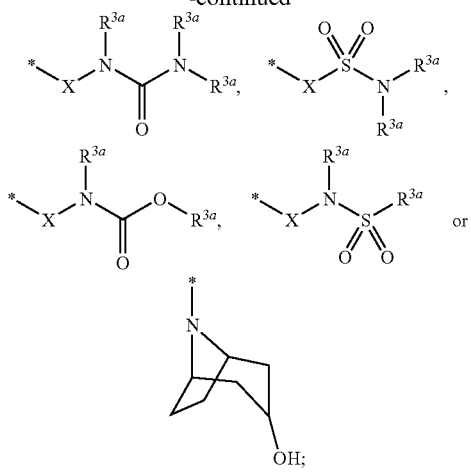

wherein

X denotes a bond or $C_{1-4}$-alkylene;

$R^{3a}$ denotes a group, which may be identical or different, selected from among $R^{3.1}$, $R^{3.2}$ and $R^{3.3}$ $R^{3.1}$ denotes spiro or het, while het may optionally be substituted by one or more $R^{3.1.1}$;

$R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, $NHCOR^{3.1.1.1}$ $R^{3.1.1.1}$ denotes a group selected from among H, $C_{1-4}$-alkyl, aryl and $C_{7-11}$-aralkyl; optionally substituted by a group selected from among halogen, OH and CN;

$R^{3.1.1.2}$ denotes H, $C_{1-4}$-alkyl;

$R^{3.2}$ denotes a group selected from among $C_{3-6}$-cycloalkyl, het, hetaryl and spiro which is optionally substituted by one or more $R^{3.2.1}$ $R^{3.2.1}$ denotes $C_{1-6}$-alkyl, $C_{3-6}$-cycloalkyl, OH, —$NR^{3.2.1.1}R^{3.2.1.2}$, $NHCOR^{3.2.1.3}$ or het, optionally substituted by one or more groups selected from among $C_{1-4}$-alkyl, $SO_2R^{3.2.1.1}$, $CH_2$—$C_{3-6}$-cycloalkyl and aryl;

$R^{3.2.1.1}$ denotes H, $C_{1-4}$-alkyl or $C_{7-11}$-aralkyl;

$R^{3.2.1.2}$ denotes H, $C_{1-4}$-alkyl or $C_{7-11}$-aralkyl;

$R^{3.2.1.3}$ denotes aryl, $C_{7-11}$-aralkyl; or $C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH, imidazolidinone;

$R^{3.2.2.1}$ denotes H or $C_{1-6}$-alkyl, aryl, $C_{7-11}$-aralkyl $R^{3.2.2.2}$ denotes H or $C_{1-6}$-alkyl; or aryl, which is optionally substituted by one or two $R^{3.2.3}$ $R^{3.2.3}$ denotes a group selected from among NH—$C_{1-6}$-alkyl-N($C_{1-6}$-alkyl)$_2$ or het, while het may optionally be substituted by a $C_{1-6}$-alkyl group;

$R^{3.3}$ denotes H or a group selected from among $C_{1-6}$-alkyl, $C_{2-4}$-alkenyl, $C_{2-4}$-alkynyl and aryl, which may optionally be substituted by one or more groups $R^{3.3.1}$;

$R^{3.3.1}$ denotes $C_{5\text{-}6}$-cycloalkyl, $C_{5\text{-}6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1\text{-}4}$-alkyl, $SO_2R^{3.2.1.1}$, $SO_2C_{1\text{-}4}$-alkyl, $SO_2C_{7\text{-}11}$-aralkyl, $CH_2$—$C_{3\text{-}6}$-cycloalkyl and aryl;

$R^{3.3.1.1}$, $R^{3.3.1.2}$ and $R^{3.3.1.3}$ denote a group selected from among $C_{1\text{-}4}$-alkyl, $C_{7\text{-}11}$-aralkyl, $C_{1\text{-}4}$-alkyl-hetaryl, $COC_{1\text{-}4}$-alkyl-hetaryl; or two of the groups $R^{3.3.1.1}$, $R^{3.3.1.2}$ and $R^{3.3.1.3}$ together form a five-, six- or seven-membered ring, consisting of carbon atoms and optionally a heteroatom selected from among oxygen, nitrogen and sulphur;

$R^b$ denotes $R^4$, $OR^4$, —$CH_2OR^4$, $COR^4$, $COOR^4$, $CONR^4R^5$, $NH_2$, $NR^5COOR^4$, $NR^5CONR^4R^5$ or $NR^5SOR^4$;

$R^4$ denotes H, $C_{1\text{-}6}$-alkyl, $C_{1\text{-}6}$-haloalkyl, $C_{1\text{-}6}$-alkylene-OH, $C_{2\text{-}6}$-alkenyl, $C_{7\text{-}11}$-aralkyl, $C_{1\text{-}4}$-alkyl-hetaryl, $C_{2\text{-}6}$-alkynyl, optionally substituted by $Si(C_{1\text{-}4}\text{-alkyl})_3$, or $R^4$ denotes a group selected from among aryl, het, hetaryl and optionally substituted by $C_{1\text{-}4}$-alkyl;

$R^5$ denotes H or $C_{1\text{-}6}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

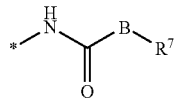

wherein
B denotes a bond, $C_{1\text{-}4}$-alkyl or $C_{2\text{-}4}$-alkynyl;
$R^6$ denotes H or a group selected from among $C_{1\text{-}4}$-alkyl, $C_{3\text{-}6}$-cycloalkyl, het, aryl, hetaryl optionally substituted by one or more groups $R^{6.1}$;
$R^{6.1}$ denotes halogen, $CF_3$, OH, CN, OMe, $SO_2(C_{1\text{-}4}$-alkyl);
$R^7$ denotes H, $C_{1\text{-}4}$-alkyl, $C_{3\text{-}6}$-cycloalkyl, $NR^{7.1}R^{7.2}$, $OR^{7.2}$, $SR^{7.2}$, hetaryl, het, optionally substituted by $C_{1\text{-}4}$-alkyl or $CONH_2$;
$R^{7.1}$ denotes H, $C_{1\text{-}4}$-alkyl, $(CH_2)_{2\text{-}4}R^{7.1.1}$ or COObutyl;
$R^{7.2}$ denotes H, $C_{1\text{-}6}$-alkyl, optionally substituted by one or more OH;
$R^{7.1.1}$ denotes $NR^{7.1.1.1}R^{7.1.1.2}$, het or 1-imidazolyl, 2-(N-ethylpyrrolidine);
$R^{7.1.1.1}$ denotes H or $C_{1\text{-}6}$-alkyl;
$R^{7.1.1.2}$ denotes H or $C_{1\text{-}6}$-alkyl;
and the pharmacologically acceptable salts, diastereomers, enantiomers, racemates, hydrates or solvates thereof.

Preferred compounds of formula 1 mentioned above are those wherein $R^a$ denotes a group selected from among aryl and $C_{7\text{-}11}$-aralkyl, which may optionally be substituted by one or more groups selected from among $R^1$, $R^2$ and $R^3$; or hetaryl optionally substituted by one or more $C_{1\text{-}4}$-alkyl;

$R^1$ denotes $C_{1\text{-}4}$-alkyl, $C_{1\text{-}4}$-haloalkyl, $C_{1\text{-}4}$-alkylene-COOH, $C_{1\text{-}4}$-alkoxy, halogen, OH, CN, $COR^{1.1}$, O—$C_{1\text{-}4}$-haloalkyl, $NO_2$ or $SO_2R^{1.1}$;

$R^{1.1}$ denotes OH, methyl, $NH_2$, NHMe, $NMe_2$,

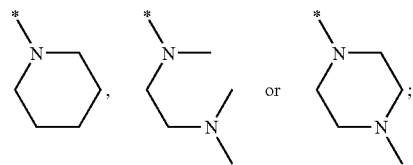

$R^2$ denotes $C_{1\text{-}4}$-alkyl, $C_{1\text{-}4}$-alkoxy or halogen;
$R^3$ denotes a group selected from among

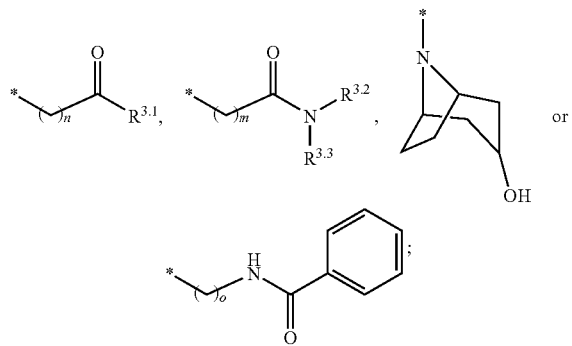

wherein
n denotes 0 or 1;
m denotes 0 or 1;
o denotes 2;
$R^{3.1}$ denotes spiro or het, while het may optionally be substituted by one or more $R^{3.1.1}$;
$R^{3.1.1}$ denotes $C_{1\text{-}4}$-alkyl, $C_{2\text{-}4}$-alkenyl, OH, $C_{1\text{-}4}$-alkylene-OH, $CH_2NEt_2$, COMe, COOH, $CONH_2$, $NH_2$, het, hetaryl,

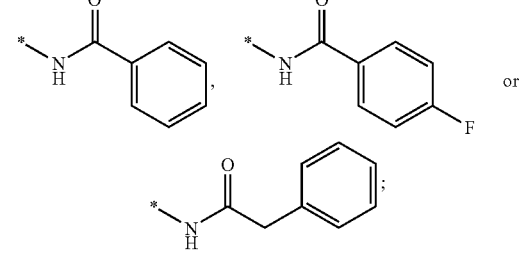

$R^{3.2}$ denotes a group selected from among $C_{3\text{-}6}$-cycloalkyl, het, hetaryl and spiro which is optionally substituted by one or two $R^{3.2.1}$ $R^{3.2.1}$ denotes $C_{1\text{-}4}$-alkyl, cyclopentyl, OH, —$NR^{3.2.1.1}R^{3.2.1.2}$ or

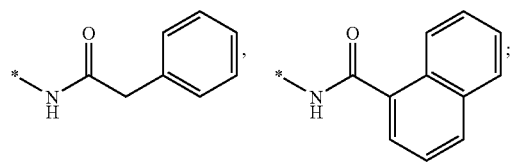

or het, is optionally substituted by one or more groups selected from among methyl, $SO_2R^{3.2.1.1}$, $R^{3.2.1.1}$ denotes H, methyl or benzyl;

$R^{3.2.1.2}$ denotes H, methyl or benzyl; or $C_{1-6}$-alkyl, which is optionally substituted by one or two $R^{3.2.2}$;

$R^{3.2.2}$ denotes $C_{2-4}$-alkenyl, $C_{2-4}$-alkynyl, $COOR^{3.2.2.1}$ $CONR^{3.2.2.1}R^{3.2.2.2}$, $NR^{3.2.2.1}R^{3.2.2.2}$, $NHCOR^{3.2.2.1}$, $C_{1-4}$-haloalkyl, CN, OH, $SO_2R^{3.2.2.1}$, $C_{3-6}$-cycloalkyl or a group selected from among or a group selected from among het, hetaryl and aryl, which is optionally substituted by one or more groups selected from among Cl, methyl, $CONR^{3.2.2.1}R^{3.2.2.2}$, OH;

$R^{3.2.2.1}$ denotes H or methyl;

$R^{3.2.2.2}$ denotes H or methyl; or aryl, which is optionally substituted by one or two $R^{3.2.3}$ $R^{3.2.3}$ denotes a group selected from among $R^{3.3}$ denotes H or a group selected from among $C_{1-6}$-alkyl and aryl, which may optionally be substituted by one or more groups $R^{3.3.1}$;

$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C(NR^{3.3.1.1}R^{3.3.1.2})NR^{3.3.1.3}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2R^{3.2.1.1}$, $SO_2$ $C_{1-4}$-alkyl, $SO_2C_{7-11}$-aralkyl, $R^{3.3.1.1}$, $R^{3.3.1.2}$ and $R^{3.3.1.3}$ denote a group selected from among $C_{1-4}$-alkyl, $C_{7-11}$-aralkyl, $C_{1-4}$-alkyl-hetaryl, $COC_{1-4}$-alkyl-hetaryl;

$R^b$ denotes $R^4$, $CH_2OR^4$, $COR^4$, $COOR^4$, $CONR^4R^5$, $NH_2$, $NHCOOR^4$, $NHCONR^4R^5$ or OH;

$R^4$ denotes H, $C_{1-4}$-alkyl, $C_{1-4}$-alkylene-OH, $C_{2-4}$-alkynyl, $C_{1-6}$-haloalkyl, aryl, het, hetaryl, $R^5$ denotes H or $C_{1-4}$-alkyl;

$R^c$ denotes $NHR^6$ or a group selected from among wherein

B denotes a bond, $C_{1-4}$-alkyl or $C_{2-4}$-alkynyl;

$R^6$ denotes H, $C_{1-4}$-alkyl, $C_{3-6}$-cycloalkyl, $C_{7-11}$-aralkyl, aryl, optionally substituted by $SO_2CH_3$;

$R^7$ denotes H, $NR^{7.1}R^{7.2}$, $OR^{7.2}$, $SR^{7.2}$, hetaryl, het, optionally substituted by $C_{1-4}$-alkyl or $CONH_2$, or a group selected from among $R^{7.1}$ denotes H, $C_{1-4}$-alkyl, $(CH_2)_2R^{7.1.1}$ or COObutyl;

$R^{7.2}$ denotes H, $C_{1-4}$-alkyl;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof.

Particularly preferred are the above-mentioned compounds of formula 1 wherein $R^a$ denotes phenyl or benzyl, in each case optionally substituted by one or more groups selected from among $R^1$, $R^2$ and $R^3$; or

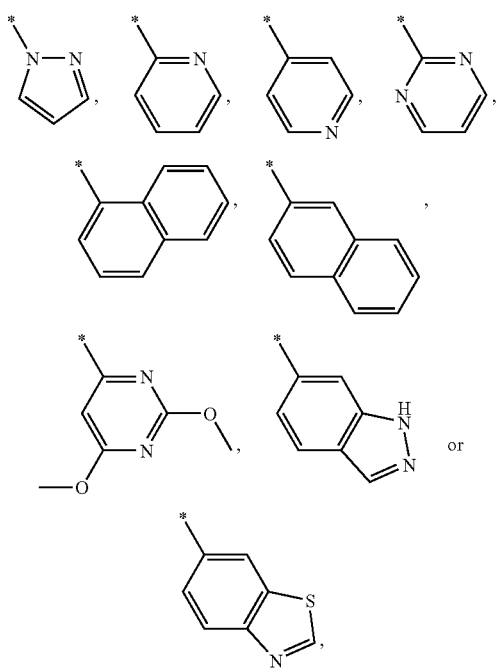

R¹ denotes methyl, ethyl, propyl, butyl, $CF_3$, $CH_2COOH$, methoxy, F, Cl, Br, OH, CN, $COR^{1.1}$, $OCF_3$, $NO_2$ or $SO_2R^{1.1}$;

$R^{1.1}$ denotes OH, methyl, $NH_2$, NHMe, $NMe_2$,

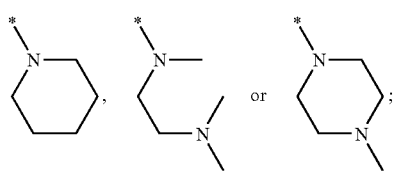

R² denotes methyl, methoxy, F, Cl or Br;
R³ denotes a group selected from among

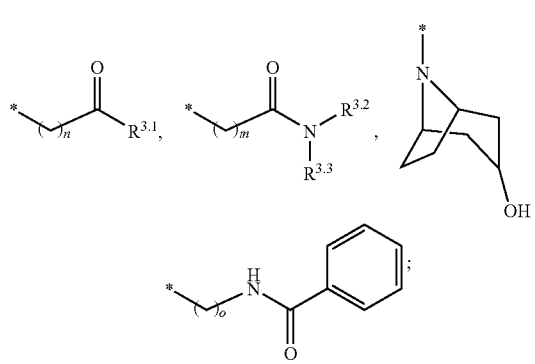

wherein
n denotes 0 or 1;
m denotes 0 or 1;
o denotes 2;

$R^{3.1}$ denotes a group selected from among

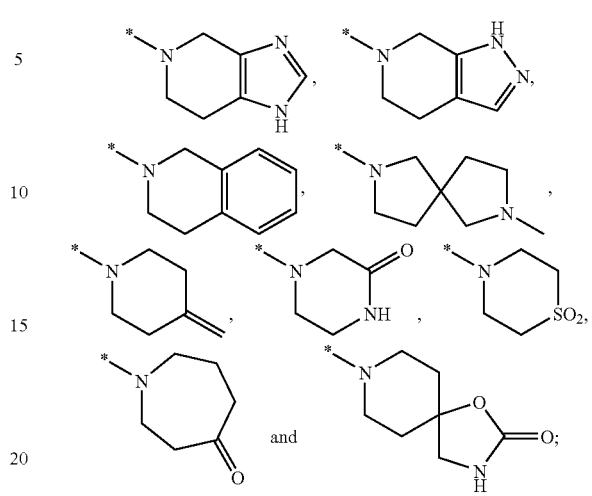

or a group selected from among

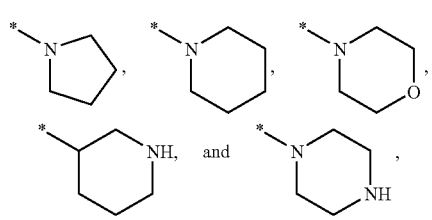

which may optionally be substituted by one or more $R^{3.1.1}$;
$R^{3.1.1}$ denotes methyl, ethyl, OH, $CH_2OH$, $CH_2CH_2OH$, $CH_2NEt_2$, COMe, COOH, $CONH_2$, $NH_2$,

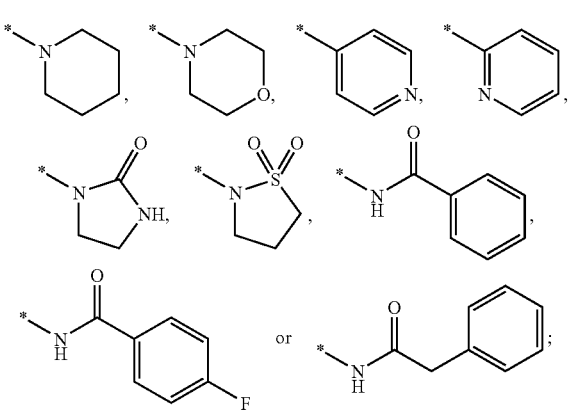

$R^{3.2}$ denotes a group selected from among

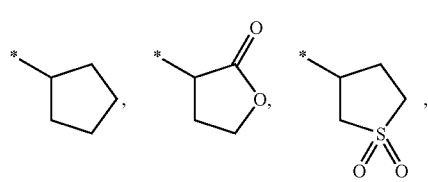

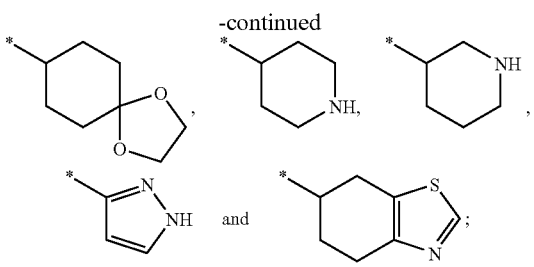

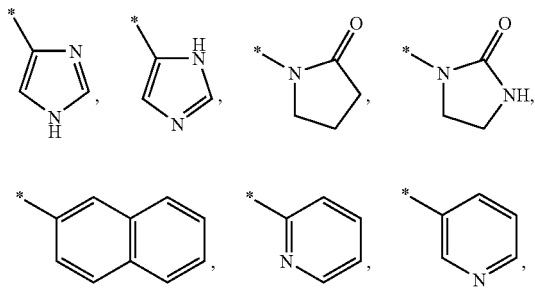

which is optionally substituted by one or more groups selected from among methyl, ethyl, cyclopentyl, OH, NH$_2$; or cyclohexyl, which is optionally substituted by one or two R$^{3.2.1}$ R$^{3.2.1}$ denotes —NR$^{3.2.1.1}$R$^{3.2.1.2}$ or a group selected from among

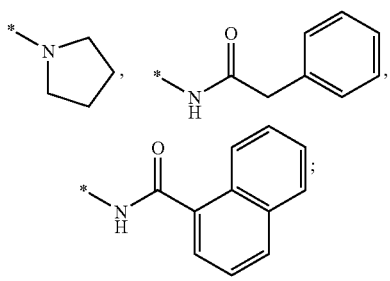

or a group selected from among

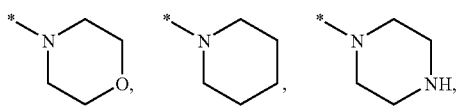

which is optionally substituted by one or more groups selected from among methyl, SO$_2$R$^{3.2.1.1}$,

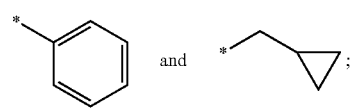

R$^{3.2.1.1}$ denotes H, methyl or benzyl;

R$^{3.2.1.2}$ denotes H, methyl or benzyl; or

—C$_{1-6}$-alkyl, straight-chain or branched, which is optionally substituted by one or two R$^{3.2.2}$;

R$^{3.2.2}$ denotes C═CH$_2$, C≡CH, COOR$^{3.2.2.1}$, CONR$^{3.2.2.1}$R$^{3.2.2.2}$, NR$^{3.2.2.1}$R$^{3.2.2.2}$, NHCOR$^{3.2.2.1}$, CF$_3$, CN, OH, SO$_2$R$^{3.2.2.1}$ or a group selected from among

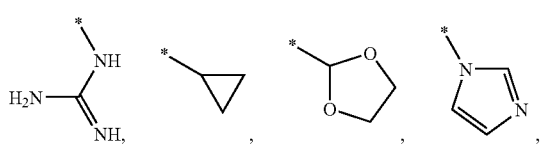

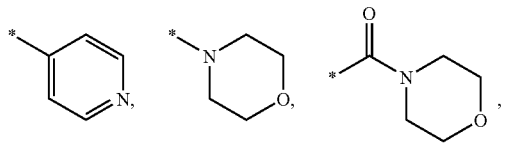

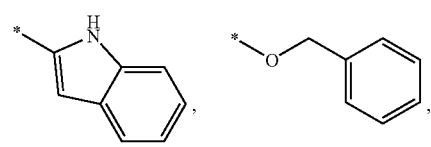

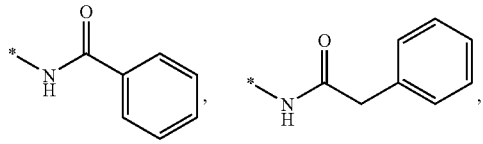

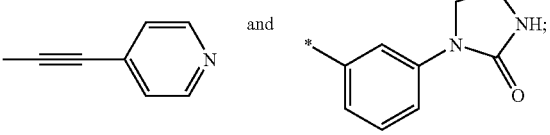

or a group selected from among

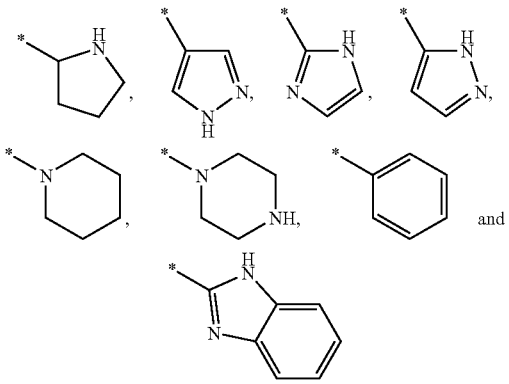

which is optionally substituted by one or more groups selected from among Cl, methyl, CONR$^{3.2.2.1}$R$^{3.2.2.2}$, OH;

R$^{3.2.2.1}$ denotes H or methyl;

R$^{3.2.2.2}$ denotes H or methyl; or phenyl, which is optionally substituted by one or two R$^{3.2.3}$ $R^{3.2.3}$ denotes a group selected from among

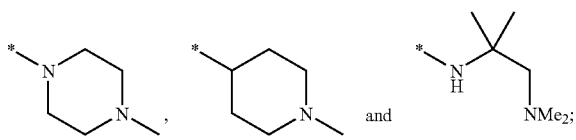

$R^{3.3}$ denotes H, methyl or ethyl;
$R^b$ denotes $R^4$, $CH_2OR^4$, $COR^4$, $COOR^4$, $CONR^4R^5$, $NH_2$, $NHCOOR^4$, $NHCONR^4R^5$ or OH;
$R^4$ denotes H, methyl, ethyl, 2-hydroxyethyl, propyl, C≡CH, $CF_3$, phenyl,

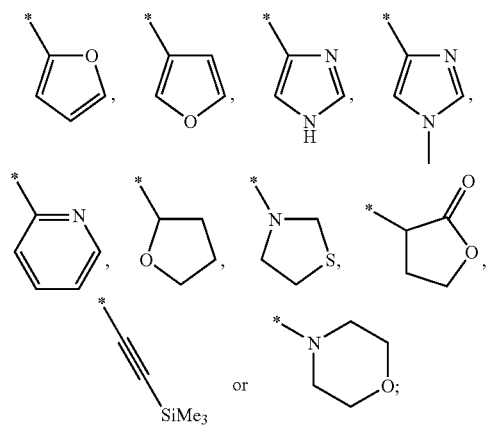

$R^5$ denotes H, methyl or ethyl;
$R^c$ denotes $NHR^6$ or a group selected from among

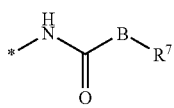

wherein
B denotes a bond, methylene, ethylene, propylene or butylene;
$R^6$ denotes H, phenyl, optionally substituted by $SO_2CH_3$;
$R^7$ denotes H, $NR^{7.1}R^{7.2}$, $OR^{7.2}$, $SR^{7.2}$ or a group selected from among

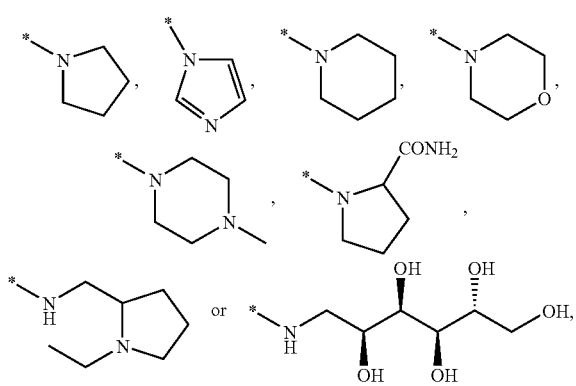

$R^{7.1}$ denotes H, methyl, ethyl, $(CH_2)_2R^{7.1.1}$ or COObutyl;
$R^{7.2}$ denotes H, methyl or ethyl;
$R^{7.11}$ denotes $NMe_2$ or 1-imidazolyl
and the pharmacologically acceptable salts, diastereomers, enantiomers, racemates, hydrates or solvates thereof.

Particularly preferred are the above-mentioned compounds of formula 1 wherein
$R^c$ denotes a group

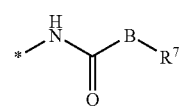

wherein
B denotes methylene, propylene;
$R^7$ denotes H, $NR^{7.1}R^{7.2}$ or 1-imidazolyl;
$R^{7.1}$ denotes H or methyl;
$R^{7.2}$ denotes H or methyl;
and the pharmacologically acceptable salts, diastereomers, enantiomers, racemates, hydrates or solvates thereof.

Particularly preferred are the above-mentioned compounds of formula 1 wherein
$R^a$ denotes phenyl, optionally substituted by one or more groups selected from among $R^1$, $R^2$ and $R^3$;
and the pharmacologically acceptable salts, diastereomers, enantiomers, racemates, hydrates or solvates thereof.

Particularly preferred are the above-mentioned compounds of formula 1 wherein
$R^a$ denotes phenyl, optionally substituted by one or more groups selected from among $R^1$ and $R^3$;
$R^1$ denotes methyl, ethyl, propyl, $CF_3$, methoxy, F, Cl or Br;
$R^3$ denotes a group

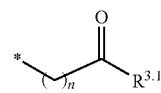

and the pharmacologically acceptable salts, diastereomers, enantiomers, racemates, hydrates or solvates thereof.

Particularly preferred are the above-mentioned compounds of formula 1 wherein
$R^a$ denotes phenyl, optionally substituted by one or more groups selected from among $R^1$ and $R^3$;
$R^1$ denotes methyl, ethyl, propyl, $CF_3$, methoxy, F, Cl or Br;
$R^3$ denotes a group

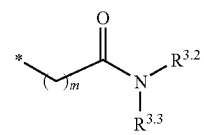

and the pharmacologically acceptable salts, diastereomers, enantiomers, racemates, hydrates or solvates thereof.

Particularly preferred of the above-mentioned compounds of formula 1 are the compounds of formula 1.1

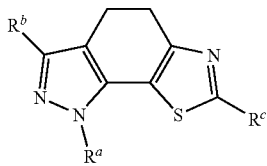
1.1 wherein $R^a$, $R^b$ and $R^c$ have the meanings given above, and the pharmacologically acceptable salts, diastereomers, enantiomers, racemates, hydrates or solvates thereof.

Particularly preferred are the above-mentioned compounds of formula 1.1; wherein $R^a$ denotes phenyl, optionally substituted by one or more groups selected from among $R^1$, $R^2$ and $R^3$; or

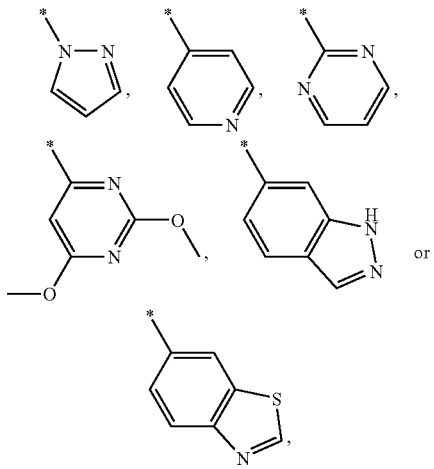

$R^1$ denotes methyl, ethyl, propyl, $CF_3$, $CH_2COOH$, methoxy, F, Cl, Br, CN, $COR^{1.1}$ or $SO_2R^{1.1}$;

$R^{1.1}$ denotes OH, methyl, $NH_2$, NHMe, $NMe_2$ or

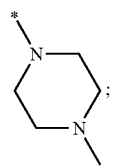

$R^2$ denotes methyl, F, Cl or Br;
$R^3$ denotes a group selected from among

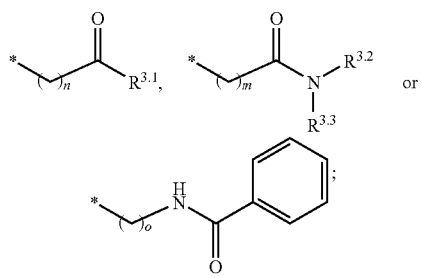

wherein
n denotes 0 or 1;
m denotes 0 or 1;
o denotes 2;
$R^{3.1}$ denotes a group selected from among

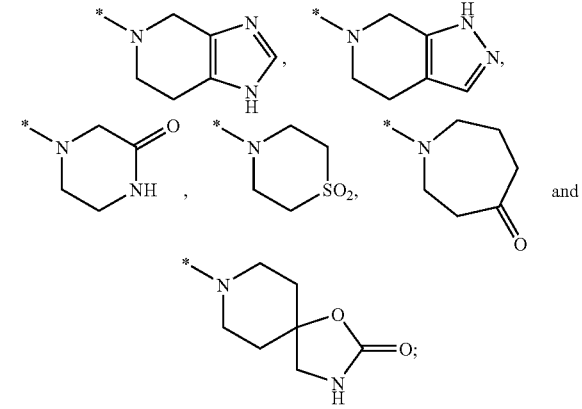

or a group selected from among

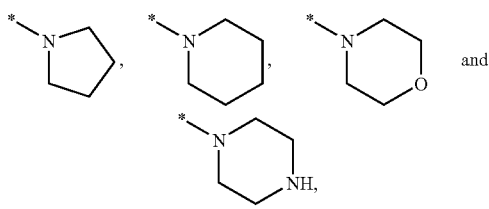

which may optionally be substituted by one or more $R^{3.1.1}$;

$R^{3.1.1}$ denotes methyl, OH, $CH_2OH$, $CH_2CH_2OH$, $CH_2NEt_2$, COMe, COOH, $CONH_2$,

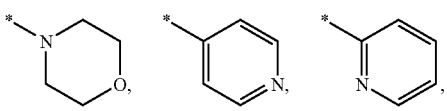

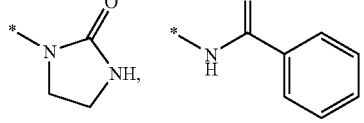

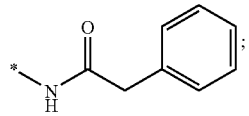

$R^{3.2}$ denotes a group selected from among

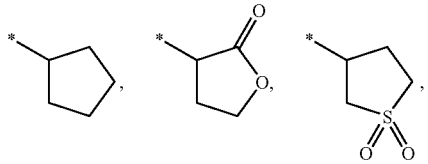

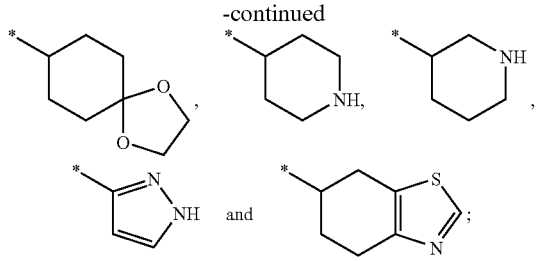

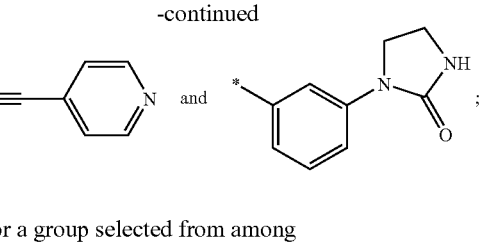

or a group selected from among

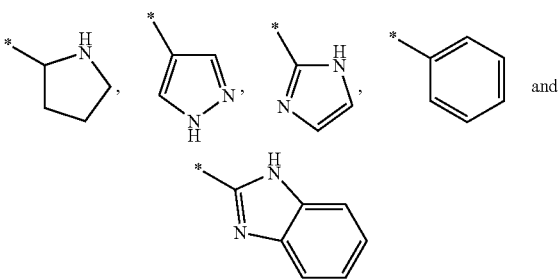

which is optionally substituted by one or more groups selected from among methyl, ethyl, cyclopentyl, OH, NH$_2$; or cyclohexyl, which is optionally substituted by one or two R$^{3.2.1}$ R$^{3.2.1}$ denotes —NR$^{3.2.1.1}$R$^{3.2.1.2}$ or a group selected from among

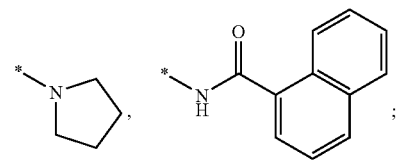

or a group selected from among

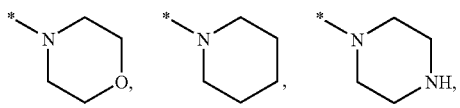

which is optionally substituted by one or more groups selected from among methyl, CONR$^{3.2.2.1}$R$^{3.2.2.2}$, OH;

R$^{3.2.2.1}$ denotes H or methyl;

R$^{3.2.2.2}$ denotes H or methyl; or phenyl, which is optionally substituted by one or two R$^{3.2.3}$ R$^{3.2.3}$ denotes a group selected from among

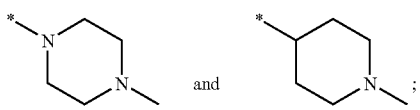

which is optionally substituted by one or more methyl groups

R$^{3.2.1.1}$ denotes H or methyl;

R$^{3.2.1.2}$ denotes H or methyl; or

—C$_{1-6}$-alkyl, straight-chain or branched, which is optionally substituted by one or two R$^{3.2.2}$;

R$^{3.2.2}$ denotes C=CH$_2$, C≡CH, COOR$^{3.2.2.1}$, CONR$^{3.2.2.1}$R$^{3.2.2.2}$, NR$^{3.2.2.1}$R$^{3.2.2.2}$, CN, OH or a group selected from among

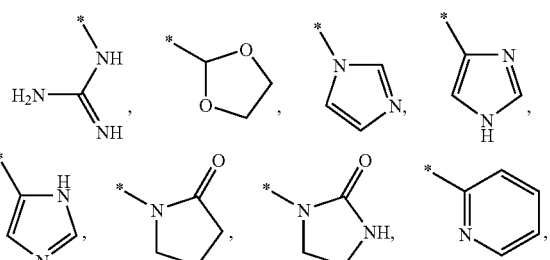

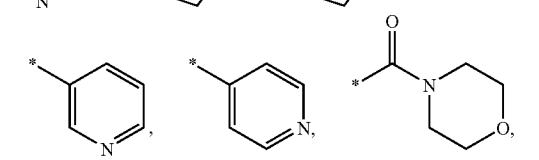

R$^{3.3}$ denotes H, methyl or ethyl;

R$^b$ R$^4$, CH$_2$OCH$_3$, COR$^4$, COOH, COOCH$_3$CONR$^4$R$^5$, NH$_2$, NHCOOR$^4$ or OH;

R$^4$ denotes H, methyl, propyl, C≡CH, phenyl,

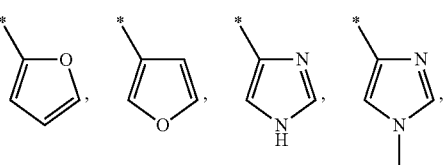

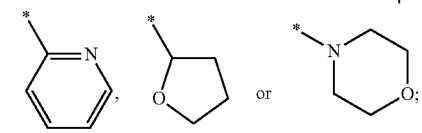

R$^5$ denotes H or methyl;

R$^c$ denotes a group

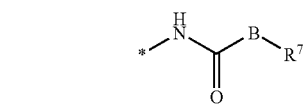

wherein

B denotes methylene, propylene;

$R^7$ denotes H, $NR^{7.1}R^{7.2}$ or 1-imidazolyl;

$R^{7.1}$ denotes H or methyl;

$R^{7.2}$ denotes H or methyl;

and the pharmacologically acceptable salts, diastereomers, enantiomers, racemates, hydrates or solvates thereof.

Most preferred are the above-mentioned compounds of formula 1.1; wherein $R^a$ denotes phenyl, optionally substituted by one or more groups selected from among $R^1$, $R^2$ and $R^3$; or

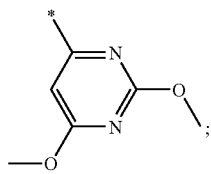

$R^1$ denotes methyl, $CF_3$, methoxy, F, Cl, Br, $COR^{1.1}$ or $SO_2R^{1.1}$;

$R^{1.1}$ denotes OH, $NH_2$, NHMe or $NMe_2$;

$R^2$ denotes Cl;

$R^3$ denotes a group selected from among

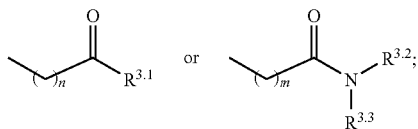

wherein n denotes 0 or 1;

m denotes 0 or 1;

$R^{3.1}$ denotes a group selected from among

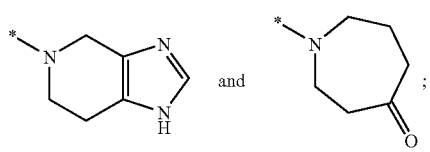

or a group selected from among

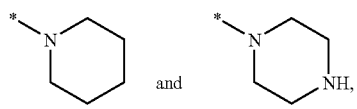

which may optionally be substituted by one or more $R^{3.1.1}$;

$R^{3.1.1}$ denotes OH, $CONH_2$ or 4-pyridinyl, $R^{3.2}$ denotes a group selected from among

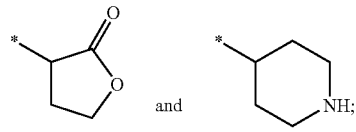

which is optionally substituted by one or more methyl groups; or cyclohexyl, which is optionally substituted by one or two $R^{3.2.1}$;

$R^{3.2.1}$ denotes a group selected from among

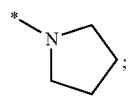

—$C_{1-6}$-alkyl, straight-chain or branched, which is optionally substituted by one or two $R^{3.2.2}$;

$R^{3.2.2}$ denotes $COOR^{3.2.2.1}$, $CONR^{3.2.2.1}R^{3.2.2.2}$, 4-pyridinyl or a group selected from among

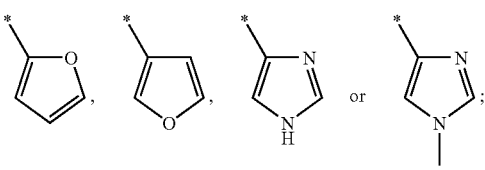

which is optionally substituted by one or more groups selected from among methyl;

$R^{3.2.2.1}$ denotes H or methyl;

$R^{3.2.2.2}$ denotes H or methyl; or $R^{3.3}$ denotes H, methyl or ethyl;

$R^b$ denotes $R^4$, $CH_2OCH_3$ or OH;

$R^4$ denotes H, C≡CH,

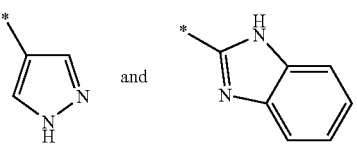

$R^c$ denotes a group

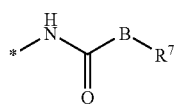

wherein

B denotes methylene, propylene;

$R^7$ denotes H or $NR^{7.1}R^{7.2}$;

$R^{7.1}$ denotes H or methyl;

$R^{7.2}$ denotes H or methyl;

and the pharmacologically acceptable salts, diastereomers, enantiomers, racemates, hydrates or solvates thereof.

Particularly preferred of the above-mentioned compounds of formula 1 are the compounds of formula 1.2

1.2

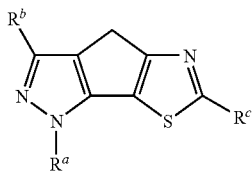

wherein $R^a$, $R^b$ and $R^c$ have the meanings given above, and the pharmacologically acceptable salts, diastereomers, enantiomers, racemates, hydrates or solvates thereof.

Particularly preferred are the above-mentioned compounds of formula 1.2; wherein $R^b$ and $R^c$ have the meanings given above and $R^a$ denotes aryl, optionally substituted by one or more groups selected from among $R^1$, $R^2$ and $R^3$;

$R^1$ and $R^2$ independently of one another denote $C_{1-6}$-alkyl, $C_{1-6}$-haloalkyl, $C_{1-6}$-alkoxy, halogen, $COR^{1.1}$, $SO_2R^{1.1}$, $R^{1.1}$ denotes $C_{1-6}$-alkyl, $NR^{1.1.1}R^{1.1.2}$ $R^{1.1.1}$ denotes H, $C_{1-6}$-alkyl, optionally substituted by a group selected from among $NH_2$, NHMe, $NMe_2$;

$R^{1.1.2}$ denotes H, $C_{1-6}$-alkyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

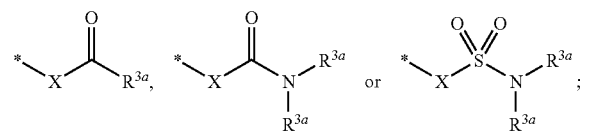

wherein
X denotes a bond or $C_{1-4}$-alkylene;
$R^{3a}$ denotes a group, which may be identical or different, selected from among $R^{3.1}$, $R^{3.2}$ and $R^{3.3}$;
$R^{3.1}$ denotes spiro or het, while het may optionally be substituted by one or more $R^{3.1.1}$;
$R^{3.1.1}$ denotes $NR^{3.1.1.1}R^{3.1.1.2}$;
$R^{3.1.1.1}$ denotes H, $C_{1-4}$-alkyl;
$R^{3.1.1.2}$ denotes H, $C_{1-4}$-alkyl;

and the pharmacologically acceptable salts, diastereomers, enantiomers, racemates, hydrates or solvates thereof.

Particularly preferred are the above-mentioned compounds of formula 1.2; wherein $R^a$ denotes phenyl, optionally substituted by one or more groups selected from among $R^1$, $R^2$ and $R^3$;

$R^1$ and $R^2$ independently of one another denote $C_{1-6}$-alkyl, $C_{1-6}$-haloalkyl, $C_{1-6}$-alkoxy, halogen, $COR^{1.1}$, $SO_2R^{1.1}$, $R^{1.1}$ denotes methyl ethyl, propyl, $NR^{1.1.1}R^{1.1.2}$ $R^{1.1.1}$ denotes H, methyl ethyl, propyl;

$R^{1.1.2}$ denotes H, methyl ethyl, propyl;

or $R^{1.1.1}$ and $R^{1.1.2}$ together form a five- or six-membered heterocyclic ring, which may optionally be substituted by a group selected from among methyl, ethyl, propyl;

$R^3$ denotes a group selected from among

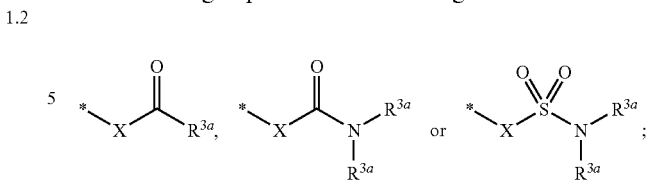

wherein
X denotes a bond or methylene, ethylene, propylene;
$R^{3a}$ denotes a group, which may be identical or different, selected from among $R^{3.1}$, $R^{3.2}$ and $R^{3.3}$;
$R^{3.1}$ denotes spiro or het, while het may optionally be substituted by one or more $R^{3.11}$
$R^{3.1.1.1}$ denotes $NR^{3.1.1.1}R^{3.1.1.2}$
$R^{3.1.1.1}$ denotes H, methyl ethyl, propyl;
$R^{3.1.1.2}$ denotes H, methyl ethyl, propyl;
$R^b$ denotes $R^4$;
$R^4$ denotes H;
$R^c$ denotes $NHR^6$ or a group

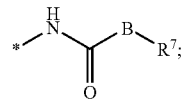

wherein
B denotes a bond, methylene, ethylene or propylene;
$R^6$ denotes H;
$R^7$ denotes H or $NR^{7.1}R^{7.2}$

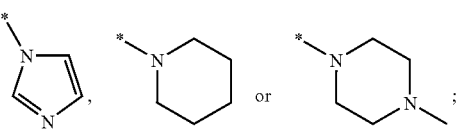

$R^{7.1}$ denotes H, methyl, ethyl, $(CH_2)_2R^{7.1.1}$ or COObutyl;
$R^{7.2}$ denotes H, methyl or ethyl;
$R^{7.1.1}$ denotes $NMe_2$ or 1-imidazolyl and the pharmacologically acceptable salts, diastereomers, enantiomers, racemates, hydrates or solvates thereof.

Particularly preferred are the above-mentioned compounds of formula 1.2; wherein $R^a$ denotes phenyl, optionally substituted by one or more groups selected from among $R^1$ and $R^2$;

$R^1$ denotes methyl, ethyl, propyl, $CF_3$, F, Cl, $COR^{1.1}$ or $SO_2R^{1.1}$;

$R^{1.1}$ denotes methyl;

$R^2$ denotes methyl, F or Cl;

$R^b$ denotes $R^4$;

$R^4$ denotes H;

$R^c$ denotes $NHR^6$ or a group

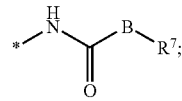

wherein
B denotes a bond, methylene, ethylene or propylene;
$R^6$ denotes H;
$R^7$ denotes H or $NR^{7.1}R^{7.2}$;

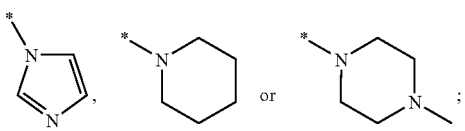

R$^{7.1}$ denotes H, methyl, ethyl, (CH$_2$)$_2$R$^{7.1.1}$ or COObutyl;
R$^{7.2}$ denotes H, methyl or ethyl;
R$^{7.1.1}$ denotes NMe$_2$ or 1-imidazolyl
and the pharmacologically acceptable salts, diastereomers, enantiomers, racemates, hydrates or solvates thereof.

Most preferred are the above-mentioned compounds of formula 1.2; wherein
R$^a$ denotes phenyl, optionally substituted by R$^1$;
R$^1$ denotes methyl, F, Cl, Br or COR$^{1.1}$;
R$^{1.1}$ denotes methyl;
R$^b$ denotes R$^4$;
R$^4$ denotes H;
R$^c$ denotes a group

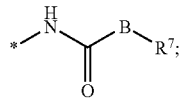

wherein
B denotes a bond, methylene or propylene;
R$^7$ denotes H or NR$^{7.1}$R$^{7.2}$,
R$^{7.1}$ denotes H or methyl;
R$^{7.2}$ denotes methyl;
and the pharmacologically acceptable salts, diastereomers, enantiomers, racemates, hydrates or solvates thereof.

Particularly preferred of the above-mentioned compounds of formula 1 are the compounds of formula 1.3

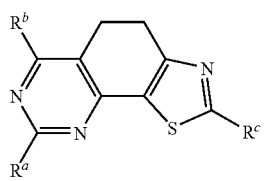

1.3 wherein R$^a$, R$^b$ and R$^c$ have the meanings given above, and the pharmacologically acceptable salts, diastereomers, enantiomers, racemates, hydrates or solvates thereof.

Particularly preferred are the above-mentioned compounds of formula 1.3; wherein R$^b$ and R$^c$ have the meanings given above and
R$^a$ denotes aryl, optionally substituted by one or more groups selected from among R$^1$, R$^2$ and R$^3$, or hetaryl;
R$^1$ and R$^2$ independently of one another denote C$_{1-6}$-alkyl, C$_{1-6}$-haloalkyl, C$_{1-6}$-alkoxy, halogen, COR$^{1.1}$;
R$^{1.1}$ denotes OH, C$_{1-6}$-alkyl, NR$^{1.1.1}$R$^{1.1.2}$
R$^{1.1.1}$ denotes H, C$_{1-6}$-alkyl, optionally substituted by a group selected from among NH$_2$, NHMe, NMe$_2$;
R$^{1.1.2}$ denotes H, C$_{1-6}$-alkyl;
or R$^{1.1.1}$ and R$^{1.1.2}$ together form a five- or six-membered heterocyclic ring, which may optionally be substituted by a group selected from among methyl, ethyl, propyl;

R$^3$ denotes a group selected from among

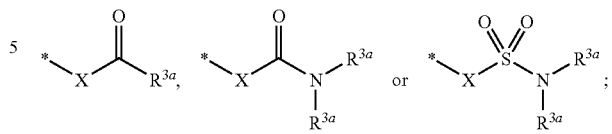

wherein
X denotes a bond or C$_{1-4}$-alkylene;
R$^{3a}$ denotes a group, which may be identical or different, selected from among R$^{3.1}$, R$^{3.2}$ and R$^{3.3}$;
R$^{3.1}$ denotes spiro or het, while het may optionally be substituted by one or more R$^{3.1.1}$;
R$^{3.1.1}$ denotes NR$^{3.1.1.1}$R$^{3.1.1.2}$;
R$^{3.1.1.1}$ denotes H, C$_{1-4}$-alkyl;
R$^{3.1.1.2}$ denotes H, C$_{1-4}$-alkyl;
and the pharmacologically acceptable salts, diastereomers, enantiomers, racemates, hydrates or solvates thereof.

Particularly preferred are the above-mentioned compounds of formula 1.3; wherein
R$^a$ denotes phenyl, optionally substituted by one or more groups selected from among R$^1$, R$^2$ and R$^3$, pyrazolyl or pyridinyl;
R$^1$ and R$^2$ independently of one another denote C$_{1-6}$-alkyl, C$_{1-6}$-haloalkyl, C$_{1-6}$-alkoxy, halogen, COR$^{1.1}$,
R$^{1.1}$ denotes methyl ethyl, propyl, NR$^{1.1.1}$R$^{1.1.2}$
R$^{1.1.1}$ denotes H, methyl ethyl, propyl;
R$^{1.1.2}$ denotes H, methyl ethyl, propyl;
or R$^{1.1.1}$ and R$^{1.1.2}$ together form a five- or six-membered heterocyclic ring, which may optionally be substituted by a group selected from among methyl, ethyl, propyl;
R$^3$ denotes a group selected from among

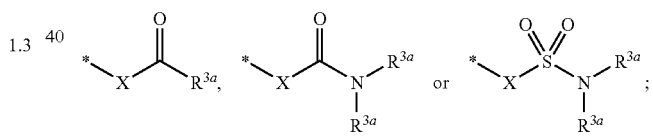

wherein
X denotes a bond or C$_{1-4}$-alkylene;
R$^{3a}$ denotes a group, which may be identical or different, selected from among R$^{3.1}$, R$^{3.2}$ and R$^{3.3}$
R$^{3.1}$ denotes spiro or het, while het may optionally be substituted by one or more R$^{3.1.1}$;
R$^{3.1}$ denotes NR$^{3.1.1.1}$R$^{3.1.1.2}$
R$^{3.1.1.1}$ denotes H, methyl ethyl, propyl;
R$^{3.1.1.2}$ denotes H, methyl ethyl, propyl;
R$^b$ denotes R$^4$ or OH;
R$^4$ denotes H;
R$^c$ denotes NHR$^6$ or a group

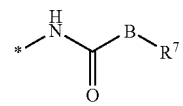

wherein
B denotes a bond, methylene, ethylene or propylene;
R$^6$ denotes H;

$R^7$ denotes H, $NR^{7.1}R^{7.2}$ or a group selected from among

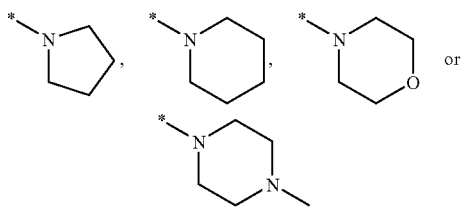

$R^{7.1}$ denotes H, methyl or $(CH_2)_2R^{7.1.1}$;
$R^{7.2}$ denotes H, methyl or ethyl;
$R^{7.1.1}$ denotes $NMe_2$;
and the pharmacologically acceptable salts, diastereomers, enantiomers, racemates, hydrates or solvates thereof.

Particularly preferred are the above-mentioned compounds of formula 1.3; wherein
$R^a$ denotes phenyl, optionally substituted by one or more groups selected from among $R^1$ and $R^2$; or

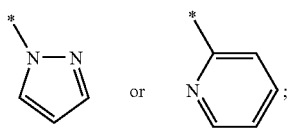

$R^1$ denotes methyl, methoxy, Cl, OH or $COR^{1.1}$;
$R^{1.1}$ denotes $NH_2$, NHMe or $NMe_2$;
$R^2$ denotes methoxy or Cl;
$R^b$ denotes $R^4$ or OH;
$R^4$ denotes H;
$R^c$ denotes $NHR^6$ or a group

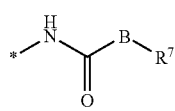

wherein
B denotes a bond, methylene, ethylene or propylene;
$R^6$ denotes H;
$R^7$ denotes H, $NR^{7.1}R^{7.2}$ or a group selected from among

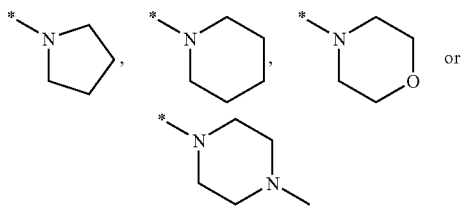

$R^{7.1}$ denotes H, methyl or $(CH_2)_2R^{7.1.1}$;
$R^{7.2}$ denotes H, methyl or ethyl;
$R^{7.1.1}$ denotes $NMe_2$;
and the pharmacologically acceptable salts, diastereomers, enantiomers, racemates, hydrates or solvates thereof.

Most preferred are the above-mentioned compounds of formula 1.3; wherein
$R^a$ denotes phenyl, optionally substituted by one or more groups selected from among $R^1$, $R^2$ and $R^3$; or $R^1$ denotes Cl or $COR^{1.1}$
$R^{1.1}$ denotes $NH_2$;
$R^2$ denotes Cl;
$R^b$ denotes $R^4$ or OH;
$R^4$ denotes H;
$R^c$ denotes $NHR^6$ or a group

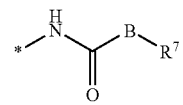

wherein
B denotes methylene;
$R^6$ denotes H;
$R^7$ denotes H;
and the pharmacologically acceptable salts, diastereomers, enantiomers, racemates, hydrates or solvates thereof.

Particularly preferred of the above-mentioned compounds of formula 1 are the above-mentioned compounds of formula 1.4

1.4

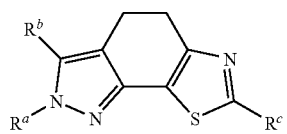

wherein $R^a$, $R^b$ and $R^c$ have the meanings given above, and the pharmacologically acceptable salts, diastereomers, enantiomers, racemates, hydrates or solvates thereof.

Particularly preferred are the above-mentioned compounds of formula 1.4; wherein
$R^a$ denotes phenyl, optionally substituted by one or more groups selected from among $R^1$ and $R^3$; or
$R^1$ denotes methyl, F, Cl or Br;
$R^3$ denotes a group selected from among

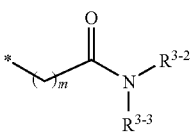

wherein
m denotes 0;
$R^{3.2}$ denotes a group

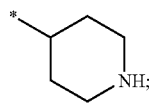

which is optionally substituted by a group selected from among methyl and cyclopentyl;
cyclohexyl, which is optionally substituted by a $R^{3.2.1}$ $R^{3.2.1}$ denotes a group

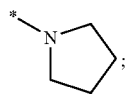

$R^{3.3}$ denotes H;
$R^b$ denotes $R^4$;
$R^4$ denotes a group selected from among

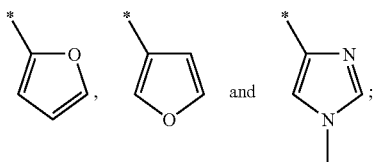

$R^c$ denotes a group

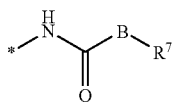

wherein
B denotes methylene;
$R^7$ denotes H;
and the pharmacologically acceptable salts, diastereomers, enantiomers, racemates, hydrates or solvates thereof.

Most preferred are the above-mentioned compounds of formula 1.4; wherein
$R^a$ denotes phenyl, optionally substituted by one or more groups selected from among $R^1$ and $R^3$; or
$R^1$ denotes Cl;
$R^3$ denotes a group selected from among

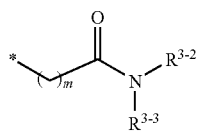

wherein
m denotes 0;
$R^{3.2}$ denotes a group

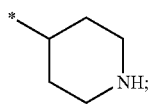

which is optionally substituted by methyl; or
cyclohexyl, which is optionally substituted by a $R^{3.2.1}$ $R^{3.2.1}$ denotes a group

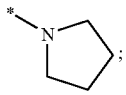

$R^{3.3}$ denotes H;
$R^b$ denotes $R^4$;
$R^4$ denotes a group

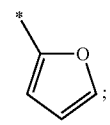

$R^c$ denotes a group

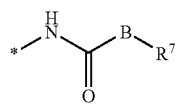

wherein
B denotes methylene;
$R^7$ denotes H;
and the pharmacologically acceptable salts, diastereomers, enantiomers, racemates, hydrates or solvates thereof.

Also preferred are the above-mentioned compounds of formula 1; wherein
$R^a$ denotes H, $C_{1-6}$-alkyl, $C_{2-6}$-alkenyl, $C_{3-8}$-cycloalkyl, $C_{3-8}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;
$R^8$ denotes $C_{1-6}$-alkyl, $C_{3-6}$-cycloalkyl, $NH_2$, hetaryl or aryl, optionally substituted by one or more halogens or $C_{1-4}$-alkyl;
$R^9$ denotes H, $COOR^{12}$, $CONR^{12}$ or $C_{1-6}$-alkyl, optionally substituted by one or more COOH, $N(C_{1-6}$-alkyl$)_2$ or het, optionally substituted by one or more $C_{1-6}$-alkyl; or $R^9$ denotes het, optionally substituted by one or more $C_{1-4}$-alkyl;
$R^{10}$ denotes H, $C_{1-6}$-alkyl, CO—$C_{1-6}$-alkyl or $C_{2-6}$-alkynyl;
$R^{11}$ denotes $C_{1-6}$-alkyl, optionally substituted by one or more $N(C_{1-4}$-alkyl$)_2$;
$R^{12}$ denotes H, $C_{1-6}$-alkyl;
$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4NR^5CONR^4R^5$, $NR^5SOR^4$ or $NR^5SO_2R^4$;
$R^4$, $R^5$ denote H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by $Si(C_{1-4}$-alkyl$)_3$, or $R^4$ denotes a group selected from among aryl, het, hetaryl and optionally substituted by $C_{1-4}$-alkyl;
or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

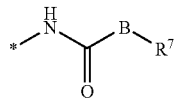

wherein

B denotes a bond, $C_{1-6}$-alkyl, $C_{2-6}$-alkenyl or $C_{2-6}$-alkynyl;

$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;

$R^{6.1}$ denotes halogen, $CF_3$, OH, CN, OMe, $SO_2(C_{1-4}$-alkyl);

$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;

$R^{7.1}$ denotes H, $C_{1-6}$-alkyl, $(CH_2)_{2-4}R^{7.1.1}$ or COObutyl;

$R^{7.2}$ denotes H, $C_{1-6}$-alkyl, optionally substituted by one or more OH;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes H, $C_{1-6}$-alkyl, $C_{2-6}$-alkenyl, $C_{3-8}$-cycloalkyl, $C_{3-8}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$ or $C_{1-4}$-alkyl, optionally substituted by one or more COOH, $N(C_{1-4}$-alkyl$)_2$ or het, optionally substituted by one or more $C_{1-4}$-alkyl; or $R^9$ denotes het, optionally substituted by one or more $C_{1-4}$-alkyl;

$R^{10}$ denotes H, $C_{1-6}$-alkyl, CO—$C_{1-4}$-alkyl or $C_{2-6}$-alkynyl;

$R^{11}$ denotes $C_{1-6}$-alkyl, optionally substituted by one or more $N(C_{1-4}$-alkyl$)_2$;

$R^{12}$ denotes $C_{1-6}$-alkyl;

$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4$, $NR^5CONR^4R^5$, $NR^5SOR^4$ or $NR^5SO_2R^4$;

$R^4$ denotes H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by $Si(C_{1-4}$-alkyl$)_3$, or $R^4$ denotes a group selected from among aryl, het, hetaryl and optionally substituted by $C_{1-4}$-alkyl;

$R^5$ denotes H or $C_{1-6}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

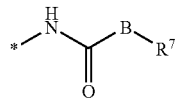

wherein

B denotes a bond, $C_{1-4}$-alkyl or $C_{2-4}$-alkynyl;

$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;

$R^{6.1}$ denotes halogen, $CF_3$, OH, CN, OMe, $SO_2(C_{1-4}$-alkyl);

$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;

$R^{7.1}$ denotes H, $C_{1-4}$-alkyl, $(CH_2)_{2-4}R^{7.1.1}$ or COObutyl;

$R^{7.2}$ denotes H, $C_{1-6}$-alkyl, optionally substituted by one or more OH;

$R^{7.1.1}$ denotes $NR^{7.1.1.1}R^{7.1.1.2}$, het or 1-imidazolyl, 2-(N-ethylpyrrolidine);

$R^{7.1.1.1}$ denotes H or $C_{1-6}$-alkyl;

$R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein $R^a$ denotes H, $C_{1-6}$-alkyl, $C_{2-6}$-alkenyl, $C_{3-6}$-cycloalkyl, $C_{3-6}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$ or $C_{1-4}$-alkyl, optionally substituted by one or more COOH, $N(C_{1-4}$-alkyl$)_2$ or het, optionally substituted by one or more $C_{1-4}$-alkyl; or $R^9$ denotes het, optionally substituted by one or more $C_{1-4}$-alkyl;

$R^{10}$ denotes H, $C_{1-6}$-alkyl, CO—$C_{1-4}$-alkyl or $C_{2-6}$-alkynyl;

$R^{11}$ denotes $C_{1-6}$-alkyl, optionally substituted by one or more $N(C_{1-4}$-alkyl$)_2$;

$R^{12}$ denotes $C_{1-6}$-alkyl;

$R^b$ denotes $R^4$, $OR^4$, —$CH_2OR^4$, $COR^4$, $COOR^4$, $CONR^4R^5$, $NH_2$, $NR^5COOR^4$, $NR^5CONR^4R^5$ or $NR^5SOR^4$;

$R^4$ denotes H, $C_{1-6}$-alkyl, $C_{1-6}$-haloalkyl, $C_{1-6}$-alkylene-OH, $C_{2-6}$-alkenyl, $C_{7-11}$-aralkyl, $C_{1-4}$-alkyl-hetaryl, $C_{2-6}$-alkynyl, optionally substituted by $Si(C_{1-4}$-alkyl$)_3$, or $R^4$ denotes a group selected from among aryl, het, hetaryl and optionally substituted by $C_{1-4}$-alkyl;

$R^5$ denotes H or $C_{1-6}$-alkyl;

or $R^4$ and $R^5$ together form a five-, six- or seven-membered ring consisting of carbon atoms and optionally a heteroatom selected from among oxygen, nitrogen and sulphur;

$R^c$ denotes $NHR^6$ or a group selected from among

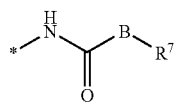

wherein
B denotes a bond, $C_{1-4}$-alkyl or $C_{2-4}$-alkynyl;
$R^6$ denotes H or a group selected from among $C_{1-4}$-alkyl, $C_{3-6}$-cycloalkyl, het, aryl, hetaryl optionally substituted by one or more groups $R^{6.1}$;
  $R^{6.1}$ denotes halogen, $CF_3$, OH, CN, OMe, $SO_2(C_{1-4}$-alkyl);
$R^7$ denotes H, $C_{1-4}$-alkyl, $C_{3-6}$-cycloalkyl, $NR^{7.1}R^{7.2}$, $OR^{7.2}$, $SR^{7.2}$, hetaryl, het, optionally substituted by $C_{1-4}$-alkyl or $CONH_2$;
  $R^{7.1}$ denotes H, $C_{1-4}$-alkyl, $(CH_2)_{2-4}R^{7.1.1}$ or COObutyl;
  $R^{7.2}$ denotes H, $C_{1-6}$-alkyl, optionally substituted by one or more OH;
    $R^{7.1.1}$ denotes $NR^{7.1.1.1}R^{7.1.1.2}$, het or 1-imidazolyl, 2-(N-ethylpyrrolidine);
      $R^{7.1.1.1}$ denotes H or $C_{1-6}$-alkyl;
      $R^{7.1.1.2}$ denotes H or $C_{1-6}$-alkyl;
and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Preferred compounds of formula 1 mentioned above are those wherein
$R^a$ denotes H, $C_{1-6}$-alkyl, $C_{2-6}$-alkenyl, $C_{3-6}$-cycloalkyl, $CF_3$, $COR^8$, $NR^9R^{10}$, $NO_2$, $S(O)_nR^{11}$, or a group selected from among

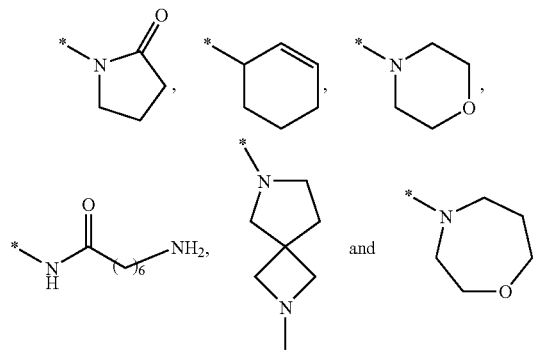

or a group selected from among

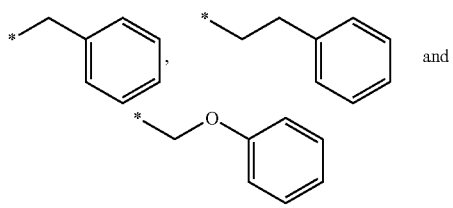

which may optionally be substituted by one or more Cl;

or a group selected from among

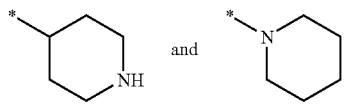

which may optionally be substituted by one or more $CH_3$, $COCF_3$, $CH_2NH_2$ or $CH_2NHCOOR^{12}$;
$R^8$ denotes $C_{1-4}$-alkyl, $C_{3-6}$-cycloalkyl, $NH_2$, furanyl or phenyl, optionally substituted by one or more chlorine;
$R^9$ denotes H, $COOR^{12}$ or piperidino, optionally substituted by one or more $CH_3$, or a group selected from among $C_{1-4}$-alkyl, which may optionally be substituted by one or more COOH, $NMe_2$ or 4-methylpiperazine;
$R^{10}$ denotes H, $C_{1-4}$-alkyl, $C_{2-4}$-alkynyl or $COCH_3$;
$R^{11}$ denotes $C_{1-4}$-alkyl, optionally substituted by one or more $NMe_2$,
$R^{12}$ denotes $C_{1-4}$-alkyl;
$R^b$ denotes $R^4$, $CH_2OR^4$, $COR^4$, $COOR^4$, $CONR^4R^5$, $NH_2$, $NHCOOR^4$, $NHCONR^4R^5$ or OH;
$R^4$ denotes H, $C_{1-4}$-alkyl, $C_{1-4}$-alkylene-OH, $C_{2-4}$-alkynyl, $C_{1-6}$-haloalkyl, aryl, het, hetaryl,

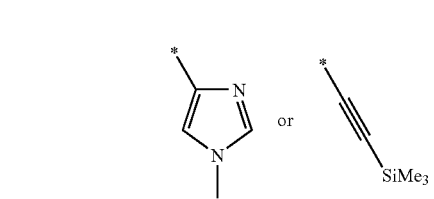

$R^5$ denotes H or $C_{1-4}$-alkyl;
$R^c$ denotes $NHR^5$ or a group selected from among

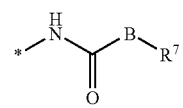

wherein
B denotes a bond, $C_{1-4}$-alkyl or $C_{2-4}$-alkynyl;
$R^6$ denotes H, $C_{1-4}$-alkyl, $C_{3-6}$-cycloalkyl, $C_{7-11}$-aralkyl, aryl, optionally substituted by $SO_2CH_3$;
$R^7$ denotes H, $NR^{7.1}R^{7.2}$, $OR^{7.2}$, $SR^{7.2}$, hetaryl, het, optionally substituted by $C_{1-4}$-alkyl or $CONH_2$, or a group selected from among

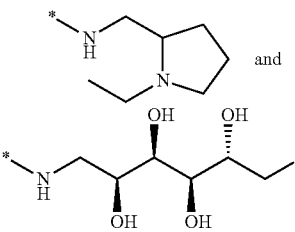

$R^{7.1}$ denotes H, $C_{1-4}$-alkyl, $(CH_2)_2R^{7.1.1}$ or COObutyl;
$R^{7.2}$ denotes H, $C_{1-4}$-alkyl;
  $R^{7.1.1}$ denotes $NR^{7.1.1.1}R^{7.1.1.2}$, het or 1-imidazolyl, 2-(N-ethylpyrrolidine);
    $R^{7.1.1.1}$ denotes H or $C_{1-6}$-alkyl;
    $R^{7.1.1.2}$ denotes H or $C_{1-6}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Particularly preferred are the above-mentioned compounds of formula 1 wherein $R^a$ denotes H, $C_{1-6}$-alkyl, $C_{2-6}$-alkenyl, $C_{3-6}$-cycloalkyl, $C_{3-6}$-cycloalkenyl, $CF_3$, $COR^8$, $NR^9R^{10}$, $NO_2$, $S(O)_nR^{11}$, spiro, NHCO—$C_{1-6}$-alkyl-$NH_2$ or a group selected from among $C_{7-11}$-aralkyl and $CH_2O$-aryl, which may optionally be substituted by one or more Cl; or a group selected from among het, which may optionally be substituted by one or more $C_{1-4}$-alkyl, $COCF_3$, $CH_2NH_2$ or $CH_2NHCOOR^{12}$;

$R^8$ denotes $C_{1-4}$-alkyl, $C_{3-6}$-cycloalkyl, $NH_2$, hetaryl, aryl, optionally substituted by one or more chlorine;

$R^9$ denotes H, $COOR^{12}$ or het, optionally substituted by one or more $C_{1-4}$-alkyl, or a group selected from among $C_{1-4}$-alkyl, which may optionally be substituted by one or more COOH, $N(C_{1-4}$-alkyl$)_2$ or 4-methylpiperazine;

$R^{10}$ denotes H, $C_{1-4}$-alkyl, $C_{2-4}$-alkynyl or $COCH_3$;

$R^{11}$ denotes $C_{1-4}$-alkyl, optionally substituted by one or more $N(C_{1-4}$-alkyl$)_2$, $R^{12}$ denotes $C_{1-4}$-alkyl;

n denotes 0 or 2;

$R^b$ denotes H, OH or COOEt;

$R^c$ denotes $NH_2$ or $NHCOR^{13}$;

$R^{13}$ denotes $C_{1-4}$-alkyl, or $NR^{13.1}R^{13.2}$, $R^{13.1}$ denotes H or $C_{1-4}$-alkyl;

$R^{13.2}$ denotes H or $C_{1-4}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Particularly preferred are the above-mentioned compounds of formula 1 wherein $R^a$ denotes H, $C_{1-6}$-alkyl, $C_{2-6}$-alkenyl, $C_{3-6}$-cycloalkyl, $CF_3$, $COR^8$, $NR^9R^{10}$, $NO_2$, $S(O)_nR^{11}$, or a group selected from among

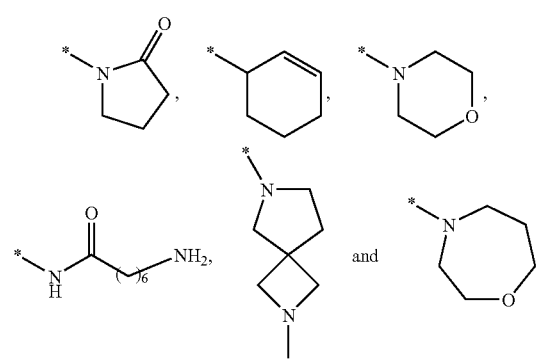

or a group selected from among

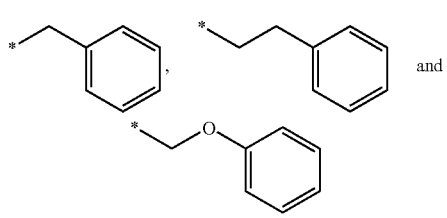

which may optionally be substituted by one or more Cl; or a group selected from among

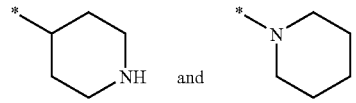

which may optionally be substituted by one or more $CH_3$, $COCF_3$, $CH_2NH_2$ or $CH_2NHCOOR^{12}$;

$R^8$ denotes $C_{1-4}$-alkyl, $C_{3-6}$-cycloalkyl, $NH_2$, furanyl or phenyl, optionally substituted by one or more chlorine;

$R^9$ denotes H, $COOR^{12}$ or piperidino, optionally substituted by one or more $CH_3$, or a group selected from among $C_{1-4}$-alkyl, which may optionally be substituted by one or more COOH, $NMe_2$ or 4-methylpiperazine;

$R^{10}$ denotes H, $C_{1-4}$-alkyl, $C_{2-4}$-alkynyl or $COCH_3$;

$R^{11}$ denotes $C_{1-4}$-alkyl, optionally substituted by one or more $NMe_2$, $R^{12}$ denotes $C_{1-4}$-alkyl;

$R^b$ denotes H, OH or COOEt;

$R^c$ denotes $NH_2$ or $NHCOR^{13}$;

$R^{13}$ denotes $C_{1-4}$-alkyl, or $NR^{13.1}R^{13.2}$, $R^{13.1}$ denotes H or $C_{1-4}$-alkyl;

$R^{13.2}$ denotes H or $C_{1-4}$-alkyl;

and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Particularly preferred are the above-mentioned compounds of formula 1 wherein $R^a$ denotes H, methyl, ethyl, propyl, butyl, 3-methyl-butyl, propenyl, cyclopropyl, cyclohexyl, $CF_3$, $COR^8$, $NR^9R^{10}$, $NO_2$, $S(O)_nR^{11}$, or a group selected from among

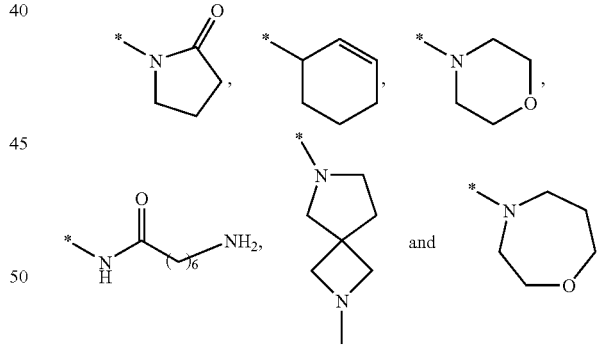

or a group selected from among

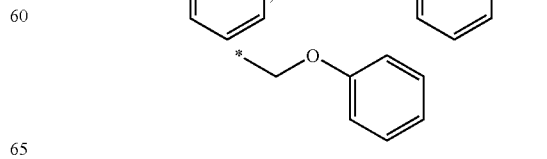

which may optionally be substituted by one or more Cl;

or a group selected from among

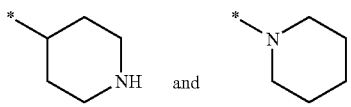

which may optionally be substituted by one or more $CH_3$, $COCF_3$, $CH_2NH_2$ or $CH_2NHCOOR^{12}$;
$R^8$ denotes methyl, propyl, cyclopropyl, $NH_2$, furanyl or phenyl, optionally substituted by one or more chlorine;
$R^9$ denotes H, $COOR^{12}$ or piperidino, optionally substituted by one or more $CH_3$, or a group selected from among methyl, ethyl and propyl, which may optionally be substituted by one or more COOH, $NMe_2$ or 4-methylpiperazine;
$R^{10}$ denotes H, methyl, $COCH_3$, C≡CH or $CH_2C$≡CH;
$R^{11}$ denotes ethyl or propyl, optionally substituted by one or more $NMe_2$,
$R^{12}$ denotes butyl
$R^b$ denotes H, OH or COOEt;
$R^c$ denotes $NH_2$ or $NHCOR^{13}$;
$R^{13}$ denotes methyl or $NR^{13.1}R^{13.2}$,
$R^{13.1}$ denotes H or methyl;
$R^{13.2}$ denotes H or methyl.
and the pharmacologically acceptable salts, diastereomers, enantiomers, racemates, hydrates or solvates thereof, with the proviso that $R^a$ cannot be H or Me if Y=nitrogen; Z=nitrogen; j=2; k=0; $R^b$=H and $R^c$=NHCONH-Et.

Most preferred are the above-mentioned compounds of formula 1; wherein
$R^a$ denotes propyl, $COR^8$, $NR^9R^{10}$, $S(O)_nR^{11}$ and

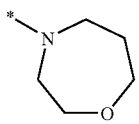

$R^8$ denotes furanyl;
$R^9$ denotes methyl;
$R^{10}$ denotes methyl;
$R^{11}$ denotes ethyl;
n denotes 0;
$R^b$ denotes H or OH;
$R^c$ denotes $NH_2$ or $NHCOCH_3$;
and the pharmacologically acceptable salts, diastereomers, enantiomers, racemates, hydrates or solvates thereof.

Particularly preferred are the above compounds, and also pharmacologically acceptable salts, diastereomers, enantiomers, racemates, hydrates or solvates thereof, with the proviso that $R^a$ cannot be H or Me if Y and Z=nitrogen; j=2; k=0; $R^b$=H and $R^c$=NHCONH-Et denotes and that $R^c$ cannot be $NH_2$ if Y and Z=nitrogen; j=2; k=1; $R^b$=H and $R^a$=

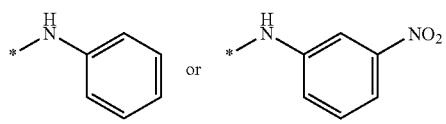

TERMS AND DEFINITIONS USED

By the term "$C_{1-6}$-alkyl" (including those which are part of other groups) are meant branched and unbranched alkyl groups with 1 to 6 carbon atoms, and by the term "$C_{1-4}$-alkyl" are meant branched and unbranched alkyl groups with 1 to 4 carbon atoms. Alkyl groups with 1 to 4 carbon atoms are preferred. Examples of these include: methyl, ethyl, n-propyl, iso-propyl, n-butyl, iso-butyl, sec-butyl, tert-butyl, n-pentyl, iso-pentyl, neo-pentyl or hexyl. The abbreviations Me, Et, n-Pr, i-Pr, n-Bu, i-Bu, t-Bu, etc. may optionally also be used for the above-mentioned groups. Unless stated otherwise, the definitions propyl, butyl, pentyl and hexyl include all the possible isomeric forms of the groups in question. Thus, for example, propyl includes n-propyl and iso-propyl, butyl includes iso-butyl, sec-butyl and tert-butyl etc.

By the term "$C_{1-6}$-alkylene" (including those which are part of other groups) are meant branched and unbranched alkylene groups with 1 to 6 carbon atoms and by the term "$C_{1-4}$-alkylene" are meant branched and unbranched alkylene groups with 1 to 4 carbon atoms. Alkylene groups with 1 to 4 carbon atoms are preferred. Examples include: methylene, ethylene, propylene, 1-methylethylene, butylene, 1-methylpropylene, 1,1-dimethylethylene, 1,2-dimethylethylene, pentylene, 1,1-dimethylpropylene, 2,2-dimethylpropylene, 1,2-dimethylpropylene, 1,3-dimethylpropylene or hexylene. Unless stated otherwise, the definitions propylene, butylene, pentylene and hexylene also include all the possible isomeric forms of the relevant groups with the same number of carbons. Thus for example propyl also includes 1-methylethylene and butylene includes 1-methylpropylene, 1,1-dimethylethylene, 1,2-dimethylethylene.

The term "$C_{2-6}$-alkenyl" (including those which are part of other groups) denotes branched and unbranched alkenyl groups with 2 to 6 carbon atoms and the term "$C_{2-4}$-alkenyl" denotes branched and unbranched alkenyl groups with 2 to 4 carbon atoms, provided that they have at least one double bond. Preferred are alkenyl groups with 2 to 4 carbon atoms. Examples include: ethenyl or vinyl, propenyl, butenyl, pentenyl, or hexenyl. Unless otherwise stated, the definitions propenyl, butenyl, pentenyl and hexenyl include all possible isomeric forms of the groups in question. Thus, for example, propenyl includes 1-propenyl and 2-propenyl, butenyl includes 1-, 2- and 3-butenyl, 1-methyl-1-propenyl, 1-methyl-2-propenyl etc.

By the term "$C_{2-6}$-alkenylene" (including those which are part of other groups) are meant branched and unbranched alkenylene groups with 2 to 6 carbon atoms and by the term "$C_{2-4}$-alkenylene" are meant branched and unbranched alkylene groups with 2 to 4 carbon atoms. Alkenylene groups with 2 to 4 carbon atoms are preferred. Examples include: ethenylene, propenylene, 1-methylethenylene, butenylene, 1-methylpropenylene, 1,1-dimethylethenylene, 1,2-dimethylethenylene, pentenylene, 1,1-dimethylpropenylene, 2,2-dimethylpropenylene, 1,2-dimethylpropenylene, 1,3-dimethylpropenylene or hexenylene. Unless stated otherwise, the definitions propenylene, butenylene, pentenylene and hexenylene include all the possible isomeric forms of the respective groups with the same number of carbons. Thus, for example, propenyl also includes 1-methylethenylene and butenylene includes 1-methylpropenylene, 1,1-dimethylethenylene, 1,2-dimethylethenylene.

By the term "$C_{2-6}$-alkynyl" (including those which are part of other groups) are meant branched and unbranched alkynyl groups with 2 to 6 carbon atoms and by the term "$C_{2-4}$-alkynyl" are meant branched and unbranched alkynyl groups with 2 to 4 carbon atoms, provided that they have at least one triple bond. Alkynyl groups with 2 to 4 carbon atoms are preferred. Examples include: ethynyl, propynyl, butynyl, pentynyl, or hexynyl. Unless stated otherwise, the definitions propynyl, butynyl, pentynyl and hexynyl include all the possible isomeric forms of the respective groups. Thus, for example, propynyl includes 1-propynyl and 2-propynyl, butynyl includes 1-, 2- and 3-butynyl, 1-methyl-1-propynyl, 1-methyl-2-propynyl etc.

By the term "$C_{2-6}$-alkynylene" (including those which are part of other groups) are meant branched and unbranched alkynylene groups with 2 to 6 carbon atoms and by the term "$C_{2-4}$-alkynylene" are meant branched and unbranched alkylene groups with 2 to 4 carbon atoms. Alkynylene groups with 2 to 4 carbon atoms are preferred. Examples include: ethynylene, propynylene, 1-methylethynylene, butynylene, 1-methylpropynylene, 1,1-dimethylethynylene, 1,2-dimethylethynylene, pentynylene, 1,1-dimethylpropynylene, 2,2-dimethylpropynylene, 1,2-dimethylpropynylene, 1,3-dimethylpropynylene or hexynylene. Unless stated otherwise, the definitions propynylene, butynylene, pentynylene and hexynylene include all the possible isomeric forms of the respective groups with the same number of carbons. Thus for example propynyl also includes 1-methylethynylene and butynylene includes 1-methylpropynylene, 1,1-dimethylethynylene, 1,2-dimethylethynylene.

By the term "$C_{1-6}$-alkoxy" (including those which are part of other groups) are meant branched and unbranched alkoxy groups with 1 to 6 carbon atoms and by the term "$C_{1-4}$-alkoxy" are meant branched and unbranched alkoxy groups with 1 to 4 carbon atoms. Alkoxy groups with 1 to 4 carbon atoms are preferred. Examples include: methoxy, ethoxy, propoxy, butoxy or pentoxy. The abbreviations OMe, OEt, OPr, etc. may optionally be used for the above-mentioned groups. Unless stated otherwise, the definitions propoxy, butoxy and pentoxy include all the possible isomeric forms of the respective groups. Thus for example propoxy includes n-propoxy and iso-propoxy, butoxy includes iso-butoxy, sec-butoxy and tert-butoxy etc.

By the term "$C_{3-8}$-cycloalkyl" (including those which are part of other groups) are meant cyclic alkyl groups with 3 to 8 carbon atoms, by the term "$C_{3-6}$-cycloalkyl" are meant cyclic alkyl groups with 3 to 8 carbon atoms and by the term "$C_{5-6}$-cycloalkyl" are meant cyclic alkyl groups with 5 to 6 carbon atoms. Examples include: cyclopropyl, cyclobutyl, cyclopentyl, cyclohexyl, cycloheptyl or cyclooctyl. By the term "$C_{3-6}$-cycloalkenyl" (including those which are part of other groups) are meant cyclic alkyl groups with 5 or 6 carbon atoms which contain one or two double bonds. Examples include: cyclopentenyl, cyclopentadienyl, cyclohexenyl or cyclohexadienyl.

By the term "$C_{1-6}$-haloalkyl" (including those which are part of other groups) are meant branched and unbranched alkyl groups with 1 to 6 carbon atoms wherein one or more hydrogen atoms are replaced by a halogen atom selected from among fluorine, chlorine or bromine, preferably fluorine and chlorine, particularly preferably fluorine. By the term "$C_{1-4}$-haloalkyl" are meant correspondingly branched and unbranched alkyl groups with 1 to 4 carbon atoms, wherein one or more hydrogen atoms are replaced analogously to what was stated above. $C_{1-4}$-haloalkyl is preferred. Examples include: $CH_2F$, $CHF_2$, $CF_3$, By the term "$C_{7-11}$-aralkyl" (including those which are part of other groups) are meant branched and unbranched alkyl groups with 1 to 4 carbon atoms which are substituted by an aromatic ring system with 6 carbon atoms. Examples include: benzyl, 1- or 2-phenylethyl. Unless otherwise stated, the aromatic groups may be substituted by one or more groups selected from among methyl, ethyl, iso-propyl, tert-butyl, hydroxy, fluorine, chlorine, bromine and iodine.

By the term "aryl" (including those which are part of other groups) are meant aromatic ring systems with 6 or 10 carbon atoms. Examples include: phenyl or naphthyl, the preferred aryl group being phenyl.

By the term heterocyclic rings ("het") are meant five-, six- or seven-membered, saturated or unsaturated heterocyclic rings or 5-10 membered, bicyclic heterorings which may contain one, two or three heteroatoms, selected from among oxygen, sulphur and nitrogen; the ring may be linked to the molecule by a carbon atom or, if present, by a nitrogen atom. The following are examples of five-, six- or seven-membered, saturated or unsaturated heterocyclic rings:

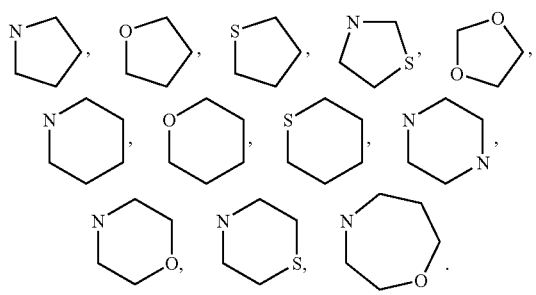

Unless stated otherwise, a heterocyclic ring may be provided with a keto group. Examples include:

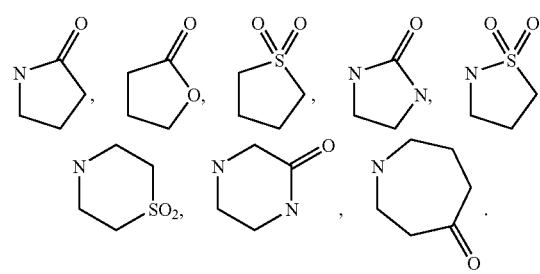

Examples of 5-10-membered bicyclic heterorings are pyrrolizine, indole, indolizine, isoindole, indazole, purine, quinoline, isoquinoline, benzimidazole, benzofuran, benzopyran, benzothiazole, benzoisothiazole, pyridopyrimidine, pteridine, pyrimidopyrimidine,

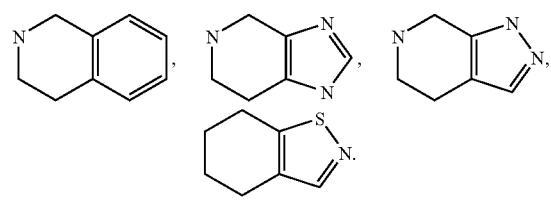

Although the term heterocyclic rings includes ("hetaryl"), the term heterocyclic aromatic groups denotes five- or six-membered heterocyclic aromatic groups or 5-10 membered, bicyclic hetaryl rings which may contain one, two or three heteroatoms, selected from among oxygen, sulphur and nitrogen, which contain sufficient conjugated double bonds that an aromatic system is formed. The ring may be linked to the molecule through a carbon atom or if present through a nitrogen atom. The following are examples of five- or six-membered heterocyclic aromatic groups:

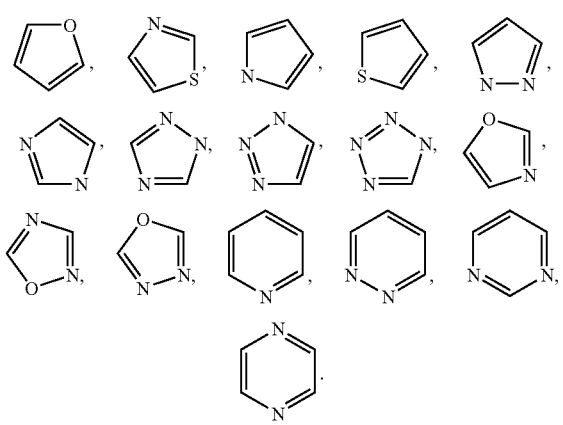

Examples of 5-10-membered bicyclic hetaryl rings include pyrrolizine, indole, indolizine, isoindole, indazole, purine, quinoline, isoquinoline, benzimidazole, benzofuran, benzopyran, benzothiazole, benzoisothiazole, pyridopyrimidine, pteridine, pyrimidopyrimidine.

By the term heterocyclic spiro rings ("spiro") are meant 5-10 membered, spirocyclic rings which may optionally contain one, two or three heteroatoms, selected from among oxygen, sulphur and nitrogen, while the ring may be connected to the molecule via a carbon atom or, if present, via a nitrogen atom. Unless otherwise stated, a spirocyclic ring may be provided with a keto group. Examples include:

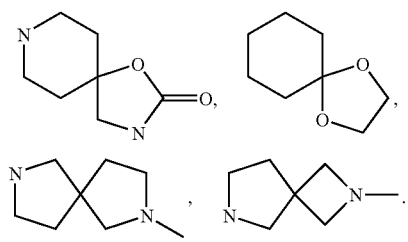

By the term "optionally substituted" is meant within the scope of the invention the above-mentioned group, optionally substituted by a lower-molecular group. Examples of lower-molecular groups regarded as chemically meaningful are groups consisting of 1-200 atoms. Preferably such groups have no negative effect on the pharmacological efficacy of the compounds.

For example the groups may comprise:

Straight-chain or branched carbon chains, optionally interrupted by heteroatoms, optionally substituted by rings, heteroatoms or other common functional groups.

Aromatic or non-aromatic ring systems consisting of carbon atoms and optionally heteroatoms, which may in turn be substituted by functional groups.

A number of aromatic or non-aromatic ring systems consisting of carbon atoms and optionally heteroatoms which may be linked by one or more carbon chains, optionally interrupted by heteroatoms, optionally substituted by heteroatoms or other common functional groups.

SYNTHESIS OF THE REAGENTS

IMIDAZOL-1-YL-[1-(2-TRIMETHYLSILANYL-ETHOXYMETHYL)-1H-IMIDAZOL-4-YL]-METHANONE

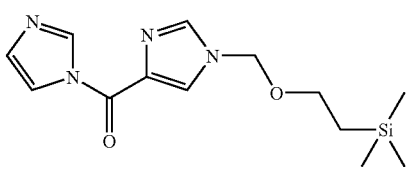

A suspension of 1.5 g (63 mmol) sodium hydride (60% suspension in mineral oil) in 80 ml DMF is combined batchwise with 8 g (63 mmol) methyl imidazole-4-carboxylate and the resulting solution is stirred for 1 hour. The reaction mixture is cooled to 5° C. and 12 ml (70 mmol) [2-(trimethylsilyl)-ethoxy]methyl chloride are added. After 12 hours the suspension is combined with 100 ml of water and extracted with ethyl acetate. The combined organic phases are washed with sodium chloride solution, dried and evaporated down.

Yield: 16 g 16 g (62 mmol) of the intermediate described above is dissolved in 20 ml dioxane and 66 ml 2 N sodium hydroxide solution and refluxed for 1.5 hours. The reaction mixture is acidified with 2 N hydrochloric acid and the precipitated solid is suction filtered, washed with water and diethyl ether and dried.

Yield: 13 g 13 g (55 mmol) of the intermediate described above are placed in 150 ml dichloromethane and combined with 22.4 g (138 mmol) carbonyldiimidazole. The reaction mixture is stirred for 1 hour at ambient temperature and then washed with semisaturated sodium chloride solution. The organic phase is dried and evaporated to dryness. Yield: 15 g

IMIDAZOL-1-YL(1-METHYL-1H-IMIDAZOL-4-YL)-METHANONE

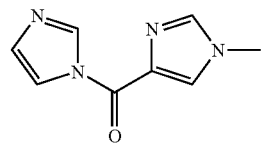

39.5 g (0.31 mol) 1-methyl-1H-imidazol-4-carboxylic acid are placed in 400 ml dichloromethane and 115.6 g (0.71 mol) carbonyldiimidazole are added. The suspension is stirred for 3 hours at ambient temperature, then extracted with saturated sodium chloride solution. The aqueous phase is extracted with dichloromethane, the combined organic phases are dried and evaporated to dryness. Yield: 60.6 g

1-IMIDAZOL-1-YL-2-METHYL-PROPAN-1-ONE

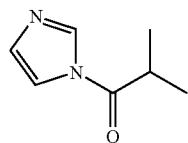

12.0 g (0.18 mol) imidazole are placed in 200 ml chloroform at 0° C. and then combined with 10.8 ml (0.10 mol) isobutyl chloride. The mixture is stirred for 1 hour at ambient temperature. Then the reaction mixture is washed with water, the organic phase is dried and evaporated to dryness. Yield: 10.7 g

(R)-IMIDAZOL-1-YL-(TETRAHYDROFURAN-2-YL)-METHANONE

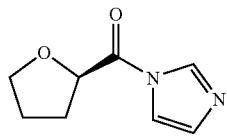

21.8 g (32 mmol) imidazole are placed in 400 ml chloroform and cooled to 0° C. 21.3 g (15.0 mol) (R)-tetrahydrofuran-2-carbonyl chloride are added dropwise, then the mixture is stirred for 1.5 hours at ambient temperature. After cooling again to 0° C. the reaction mixture is extracted with semisaturated sodium chloride solution. The organic phase is dried and evaporated to dryness. Yield: 24.0 g

(S)-IMIDAZOL-1-YL-(TETRAHYDROFURAN-2-YL)-METHANONE

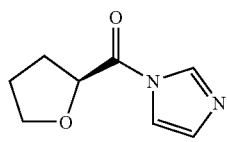

21.8 g (32.0 mmol) imidazole are placed in 400 ml chloroform and cooled to 0° C. 21.5 g (15.0 mmol) (S)-tetrahydrofuran-2-carbonyl chloride are added dropwise, then stirred for 1.5 hours at ambient temperature. After cooling again to 0° C. the reaction mixture is extracted with semisaturated sodium chloride solution. The organic phase is dried and evaporated to dryness. Yield: 23.5 g

1-IMIDAZOL-1-YL-2-METHOXY-ETHANONE

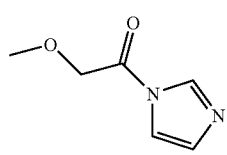

Analogously to the method described above 5.6 g of the desired product are obtained from 14.9 g (219 mmol) imidazole and 10 ml (109 mmol) methoxyacetic acid chloride.

1-IMIDAZOL-1-YL-3-TRIMETHYLSILANYL-PROPYNONE

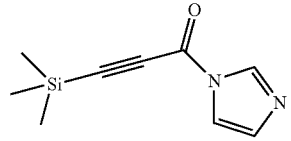

0.5 g (3.5 mmol) 3-trimethylsilylpropynoic acid are dissolved in 10 ml THF and combined with 1.7 g (10.6 mmol) carbonyldiimidazole. The reaction mixture is stirred overnight at ambient temperature and then filtered. The filtrate is diluted with diethyl ether and washed twice with cold water. The organic phase is dried over magnesium sulphate and evaporated down. Yield: 0.4 g

(4-HYDRAZINO-PHENYL)-ACETIC ACID HYDROCHLORIDE

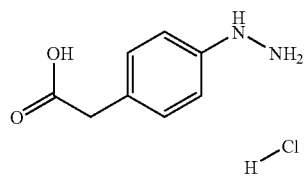

15.1 g (10.0 mmol) 4-aminophenylacetic acid are placed in a solution of 10.6 g (10.0 mmol) sodium carbonate in 100 ml of water. The mixture is cooled to 0° C., then 6.9 g (10.0 mmol) sodium nitrite in 50 ml of water are added. This mixture is added dropwise to 100 ml of conc. hydrochloric acid while being cooled, then stirred for 0.1 hours. 45.1 g (20.0 mmol) tin(II)-chloride in 40 ml of conc. hydrochloric acid are added dropwise with vigorous stirring, during which time a precipitate is formed. The reaction mixture is stirred for 1 hour at ambient temperature, then suction filtered. The precipitate is washed with water and dried.
Yield: 22.0 g

3-CHLORO-5-HYDRAZINO-PHENOL

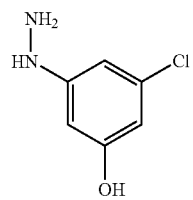

2.1 g (14.3 mmol) 3-amino-5-chloro-phenol are dissolved in 20 ml of conc. hydrochloric acid and 20 ml of water and cooled to 0° C. 1.0 g (15.0 mmol) sodium nitrite in 4 ml of water are added. Then a solution of 12.1 g (53.5 mmol) tin(II)-chloride in 16 ml hydrochloric acid is slowly added dropwise at −5° C. It is stirred for 1 hour at 0° C., then adjusted to pH 7 with sodium hydrogen carbonate. The precipitate formed is suction filtered and washed with water. The filtrate is extracted with diethyl ether. The organic phase is dried and evaporated to dryness. The residue is extracted with hexane.

Yield: 1.2 g

CHLORO-4-HYDRAZINO-PHENOL

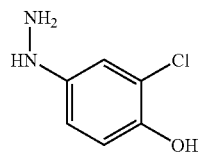

analogously to the method described above 2.3 g hydrazine are obtained from 2.2 g (15 mmol) 4-amino-2-chloro-phenol.

METHYL 3-CHLORO-4-HYDRAZINO-BENZOATE

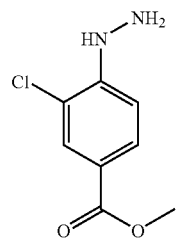

3.0 g (16.0 mmol) methyl-4-amino-3-chlorobenzoate are suspended in 15 ml of conc. hydrochloric acid and cooled to −10° C. First a solution of 1.1 g (16.0 mmol) sodium nitrite in 15 ml of water is added dropwise, then a solution of 16.1 g (71.0 mmol) tin(II)-chloride in 13.5 ml hydrochloric acid. A precipitate settles out. The reaction mixture is made basic with 3 molar sodium hydroxide solution, then suction filtered. The precipitate is extracted with dichloromethane and water, the organic phase is dried, combined with activated charcoal and evaporated to dryness. The residue is purified by chromatography. Yield: 1.4 g (M.p.: 120° C.)

CHLORO-4-HYDRAZINO-BENZOIC ACID

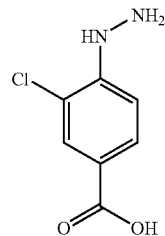

4.0 g (20.0 mmol) methyl 3-chloro-4-hydrazino-benzoate are taken and 75 ml 3 molar sodium hydroxide solution are added thereto. This is stirred for 16 hours at ambient temperature. Then the reaction mixture is adjusted to pH 6 with glacial acetic acid and the precipitated solid is suction filtered. This is extracted with diethyl ether. Yield: 2.4 g

(4-BROMO-2-TRIFLUOROMETHYL-PHENYL)-HYDRAZINE

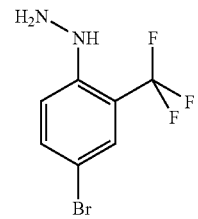

A suspension of 25.6 g (0.11 mol) 4-bromo-2-(trifluoromethyl)-aniline in 125 ml of conc. hydrochloric acid is cooled to −10° C. and a solution of 7.7 g (0.11 mol) sodium nitrite in 125 ml of water is added. The reaction mixture is stirred for 3 hours at −10 to −5° C., then a solution of 103 g (0.46 mol) tin-(II)-chloride-dihydrate in 125 ml of conc. hydrochloric acid is added dropwise. The mixture is stirred for 1 hour at −5° C. The precipitate formed is suction filtered and washed with water. The aqueous mother liquor is extracted with petroleum ether, then made basic with sodium hydroxide. The precipitate formed is extracted with diethyl ether. The organic phase is dried and evaporated to dryness. Yield: 12.9 g

2,2,2-TRIFLUORO-1-(4-HYDRAZINO-PIPERIDIN-1-YL)-ETHANONE-TRIFLUOROACETATE

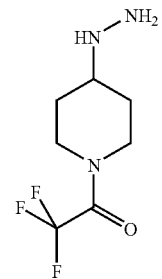

100 g (0.65 mol) 4-piperidinone-hydrate-hydrochloride and 274.6 ml (1.97 mol) triethylamine are placed in 1000 ml dichloromethane and then cooled to 0° C. 182.1 ml (1.31 mol) trifluoroacetic anhydride are slowly added and the mixture is stirred for 0.5 hours. The reaction mixture is washed with water and sodium bicarbonate solution, the organic phase is dried and evaporated to dryness. The residue is stirred with methyl-tert-butylether, the precipitate is suction filtered, washed and dried. Yield: 106.0 g 106.0 g (0.54 mol) 1-(2,2,2-trifluoro-acetyl)-piperidin-4-one are dissolved in 1000 ml of ethanol and combined with 71.8 g (0.54 mol) tert-butyl hydrazinoformate. The reaction mixture is stirred for 3.5 hours at ambient temperature, then evaporated to dryness. Yield: 172.0 g 172.0 g (0.56 mol) tert-butyl N'-[1-(2,2,2-trifluoro-acetyl)-piperidin-4-ylidene]-hydrazine-carboxylate are dissolved in 2000 ml of methanol. 17.0 g palladium on charcoal (10%) are added and the mixture is hydrogenated at 1 bar hydrogen. After the hydrogen uptake has ended the catalyst is suction filtered and the mother liquor concentrated by evaporation. The residue crystallises out overnight. Yield: 168.0 g 5.0 g (16.1 mmol) tert-butyl N'-[1-(2,2,2-trifluoro-acetyl)-piperidin-4-yl]-hydrazine-carboxylate are dissolved in 50 ml dichloromethane and combined with 6.0 ml (77.9 mmol) trifluoroacetic acid. The reaction mixture is stirred for 5 hours at ambient temperature, then concentrated by evaporation. Yield: 6.70 g 4-(4-METHYL-PIPERAZIN-1-YL)-PHENYLAMINE

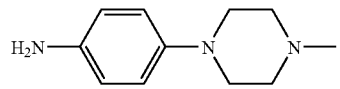

18.1 g (0.18 mol) 1-methyl-piperazine, 25.5 g (0.18 mol) 1-fluoro-4-nitrobenzene and 50 g (0.36 mol) potassium carbonate are placed in 200 ml of dimethylformamide and stirred for 15 hours at 130° C. After cooling 300 ml of water are added, during which time a precipitate is formed. The aqueous phase with the precipitate is cooled, then suction filtered and washed with water. The precipitate is recrystallised from ethanol.

Yield: 23.2 g 10.0 g (45 mmol) 1-methyl-4-(4-nitro-phenyl)-piperazine are dissolved in 250 ml of ethanol, then combined with 2 g palladium/charcoal (10%) and hydrogenated at 5 bar hydrogen for 2 hours. Then the reaction mixture is suction filtered and the filtrate is concentrated by evaporation. The residue is recrystallised from cyclohexane. Yield: 7.7 g 4-(1-METHYL-PIPERIDIN-4-YL)-PHENYLAMINE

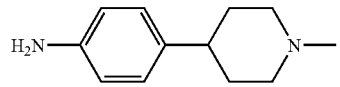

125 g (0.78 mol) 4-phenylpiperidine are dissolved in 1300 ml dichloromethane and combined with 149 ml (0.85 mol) diisopropylethylamine. The reaction mixture is cooled to −5° C., then within 2 hours 120 ml (0.85 mol) trifluoroacetic anhydride are added dropwise. The mixture is then stirred for 1 hour while cooling with ice and for 16 hours at ambient temperature. 400 ml of water are added and the phases are separated. The organic phase is washed with water, dried and evaporated to dryness. Yield: 193 g 80 g (0.31 mol) 2,2,2-trifluoro-1-(4-phenyl-piperidin-1-yl)-ethanone are dissolved in 400 ml glacial acetic acid and 200 ml acetic anhydride and cooled to 0° C. 1.6 g sodium nitrite are added, then 52 ml (1.24 mol) fuming nitric acid are added dropwise. The reaction mixture is stirred for 16 hours at ambient temperature. Then the reaction mixture is poured onto 1200 ml ice water and adjusted to pH 8 with 8 N sodium hydroxide solution (temp. <20° C.). After the addition of dichloromethane the phases are separated and the aqueous phase is extracted with dichloromethane. The combined organic phases are washed with 0.1 N sodium hydroxide solution and water, dried and evaporated to dryness. The product is recrystallised from cyclohexane/ethyl acetate. Yield: 47 g 20 g (66.2 mmol) 2,2,2-trifluoro-1-[4-(4-nitro-phenyl)-piperidin-1-yl]-ethanone and 32 g (23.2 mmol) potassium carbonate are placed in 400 ml of methanol and stirred for 48 hours at ambient temperature. Then the reaction mixture is concentrated by evaporation, the residue is extracted with water and dichloromethane. The organic phase is dried and evaporated to dryness. The hydrochloride is precipitated. Yield: 15 g 6.0 g (24.7 mmol) 4-(4-nitro-phenyl)-piperidine-hydrochloride are placed in 300 ml of tetrahydrofuran and combined successively with 11 ml (61.8 mmol) diisopropylethylamine, 5 ml (49.4 mmol) formaldehyde (37% in water) and 13 g (61.8 mmol) sodium triacetoxyborohydride. The reaction mixture is stirred for 16 hours at ambient temperature, then poured onto water and concentrated by evaporation. The aqueous residue is made basic with 2 N sodium hydroxide solution and extracted with dichloromethane. The combined organic phases are dried and evaporated to dryness. Yield: 4.5 g 4.3 g (19.5 mmol) 1-methyl-4-(4-nitro-phenyl)-piperidine are dissolved in a mixture of 60 ml of ethanol and 60 ml THF, combined with 2 g palladium/charcoal (10%) and hydrogenated at 1 bar hydrogen. Then the reaction mixture is suction filtered and the filtrate is concentrated by evaporation. Yield: 3.5 g 4-(1-CYCLOPROPYLMETHYL-PIPERIDIN-4-YL)-PHENYLAMINE

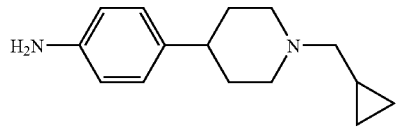

6.0 g (24.7 mmol) of the intermediate described above, 4-(4-nitro-phenyl)-piperidine-hydrochloride, are placed in 300 ml of tetrahydrofuran and combined successively with 11 ml (61.8 mmol) diisopropylethylamine, 3.7 ml (49.4 mmol) cyclopropane carboxaldehyde and 13 g (61.8 mmol) sodium triacetoxyborohydride. The reaction mixture is stirred for 3 hours at ambient temperature, then poured onto water and concentrated by evaporation. The aqueous residue is extracted with dichloromethane, the organic phase is dried and evaporated to dryness. The aqueous phase is made basic with 2 N sodium hydroxide solution, then extracted with dichloromethane. The organic phase is dried and evaporated to dryness. Yield: 5.6 g 3.3 g (12.5 mmol) 1-cyclopropylmethyl-4-(4-nitro-phenyl)-piperidine are dissolved in a mixture of 40 ml of ethanol and 40 ml THF, combined with 1.3 g palladium/charcoal (10%) and hydrogenated at 1 bar hydrogen. Then the reaction mixture is suction filtered and the filtrate is concentrated by evaporation. Yield: 2.7 g 1,1-DIMETHYL-2-DIMETHYLAMINO-1-YL-ETHYLAMINE AND 1,1-DIMETHYL-2-PIPERIDIN-1-YL-ETHYLAMINE

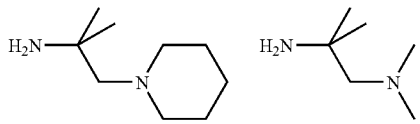

The compounds were prepared according to the following references: a) S. Schuetz et al. *Arzneimittel-Forschung* 1971, 21, 739-763 b) V. M. Belikov et al. *Tetrahedron* 1970, 26, 1199-1216. c) E. B. Butler and McMillan *J. Amer. Chem. Soc.* 1950, 72, 2978.

Other amines were prepared as follows according to a modification of the literature mentioned above.

1,1-DIMETHYL-2-MORPHOLIN-1-YL-ETHYLAMINE

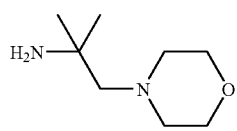

8.7 ml morpholine and 9.3 ml 2-nitropropane are taken, while cooling with ice, and 7.5 ml formaldehyde (37% in water) and 4 ml of a 0.5 mol/L NaOH solution are slowly added dropwise (<10° C.). Then the mixture is stirred for 1 h at 25° C. and for 1 h at 50° C. The solution is treated with water and ether and the aqueous phase is extracted 3× with ether. The combined organic phases are dried over sodium sulphate and combined with hydrochloric acid in dioxane (4 mol/L), the precipitate formed is suction filtered.

Yield: 21.7 g of colourless powder 5 g of the white powder are dissolved in 80 ml of methanol and with the addition of 2 g RaNi treated with hydrogen at 35° C. and 50 psi for 40 minutes. This yields 3.6 g of 1,1-dimethyl-2-morpholin-1-yl-ethylamine.

The following amine is prepared analogously to this method:

1,1-DIMETHYL-N-METHYLPIPERAZIN-1-YL-ETHYLAMINE

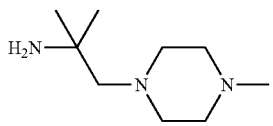

1,3-DIMORPHOLIN-2-AMINO-PROPANE

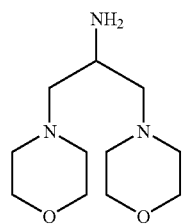

5 g 1,3-dimorpholine-2-nitropropane are dissolved in 80 ml of methanol and with the addition of 2 g RaNi treated with hydrogen at 30° C. and 50 psi for 5.5 h. This yields 4.2 g 1,3-dimorpholin-2-amino-propane.

TRANS-N,N-DIBENZYL-CYCLOHEXANE-1,4-DIAMINE

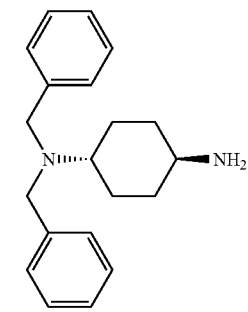

33 g (112 mmol) 4-dibenzylaminocyclohexanone are dissolved in 300 ml of methanol, combined with 17.4 g (250 mmol) hydroxylamine hydrochloride and stirred for 4 h at 60° C. The solvent is evaporated down in vacuo, combined with 500 ml of water and 50 g potassium carbonate and extracted twice with 300 ml dichloromethane. The organic phase is dried, evaporated down in vacuo, the residue is crystallised from petroleum ether, dissolved in 1.5 L ethanol and heated to 70° C. 166 g sodium are added batchwise and the mixture is refluxed until the sodium dissolves. The solvent is eliminated in vacuo, the residue is combined with 100 ml of water and extracted twice with 400 ml ether. The org. phase is washed with water, dried, evaporated down in vacuo and the trans-isomer is isolated through a column (approx. 1.5 L silica gel; approx. 2 L ethyl acetate 80/methanol 20+2% conc. ammonia). Yield: 12.6 g

TRANS-N,N-DIMETHYL-CYCLOHEXANE-1,4-DIAMINE (DIMETHANESULPHONATE)

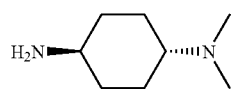

4 g (13.6 mmol) trans-N,N-dibenzyl-cyclohexane-1,4-diamine are placed in 8.1 g (100 mmol) formalin solution (37% in water) and 20 ml (43.4 mmol) formic acid and refluxed for 2 hours. The reaction mixture is added to ice water and combined with conc. ammonia. It is extracted with ethyl acetate. The organic phase is washed with water, dried and evaporated to dryness. The residue is crystallised from acetone and methanesulphonic acid. Yield: 6 g (M.p.: 203-204° C. 6 g (11.7 mmol) trans-N,N-dibenzyl-N',N'-dimethyl-cyclohexane-1,4-diamine-dimethanesulphonate are placed in 120 ml of methanol, 1.2 g palladium/charcoal (10%) are added and then the mixture is hydrogenated at 50 psi and 20° C. The reaction mixture is suction filtered through kieselguhr, the mother liquor is concentrated by evaporation. The residue is crystallised from acetone. Yield: 3.5 g

CIS- AND TRANS-4-MORPHOLINO-CYCLOHEXYLAMINE

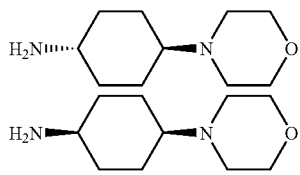

3.9 g (30 mmol) 4-dibenzylaminocyclohexanone are dissolved in 100 ml dichloromethane and stirred with 3.9 g (45 mmol) morpholine and 9.5 g (45 mmol) sodium triacetoxyborohydride for 12 h at RT. Then the mixture is combined with water and potassium carbonate, the organic phase is separated off, dried and the solvent is eliminated in vacuo. The residue is purified through a silica gel column (approx 20 ml silica gel; approx 500 ml of ethyl acetate 90/methanol 10+1% conc. ammonia). The required fractions are evaporated down in vacuo.

Yield: 6.6 g cis-isomer and 2 g trans-isomer.

Alternatively the trans-dibenzyl-4-morpholino-cyclohexylamine may be prepared as follows:

6.8 g (23 mmol) trans-N,N-dibenzyl-cyclohexane-1,4-diamine are dissolved in 90 ml DMF and stirred with 5 ml (42 mmol) 2,2'-dichloroethylether and 5 g potassium carbonate for 8 h at 100° C. After cooling the mixture is combined with 30 ml of water, precipitated crystals are suction filtered and purified through a short column (approx. 20 ml silica gel, approx. 100 ml of ethyl acetate). The residue is crystallised from methanol and conc. HCl as the dihydrochloride. Yield: 7.3 g 7.2 g (16.4 mmol) trans-dibenzyl-4-morpholino-cyclohexylamine are dissolved in 100 ml of methanol and hydrogenated on 1.4 g Pd/C (10%) at 30-50° C. The solvent is eliminated in vacuo and the residue crystallised from ethanol and conc. HCl.

Yield: 3.9 g (M.p. 312° C.). The cis-isomer may be prepared analogously.

CIS- AND TRANS-4-PIPERIDINO-CYCLOHEXYLAMINE

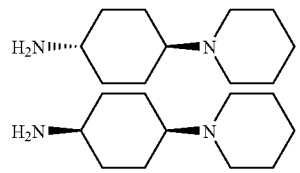

2.0 g (6.8 mmol) trans-1-amino-4-dibenzylaminocyclohexane (see preceding Example) are dissolved in 50 ml DMF and stirred with 1.6 g (7 mmol) 1,5-dibromopentane and 2 g potassium carbonate 48 h at RT. It is cooled, combined with water, extracted twice with 100 ml dichloromethane, dried and the solvent is eliminated in vacuo. The residue is purified through a column (approx. 100 ml silica gel, approx. 500 ml of ethyl acetate 80/methanol 20+1% conc. ammonia). The required fractions are evaporated down in vacuo and crystallised from petroleum ether. Yield: 1.2 g 1.7 g (4.8 mmol) trans-dibenzyl-4-piperidino-cyclohexylamine are dissolved in 35 ml of methanol and hydrogenated on 350 mg Pd/C (10%) at 20° C. The solvent is eliminated in vacuo and the residue is crystallised from ethanol and conc. HCl. Yield: 1.1 g. The cis-isomer may be prepared analogously.

CIS- AND TRANS-4-(4-PHENYL-PIPERAZIN-1-YL)-CYCLOHEXYLAMINE

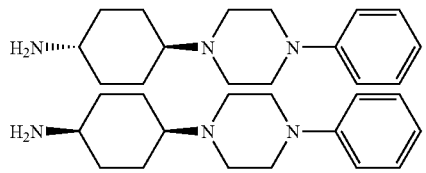

4.1 g (25.3 mmol) 4-dibenzylaminocyclohexanone are dissolved in 50 ml dichloromethane and stirred with 7.4 g (25.3 mmol) N-phenylpiperazine and 7.4 g (35 mmol) sodium triacetoxyborohydride for 12 h at RT. Then the mixture is combined with water and potassium carbonate, the organic phase is separated off, dried and the solvent is eliminated in vacuo. The residue is purified through a silica gel column (ethyl acetate 80/methanol 20+0.5% conc. ammonia). Yield: 1.7 g cis-isomer and 0.27 g trans-isomer.

270 mg (0.61 mmol) trans-dibenzyl-[4-(4-phenyl-piperazin-1-yl)-cyclohexyl]-amine are dissolved in 5 ml of methanol and hydrogenated on 40 mg Pd/C (10%) at 20-30° C. The solvent is eliminated in vacuo and the residue is crystallised from ethanol and conc. HCl. Yield: 110 mg. The cis-isomer may be prepared analogously.

CIS-4-(4-CYCLOPROPYLMETHYL-PIPERAZIN-1-YL)-CYCLOHEXYLAMINE

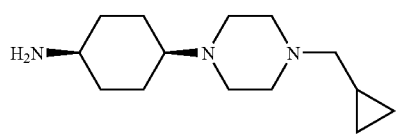

9.8 g (33.4 mmol) 4-dibenzylcyclohexanone are dissolved in 100 ml dichloromethane and stirred with 5.6 g (40 mmol) N-cyclopropylmethylpiperazine and 8.5 g (40 mmol) sodium triacetoxyborohydride for 12 h at RT. Then the mixture is combined with water and potassium carbonate, the organic phase is separated off, dried and the solvent is eliminated in vacuo. The residue is purified through a silica gel column (approx. 50 ml silica gel, approx. 3 L ethyl acetate 95/methanol 5+0.25% conc. ammonia). The required fractions are evaporated down in vacuo.

Yield: 8.5 g cis-isomer and 2.2 trans-isomer.

8.5 g (20 mmol) cis-dibenzyl-[4-(4-cyclopropyl methyl-piperazin-1-yl)-cyclohexyl]-amine are dissolved in 170 ml of methanol and hydrogenated on 1.7 g Pd/C (10%) at 30-50° C. The solvent is eliminated in vacuo and the residue is crystallised from ethanol and conc. HCl. Yield: 4.4 g

4-(4,4-DIMETHYL-PIPERIDIN-1YL)-CYCLOHEXYLAMINE

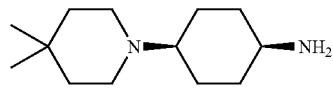

8.8 g (30 mmol) 4-dibenzylamino-cyclohexanone, 6.7 g (45 mmol) 4,4-dimethyl-piperidine-hydrochloride and 9.5 g (45 mmol) sodium triacetoxyborohydride are stirred in 100 ml dichloromethane for 16 hours at ambient temperature. 200 ml of water and 20 g potassium carbonate are added, the organic phase is separated off and evaporated to dryness. The residue is purified by chromatography.

Yield: 0.7 g cis-isomer (M.p.: 125-126° C.) and 0.4 g trans-isomer.

0.7 g (1.8 mmol) cis-dibenzyl-[4-(4,4-dimethyl-piperidin-1-yl)-cyclohexyl]-amine are placed in 14 ml of methanol, 0.14 g palladium/charcoal (10%) are added and the mixture is hydrogenated at 50 psi and 20° C. Then the catalyst is suction filtered and the mother liquor is concentrated by evaporation. Yield: 0.3 g

CIS- AND TRANS-4-PYRROLIDIN-1-YL-CYCLOHEXYLAMINE (HYDROCHLORIDE)

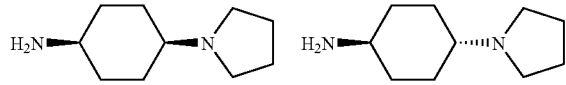

0.8 g (21 mmol) lithium aluminium hydride are placed in 50 ml of tetrahydrofuran and 6.2 g (20 mmol) 4-dibenzylamino-cyclohexanone oxime (for preparation see above) dissolved in 62 ml of tetrahydrofuran are added dropwise. Then the reaction mixture is refluxed for 3 hours with stirring. After cooling 0.8 ml of water and 2.4 ml 15% sodium hydroxide solution are added dropwise. The precipitate formed is suction filtered and washed with tetrahydrofuran. The mother liquor is evaporated to dryness.

Yield: 4.9 g (cis/trans-mixture)

2.9 g (10 mmol) cis/trans-N,N-dibenzyl-cyclohexane-1,4-diamine, 2.4 g (11 mmol)) 1,4-dibromobutane and 2.7 g potassium carbonate are placed in 70 ml of dimethylformamide and stirred for 48 hours at ambient temperature. Then the reaction mixture is concentrated by evaporation, the residue is extracted with water and dichloromethane. The organic phase is washed with water, dried and evaporated to dryness. The residue is purified by chromatography, corresponding fractions are combined, concentrated by evaporation and crystallised from petroleum ether.

Yield: 0.8 g cis-isomer (M.p.: 81-82° C.) and 0.9 g trans-isomer (122-124° C.).

2.2 g (6.1 mmol) trans-dibenzyl-(4-pyrrolidin-1-yl-cyclohexyl)-amine are placed in 40 ml of methanol and 0.4 g palladium/charcoal (10%) are added. The mixture is hydrogenated at 5 bar and 20° C. Then the catalyst is suction filtered, the mother liquor is combined with conc. hydrochloric acid and concentrated by evaporation. The residue is stirred out with acetone.

Yield: 1.20 g. The cis isomer may be prepared analogously.

TRANS-4-(4-METHANESULPHONYL-PIPERAZIN-1-YL)-CYCLOHEXYLAMINE

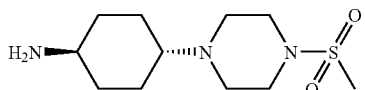

14 g (47 mmol) 4-dibenzylamino-cyclohexanone, 8.5 g (51 mmol) 1-methanesulphonyl-piperazine and 17.5 g (78 mmol) sodium triacetoxyborohydride are stirred in 250 ml dichloromethane for 4 hours at ambient temperature. Then the reaction mixture is combined with 200 ml of water and 20 g potassium carbonate. The organic phase is separated off, dried and evaporated to dryness. The residue is purified by chromatography. Yield: 4.8 g trans-isomer 4.8 g (11 mmol) trans-dibenzyl-[4-(4-methanesulphonyl-piperazin-1-yl)-cyclohexyl]-amine are dissolved in 100 ml of methanol and 2 g palladium/charcoal (10%) are added. The mixture is hydrogenated at 50 psi and 50° C. Then the catalyst is suction filtered, the mother liquor is concentrated by evaporation. The precipitate formed is suction filtered and washed with diethyl ether. Yield: 2.4 g

CIS- AND TRANS-4-(2,6-DIMETHYL-MORPHOLIN-4-YL)-CYCLOHEXYLAMINE-DIHYDROCHLORIDE

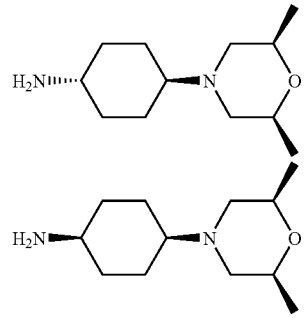

9 g (31 mmol) 4-dibenzylamino-cyclohexanone, 7.5 g (65 mmol) cis-2,6-dimethyl-morpholine and 9.5 g (45 mmol) sodium triacetoxyborohydride are stirred in 100 ml dichloromethane for 2 hours at ambient temperature. Then 200 ml of water are added and the mixture is made basic with potassium carbonate. The organic phase is separated off, dried and evaporated to dryness. The residue is purified by chromatography. Corresponding fractions are combined and concentrated by evaporation, then the hydrochloride is precipitated.

Yield: 10 g cis-isomer (M.p.: 304-305° C.) and 3.5 g trans-isomer (334-335° C.).

9.8 g (21 mmol) cis-dibenzyl-[4-(2,6-dimethyl-morpholin-4-yl)-cyclohexyl]-amine-dihydrochloride are placed in 150 ml of methanol and 2 g palladium/charcoal (10%) are added. The mixture is hydrogenated at 50 psi and 50° C. Then the catalyst is suction filtered, the mother liquor is concentrated by evaporation. The precipitate formed is suction filtered and washed with diethyl ether. Yield: 5.5 g. The trans isomer may be prepared analogously.

CIS- AND TRANS-4-(4-METHYL-PIPERAZIN-1YL)-CYCLOHEXYLAMINE

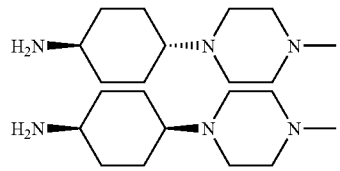

14.7 g (50 mmol) 4-dibenzylamino-cyclohexanone, 15.8 g (100 mmol) ethyl piperazine-N-carboxylate and 10.6 g (50 mmol) sodium triacetoxyborohydride are stirred in 200 ml dichloromethane for 16 hours at ambient temperature. Then the reaction mixture is combined with 200 ml of water and 20 g potassium carbonate. The organic phase is separated off and evaporated to dryness. The residue is purified by chromatography. Yield: 12 g cis-isomer (M.p.: 143-144° C.) and 4 g trans-isomer (281-282° C.).

12 g (27.5 mmol) ethyl cis-4-(4-dibenzylamino-cyclohexyl)-piperazin-1-carboxylate are placed in 50 ml of water and 50 ml of conc. hydrochloric acid, then refluxed for 72 hours. Then the reaction mixture is concentrated by evaporation, the residue is combined with 200 ml of water and 20 g potassium carbonate and extracted with dichloromethane. The organic phase is separated off, dried and evaporated to dryness. The residue is crystallised from ethyl acetate. Yield: 8.6 g (M.p.: 100-101° C.)

4 g (11 mmol) cis-dibenzyl-(4-piperazin-1-yl-cyclohexyl)-amine are placed in 5 ml (16.7 mmol) formalin solution (37% in water) and 10 ml (22 mmol) formic acid, then refluxed for 2 hours with stirring. The reaction mixture is added to ice water and combined with conc. ammonia. It is extracted with diethyl ether. The organic phase is washed with water, dried and evaporated to dryness. The residue is stirred out with petroleum ether, suction filtered and dried. Yield: 4.10 g (M.p.: 93-94° C.)

4.1 g (11 mmol) cis-dibenzyl-[4-(4-methyl-piperazin-1-yl)-cyclohexyl]-amine are placed in 80 ml of methanol, 0.8 g palladium/charcoal (10%) are added and then the mixture is hydrogenated at 50 psi and 20° C. The reaction mixture is suction filtered through kieselguhr, the mother liquor is concentrated by evaporation. Yield: 1.90 g. The trans-isomer may be prepared analogously.

SYNTHESIS OF THE INTERMEDIATE COMPOUNDS

INTERMEDIATE COMPOUND 1. N-(7-OXO-4,5,6,7-TETRAHYDRO-BENZOTHIAZOL-2-YL)-ACETAMIDE

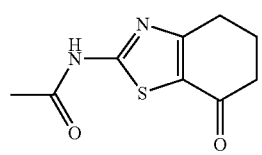

Z4a 112 g (1.0 mol) 1,3-cyclohexanedione are suspended in 700 ml ice water and 51.6 ml (1.0 mol) bromine are added dropwise at 0° C. within 45 minutes. The suspension is stirred for 3.5 hours at max. 10° C. Then it is suction filtered and the solid is stirred out in 800 ml of water, suction filtered, washed with 3 L water and dried. The solid obtained is recrystallised from ethanol. Yield: 37 g Z2a (m.p.: 159-160° C.)

15.5 g (0.2 mol) thiourea are placed in 200 ml of ethanol at ambient temperature. 37.1 g (0.2 mol) Z2a are added batchwise to this suspension, then it is rinsed with 60 ml of ethanol. The solution gradually formed is refluxed for 2 hours with stirring and then concentrated by evaporation. The residue is extracted with water and diethyl ether, the aqueous phase is made basic with sodium carbonate solution. The resulting solid is suction filtered, washed with water, then stirred out with methanol and evaporated to dryness. Yield: 22 g Z3a (m.p.: 265-268° C.) ml (2.4 mol) acetic anhydride are taken at ambient temperature, 22 g (0.13 mol) Z3a are added and the mixture is refluxed for 3 hours with stirring. The suspension goes partially into solution. After cooling with ice/saline bath the solid is suction filtered, decocted 2× in 150 ml acetone, suction filtered and dried. Yield: 25 g Z4a (m.p.: 268-272° C.)

INTERMEDIATE COMPOUND 2. N-(6-FORMYL-7-OXO-4,5,6,7-TETRAHYDRO-BENZOTHIAZOL-2-YL)-ACETAMIDE

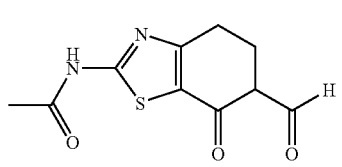

Z5a 20 g (0.37 mol) sodium methoxide are suspended in 50 ml of dimethylformamide, a suspension of 21 g (0.1 mol) intermediate compound 1 in 100 ml of dimethylformamide is added dropwise. The mixture is stirred for 15 minutes, then cooled to 0° C. A mixture of 29.9 ml (0.37 mol) ethyl formate and 60 ml benzene is added dropwise and the reaction mixture is diluted with another 100 ml benzene. Gradually a precipitate is formed and stirring is continued at 0° C. for 3.5 hours. The suspension is hydrolysed with 370 ml 1 molar hydrochloric acid, the solid thus precipitated is suction filtered. The two phases of the mother liquor are separated, the aqueous phase is extracted with dichloromethane. The resulting organic phase is dried and evaporated to dryness. The solid and the residue from the extraction are recrystallised from acetonitrile.

Yield: 20 g Z5a

INTERMEDIATE COMPOUND 3. N-(6-DIMETHYLAMINOMETHYLENE-7-OXO-4,5,6,7-TETRAHYDRO-BENZOTHIAZOL-2-YL)-ACETAMIDE

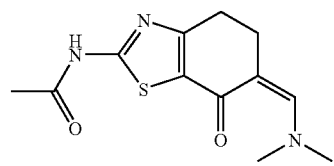

Z5b 30 g (0.13 mol) intermediate compound 2 are suspended in 750 ml dichloromethane and while cooling with ice combined with 1 ml glacial acetic acid and 30 ml dimethylamine (33% solution in THF). The reaction mixture is stirred overnight at ambient temperature, evaporated down and the solid remaining is extracted with cyclohexane. Yield: 33 g Z5b

INTERMEDIATE COMPOUND 4. N-[6-(FURAN-2-CARBONYL)-7-OXO-4,5,6,7-TETRAHYDRO-BENZOTHIAZOL-2-YL]-ACETAMIDE

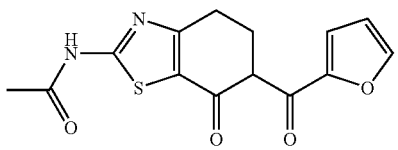

Analogously to the preparation of intermediate compound 21.7 g product Z5c are obtained from 2 g (10 mmol) intermediate compound 1, 1.6 g (30 mmol) sodium methoxide and 3.8 g (30 mmol) methyl 2-furanoate. (m.p.: 255-256° C.)

INTERMEDIATE COMPOUND 5. N-(6-BENZOYL-7-OXO-4,5,6,7-TETRAHYDRO-BENZOTHIAZOL-2-YL)-ACETAMIDE

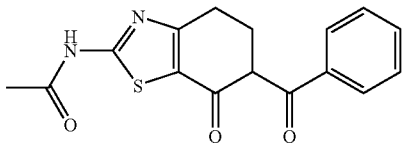

Analogously to the preparation of intermediate compound 23.6 g product Z5d are obtained from 10 g (50 mmol) intermediate compound 1, 7.8 g (140 mmol) sodium methoxide and 17.9 ml (140 mmol) methyl benzoate.

INTERMEDIATE COMPOUND 6. N-[6-(FURAN-3-CARBONYL)-7-OXO-4,5,6,7-TETRAHYDRO-BENZOTHIAZOL-2-YL]-ACETAMIDE

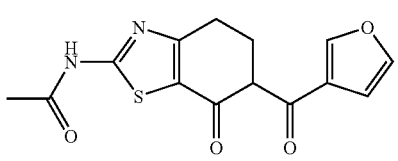

Analogously to the preparation of intermediate compound 24.8 g product Z5e are obtained from 7.5 g (40 mmol) intermediate compound 1, 7.7 g (110 mmol) sodium methoxide and 15.1 ml (110 mmol) ethyl furan-3-carboxylate.

INTERMEDIATE COMPOUND 7. METHYL (2-ACETYLAMINO-7-OXO-4,5,6,7-TETRAHYDRO-BENZOTHIAZOL-6-YL)-OXO-ACETATE

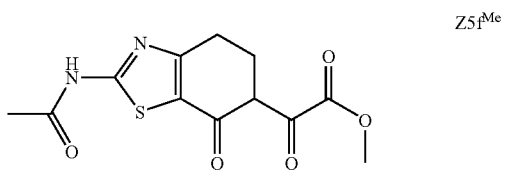

Analogously to the preparation of intermediate compound 252 g product Z5f$^{Me}$ are obtained from 40 g (190 mmol) intermediate compound 1, 38 g (0.7 mol) sodium methoxide and 84 g (0.7 mol) dimethyl oxalate.

INTERMEDIATE COMPOUND 8. ETHYL (2-ACETYLAMINO-7-OXO-4,5,6,7-TETRAHYDRO-BENZOTHIAZOL-6-YL)-OXO-ACETATE

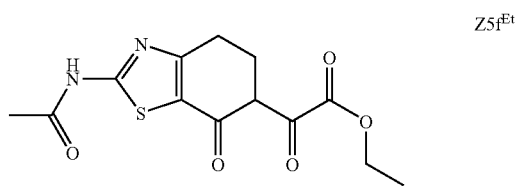

Analogously to the preparation of intermediate compound 278 g product Z5f$^{Et}$ are obtained from 73 g (348 mmol) intermediate compound 1, 54 g (1 mol) sodium methoxide and 152 g (1 mol) diethyl oxalate.

INTERMEDIATE COMPOUND 9. N-[7-OXO-6-(PYRIDINE-3-CARBONYL)-4,5,6,7-TETRAHYDRO-BENZOTHIAZOL-2-YL]-ACETAMIDE

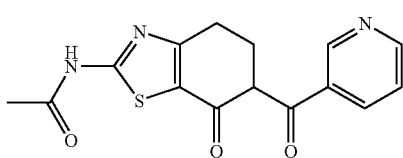

Analogously to the preparation of intermediate compound 23.1 g product Z5g are obtained from 4 g (19 mmol) intermediate compound 1, 3.9 g (57 mmol) sodium ethoxide and 7.9 g (57 mmol) methyl nicotinate.

INTERMEDIATE COMPOUND 10. N-(6-ACETYL-7-OXO-4,5,6,7-TETRAHYDRO-BENZOTHIAZOL-2-YL)-ACETAMIDE

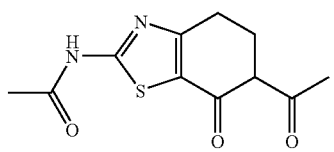

1 g (4.8 mmol) intermediate compound 1 are dissolved in 20 ml THF, cooled to −20° C. and combined with 12 ml (12 mmol) of a 1 N solution of lithium hexamethyl disilazide in hexane. After 45 minutes at −20° C. 0.8 g (7.2 mmol) 1-imidazol-1-yl-ethanone are added and the reaction mixture is slowly heated to ambient temperature. After one hour at this temperature the pH is adjusted to 6 with 2 N hydrochloric acid and the mixture is extracted with ethyl acetate. The combined organic phases are dried and evaporated down. Yield: 1.2 g Z5h INTERMEDIATE COMPOUND 11. N-[6-(1-METHYL-1H-IMIDAZOL-4-CARBONYL)-7-OXO-4,5,6,7-TETRAHYDRO-BENZOTHIAZOL-2-YL]-ACETAMIDE

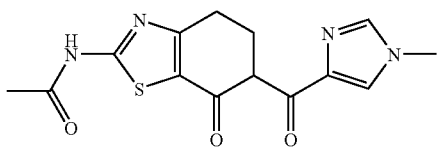

Z5i

Analogously to the preparation of intermediate compound 10 57 g product Z5i are obtained from 50 g (0.24 mol) intermediate compound 1, 714 ml (0.71 mol) LiHMDS (1 M in THF) and 55 g (0.31 mol) imidazol-1-yl-(1-methyl-1H-imidazol-4-yl)-methanone.

INTERMEDIATE COMPOUND 12. N-(6-ISOBUTYRYL-7-OXO-4,5,6,7-TETRAHYDRO-BENZOTHIAZOL-2-YL)-ACETAMIDE

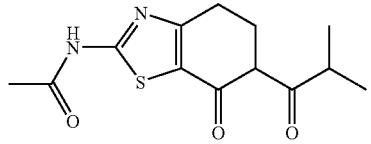

Z5j

Analogously to the preparation of intermediate compound 10 4.4 g product Z5j are obtained from 4.8 g (23 mmol) intermediate compound 1, 71 ml (71 mmol) LiHMDS (1 M in hexane) and 6.3 g (46 mmol) 1-imidazol-1-yl-2-methyl-propan-1-one.

INTERMEDIATE COMPOUND 13. N-[6-(2-METHOXY-ACETYL)-7-OXO-4,5,6,7-TETRAHYDRO-BENZOTHIAZOL-2-YL]-ACETAMIDE

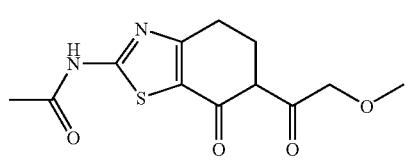

Z5k

Analogously to the preparation of intermediate compound 10 1.8 g product Z5k are obtained from 4.2 g (20 mmol) intermediate compound 1, 60 ml (60 mmol) LiHMDS (1 M in hexane) and 5.6 g (40 mmol) 1-imidazol-1-yl-2-methoxyethanone.

INTERMEDIATE COMPOUND 14. (R)—N-[7-OXO-6-(TETRAHYDRO-FURAN-2-CARBONYL)-4,5,6,7-TETRAHYDRO-BENZOTHIAZOL-2-YL]-ACETAMIDE

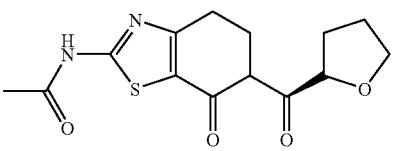

Z5l

Analogously to the preparation of intermediate compound 10 1 g product Z5l are obtained from 10 g (48 mmol) intermediate compound 1,145 ml (145 mmol) LiHMDS (1 M in hexane) and 23.5 g (52 mmol) (R)-imidazol-1-yl-(tetrahydro-furan-2-yl)-methanone.

INTERMEDIATE COMPOUND 15. (S)—N-[7-OXO-6-(TETRAHYDRO-FURAN-2-CARBONYL)-4,5,6,7-TETRAHYDRO-BENZOTHIAZOL-2-YL]-ACETAMIDE

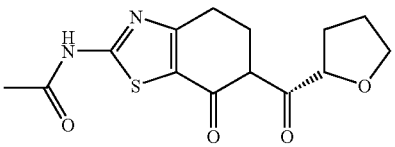

Z5m

Analogously to the preparation of intermediate compound 10 3.1 g product Z5m are obtained from 19.4 g (92 mmol) intermediate compound 1, 277 ml (277 mmol) LiHMDS (1 M in hexane) and 23.5 g (141 mmol) (S)-imidazol-1-yl-(tetrahydro-furan-2-yl)-methanone.

INTERMEDIATE COMPOUND 16. N-[7-Oxo-6-(3-TRIMETHYLSILANYL-PROPYNOYL)-4,5,6,7-TETRAHYDRO-BENZOTHIAZOL-2-YL]-ACETAMIDE

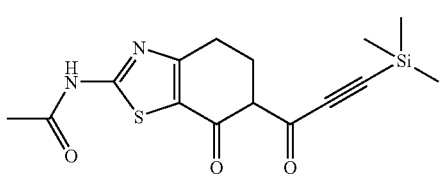

Z5n

Analogously to the preparation of intermediate compound 10 1.1 g product Z5n are obtained from 1.1 g (5.7 mmol)

intermediate compound 1, 17.5 ml (17.5 mmol) LiHMDS (1 M in hexane) and 4.6 g (8.4 mmol) 1-imidazol-1-yl-3-trimethylsilanyl-propynone.

INTERMEDIATE COMPOUND 17. N-{7-OXO-6-[1-(2-TRIMETHYLSILANYL-ETHOXYMETHYL)-1H-IMIDAZOL-4-CARBONYL]-4,5,6,7-TETRAHYDRO-BENZOTHIAZOL-2-YL}-ACETAMIDE

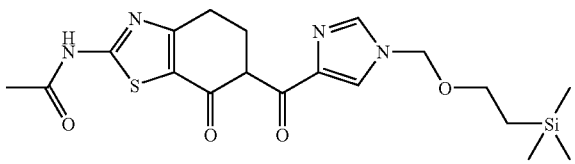

Z5s

A solution of 125 ml (0.125 mol) LHMDS (lithium hexamethyl disilazide) in 100 mL tetrahydrofuran is combined with 10.5 g (50 mmol) intermediate compound 1 at −20° C. and stirred for 0.75 hours. 15.6 g (53 mmol) imidazol-1-yl-[1-(2-trimethylsilanyl-ethoxymethyl)-1H-imidazol-4-yl]-methanone dissolved in 80 ml of tetrahydrofuran are added. The resulting suspension is stirred for 16 hours at ambient temperature. Then it is hydrolysed with 2 N hydrochloric acid and extracted with methyl-tert-butylether. The organic phase is dried and evaporated to dryness. The residue is purified by chromatography. Yield: 1.5 g

INTERMEDIATE COMPOUND 18. ETHYL 2-ACETYLAMINO-7-OXO-4,5,6,7-TETRAHYDRO-BENZOTHIAZOL-6-CARBOXYLATE

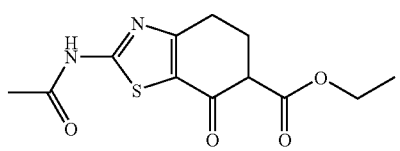

Z5o 4.0 g (19 mmol) intermediate compound 1 are placed in 120 ml of tetrahydrofuran and cooled to −50° C. 80 ml (60 mmol) of a 1 molar solution of lithium bis(trimethylsilylamide) in tetrahydrofuran are added and the mixture is stirred for 5 hours at −30° C. to −50° C. Then the reaction mixture is combined with 6.5 ml (80 mmol) chloroethyl formate, then stirred for 1 hour. 50 ml of water are added, the mixture is acidified with 2 N hydrochloric acid and extracted with ethyl acetate. The organic phase is dried and evaporated to dryness. The residue is purified by chromatography, corresponding fractions are combined and concentrated by evaporation. The crude product is triturated with diethyl ether and suction filtered. Yield: 2.3 g Z5o

INTERMEDIATE COMPOUND 19. N-[7-OXO-6-(2,2,2-TRIFLUORO-ACETYL)-4,5,6,7-TETRAHYDRO-BENZOTHIAZOL-2-YL]-ACETAMIDE

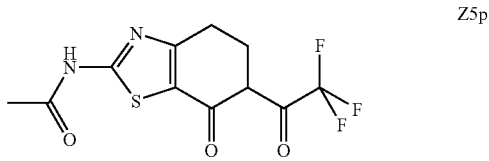

Z5p 140 g (1.25 mol) 1,3-cyclohexanedione are dissolved in 625 ml chloroform, then 145 ml (2.49 mol) ethanol and 3.4 g (18 mmol) p-toluenesulphonic acid are added. The reaction mixture is refluxed for 72 hours with stirring, while the resulting water is separated off using the water separator. Then the mixture is concentrated by evaporation and the residue is combined with diethyl ether, dried and evaporated to dryness. The residue is purified by distillation. Yield: 166 g 4.6 g (0.115 mol) sodium hydride are suspended in 250 ml diethyl ether and heated to 40° C. Then a solution of 17 ml (0.14 mol) ethyl trifluoroacetate and 10 g (71 mmol) of the intermediate described above in 50 ml diethyl ether is added dropwise. The mixture is refluxed for 24 hours with stirring. After cooling to ambient temperature 150 ml of water are added and the mixture is stirred for 0.1 hour at ambient temperature. The phases are separated, the organic phase is extracted with 5% sodium hydroxide solution. The combined basic aqueous phases are acidified and extracted with ethyl acetate. The ethyl acetate phases are dried and evaporated to dryness. The crude product is purified by chromatography. Yield: 4.1 g 0.4 g (1.7 mmol) of the intermediate described above are dissolved in 10 ml dioxane and 10 ml of water, cooled to −10° C. and then combined with 0.3 g (1.9 mmol) N-bromosuccinimide. The mixture is stirred for 1 hour at ambient temperature and then 0.13 g (1.7 mmol) thiourea are added. The mixture is stirred for 0.5 hours at ambient temperature and for 3 hours at 80° C. After cooling the reaction mixture is made basic and extracted with dichloromethane. The organic phase is dried and evaporated to dryness. Yield: 0.2 g 0.2 g (0.76 mmol) of the intermediate described above are suspended in 10 ml (0.1 mol) acetic anhydride and then heated to 100° C. The mixture is stirred for 3 hours at 100° C. and for 16 hours at ambient temperature. Then the reaction mixture is concentrated by evaporation, the residue is combined with glacial acetic acid and concentrated by evaporation. Yield: 0.3 g Z5p

INTERMEDIATE COMPOUND 20. 1-PHENYL-4,5-DIHYDRO-1H-PYRAZOLO[3',4':3,4]BENZO[1,2-d]THIAZOL-7-YLAMINE

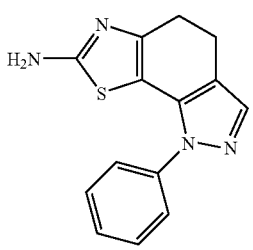

650 ml 37% hydrochloric acid are placed in 650 ml of water and 99 g (0.27 mol) N-(1-phenyl-4,5-dihydro-1H-pyrazolo[3',4':3,4]benzo[1,2-d]thiazol-7-yl)-acetamide (prepared analogously to Example 1) are dissolved therein. The solution is refluxed for 2 hours with stirring. After cooling to ambient temperature the mixture is carefully made basic (pH 10-11) with sodium hydroxide solution. The precipitate formed is suction filtered and stirred out with methanol. Yield: 66 g (m.p.: 307-308° C.)

INTERMEDIATE COMPOUND 21. N-(6-BROMO-7-OXO-4,5,6,7-TETRAHYDRO-BENZOTHIAZOL-2-YL)-ACETAMIDE

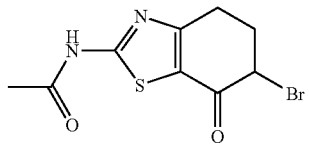

A solution of 2 g (9.5 mmol) intermediate compound 1 in 60 ml glacial acetic acid is combined at ambient temperature with a solution of 1.5 g (9.5 mmol) bromine in 10 ml glacial acetic acid. The reaction mixture is slowly heated to 75° C., during which time rapid decolorisation sets in. It is evaporated to dryness, the residue is dissolved in methanol and the product is precipitated by the addition of water. Yield: 2.2 g (M.p.: 180-182° C.)

INTERMEDIATE COMPOUND 22. N-(5-FORMYL-6-OXO-4,5,6,6A-TETRAHYDRO-3AH-CYCLOPENTATHIAZOL-2-YL)-ACETAMIDE

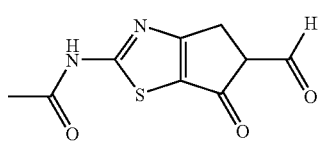

Z5q 100 g (0.36 mol) 2-bromo-cyclopentane-1,3-dione (see M. Vanderwalle et al., *Bull. Soc. Chim. Belg.* 1966, 75, 648-654) are dissolved in 370 ml of dimethylformamide and combined with 43 g (0.36 mol) N-acetylthiourea. The mixture is stirred for 3 hours at 75° C., then at 50° C. 15 g activated charcoal are added. After filtration through kieselguhr the filtrate is cooled to 10° C. and combined with 1200 ml of water. The precipitate formed is stirred for 16 hours at ambient temperature, suction filtered and dried.

Yield: 20.4 g Z4b (m.p.: 270-272° C.)

27.6 g (0.51 mol) sodium methoxide are suspended in 50 ml of dimethylformamide and at ambient temperature a suspension of 20.0 g (0.10 mol) Z4b in 350 ml of dimethylformamide is added dropwise in batches within 0.25 hours. The reaction mixture is stirred for 1 hour at ambient temperature, then heated to an internal temperature of 60° C. A solution of 41 ml (0.51 mol) ethyl formate in 40 ml benzene is added dropwise and the mixture is stirred for 2 hours. After cooling to 5° C. 100 ml semiconcentrated hydrochloric acid are added and the mixture is diluted with water to 3000 ml. A precipitate is formed which is suction filtered. The filtrate is extracted with dichloromethane, the organic phase is dried and evaporated to dryness. The residue is stirred with dichloromethane/diethyl ether 1:5, suction filtered and dried.

Yield: 12.3 g Z5q

INTERMEDIATE COMPOUND 23. N-(7-FORMYL-8-OXO-5,6,7,8-TETRAHYDRO-4H-CYCLOHEPTATHIAZOL-2-YL)-ACETAMIDE

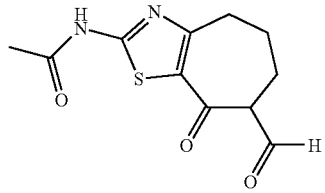

Z5r

A solution of 7.4 g (90 mmol) sodium acetate and 9.9 g (79 mmol) 1,3-cycloheptadiene in 300 ml glacial acetic acid is combined at 15° C. with 12.6 g (79 mmol) bromine and stirred for 30 min. Then 6.0 g (79 mmol) thiourea are added and the suspension is refluxed for 5 hours. The acetic acid is eliminated in vacuo and the residue is taken up in saturated saline solution. Insoluble constituents are suction filtered and the aqueous phase is first of all extracted with ether and then made alkaline with ammonia. The precipitated solid is suction filtered and dried. Yield: 3.7 g Z3b 3.7 g (20 mmol) of compound Z3b are refluxed in 50 ml acetic anhydride for 1 hour. The solid precipitated after cooling is suction filtered and stirred with ether. Yield: 2.4 g Z4c 1.7 g (31 mmol) sodium methoxide are suspended in 20 ml DMF and combined batchwise with 2.4 g (11 mmol) of compound Z4c. After 30 min the mixture is cooled to −5° C., a solution of 2.5 ml (31 mmol) ethyl formate in 10 ml benzene is added dropwise and the resulting mixture is stirred overnight at ambient temperature. It is combined with 70 ml 1N hydrochloric acid, the precipitate formed is suction filtered and washed with water. Yield: 2 g Z5r

SYNTHESIS OF COMPOUNDS OF FORMULA 1

EXAMPLE 1

N-(1-P-TOLYL-4,5-DIHYDRO-1H-PYRAZOLO[3',4':3,4]BENZO[1,2-d]THIAZOL-7-YL)-ACETAMIDE

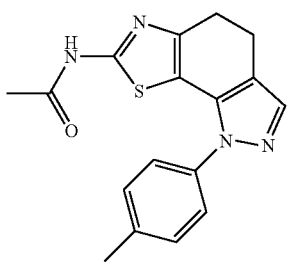

0.5 g (2 mmol) intermediate compound 2 are placed in 7.5 ml glacial acetic acid, combined with 0.32 g (2 mmol) p-tolyl-hydrazine-hydrochloride and heated to 60° C. for 3.5 hours. The precipitate formed after the addition of 20 ml of water is suction filtered and recrystallised from acetonitrile with the addition of activated charcoal. Yield: 0.32 g (m.p.: 240-242° C.)

EXAMPLE 2

N-[1-(5-FLUORO-2-METHYL-PHENYL)-4,5-DI-HYDRO-1H-PYRAZOLO[3',4':3,4]BENZO[1,2-d]THIAZOL-7-YL]-ACETAMIDE

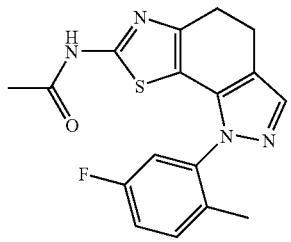

8.8 mg (0.05 mmol) 5-Fluoro-2-methyl-phenylhydrazine-hydrochloride are placed in 2.5 ml of ethanol and combined with 13.3 mg (0.05 mmol) intermediate compound 3, dissolved in 2.5 ml of ethanol. The reaction mixture is heated overnight to 50° C., evaporated down and the residue is purified by RP-HPLC. Yield: 13.3 mg

EXAMPLE 3

7-ACETYLAMINO-4,5-DIHYDRO-PYRAZOLO[3',4':3,4]BENZO[1,2-d]THIAZOLE-1-CARBOXYLIC ACID AMIDE

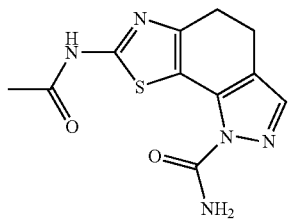

14 g (59 mmol) intermediate compound 2 and 6.7 g (60 mmol) semicarbazide are suspended in 130 ml of water and refluxed for 1 hour. The solid is suction filtered and purified by chromatography. Yield: 5.6 g (M.p.: 265-270° C.)

EXAMPLE 4

1-(4-NITRO-PHENYL)-4,5-DIHYDRO-1H-PYRAZOLO[3',4':3,4]BENZO[1,2-d]THIAZOL-7-YLAMINE

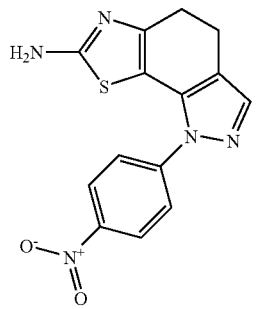

Analogously to Example 1 14 g product are obtained from 15 g (63 mmol) intermediate compound 2 and 9.8 g (64 mmol) 4-nitrophenylhydrazine (M.p.: 300-310° C.).

7 g (20 mmol) of this intermediate are saponified with 90 ml semiconcentrated hydrochloric acid as described for intermediate 20.

5.2 g product are obtained (M.p.: 273-278° C.).

EXAMPLE 5

N-(1-PHENYL-4,5-DIHYDRO-1H-PYRAZOLO[3',4':3,4]BENZO[1,2-d]THIAZOL-7-YL)-FORMAMIDE

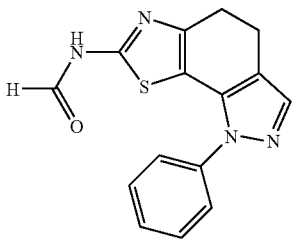

A mixture of 0.25 g (0.9 mmol) intermediate compound 20 in 8 ml phenyl formate is stirred for 4 hours at 60° C. After cooling to ambient temperature the precipitate is suction filtered and washed with a little acetone. The crude product is recrystallised from acetonitrile with the addition of activated charcoal. Yield: 0.11 g (m.p.: 273-277° C.)

EXAMPLE 6

METHYL (1-PHENYL-4,5-DIHYDRO-1H-PYRAZOLO[3',4':3,4]BENZO[1,2-d]THIAZOL-7-YL)-CARBAMOYLATE

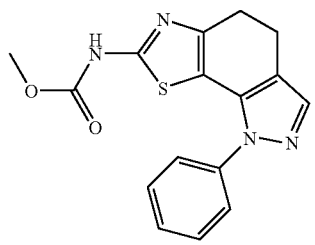

0.50 g (1.9 mmol) intermediate compound 20 are suspended in 10 ml of pyridine and heated to 50° C. 0.6 ml (7.6 mmol) chloroethyl formate are slowly added and the reaction mixture is then stirred for 48 hours at 50° C. During this time a further 2×0.6 ml of chloroethyl formate are added. The mixture is stirred for another 72 hours at ambient temperature. The suspension is filtered, the filtrate is combined with 130 ml of water. The precipitate formed is suction filtered, washed and dried. The crude product is recrystallised from methanol. Yield: 0.15 g (m.p.: 283-287° C.)

EXAMPLE 7

4-DIMETHYLAMINO-N-(1-PHENYL-4,5-DIHYDRO-1H-PYRAZOLO-[3',4':3,4]BENZO[1,2-D]THIAZOL-7-YL)-BUTYRAMIDE

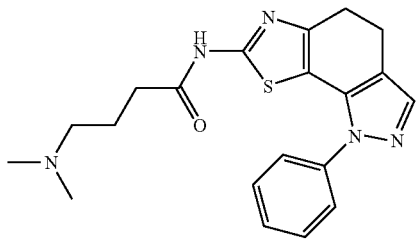

In a sealable pressure tube 0.9 g (4.8 mmol) freshly prepared 4-(dimethylamino)-butyric acid chloride-hydrochloride are suspended in 30 ml of tetrahydrofuran and heated to 50° C. 0.6 ml triethylamine are added, followed by 0.5 g (1.9 mmol) intermediate compound 20 added batchwise. The reaction mixture is stirred for 71 hours at 70° C. After cooling to ambient temperature the precipitate formed is suction filtered, washed and taken up in saturated sodium hydrogen carbonate solution and chloroform. The organic phase is washed with water, dried and evaporated to dryness. The crude product is recrystallised from acetonitrile with the addition of activated charcoal. Yield: 0.2 g (m.p.: 165-166° C.)

EXAMPLE 8

S-ETHYL (1-PHENYL-4,5-DIHYDRO-1H-PYRAZOLO[3',4':3,4]BENZO[1,2-d]THIAZOL-7-YL)-THIOCARBAMOYLATE

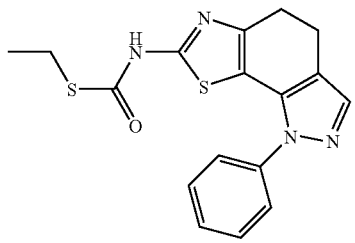

2.7 g (9.9 mmol) intermediate compound 20 are placed in 70 ml of pyridine and heated to 50° C. 1.6 ml (15 mmol) ethyl thiochloroformate are added to this suspension. The resulting solution is stirred for 2 hours at 50° C. After cooling to ambient temperature the solution is added to 700 ml of water, the precipitate formed is suction filtered, washed and dried. Yield: 2.2 g

EXAMPLE 9

(1-PHENYL-4,5-DIHYDRO-1H-PYRAZOLO[3',4':3,4]BENZO[1,2-d]THIAZOL-7-YL)-UREA

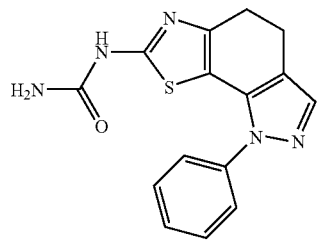

In a sealable pressure tube 7 ml (14 mmol) 2 molar ethanolic ammonia solution are added to a suspension of 0.5 g (1.4 mmol) of the compound described in Example 8 in 9 ml of ethanol. The tube is sealed and the reaction mixture is stirred for a total of 24 hours at 80° C. After 5 hours reaction a further 3 ml (6 mmol) of the ammonia solution are added. After cooling to ambient temperature the precipitate formed is suction filtered, washed and dried. The crude product is recrystallised from isopropanol with the addition of activated charcoal. Yield: 0.16 g (m.p.: 321-325° C.)

EXAMPLE 10

3-METHANESULPHONYL-PHENYL-(1-PHENYL-4,5-DIHYDRO-1H-PYRAZOLO[3',4':3,4]BENZO[1,2-d]THIAZOL-7-YL)-AMINE

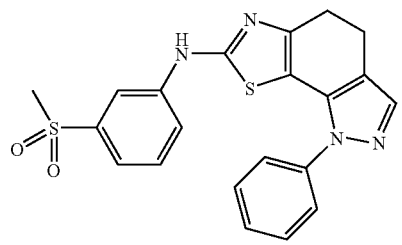

A mixture of 0.5 g (2 mmol) intermediate compound 20, 0.5 g (2 mmol) 1-bromo-3-methanesulphonylbenzene, 0.13 g (0.4 mmol) tri-tert-butylphosphine tetrafluoroborate, 0.2 g (0.2 mmol) tris(dibenzylideneacetone)-dipalladium (0) and 0.2 g (2 mmol) sodium carbonate in 10 ml DMF is stirred for 48 hours at 90° C. The reaction mixture is combined with dichloromethane and water and the aqueous phase is extracted with dichloromethane. The combined organic phases are dried, evaporated down and the residue remaining is purified by column chromatography. Yield: 25 mg

EXAMPLE 11

1-TERT-BUTYL-3-{4-[3-(1-PHENYL-4,5-DIHYDRO-1H-PYRAZOLO[3',4':3,4]BENZO[1,2-d]THIAZOL-7-YL)-UREIDO]-BUT-2-YNYL}-UREA

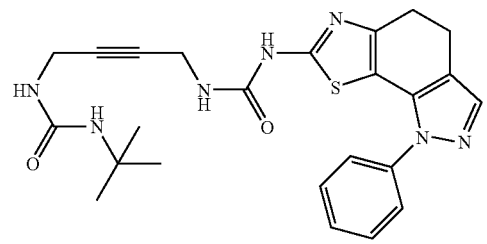

A solution of 0.4 g (1.5 mmol) intermediate compound 20 in 0.5 ml of pyridine, 3 ml dichloromethane and 0.5 ml THF is combined with 0.4 g (2 mmol) 4-nitrophenyl chloroformate and stirred for 2 hours at ambient temperature. Then the reaction mixture is combined with 0.5 g (2.7 mmol) tert-butyl (4-amino-but-2-ynyl)-carbamoylate and 1 ml of pyridine and stirred for a further 24 hours. After the addition of dichloromethane and water the aqueous phase is extracted with dichloromethane. The combined organic phases are evaporated down and the residue remaining is purified by column chromatography. Yield: 0.2 g (M.p.: 196° C.)

EXAMPLE 12

1-(4-AMINO-BUT-2-YNYL)-3-(1-PHENYL-4,5-DIHYDRO-1H-PYRAZOLO[3',4':3,4]BENZO[1,2-d]THIAZOL-7-YL)-UREA

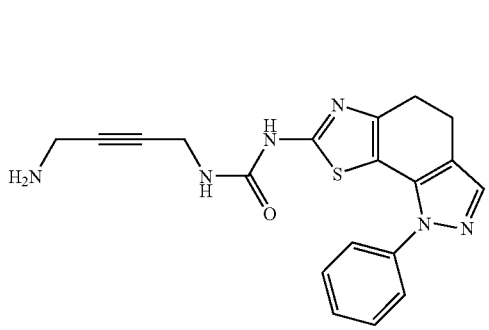

0.1 g (0.2 mmol) of the compound obtained in Example 11 are suspended in 0.5 ml trifluoroacetic acid and 2 ml dichloromethane and stirred overnight at ambient temperature. The reaction mixture is evaporated down, the residue taken up in acetone and the product is precipitated by the addition of ethereal hydrochloric acid.

Yield: 0.1 g (M.p.: 232° C.)

EXAMPLE 13

2-[(1-ETHYL-PYRROLIDIN-2-YLMETHYL)-AMINO]-N-(1-PHENYL-4,5-DIHYDRO-1H-PYRAZOLO[3',4':3,4]BENZO[1,2-d]THIAZOL-7-YL)-ACETAMIDE

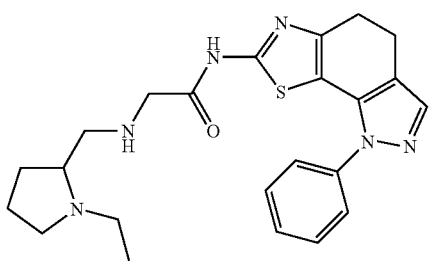

0.8 g (6.2 mmol) bromoacetic acid are dissolved in 20 ml DMF, combined with 4.9 g N-cyclohexylcarbodiimide-N'-methyl-polystyrene HL (1.9 mmol/g) and stirred for 30 minutes at ambient temperature. Then a solution of 0.83 g (3.1 mmol) intermediate compound 20 is added and the mixture is stirred overnight. The polymer is suction filtered and washed with DMF. The filtrate is evaporated down and the residue is triturated in ethyl acetate/diisopropylether. Yield: 1 g 6 mg (0.048 mmol) C-(1-ethyl-pyrrolidin-2-yl)-methylamine are dissolved in 0.4 ml DMF and combined with 0.02 ml (0.12 mmol) triethylamine, dissolved in 0.1 ml DMF. Then 16 mg (0.04 mmol) of a solution of the bromide intermediate described above in 0.5 ml DMF are added. The reaction mixture is stirred overnight and then evaporated down. Yield: 4 mg.

EXAMPLE 14

2-AMINO-N-(1-PHENYL-4,5-DIHYDRO-1H-PYRAZOLO-[3',4':3,4]BENZO[1,2-d]THIAZOL-7-YL)-ACETAMIDE

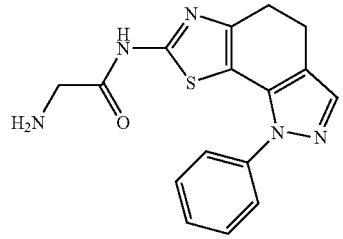

26 mg of the bromide intermediate obtained in the first part of Example 13 are suspended in 3 ml 33% aqueous ammonia solution and stirred overnight at ambient temperature. The reaction mixture is extracted with dichloromethane and the combined organic phases are evaporated down. The residue is purified by RP-HPLC. Yield: 8 mg

EXAMPLE 15

2-HYDROXY-N-(1-PHENYL-4,5-DIHYDRO-1H-PYRAZOLO[3',4':3,4]BENZO[1,2-d]THIAZOL-7-YL)-ACETAMIDE

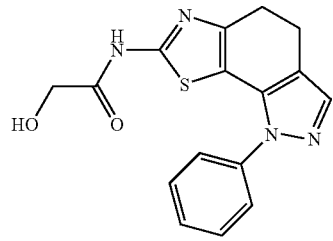

26 mg of the bromide intermediate obtained in the first part of Example 13 are suspended in 2 ml of water and 1 ml DMF and stirred for 48 hours at 100° C. The reaction mixture is purified by RP-HPLC. Yield: 9 mg

EXAMPLE 16

N-{1-[4-(MORPHOLIN-4-CARBONYL)-PHENYL]-4,5-DIHYDRO-1H-PYRAZOLO[3',4':3,4]BENZO[1,2-d]THIAZOL-7-YL}-ACETAMIDE

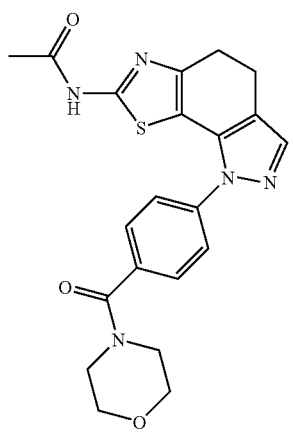

A solution of 3.5 mg (0.01 mmol) 4-(7-acetylamino-4,5-dihydro-pyrazolo[3',4':3,4]benzo[1,2-d]thiazol-1-yl)-benzoic acid (prepared analogously to Example 1) in 0.5 ml DMF is combined with 4 μL (0.03 mmol) triethylamine and 4 mg (0.01 mmol) O-pentafluorophenyl-1,1,3,3-tetramethyluronium hexafluorophosphate (PFTU) and stirred for 15 minutes. A solution of 1 mg (0.01 mmol) morpholine in 0.5 ml DMF is added to this mixture and it is shaken for 12 hours at ambient temperature. Then 3 mg polyamine resin HL (0.01 mmol, 200-400 mesh) are added and the mixture is shaken for a further 8 hours. The resin is filtered off and the filtrate is evaporated to dryness in vacuo.

EXAMPLE 17

N-{1-[4-(4-AMINO-PIPERIDINE-1-CARBONYL)-PHENYL]-4,5-DIHYDRO-1H-PYRAZOLO[3',4':3,4]BENZO[1,2-d]THIAZOL-7-YL}-ACETAMIDE

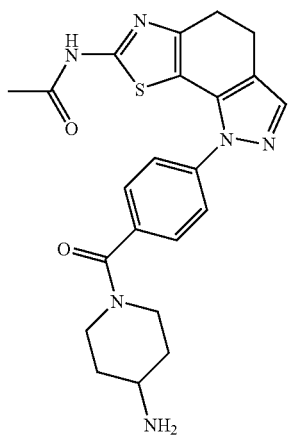

A solution of 0.3 g (0.85 mmol)) 4-(7-acetylamino-4,5-dihydro-pyrazolo[3',4':3,4]benzo[1,2-d]thiazol-1-yl)-benzoic acid (prepared analogously to Example 1), 0.32 g (1.00 mmol) TBTU and 0.75 ml (4.38 mmol) diisopropylethylamine in 25 ml dichloromethane is stirred for 15 minutes at ambient temperature and then combined with 0.17 g (0.86 mmol) 4-N-Boc-aminopiperidine. After 2.5 hours the reaction mixture is poured onto 25 ml 5% potassium carbonate solution. The organic phase is dried and evaporated down. The residue is triturated with ethyl acetate/ether.

Yield: 0.43 mg (M.p.: 230° C.)

0.40 g (0.75 mmol) of the compound described previously are suspended in 10 ml ethereal hydrochloric acid and stirred for 72 hours at ambient temperature. The solid is suction filtered and washed with ether. Yield: 0.35 mg (M.p.: 269-270° C.)

EXAMPLE 18

N-{1-[4-(7-ACETYLAMINO-4,5-DIHYDRO-PYRAZOLO[3',4':3,4]-BENZO[1,2-d]THIAZOL-1-YL)-BENZOYL]-PIPERIDIN-4-YL}-2-PHENYL-ACETAMIDE

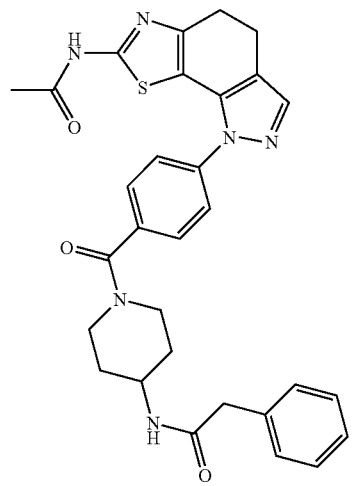

A solution of 12 mg (0.09 mmol) phenylacetic acid, 33 mg (0.09 mmol) TBTU and 80 μL (0.47 mmol) diisopropylethylamine in 2 ml dichloromethane is stirred for 15 minutes at ambient temperature and then combined with 40 mg (0.09 mmol) of the compound described in Example 17. After 2.5 hours the reaction mixture is poured onto 5% potassium carbonate solution. The organic phase is dried and evaporated down. The residue is triturated with ethyl acetate. Yield: 34 mg (M.p.: 271-272° C.)

EXAMPLE 19

N-[1-(4-METHYLSULPHAMOYL-PHENYL)-4,5-DIHYDRO-PYRAZOLO[3',4':3,4]BENZO[1,2-d]THIAZOL-7-YL]-ACETAMIDE

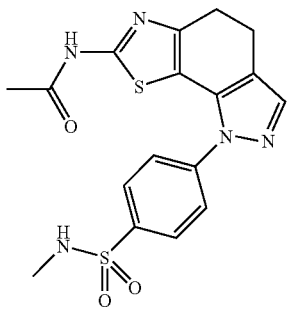

3.0 g (7.7 mmol) 4-(7-acetylamino-4,5-dihydro-pyrazolo[3',4':3,4]benzo[1,2-d]thiazol-1-yl)-benzenesulphonic acid (prepared analogously to Example 1) are placed in 180 ml phosphorus oxychloride, and 1.6 g (7.7 mmol) phosphorus pentachloride are added with cooling. The suspension is stirred for 3 hours at 90° C. and for 16 hours at ambient temperature, then cooled to 5° C. Within 0.75 hours the reaction solution is added dropwise to ice, then extracted with chloroform. The organic phase is dried and evaporated to dryness. Yield: 1.3 g 0.15 g (0.37 mmol) of the sulphonic acid chloride described previously and 2 ml (4.0 mmol) methylamine (2 M in THF) are placed In a pressurised reaction vessel, then the mixture is stirred for 1 hour at ambient temperature. The solution is concentrated by evaporation, the residue is crystallised from ethanol. The crude product is recrystallised from methanol. Yield: 0.02 g (m.p.: >260° C.)

EXAMPLE 20

N-(1-CYCLOHEX-2-ENYL-4,5-DIHYDRO-1H-PYRAZOLO[3',4':3,4]BENZO[1,2-d]THIAZOL-7-YL)-ACETAMIDE

EXAMPLE 21

N-(2-CYCLOHEX-2-ENYL-4,5-DIHYDRO-2H-PYRAZOLO[3',4':3,4]BENZO[1,2-d]THIAZOL-7-YL)-ACETAMIDE

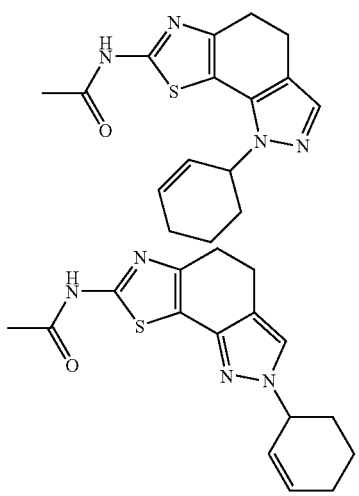

4.0 g (16.8 mmol) intermediate compound 2 are suspended in 50 ml glacial acetic acid and combined with 1.6 g (16.8 mol) hydrazine-acetate. The mixture is stirred for 3.5 hours at 60° C. stirred and then 150 ml of water are added. The precipitate formed is suction filtered, washed and dried. Yield: 2.8 g (m.p.: 261-264° C.)

0.2 g (0.85 mmol) of the intermediate described above are dissolved in 2 ml dimethylacetamide and combined with 0.1 g (2.5 mmol) sodium hydroxide (ground). It is stirred for 0.5 hours at ambient temperature. Then 12 mg (0.035 mmol) tetrabutylammonium hydrogen sulphate and 0.09 ml (0.9 mmol) 3-bromocyclohexene are added. The reaction mixture is stirred for 3 hours at 120° C. It is concentrated by evaporation, the residue is extracted with water and dichloromethane. The combined organic phases are dried and evaporated to dryness. The crude product is purified by chromatography.

Yield: 0.020 g (m.p.: 247-249° C., Example 21);
Yield: 0.060 g (m.p.: 213-214° C., Example 20)

EXAMPLE 22

N-(1-BENZOYL-4,5-DIHYDRO-1H-PYRAZOLO[3',4':3,4]BENZO[1,2-d]THIAZOL-7-YL)-ACETAMIDE

EXAMPLE 23

N-(2-BENZOYL-4,5-DIHYDRO-2H-PYRAZOLO[3',4':3,4]BENZO[1,2-d]THIAZOL-7-YL)-ACETAMIDE

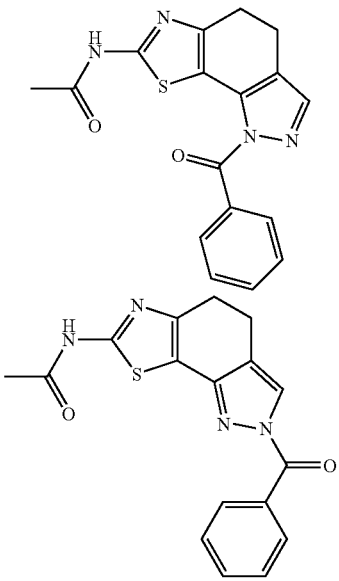

0.2 g (0.85 mmol) of the intermediate described in Example 20/21 are suspended in 2 ml benzene and combined with 0.25 ml (1.80 mmol) triethylamine and 0.18 ml (1.55 mmol) benzoyl chloride. The reaction mixture is stirred for 2 hours at 75° C. Then the suspension is suction filtered, the precipitate is washed with ethyl acetate and water. Yield: 0.12 g (m.p.: 266-267° C., Example 23)

The mother liquor is concentrated by evaporation and the residue is purified by chromatography.

Yield: 7 mg (Example 22)

EXAMPLE 24

N-[1-(2-CHLORO-PHENYL)-3-FURAN-2-YL-4,5-DIHYDRO-1H-PYRAZOLO[3',4':3,4]BENZO[1,2-d]THIAZOL-7-YL]-ACETAMIDE

EXAMPLE 25

N-[2-(2-CHLORO-PHENYL)-3-FURAN-2-YL-4,5-DIHYDRO-2H-PYRAZOLO[3',4':3,4]BENZO[1,2-d]THIAZOL-7-YL]-ACETAMIDE

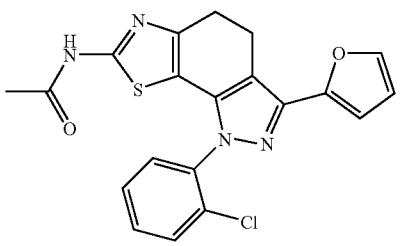

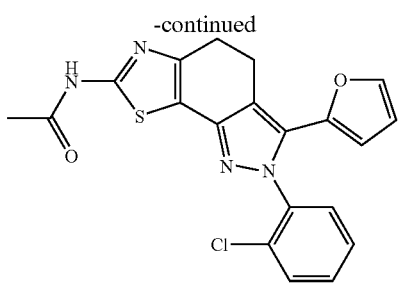

220 mg (0.7 mmol) intermediate compound 4 are placed in 3 ml glacial acetic acid and combined with 179 mg (0.7 mmol) 2-chloro-phenylhydrazine-hydrochloride. The suspension is heated overnight to 50° C., then combined with 20 ml of water and the precipitate formed is suction filtered. The solid is purified by column chromatography (eluant: dichloromethane/methanol 98:2).

Yield: 120 mg (yellow solid, m.p.: 265-266° C., Example 24); 38 mg (m.p.: >300° C., Example 25)

EXAMPLE 26

4-(7-ACETYLAMINO-3-FURAN-2-YL-4,5-DIHYDRO-PYRAZOLO[3',4':3,4]BENZO[1,2-d]THIAZOL-1-YL)-3-CHLORO-N-(1-METHYL-PIPERIDIN-4-YL)-BENZAMIDE

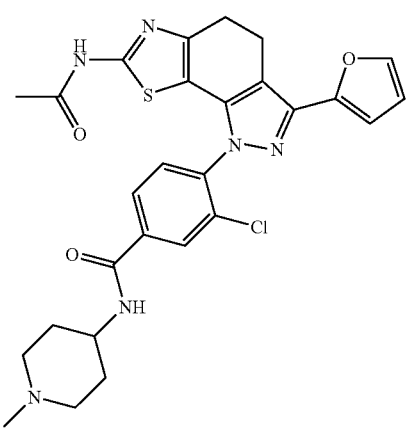

Analogously to Example 1 a mixture of the two possible pyrazole isomers is obtained from 3.3 g (11 mmol) intermediate compound 4 and 2.1 g (11 mmol) methyl 3-chloro-4-hydrazino-benzoate, and these are separated by column chromatography.

Yield: 0.6 g isomer A; 0.7 g isomer B 0.7 g (1.5 mmol) of the isomer B described above are dissolved in 8 ml dioxane and combined with a solution of 0.1 g (4.4 mmol) lithium hydroxide in 1 ml of water. After 1.5 hours the reaction mixture is acidified with 2 N hydrochloric acid and the precipitated solid is suction filtered. The product is stirred with ether. Yield: 0.5 g 40 mg (0.09 mmol) of the acid described previously, 33 mg (0.09 mmol) HATU and 46 µL diisopropylethylamine are dissolved in 3 ml DMF and stirred for 10 minutes. Then a solution of 10 mg (0.09 mmol) methylaminopiperidine in 2 ml DMF is added and the mixture is stirred for 2 hours. The reaction mixture is diluted with 15 ml 5% potassium hydrogen carbonate solution and extracted with dichloromethane. The combined organic phases are washed with water, dried and evaporated down. The crude product is purified by column chromatography. Yield: 24 mg

EXAMPLE 27

N-[1-(2-CHLORO-PHENYL)-3-FURAN-3-YL-4,5-DIHYDRO-1H-PYRAZOLO[3',4':3,4]BENZO[1,2-d]THIAZOL-7-YL]-ACETAMIDE

EXAMPLE 28

N-[2-(2-CHLORO-PHENYL)-3-FURAN-3-YL-4,5-DIHYDRO-2H-PYRAZOLO[3',4':3,4]BENZO[1,2-d]THIAZOL-7-YL]-ACETAMIDE

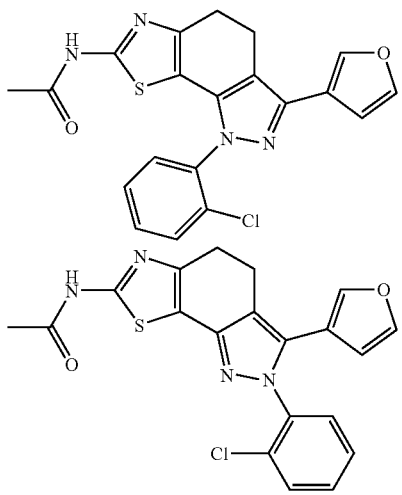

Analogously to Example 1, 102 mg (M.p. 265-266° C., Example 27); 12 mg (m.p.: >300° C., Example 28) are obtained from 0.5 g (1.2 mmol) intermediate compound 6 and 0.2 g (1.2 mmol) 2-chloro-phenylhydrazine-hydrochloride after purification by column chromatography.

EXAMPLE 29

N-[1-(2-CHLORO-PHENYL)-3-ISOPROPYL-4,5-DIHYDRO-1H-PYRAZOLO[3',4':3,4]BENZO[1,2-d]THIAZOL-7-YL]-ACETAMIDE

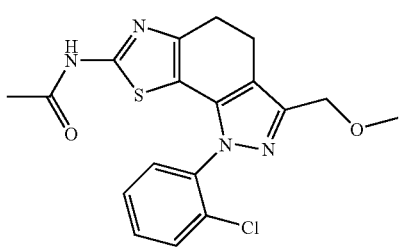

Analogously to Example 1, 0.22 g product are obtained from 0.2 g (0.7 mmol) intermediate compound 13 and 0.13 g (0.7 mmol) 2-chloro-phenylhydrazine hydrochloride.

EXAMPLE 30

4-(7-ACETYLAMINO-3-METHOXYMETHYL-4, 5-DIHYDRO-PYRAZOLO[3',4':3,4]BENZO[1,2-d] THIAZOL-1-YL)-3-CHLORO-N-(1-METHYL-PIPERIDIN-4-YL)-BENZAMIDE

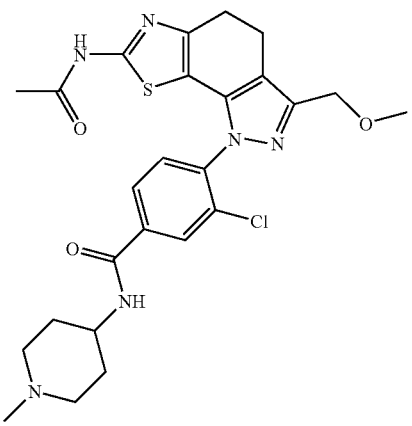

Analogously to Example 1, 1.2 g of product, whose ester function is saponified with 0.2 g (8.4 mmol) lithium hydroxide analogously to Example 26, is obtained from 0.9 g (3.2 mmol) intermediate compound 13 and 0.7 g (3.2 mmol) methyl 3-chloro-4-hydrazino-benzoate. Then 50 mg of the acid obtained are subjected to amide coupling with methylaminopiperidine as described in Example 26.

EXAMPLE 31

METHYL 7-ACETYLAMINO-1-(2-CHLORO-PHENYL)-4,5-DIHYDRO-1H-PYRAZOLO[3',4':3, 4]BENZO[1,2-d]THIAZOLE-3-CARBOXYLATE

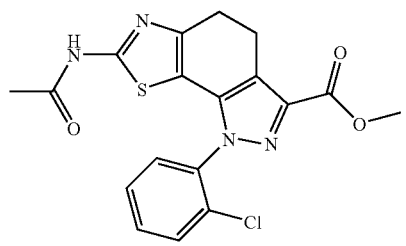

Analogously to Example 1, 0.8 g product (M.p.: 294-297° C.) are obtained from 1.0 g (3.4 mmol) intermediate compound 7 and 0.6 g (3.4 mmol) 2-chloro-phenylhydrazine hydrochloride.

EXAMPLE 32

7-ACETYLAMINO-1-(2-CHLORO-PHENYL)-4,5-DIHYDRO-1H-PYRAZOLO[3',4':3,4]BENZO[1,2-d]THIAZOLE-3-CARBOXYLIC ACID

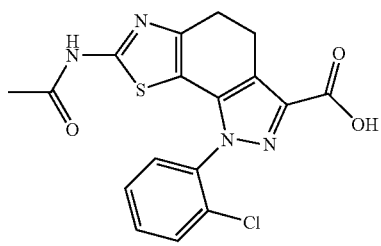

24 g (1 mol) of the compound described in Example 31 are placed in 250 ml dioxane and a solution of 4 g (10 mmol) lithium hydroxide in 35 ml of water is added. The mixture is stirred for 16 hours at ambient temperature. Then the solution is acidified slightly and the dioxane is concentrated by evaporation. The suspension is diluted with water, then suction filtered. The precipitate is dried. Yield: 23 g

EXAMPLE 33

7-ACETYLAMINO-1-PHENYL-4,5-DIHYDRO-1H-PYRAZOLO[3',4':3,4]BENZO[1,2-d]THIAZOLE-3-CARBOXYLIC ACID

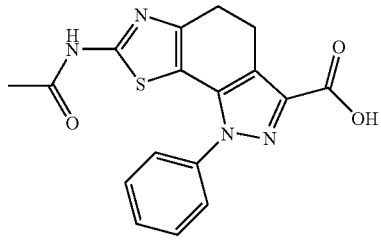

Analogously to Example 1, 27 g product (M.p.: 298-300° C.) are obtained from 30 g (0.1 mol) intermediate compound 7 and 10.3 ml (0.1 mol) phenylhydrazine. Of this, 0.1 g (0.3 mmol) are suspended in 12 ml of methanol/water (1:1) and combined with 0.4 ml 10% potassium hydroxide solution. After 1.5 hours the reaction mixture is evaporated down and the solution is acidified with dilute hydrochloric acid. The precipitate formed is recrystallised from acetonitrile. Yield: 0.1 g (M.p.: >300° C.)

EXAMPLE 34

N-[3-AMINO-1-(2-CHLOROPHENYL)-4,5-DIHY-DRO-1H-PYRAZOLE[3',4':3,4]BENZO[1,2-d]THIAZOL-7-YL]-ACETAMIDE

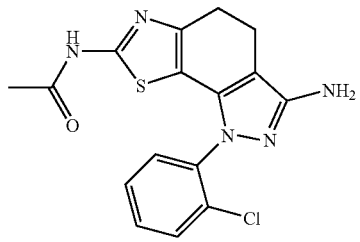

0.1 g (0.26 mmol) of the compound described in Example 32, 0.06 ml (0.27 mmol) diphenyl phosphate azide (DPPA) and 0.04 ml (0.29 mmol) triethylamine are placed in 5 ml dimethylacetamide and stirred for 2 hours at 50° C. 0.05 g (0.29 mmol) p-toluenesulphonic acid and 0.10 ml of water are added and the mixture is stirred for 16 hours at 50° C. Then the reaction mixture is purified by chromatography, corresponding fractions are combined and concentrated by evaporation. The residue is crystallised from ethyl acetate/petroleum ether. Yield: 0.02 g

EXAMPLE 35

N-(3-AMINO-1-PHENYL-4,5-DIHYDRO-1H-PYRAZOLO[3',4':3,4]BENZO[1,2-d]THIAZOL-7-YL)-ACETAMIDE

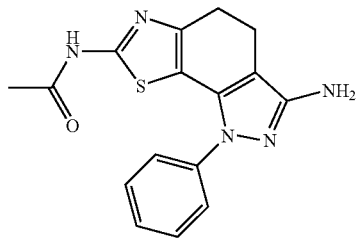

Analogously to Example 34, 0.5 g product is obtained from 1.5 g of the acid described in Example 33, 1 ml (4.6 mmol) DPPA and 0.6 ml (4.4 mmol) triethylamine in 20 ml dimethylacetamide and subsequent reaction with 2 g p-toluenesulphonic acid and 10 ml of water.

EXAMPLE 36

N-[1-(2-CHLOROPHENYL)-3-(3-ISOPROPYL-UREIDO)-4,5-DIHYDRO-1H-PYRAZOLE[3',4':3,4]BENZO[1,2-d]THIAZOL-7-YL]-ACETAMIDE

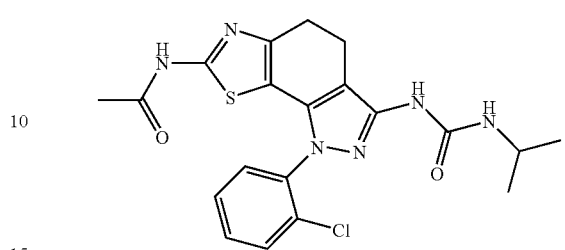

1.0 g (3.1 mmol) of the compound described in Example 35 and 1.0 ml (12.1 mmol) pyridine are suspended in 10 ml dichloromethane and 2 ml of tetrahydrofuran and combined with a solution of 0.8 g (4.0 mmol) 4-nitrophenyl chloroformate in 5 ml dichloromethane. The mixture is stirred for 0.5 hours at ambient temperature. 1.8 ml of this solution is combined with 0.05 ml (0.53 mmol) isopropylamine. It is stirred for 16 hours at ambient temperature, then extracted with dichloromethane and water. The organic phase is dried and evaporated to dryness. The residue is purified by chromatography, corresponding fractions are combined and concentrated by evaporation. The residue is dissolved in water, made basic with sodium hydrogen carbonate solution and precipitated crystals are suction filtered. Yield: 0.010 g

EXAMPLE 37

N-[1-(2-CHLORO-PHENYL)-3-(3-METHYL-URE-IDO)-4,5-DIHYDRO-1H-PYRAZOLO[3',4':3,4]BENZO[1,2-d]THIAZOL-7-YL]-ACETAMIDE

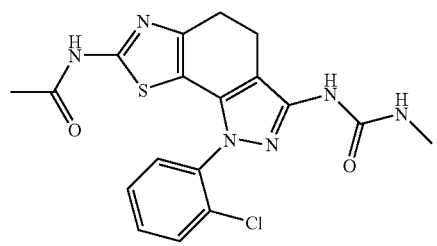

Analogously to Example 36 the desired product is obtained by using methylamine.

EXAMPLE 38

ISOPROPYL [7-ACETYLAMINO-1-(2-CHLOROPHENYL)-4,5-DIHYDRO-1H-PYRAZOLE[3',4':3,4]BENZO[1,2-d]THIAZOLE-73-YL]-CARBAMATE

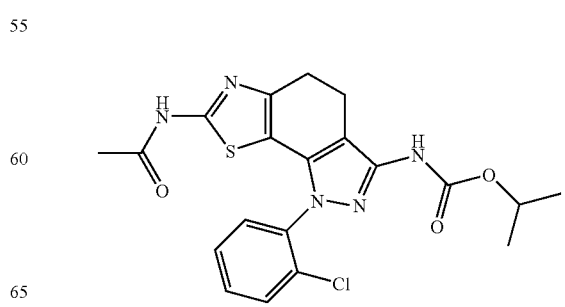

10 g (25 mmol) of the compound described in Example 32, 6.0 ml (27 mmol) diphenyl phosphate azide (DPPA) and 4.0 ml (29 mmol) triethylamine are placed in 80 ml dimethylacetamide and stirred for 2 hours at 50° C. 9 ml of this solution are combined with 2 ml isopropanol and stirred for 48 hours at 50° C. Then the mixture is diluted with dichloromethane, then washed with potassium hydrogen sulphate solution and sodium hydrogen carbonate solution. The organic phase is dried and evaporated to dryness. The residue is dissolved in dichloromethane and shaken with 0.3 g anhydride catching resin (MP anhydride resin) for 3 hours. Then the resin is suction filtered, washed with dichloromethane and the organic phase is concentrated by evaporation. The residue is purified by chromatography, corresponding fractions are combined and concentrated by evaporation. Yield: 0.09 g (m.p.: 196° C.)

EXAMPLE 39

N-[1-(2-CHLORO-PHENYL)-3-(MORPHOLINE-4-CARBONYL)-4,5-DIHYDRO-1H-PYRAZOLO[3',4':3,4]BENZO[1,2-d]THIAZOL-7-YL]-ACETAMIDE

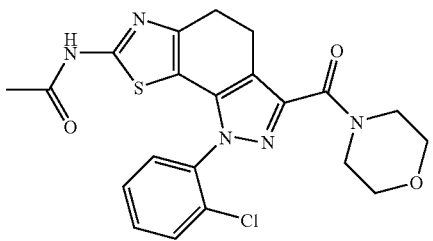

0.1 g (0.26 mmol) of the compound described in Example 32 are placed in 5 ml dichloromethane and 0.1 g (0.28 mmol) HATU (o-7-azabenzotriazol-1-yl)-N,N,N',N'-tetramethyluronium-hexafluorophosphate) are added. Then the mixture is combined with 0.09 ml (0.53 mmol) diisopropylethylamine and 0.03 ml (0.28 mmol) morpholine. The reaction mixture is stirred for 4 hours at ambient temperature, then extracted with dichloromethane and water. The organic phase is dried and evaporated to dryness. The residue is purified by chromatography. Corresponding fractions are combined, concentrated by evaporation, dissolved in water and made basic with sodium hydrogen carbonate solution. The precipitated solid is suction filtered and dried. Yield: 0.02 g

EXAMPLE 40

7-ACETYLAMINO-1-PHENYL-4,5-DIHYDRO-1H-PYRAZOLO[3',4':3,4]BENZO[1,2-d]THIAZOLE-3-CARBOXYLIC ACID (2-HYDROXY-ETHYL)-METHYLAMIDE

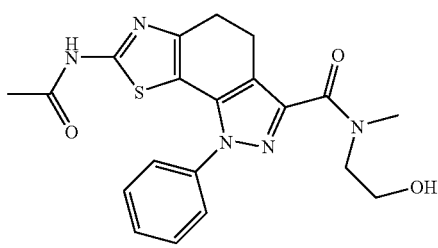

0.09 g (0.25 mmol) of the compound described in Example 33 are placed in 5 ml of dimethylformamide, and 0.1 ml (0.75 mmol) triethylamine and 0.1 g (0.25 mmol) (dimethylamino-pentafluorophenyloxymethylene)-dimethyl-ammonium-hexafluorophosphate are added. The mixture is stirred for 0.1 hours at ambient temperature, then 0.02 g (0.25 mmol) 2-methylamino-ethanol are added. The reaction mixture is stirred for 16 hours at ambient temperature and 24 hours at 70° C. Then it is concentrated by evaporation, the residue is purified by chromatography. Corresponding fractions are combined and freeze-dried. Yield: 0.04 g

EXAMPLE 41

ETHYL 7-ACETYLAMINO-4,5-DIHYDRO-1H-PYRAZOLO[3',4':3,4]BENZO[1,2-d]THIAZOLE-3-CARBOXYLATE

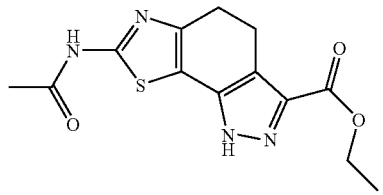

Analogously to Example 16.4 g product are obtained from 10 g (32 mmol) intermediate compound 8 and 1.7 g (33 mmol) hydrazine-hydrate.

EXAMPLE 42

N-[1-(2-CHLORO-PHENYL)-3-(1-METHYL-1H-IMIDAZOL-4-YL)-4,5-DIHYDRO-1H-PYRAZOLO[3',4':3,4]BENZO[1,2-d]THIAZOL-7-YL]-ACETAMIDE

EXAMPLE 43

N-[2-(2-CHLORO-PHENYL)-3-(1-METHYL-1H-IMIDAZOL-4-YL)-4,5-DIHYDRO-2H-PYRAZOLO[3',4':3,4]BENZO[1,2-d]THIAZOL-7-YL]-ACETAMIDE

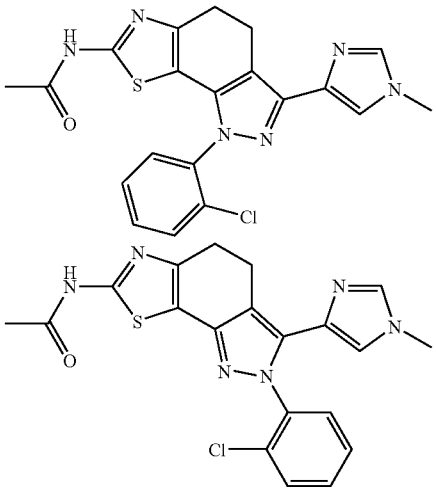

Analogously to Example 1, 100 mg (M.p.: >300° C., Example 42) and 4 mg (Example 43) are obtained from 0.25 g (0.8 mmol) intermediate compound 11 and 0.14 g (0.8 mmol) 2-chloro-phenylhydrazine-hydrochloride after purification by column chromatography.

EXAMPLE 44

N-[1-(2-CHLORO-PHENYL)-3-ISOPROPYL-4,5-DIHYDRO-1H-PYRAZOLO[3',4':3,4]BENZO[1,2-d]THIAZOL-7-YL]-ACETAMIDE

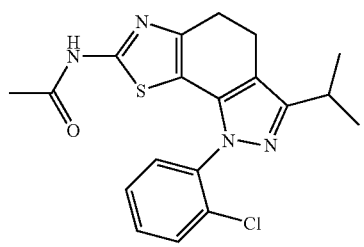

Analogously to Example 1, 0.2 g product are obtained from 0.25 g (0.9 mmol) intermediate compound 12 and 0.16 g (0.9 mmol) 2-chloro-phenylhydrazine-hydrochloride after purification by column chromatography.

EXAMPLE 45

4-(7-ACETYLAMINO-3-ISOPROPYL-4,5-DIHYDRO-PYRAZOLO-[3',4':3,4]BENZO[1,2-d]THIAZOL-1-YL)-3-CHLORO-N-(1-METHYL-PIPERIDIN-4-YL)-BENZAMIDE

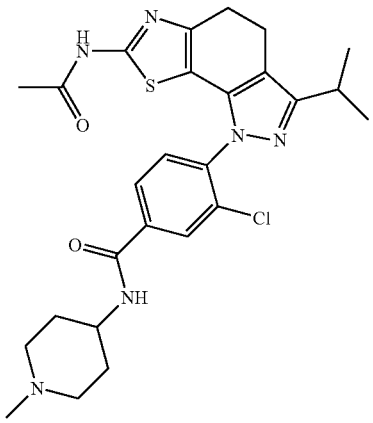

Analogously to Example 1, 0.68 g product, the ester function of which is saponified with 0.1 g lithium hydroxide analogously to Example 26, is obtained from 3.25 g (10.7 mmol) intermediate compound 12 and 2.14 g (10.7 mmol) methyl 3-chloro-4-hydrazinebenzoate. Then 40 mg of the acid obtained are subjected to amide coupling with methylaminopiperidine as described in Example 26.

EXAMPLE 46

N-[1-(2-CHLORO-PHENYL)-3-METHYL-4,5-DIHYDRO-1H-PYRAZOLO[3',4':3,4]BENZO[1,2-d]THIAZOL-7-YL]-ACETAMIDE

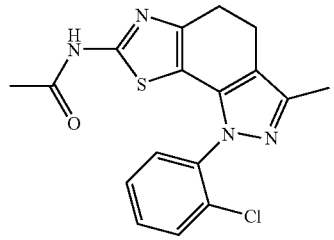

Analogously to Example 10.16 g product are obtained from 0.25 g (1.0 mmol) intermediate compound 10 and 0.18 g (1.0 mmol) 2-chloro-phenylhydrazine-hydrochloride.

EXAMPLE 47

N-[1-(2-CHLORO-PHENYL)-3-PYRIDIN-3-YL-4,5-DIHYDRO-1H-PYRAZOLO[3',4':3,4]BENZO[1,2-d]THIAZOL-7-YL]-ACETAMIDE

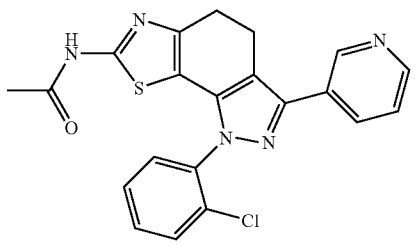

Analogously to Example 10.06 g product are obtained from 0.1 g (0.3 mmol) intermediate compound 9 and 0.06 g (0.3 mmol) 2-chloro-phenylhydrazine-hydrochloride after purification by column chromatography.

EXAMPLE 48

N-[1-(2-CHLORO-PHENYL)-3-PHENYL-4,5-DIHYDRO-1H-PYRAZOLO[3',4':3,4]BENZO[1,2-d]THIAZOL-7-YL]-ACETAMIDE

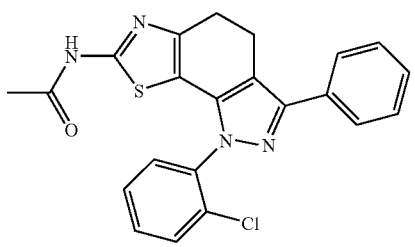

Analogously to Example 1, 0.2 g product (M.p.: 232-234° C.) are obtained from 0.3 g (1.0 mmol) intermediate compound 5 and 0.18 g (1.0 mmol) 2-chloro-phenylhydrazine-hydrochloride.

EXAMPLE 49

N-[1-(2-CHLORO-PHENYL)-3-PHENYL-4,5-DIHYDRO-1H-PYRAZOLO[3',4':3,4]BENZO[1,2-d]THIAZOL-7-YL]-4-DIMETHYLAMINO-BUTYRAMIDE

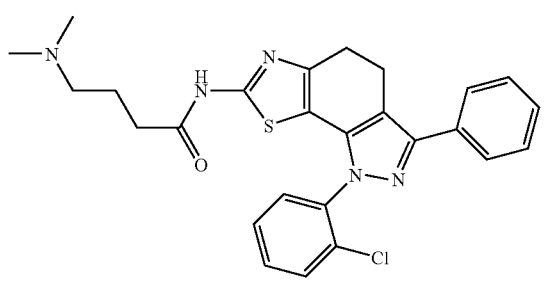

A mixture of 0.5 g (1.2 mmol) of the compound obtained in Example 48 in 5 ml of water and 5 ml hydrochloric acid is refluxed for 2 hours. The solid precipitated after the solution is cooled is suction filtered and dried. Yield: 0.4 g (M.p.: 182-185° C.)

0.1 g of the intermediate compound described previously are suspended in 5 ml dichloromethane, combined with 0.16 ml (1.2 mmol) triethylamine and stirred for 15 minutes at ambient temperature, forming a solution. This is heated to 40° C. and 0.17 g (0.9 mmol) 4-dimethylamino-butanoic acid chloride are added. The reaction mixture is stirred for 3 hours at 40° C. and then washed with 5% sodium carbonate solution and water. The organic phase is dried, evaporated down and the residue is recrystallised from isopropanol. Yield: 11 mg (M.p. 290-291° C.)

EXAMPLE 50

N-[3-(1H-IMIDAZOL-4-YL)-1-(2-TRIFLUOROMETHYL-PHENYL)-4,5-DIHYDRO-1H-PYRAZOLO[3',4':3,4]BENZO[1,2-d]THIAZOL-7-YL]-ACETAMIDE

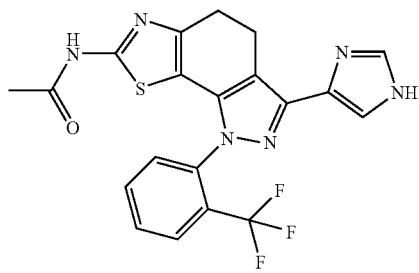

Analogously to Example 11.26 g intermediate product are obtained from 1.36 g (3.1 mmol) intermediate compound 17 and 0.55 g (3.1 mmol) 2-trifluoromethyl-phenylhydrazine. Of this, 75 mg (0.13 mmol) are suspended in 0.65 ml (0.65 mmol) tetrabutylammonium fluoride solution (1 M in THF) and refluxed for 5.5 hours. The solution is combined with 5 ml pH 7-buffer solution, diluted with 10 ml of water and extracted with ethyl acetate. The organic phase is washed with buffer solution, dried and evaporated to dryness. The residue is purified by chromatography, the corresponding fraction is stirred out with diethyl ether. Yield: 5 mg (M.p.: >300° C.)

EXAMPLE 51

N-[1-(2-CHLORO-PHENYL)-3-(1H-IMIDAZOL-4-YL)-4,5-DIHYDRO-1H-PYRAZOLO[3',4':3,4]BENZO[1,2-d]THIAZOL-7-YL]-ACETAMIDE

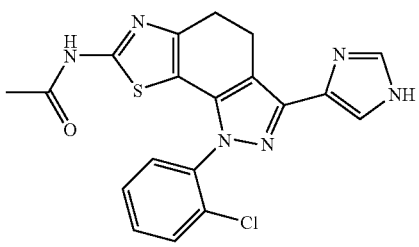

Analogously to Example 1, 0.5 g intermediate product are obtained from 0.6 g (1.4 mmol) intermediate compound 17 and 0.3 g (1.4 mmol) 2-chlorophenylhydrazine hydrochloride. This is converted into the desired product with 1.7 ml (1.7 mmol) tetrabutylammonium fluoride solution (1 M in THF) as described in Example 50. Yield: 35 mg (M.p.: 287-288° C.)

EXAMPLE 52

(R)—N-[1-(2-CHLORO-PHENYL)-3-(TETRAHYDRO-FURAN-2-YL)-4,5-DIHYDRO-1H-PYRAZOLO[3',4':3,4]BENZO[1,2-d]THIAZOL-7-YL]-ACETAMIDE

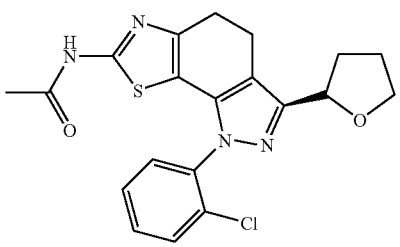

Analogously to Example 10.23 g product are obtained from 0.25 g (0.8 mmol) intermediate compound 14 and 0.15 g (0.8 mmol) 2-chloro-phenylhydrazine-hydrochloride after purification by column chromatography.

EXAMPLE 53

(R)-4-[7-ACETYLAMINO-3-(TETRAHYDRO-FURAN-2-YL)-4,5-DIHYDRO-PYRAZOLO[3',4':3,4]BENZO[1,2-d]THIAZOL-1-YL]-3-CHLORO-N-PYRIDIN-4-YLMETHYL-BENZAMIDE

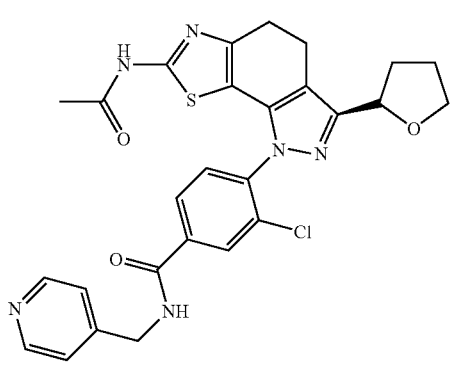

Analogously to Example 11.16 g product, the ester function of which is saponified with 0.2 g lithium hydroxide analogously to Example 26, is obtained from 1.25 g (4.1 mmol) intermediate compound 14 and 0.82 g (4.1 mmol) methyl 3-chloro-4-hydrazine benzoate. Then 50 mg of the acid obtained are subjected to amide coupling with 4-picolylamine as described in Example 26.

EXAMPLE 54

(S)—N-[1-(2-CHLORO-PHENYL)-3-(TETRAHYDRO-FURAN-2-YL)-4,5-DIHYDRO-1H-PYRAZOLO[3',4':3,4]BENZO[1,2-d]THIAZOL-7-YL]-ACETAMIDE

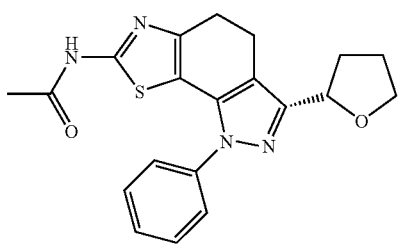

Analogously to Example 10.08 g product are obtained from 0.1 g (0.3 mmol) intermediate compound 15 and 0.05 g (0.3 mmol) 2-chloro-phenylhydrazine-hydrochloride after purification by column chromatography.

EXAMPLE 55

N-[1-(2-CHLORO-PHENYL)-3-TRIMETHYLSILANYLETHYNYL-4,5-DIHYDRO-1H-PYRAZOLO[3',4':3,4]BENZO[1,2-d]THIAZOL-7-YL]-ACETAMIDE

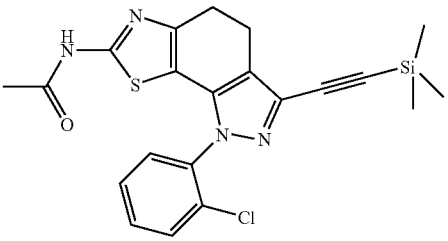

Analogously to Example 10.02 g product are obtained from 0.1 g (0.3 mmol) intermediate compound 16 and 0.06 g (0.3 mmol) 2-chlorophenylhydrazine-hydrochloride after purification by column chromatography.

EXAMPLE 56

N-[3-ETHYNYL-1-(2-TRIFLUOROMETHYL-PHENYL)-4,5-DIHYDRO-1H-PYRAZOLO[3',4':3,4]BENZO[1,2-d]THIAZOL-7-YL]-ACETAMIDE

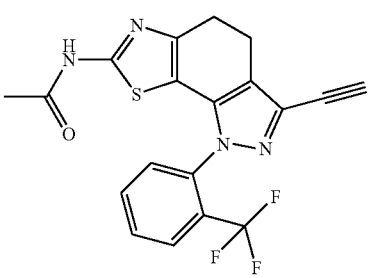

Analogously to Example 10.05 g product are obtained from 0.3 g (0.9 mmol) intermediate compound 16 and 0.16 g (0.9 mmol) 2-(trifluoromethyl)phenylhydrazine after purification by column chromatography. Of this, 0.04 g are placed in 5 ml THF and combined with 0.1 ml (0.1 mmol) tetrabutylammonium fluoride solution (1 M in THF). The mixture is stirred for 0.5 hours at ambient temperature and then water is added. The aqueous phase is extracted with ethyl acetate, the organic phase is washed with water and 1 N hydrochloric acid. The organic phase is dried and evaporated to dryness. The residue is purified by chromatography. Yield: 0.012 g

EXAMPLE 57

N-(1-PHENYL-3-TRIFLUOROMETHYL-4,5-DI-HYDRO-1H-PYRAZOLO[3',4':3,4]BENZO[1,2-d]THIAZOL-7-YL)-ACETAMIDE

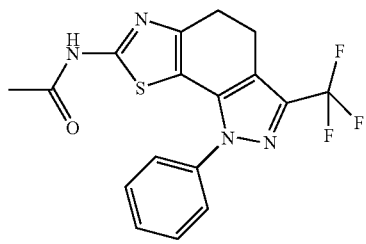

Analogously to Example 10.04 g product are obtained from 0.3 g (1.0 mmol) intermediate compound 19 and 0.15 g (1.0 mmol) phenylhydrazine-hydrochloride.

EXAMPLE 58

N-[4-(4-CHLORO-PHENYL)-4,7-DIHYDRO-3-THIA-1,4,5-TRIAZA-CYCLOPENTA[A]PENTALEN-2-YL]-ACETAMIDE

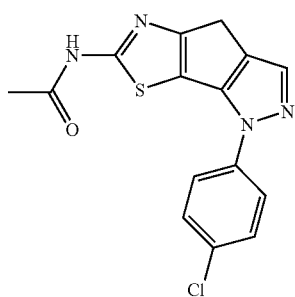

0.50 g (1.56 mmol) intermediate compound 22 are suspended in 8 ml glacial acetic acid, combined with 0.34 g (1.88 mmol) 4-chlorophenylhydrazine-hydrochloride. The mixture is stirred for 1.5 hours at 60° C., then cooled to ambient temperature. After the addition of 50 ml of water a precipitate is formed. This is stirred for 0.1 hours at 5° C., suction filtered and recrystallised from methanol. Yield: 0.19 g (m.p.: 296-305° C.)

EXAMPLE 59

4-PHENYL-4,7-DIHYDRO-3-THIA-1,4,5-TRIAZA-CYCLOPENTA[A]PENTALEN-2-YL-AMINE

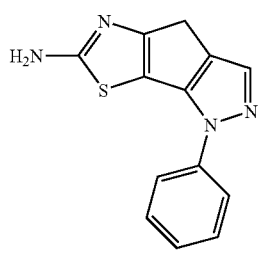

2.9 g (8.71 mmol) N-(4-phenyl-4,7-dihydro-3-thia-1,4,5-triaza-cyclopenta[A]pentalen-2-yl)-acetamide (prepared analogously to Example 58 from intermediate compound 22) are suspended in 20 ml of water and 20 ml 32% hydrochloric acid and refluxed for 2 hours with stirring. After cooling to ambient temperature the mixture is extracted with diethyl ether and the aqueous phase is made basic. The precipitate formed is stirred for 0.25 hours at 5° C., suction filtered and dried. The crude product is suspended in 150 ml of tetrahydrofuran and combined with 5 ml of conc. hydrochloric acid, then stirred for 16 hours at 60° C. After cooling to 5° C. the precipitate is suction filtered and dried.
Yield: 1.8 g

EXAMPLE 60

4-o-TOLYL-3A,4,7,7A-TETRAHYDRO-3-THIA-1,4,5-TRIAZA-CYCLOPENTA[A]PENTALEN-2-YLAMINE

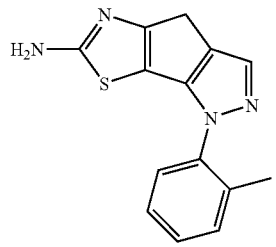

Analogously to Example 5914 mg product are obtained from 140 mg (0.5 mmol) N-(4-o-tolyl-4,7-dihydro-3-thia-1,4,5-triaza-cyclopenta[A]pentalen-2-yl)-acetamide (prepared analogously to Example 58) in 1 ml of water and 1 ml hydrochloric acid after purification by column chromatography.

EXAMPLE 61

4-DIMETHYLAMINO-N-(4-PHENYL-4,7-DIHYDRO-3-THIA-1,4,5-TRIAZA-CYCLOPENTA[A]PENTALEN-2-YL)-BUTANOIC ACID AMIDE

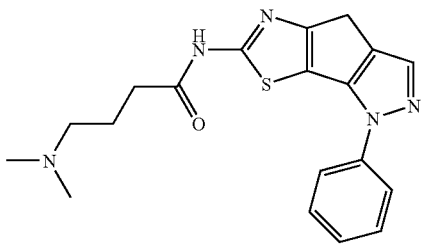

0.5 g (1.72 mmol) of the compound described under Example 59 are suspended in 25 ml dichloromethane, combined with 0.8 ml (6.02 mmol) triethylamine and refluxed. 0.8 g (4.30 mmol) 4-dimethylamine-butyric acid chloride-hydrochloride in 5 ml dichloromethane are added dropwise within 0.1 hours and the reaction mixture is refluxed for 16 hours. After cooling to ambient temperature the precipitate is suction filtered and the filtrate is washed with 5% sodium hydrogen carbonate solution and water. The organic phase is dried and evaporated to dryness. The residue is triturated with diethyl ether and suction filtered. Yield: 0.2 g (m.p.: 218-222° C.)

EXAMPLE 62

N-[4-(2-CHLORO-PHENYL)-4,7-DIHYDRO-3-THIA-1,4,5-TRIAZA-CYCLOPENTA[A]PENTALEN-2-YL]-4-DIMETHYLAMINO-BUTANOIC ACID AMIDE

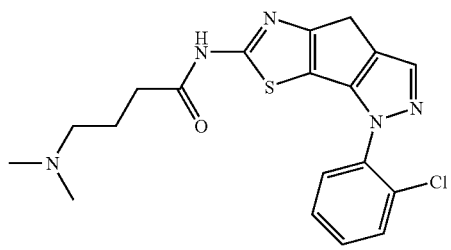

Analogously to Example 59, 2.5 g of a compound are obtained from 3.9 g (11.7 mmol) 4-(2-chloro-phenyl)-4,7-dihydro-3-thia-1,4,5-triaza-cyclopenta[a]pentalen-2-ylamine (prepared analogously to Example 58), of which 0.7 g (1.7 mmol) are reacted as in Example 61 to form 0.2 g product (m.p.: 167-170° C.).

EXAMPLE 63

PIPERIDINE-1-CARBOXYLIC ACID-(4-PHENYL-4,7-DIHYDRO-3-THIA-1,4,5-TRIAZA-CYCLOPENTA[A]PENTALEN-2-YL)-AMIDE

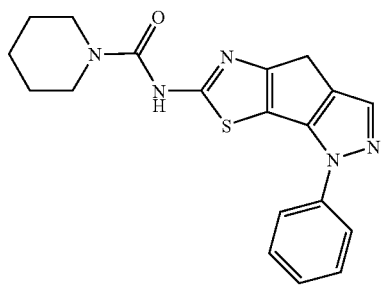

A suspension of 2.3 g (8 mol) of the compound obtained under Example 59 in 60 ml of pyridine is heated to 50° C., then combined with 1.6 ml (10 mmol) ethyl chlorothioformate. The reaction mixture is stirred for 12 hours at 70° C., then stirred into 600 ml of water. The precipitate formed is suction filtered and washed with water and ether. Yield: 2.3 g (M.p.: 142-145° C.)

In a sealable pressurised glass tube 0.3 g (0.7 mmol) of the compound described previously are suspended in 8 ml of ethanol, combined with 1 ml (10.5 mmol) piperidine and refluxed for 16 hours with stirring. After cooling to ambient temperature the reaction mixture is concentrated by evaporation. The crude product is filtered through silica gel. The residue is triturated with 20 ml of water and 5 drops of acetonitrile, suction filtered and dried. Yield: 0.07 g (m.p.: 120-125° C.)

EXAMPLE 64

N-[8-(4-HYDROXY-PHENYL)-4,5-DIHYDRO-THIAZOLO[4,5-h]QUINAZOLIN-2-YL]-ACETAMIDE

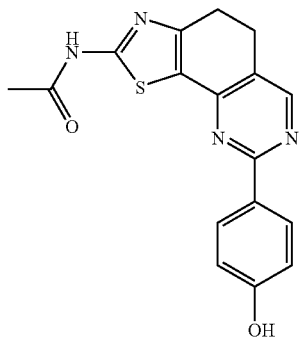

2.7 g (11.3 mmol) intermediate compound 2 and 1.7 g (12.6 mmol) 4-hydroxybenzamidine are suspended in 6 ml of pyridine and heated to 100° C. for 2 hours. The reaction mixture is combined with ether and the precipitate formed is stirred with methanol. Yield: 2.1 g

EXAMPLE 65

4,5-DIHYDRO-THIAZOLO[4,5-h]QUINAZOLINE-2,8-DIAMINE

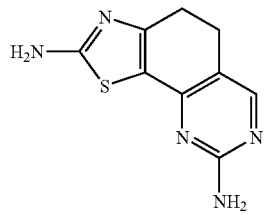

10 g (42 mmol) intermediate compound 2, 4 g (42 mmol) guanidine-hydrochloride and 2.2 g (21 mmol) sodium carbonate are suspended in 30 ml amyl alcohol and refluxed for 1 hour using the water separator. The reaction mixture is evaporated down, the residue is distilled off with xylene several times and then purified by chromatography. The product is taken up in methanol and precipitated with methanolic hydrochloric acid as the hydrochloride. Yield: 1.2 g (M.p.: 293-300° C.)

EXAMPLE 66

N-(8-ACETYLAMINO-4,5-DIHYDRO-THIAZOLO[4,5-h]QUINAZOLIN-2-YL)-ACETAMIDE

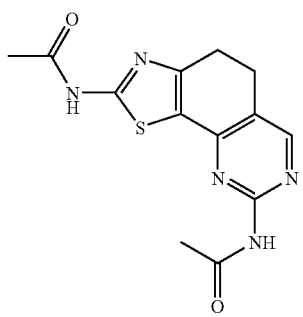

0.5 g (1.7 mmol) of the compound described in Example 65 and 0.4 g (4.6 mmol) sodium acetate are suspended in 15 ml acetic anhydride and stirred for 2 hours at 100° C. The mixture is cooled to 5° C., the resulting solid is suction filtered and washed with water. The crude product is stirred with methanol. Yield: 0.4 g (M.p.: >310° C.)

EXAMPLE 67

N-(6-OXO-8-PHENYL-4,5,6,7-TETRAHYDRO-THIAZOLO[4,5-h]QUINAZOLIN-2-YL)-ACETAMIDE

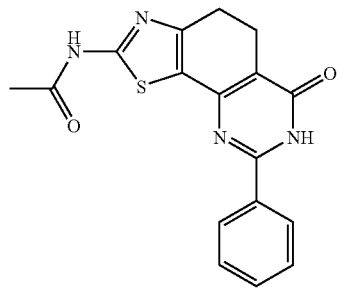

In a pressurised glass tube 0.1 g (0.35 mmol) intermediate compound 18 and 0.1 g (0.83 mmol) benzamidine are placed in 1 ml of pyridine and heated to 160° C. for 4 hours. The solvent is concentrated by evaporation, the residue is stirred with hot ethanol and suction filtered. Yield: 14 mg

EXAMPLE 68

N-(8-ETHYLSULPHANYL-4,5-DIHYDRO-THIAZOLO[4,5-h]QUINAZOLIN-2-YL)-ACETAMIDE

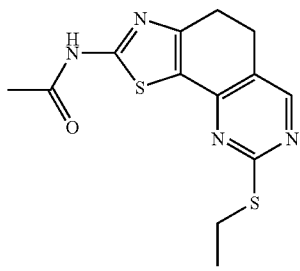

10.0 g (42 mmol) intermediate compound 2 and 14.6 g (80 mmol) ethylisothiourea-hydrobromide are suspended in 20 ml of pyridine and then stirred for 3 hours at 110° C. After cooling to ambient temperature the reaction mixture is triturated with a little methanol, suction filtered and dried. Yield: 10.2 g

EXAMPLE 69

N-(8-ETHANESULPHONYL-4,5-DIHYDRO-THIAZOLO[4,5-h]QUINAZOLIN-2-YL)-ACETAMIDE

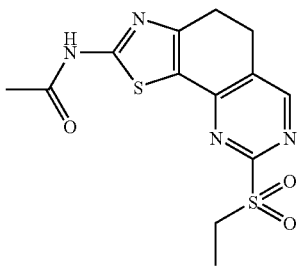

10.6 g (34.6 mmol) of the compound prepared under Example 68 are dissolved in 100 ml dichloromethane, 17.0 g (75.9 mmol) m-chloroperbenzoic acid are added and the mixture is then stirred for 24 hours at ambient temperature. The reaction mixture is diluted with dichloromethane and extracted with sodium carbonate solution. The organic phase is washed with water, dried and evaporated to dryness. Yield: 8.8 g

EXAMPLE 70

TERT-BUTYL [1-(2-ACETYLAMINO-4,5-DIHYDRO-THIAZOLO[4,5-h]QUINAZOLIN-8-YL)-PIPERIDIN-3-YLMETHYL]-CARBAMATE

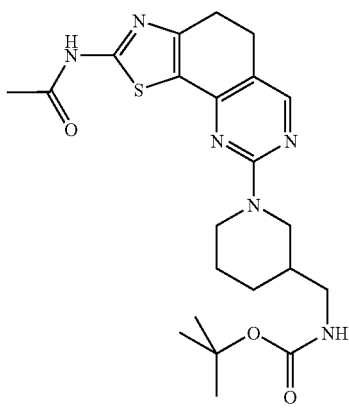

0.2 g (0.6 mmol) of the compound prepared under Example 69 and 0.25 g (1.2 mmol) tert-butyl piperidin-3-ylmethyl-carbamate are placed in 2 ml N-methyl-pyrrolidine and refluxed for 24 hours with stirring. Then the reaction mixture is combined with dilute potassium carbonate solution and dichloromethane and extracted. The organic phase is washed with water, dried and evaporated to dryness. The residue is purified by chromatography. Yield: 0.03 g (m.p.: 250-255° C.)

EXAMPLE 71

8-PHENYL-4,5-DIHYDRO-THIAZOLO[4,5-h]QUINAZOLIN-2-YLAMINE

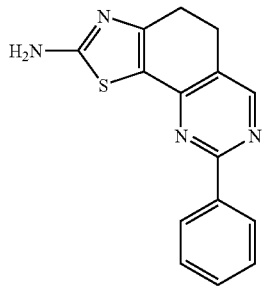

9.0 g (28 mmol) N-(8-phenyl-4,5-dihydro-thiazolo[4,5-h]quinazolin-2-yl)-acetamide (prepared analogously to Example 64) are refluxed for 2 hours in 130 ml semi-concentrated hydrochloric acid. After cooling the reaction mixture is made basic, the precipitate formed is suction filtered and dried. Yield: 7.3 g

EXAMPLE 72

$N^8,N^8$-DIMETHYL-4,5-DIHYDRO-THIAZOLO[4,5-h]QUINAZOLINE-2,8-DIAMINE

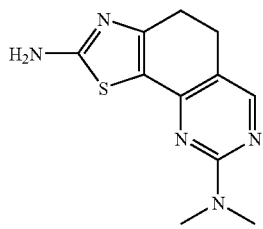

Analogously to Example 710.14 g product (M.p.: 292-295° C.) may be obtained from 0.20 g (0.7 mmol) N-(8-dimethylamino-4,5-dihydro-thiazolo[4,5-h]quinazolin-2-yl)-acetamide (obtained analogously to Example 58).

EXAMPLE 73

N-(8-PHENYL-4,5-DIHYDRO-THIAZOLO[4,5-h]QUINAZOLIN-2-YL)-PROPIONIC ACID AMIDE

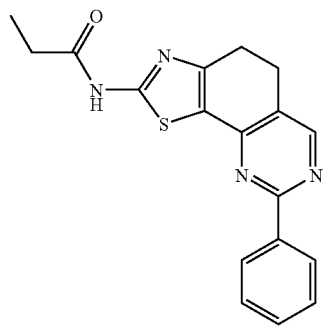

0.3 g (1.1 mmol) of the compound obtained in Example 71 are suspended in 15 ml dichloromethane, combined with 0.4 ml (2.5 mmol) triethylamine and gently refluxed. 0.2 ml (2.3 mmol) propionic acid chloride are added and the mixture is refluxed for 5 hours with stirring. After cooling to ambient temperature the reaction solution is washed with sodium hydrogen carbonate and water, dried and evaporated to dryness. The residue is stirred with diethyl ether and suction filtered. Yield: 0.2 g (m.p.: 274-275° C.)

EXAMPLE 74

4-DIMETHYLAMINO-N-(8-PHENYL-4,5-DIHYDRO-THIAZOLO[4,5-h]QUINAZOLIN-2-YL)-BUTYRIC ACID AMIDE

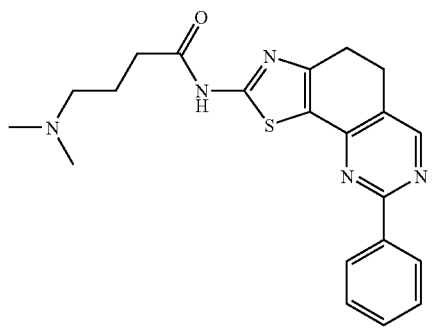

Analogously to Example 73, 0.03 g product are obtained from 0.15 g (0.5 mmol) of the compound obtained in Example 71, 1 ml triethylamine and 0.2 g (1.3 mmol) 4-dimethylamine-butyric acid chloride-hydrochloride.

EXAMPLE 75

N-(8-PHENYL-4,5-DIHYDRO-THIAZOLO[4,5-h]QUINAZOLIN-2-YL)-FORMAMIDE

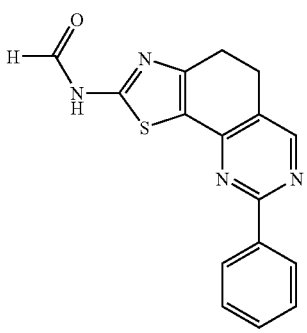

0.2 g (0.71 mmol) of the compound described in Example 71 and 2.5 ml (22.7 mmol) phenyl formate are placed in a pressurised glass tube and stirred for 16 hours at 80° C. Then the reaction mixture is concentrated by evaporation and the residue is triturated with diethyl ether/ethanol. Yield: 0.17 g (m.p.: 304-306° C.)

EXAMPLE 76

MORPHOLINE-4-CARBOXYLIC ACID-(8-PHENYL-4,5-DIHYDRO-THIAZOLO[4,5-h]QUINAZOLIN-2-YL)-AMIDE

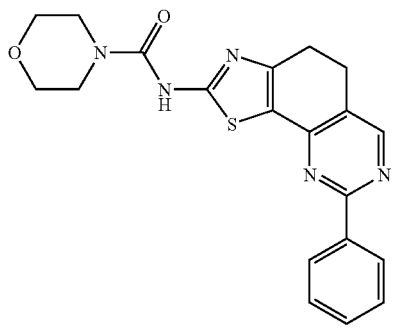

2.5 g (8.9 mmol) of the compound obtained in Example 71 are placed in 50 ml of pyridine and heated to 50° C. 1.5 ml (13.8 mmol) ethyl chlorothioformate are added and the mixture is stirred for 20 hours at 50° C. After cooling to ambient temperature the reaction solution is added to water and extracted with dichloromethane. The organic phase is dried and evaporated to dryness. The residue is crystallised with diethyl ether. Yield: 1.0 g 0.2 g (0.54 mmol) of the intermediate described above and 0.1 g (1.15 mmol) morpholine in 5 ml of ethanol are placed in a pressurised glass tube and then stirred for 16 hours at 80° C. After cooling to ambient temperature the precipitate formed is suction filtered and dried. Yield: 0.14 g (m.p.: 165-168° C.)

EXAMPLE 77

4-(2-ACETYLAMINO-4,5-DIHYDRO-THIAZOLO[4,5-h]QUINAZOLIN-8-YL)-N,N-DIMETHYL-BENZAMIDE

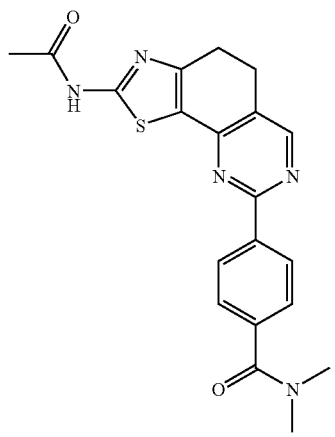

1.0 g (3.8 mmol) of the intermediate compound 2 and 0.8 g (3.1 mmol) carbamimidoyl-benzoic acid-methanesulphonate are placed in 5 ml of pyridine and heated to 180° C. for 5 hours. After cooling to ambient temperature the reaction mixture is stirred with ethanol and suction filtered. Yield: 0.6 g 0.1 g (0.27 mmol) of the previously prepared compound and 0.1 g O-(1H-benzotriazol-1-yl)-N,N,N',N'-tetramethyluronium-tetrafluoroborate (TBTU) are placed in 2 ml of dimethylformamide, combined with 0.2 ml diisopropylethylamine and stirred for 0.5 hours at ambient temperature. 0.2 ml (4.0 mmol) dimethylamine (2 M in THF) are added and the mixture is stirred for a further 16 hours at ambient temperature. The resulting suspension is dissolved with dimethylformamide, then purified by RP-HPLC. Corresponding fractions are combined and freeze-dried. Yield: 0.04 g (m.p.: >300° C.)

EXAMPLE 78

N-[8-(2-OXO-PYRROLIDIN-1-YL)-4,5-DIHYDRO-THIAZOLO[4,5-h]QUINAZOLIN-2-YL]-ACETAMIDE

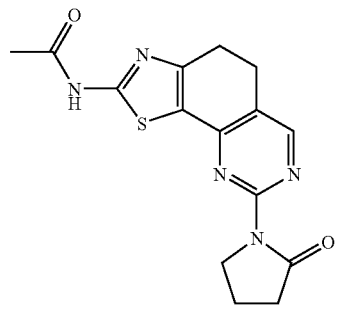

2.0 g (8.4 mmol) intermediate compound 2 and 2.4 g (16.8 mmol) 4-guanidine-butyric acid in 30 ml of pyridine are placed in a pressurised glass tube and then heated to 190° C. for 20 hours. The reaction mixture is concentrated by evaporation, the residue is boiled with methanol and insoluble constituents are filtered off. The crude product is precipitated from the mother liquor in the form of the hydrochloride, suction filtered and dried. The solid is purified by column chromatography. Yield: 0.02 g (m.p.: >160° C.)

EXAMPLE 79

N-[8-(3-AMINOMETHYL-PIPERIDIN-1-YL)-4,5-DIHYDRO-THIAZOLO[4,5-h]QUINAZOLIN-2-YL]-ACETAMIDE

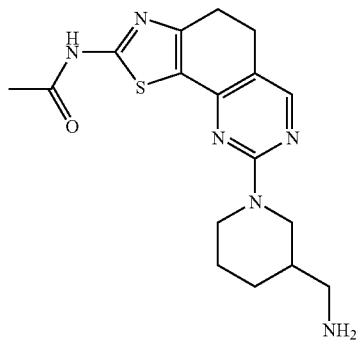

0.05 g (0.1 mmol) of the compound described under Example 70 are dissolved in 5 ml ethereal hydrochloric acid and stirred for 16 hours at ambient temperature. The resulting solid is suction filtered, washed with diethyl ether and dried. Yield: 0.035 g

EXAMPLE 80

N-{8-[3-(ISOPROPYLAMINO-METHYL)-PIPERIDIN-1-YL]-4,5-DIHYDRO-THIAZOLO[4,5-h]QUINAZOLIN-2-YL}-ACETAMIDE

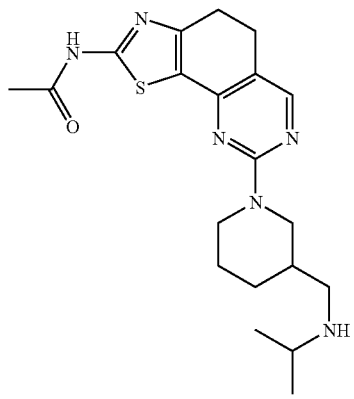

0.2 g (0.5 mmol) of the compound obtained in Example 79, 0.05 ml (0.6 mmol) acetone and 0.02 g (0.5 mol) sodium borohydride are dissolved in methanol and stirred for 0.5 hours at 40° C. The same amounts of acetone and sodium borohydride are added again and the mixture is stirred for a further 16 hours at ambient temperature. Then the reaction mixture is concentrated by evaporation, the residue is extracted with dichloromethane and water. The organic phase is dried and evaporated to dryness. The crude product is triturated with diethyl ether and suction filtered. Yield: 0.040 g

EXAMPLE 81

N-{8-[ACETYL-(2-DIMETHYLAMINO-ETHYL)-AMINO]-4,5-DIHYDRO-THIAZOLO[4,5-h]QUINAZOLIN-2-YL}-ACETAMIDE

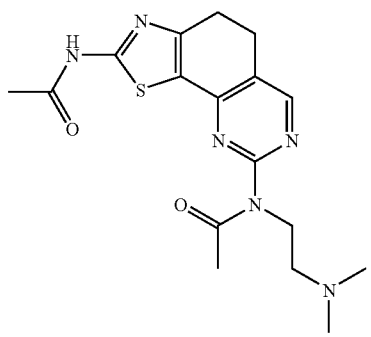

0.4 g (1.2 mmol) of the compound obtained under Example 69 and 0.4 ml (4.5 mmol) $N^1,N^1$-dimethylethane-1,2-diamine are placed in 5 ml N-methylpyrrolidine and stirred for 48 hours at 90° C. The reaction mixture is extracted with dichloromethane and 10% potassium carbonate solution. The organic phase is dried and evaporated to dryness. Yield: 0.08 g 0.08 g (0.28 mmol) of the compound described previously are dissolved in 5 ml (49 mmol) acetic anhydride and stirred for 1 hour at 140° C. The reaction mixture is concentrated by evaporation, the residue is stirred with acetonitrile and suction filtered. Yield: 0.07 g

EXAMPLE 82

TERT-BUTYL (2-ACETYLAMINO-4,5-DIHYDRO-THIAZOLO[4,5-h]QUINAZOLIN-8-YL)-PROP-2-YNYL-CARBAMATE

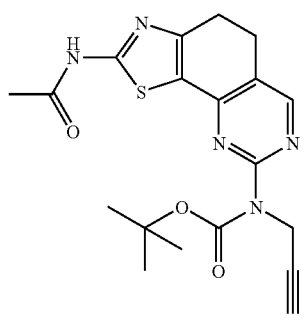

0.34 g (2.2 mmol) tert-butyl prop-2-ynyl-carbamate are placed in 3 ml of tetrahydrofuran and cooled to −30° C. 2.3 ml (4.4 mmol) 2 M isopropylmethyl-magnesium chloride solution in tetrahydrofuran are slowly added dropwise and the mixture is stirred for 0.5 hours. Then a solution of 0.34 g (1.0 mmol) of the compound described in Example 69 in 4 ml of tetrahydrofuran is added at −10° C. and the mixture is stirred for 4 hours, while heating to ambient temperature. The reaction mixture is extracted with water and dichloromethane, the organic phase is dried and evaporated to dryness. The residue is triturated with diethyl ether. Yield: 0.18 g

EXAMPLE 83

N-(8-PROP-2-YNYLAMINO-4,5-DIHYDRO-THIAZOLO[4,5-h]QUINAZOLIN-2-YL)-ACETAMIDE

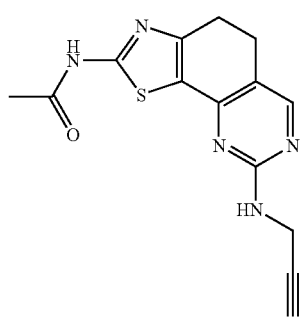

0.05 g (0.13 mmol) of the compound obtained in Example 82 are dissolved in 5 ml ethereal hydrochloric acid and stirred for 16 hours at ambient temperature. The resulting solid is

EXAMPLE 84

N-[1-(4-METHOXY-PHENYL)-1,4,5,6-TETRAHYDRO-9-THIA-1,2,7-TRIAZA-CYCLOPENTA[E]AZULEN-8-YL]-ACETAMIDE

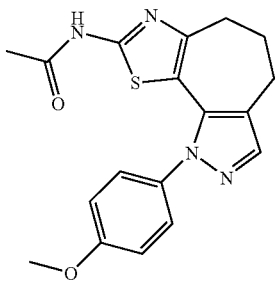

A solution of 0.25 g (1 mmol) intermediate compound 23 and 0.18 mg (1 mmol) 4-methoxyphenylhydrazine-hydrochloride in 5 ml glacial acetic acid is heated to 60° C. for 2 h. The mixture is combined with water and extracted three times with ethyl acetate. The combined organic phases are dried over magnesium sulphate and evaporated down. The residue is purified first of all by column chromatography (eluant: dichloromethane/methanol 95:5), then by RP-HPLC.

Yield: 0.07 g

EXAMPLE 85

N-(8-NITRO-4,5-DIHYDRO-3H-1$\lambda^4$-NAPHTHO[2,1-d]THIAZOL-2-YL)-ACETAMIDE

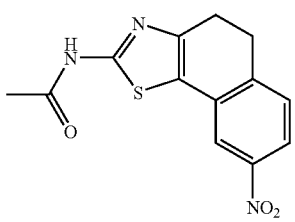

0.8 g (10.0 mmol) sodium acetate and 1.9 g (9.40 mmol) 7-nitro-3,4-dihydro-1H-naphthalen-2-one (prepared according to D. E. Nichols et al., *J. Med. Chem.* 1989, 32, 2128-2134) are dissolved in 40 ml acetic acid and cooled to 15° C. 0.5 g (3.19 mmol) bromine are added and the mixture is stirred for 0.1 hours, until the bromine has finished reacting completely. Then 0.8 g (10.5 mmol) thiourea are added. The reaction mixture is heated to 60° C. for 0.25 hours, then suction filtered and washed. The crystals are recrystallised from ethanol. Yield: 0.75 g (M.p.: 247-248° C.) 0.75 g (3.0 mmol) of the compound described previously are placed in 5 ml (49 mmol) acetic anhydride and refluxed for 0.1 hours. After cooling to ambient temperature the precipitate formed is suction filtered, washed with ethyl acetate and diethyl ether and dried. Yield: 0.8 g (M.p.: >315° C.)

EXAMPLE 86

N-(8-ACETYLAMINO-4,5-DIHYDRO-3H-1$\lambda^4$-NAPHTHO[2,1-d]THIAZOL-2-YL)-ACETAMIDE

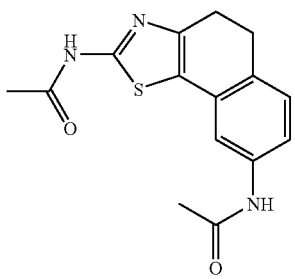

0.5 g (1.7 mmol) of the compound described in Example 85 are suspended in 10 ml acetic acid and combined with 2 g iron powder. The reaction mixture is heated to 70° C. and stirred for 0.1 hours. Then it is suction filtered and the mother liquor is concentrated by evaporation. The residue is combined with water, the precipitate is suction filtered, washed and dried. Yield: 0.4 g 0.1 g (0.4 mmol) of the compound described previously, 0.1 g (1.0 mmol) acetic anhydride and 0.1 ml triethylamine are placed in 5 ml dichloromethane and stirred for 1 hour at ambient temperature. Then the reaction mixture is washed with 2 N hydrochloric acid and 2 N sodium hydroxide solution. The organic phase is dried and evaporated to dryness. The residue is crystallised from ethyl acetate. Yield: 0.07 g (m.p.: 181-183° C.)

EXAMPLE 87

N-(2-ACETYLAMINO-4,5-DIHYDRO-NAPHTHO[2,1-d]THIAZOL-8-YL)-ISOBUTYRIC ACID AMIDE

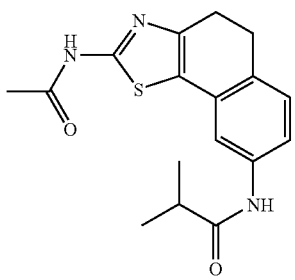

Analogously to Example 86 0.075 g product (M.p.: 272-274° C.) may be obtained from 0.1 g (0.4 mmol) of the intermediate described therein, 0.045 g (0.4 mmol) isobutyric acid chloride and 0.1 ml triethylamine in 5 ml dichloromethane.

EXAMPLE 88

N-(8-ISOPROPYLAMINO-4,5-DIHYDRO-3H-1λ⁴-NAPHTHO[2,1-d]THIAZOL-2-YL)-ACETAMIDE

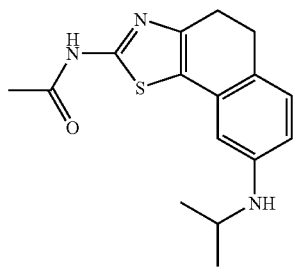

0.15 g (0.58 mmol) of the intermediate described in Example 86, 1.0 g (17.2 mmol) acetone and 0.4 g sodium triacetoxyborohydride are placed in 10 ml dichloromethane and stirred for 4 hours at ambient temperature. The reaction mixture is combined with 50 ml of water and 2 g potassium carbonate, the organic phase is separated off, dried and evaporated to dryness. The residue is purified by chromatography, then crystallised from diethyl ether. Yield: 0.11 g (m.p.: 183-184° C.)

EXAMPLE 89

N-[5-(2-CHLORO-PHENYL)-8H-3-THIA-1,4,6-TRIAZA-CYCLOPENTA[A]INDEN-2-YL]-ACETAMIDE

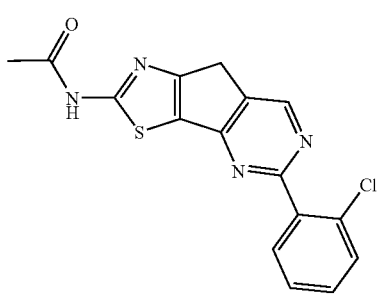

350 mg (1.56 mmol) intermediate compound 22 and 298 mg (1.56 mmol) 2-chlorobenzamidine are suspended in 1.5 mL pyridine and heated to 160° C. for 1 hour. The reaction mixture is evaporated down and purified by RP-HPLC. Yield: 14 mg (m.p.: 257° C.)

EXAMPLE 90

N-(5-MORPHOLIN-4-YL-8H-3-THIA-1,4,6-TRIAZA-CYCLOPENTA[A]INDEN-2-YL)-ACETAMIDE

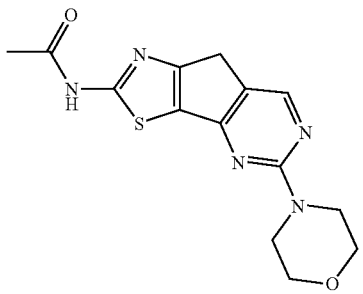

350 mg (1.56 mmol) intermediate compound 22 and 260 mg (1.57 mmol) morpholinecarboxamidine are suspended in 1.5 mL pyridine and heated to 160° C. for 1 hour. The reaction mixture is evaporated down and purified by RP-HPLC.
Yield: 11 mg (m.p.: >300° C.)

EXAMPLE 91

N-(5-PHENYL-8H-3-THIA-1,4,6-TRIAZA-CYCLOPENTA[A]INDEN-2-YL)-ACETAMIDE

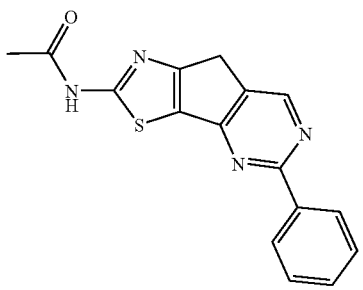

350 mg (1.56 mmol) intermediate compound 22 and 190 mg (1.58 mmol) benzamidine are suspended in 1.5 mL pyridine and heated to 160° C. for 1 hour. The reaction mixture is evaporated down and purified by RP-HPLC. Yield: 16 mg (m.p.: >300° C.)

Some compounds which may be prepared by one of the methods of synthesis described above are hereinafter listed by way of example. All the melting points ($m_p$) are given in ° C. In order to determine the inhibitory activity of the compounds on PI3Kγ, an in-vitro kinase assay is set up which is based on the transfer of the terminal γ-phosphate of ATP to phosphatidylinositol-4,5-bisphosphate ($PIP_2$). The enzyme activity used is the $G\beta_1\gamma_2$-His stimulated PI3Kγ. The expression and purification of $G\beta_1\gamma_2$-His and p101-GST/p110γ from Sf9-cells (*Spodoptera frugiperda* 9) has already been described (Maier et al., J. Biol. Chem. 1999 (274) 29311-29317).

The kinase assay is carried out in white 384-well flat-bottomed dishes. Each well contained 5 μl of the compound to be tested which had been dissolved in assay buffer (40 mM Hepes, pH 7.5, 100 mM NaCl, 1 mM EGTA, 1 mM β-glycerophosphate, 1 mM DTT, 7 mM $MgCl_2$ and 0.1% BSA; 6%

DMSO). 15 µl of lipid vesicles containing 10 ng of PI3Kγ and 31.5 ng of Gβ$_1$γ$_2$-His were added in each case. The lipid vesicles in turn were generated by suspending PIP$_2$ (0.35 µg/well), phosphatidyl ethanolamine (3.75 µg/well), phosphatidyl serine (3.5 µg/well), sphingomyelin (0.35 µg/well) and phosphatidyl choline (1.6 µg/well) in lipid buffer (assay buffer without DMSO) by ultrasound treatment. After the addition of the lipid vesicles the reaction is started by the addition of 10 µl reaction buffer (40 mM Hepes, pH 7.5, 100 mM NaCl, 1 mM EGTA, 1 mM β-glycerophosphate, 1 mM DTT, 7 mM MgCl$_2$ and 0.1% BSA; 1 µM ATP and 0.2 µCi [γ-$^{33}$P]-ATP). The reaction mixture is incubated in this way for 1 h and then stopped by the addition of a suspension of 0.12 mg LEADseeker beads (Amersham Biosciences) in stop buffer (40 mM Hepes, pH 7.5, 100 mM NaCl, 1 mM EGTA, 12 mM EDTA, 1 mM β-glycerophosphate, 1 mM DTT). After 1 minute's centrifugation at 500×g the plates were read and analysed using a LEADseeker apparatus. All the compounds shown have an IC$_{50}$ value of less than 800 nM in the test.

EXAMPLES A

| # | R$^a$ | R$^b$ | R$^c$ | m$_p$ |
|---|---|---|---|---|
| 1. | phenyl | H | –NH–C(=O)–CH$_3$ | |
| 2. | 4-Cl-3-*-phenyl-SO$_2$NH$_2$ | H | –NH–C(=O)–CH$_3$ | |
| 3. | phenyl | –CH$_3$ | –NH–C(=O)–CH$_3$ | >280 |
| 4. | 2-F-phenyl | phenyl | –NH–C(=O)–CH$_3$ | 258-260 |
| 5. | 2-CF$_3$-phenyl | phenyl | –NH–C(=O)–CH$_3$ | 282-283 |
| 6. | 2-Br-phenyl | phenyl | –NH–C(=O)–CH$_3$ | 286-288 |
| 7. | 2-F-phenyl | furan-2-yl | –NH–C(=O)–CH$_3$ | 280-282 |
| 8. | phenyl | furan-2-yl | –NH–C(=O)–CH$_3$ | >300 |

-continued
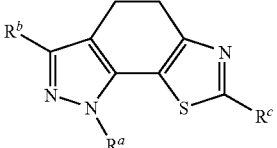
| | Rᵃ | Rᵇ | Rᶜ | m_p |
|---|---|---|---|---|
| 9. | 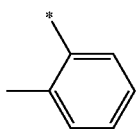 | 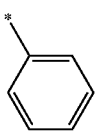 | 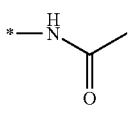 | 261-263 |
| 10. | 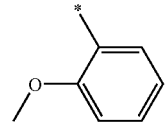 | 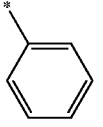 | 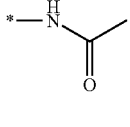 | 295-298 |
| 11. | 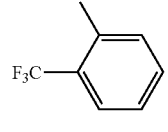 | 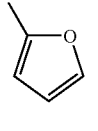 | 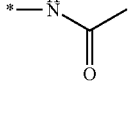 | >300 |
| 12. | 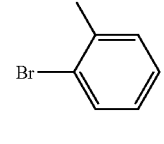 | 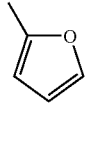 | 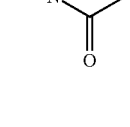 | >300 |
| 13. | 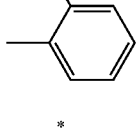 | 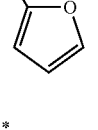 | 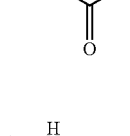 | 297-299 |
| 14. | 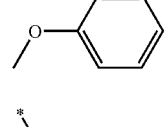 | 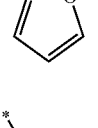 | 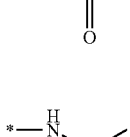 | >300 |
| 15. | 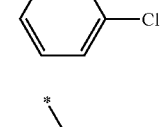 | 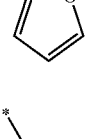 | 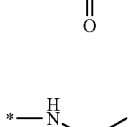 | >300 |
| 16. | 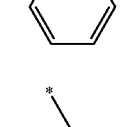 | 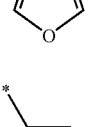 | 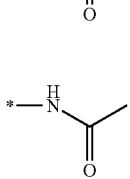 | >300 |
| 17. | 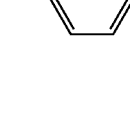 | 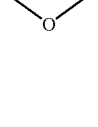 |  | 259-261 |

-continued
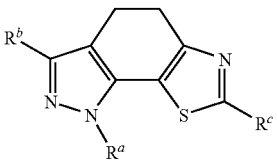
| | $R^a$ | $R^b$ | $R^c$ | $m_p$ |
|---|---|---|---|---|
| 18. | 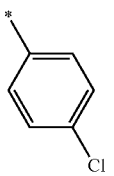 | 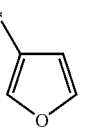 | 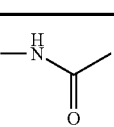 | >300 |
| 19. | 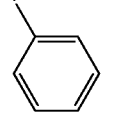 | H | 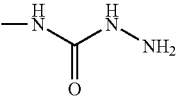 | |
| 20. | 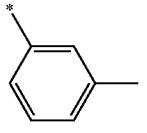 | H | 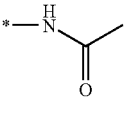 | 214-216 |
| 21. | 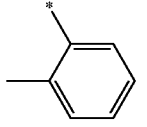 | H | 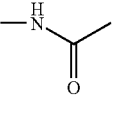 | 227-229 |
| 22. | 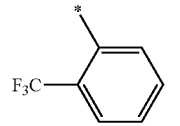 | H | 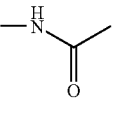 | 244-246 |
| 23. | 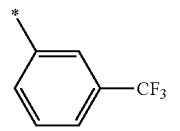 | H | 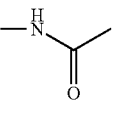 | 211-213 |
| 24. | 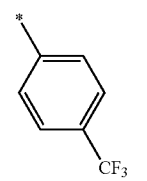 | H | 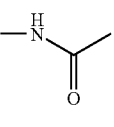 | 242-244 |
| 25. | 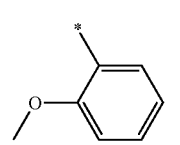 | H | 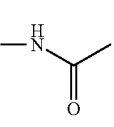 | 270-273 |
| 26. | 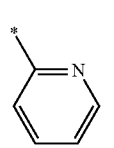 | H | 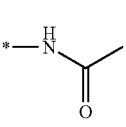 | 251-253 |

-continued
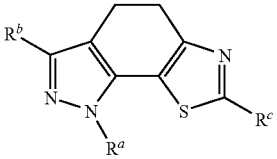
| | R$^a$ | R$^b$ | R$^c$ | m$_p$ |
|---|---|---|---|---|
| 27. | phenyl | H | *—NH-C(O)-NH-CH$_2$CH$_2$-NMe$_2$ | |
| 28. | 2-methylphenyl | *-C(O)-OMe | *—NH-C(O)-CH$_3$ | 277-290 Decomp. |
| 29. | 4-methylphenyl | *-C(O)-OMe | *—NH-C(O)-CH$_3$ | 113-120 Decomp. |
| 30. | phenyl | H | *—NH-C(O)-NH-(CH$_2$)$_2$-morpholine | |
| 31. | 4-pyridyl | H | *—NH-C(O)-CH$_3$ | |
| 32. | phenyl | H | *—NH-C(O)-CH$_2$CH$_3$ | 236-237.5 |
| 33. | phenyl | H | *—NH-C(O)-NH-Et | 298-304 Decomp. |
| 34. | phenyl | H | *—NH-C(O)-NH-Me | 303.5-306 |
| 35. | 3-methoxyphenyl | H | *—NH-C(O)-CH$_3$ | |

-continued
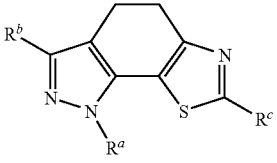
| | R$^a$ | R$^b$ | R$^c$ | m$_p$ |
|---|---|---|---|---|
| 36. | 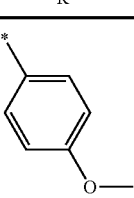 | H | 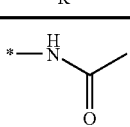 | |
| 37. | 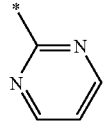 | H | 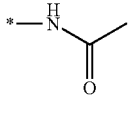 | >300 |
| 38. | 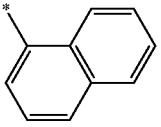 | H | 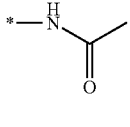 | |
| 39. | 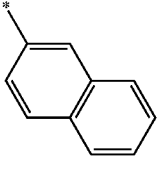 | H | 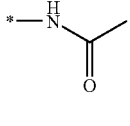 | 154-157 |
| 40. | 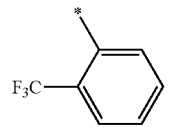 | 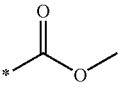 | 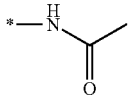 | 295-300 |
| 41. | 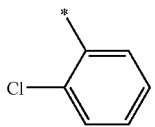 | H | 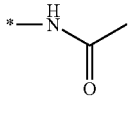 | 256-259 |
| 42. | 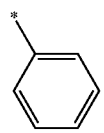 | H | 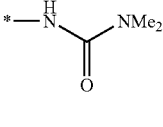 | 228-230 |
| 43. | 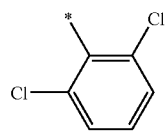 | H | 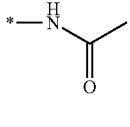 | 270-273 |
| 44. | 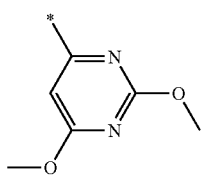 | H | 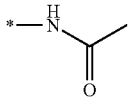 | 202-204 |

-continued
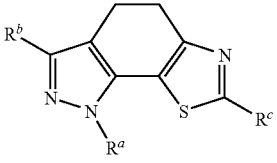
| | R$^a$ | R$^b$ | R$^c$ | m$_p$ |
|---|---|---|---|---|
| 45. | 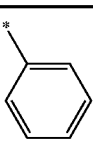 | H | 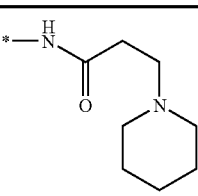 | 202-204 |
| 46. | 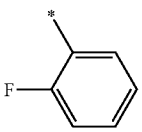 | H | 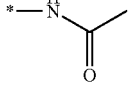 | >300° |
| 47. | 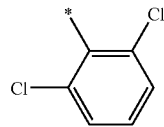 | 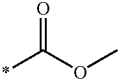 | 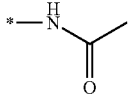 | 295-305 |
| 48. | 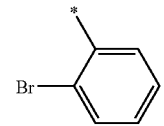 | H | 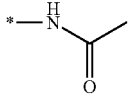 | 264-266 |
| 49. | 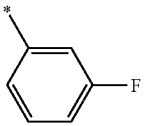 | H | 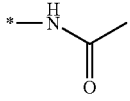 | 294-296 |
| 50. | 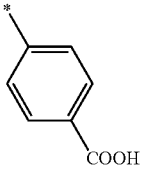 | H | 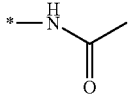 | >300 |
| 51. | 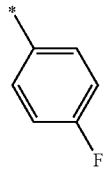 | H | 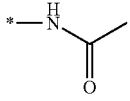 | |
| 52. | 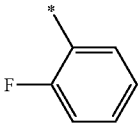 | 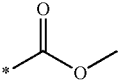 | 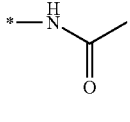 | 296->Decomp. |
| 53. | 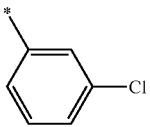 | H | 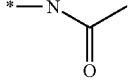 | 233-235 |

-continued
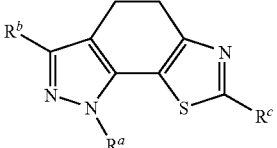
| | R<sup>a</sup> | R<sup>b</sup> | R<sup>c</sup> | m<sub>p</sub> |
|---|---|---|---|---|
| 54. | 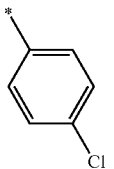 | H | 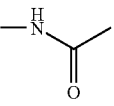 | 234–235 |
| 55. | 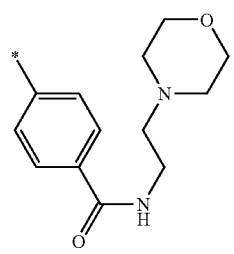 | H | 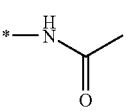 | |
| 56. | 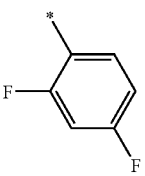 | H | 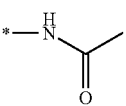 | 249–251 |
| 57. | 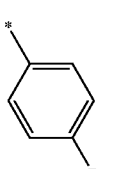 | H | 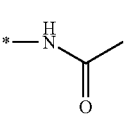 | 248–249 |
| 58. | 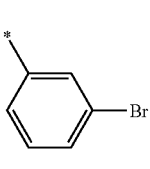 | H | 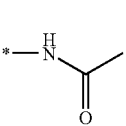 | 135–137 |
| 59. | 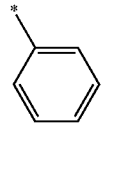 | H | 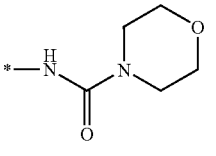 | 239 |
| 60. | 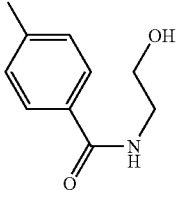 | H | 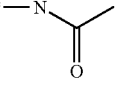 | |

-continued

| | $R^a$ | $R^b$ | $R^c$ | $m_p$ |
|---|---|---|---|---|
| 61. | 4-[(1,4,6,7-tetrahydro-5H-imidazo[4,5-c]pyridin-5-yl)carbonyl]phenyl | H | *—NH—C(O)CH$_3$ | |
| 62. | 4-[(4-hydroxypiperidin-1-yl)carbonyl]phenyl | H | *—NH—C(O)CH$_3$ | |
| 63. | 4-{[(2,2,2-trifluoroethyl)amino]carbonyl}phenyl | H | *—NH—C(O)CH$_3$ | |
| 64. | 4-{[(2-oxotetrahydrofuran-3-yl)amino]carbonyl}phenyl | H | *—NH—C(O)CH$_3$ | |
| 65. | 4-{[4-(aminocarbonyl)piperidin-1-yl]carbonyl}phenyl | H | *—NH—C(O)CH$_3$ | |
| 66. | 4-{[(2-hydroxypropyl)(methyl)amino]carbonyl}phenyl | H | *—NH—C(O)CH$_3$ | |

-continued
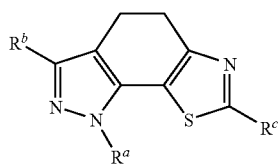
| | Rᵃ | Rᵇ | Rᶜ | mₚ |
|---|---|---|---|---|
| 67. | 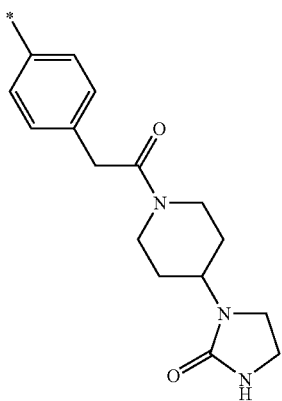 | H | 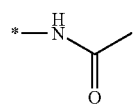 | |
| 68. | 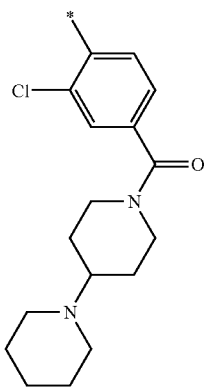 | H | 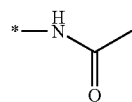 | |
| 69. | 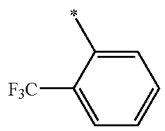 | 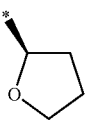 | 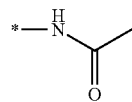 | |
| 70. | 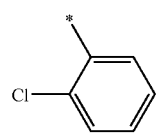 |  | 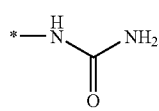 | |

-continued
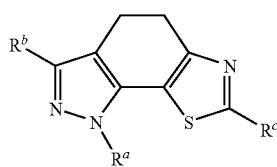
| | Rᵃ | Rᵇ | Rᶜ | m_p |
|---|---|---|---|---|
| 71. | 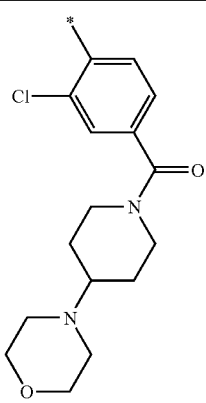 | H | 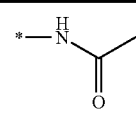 | |
| 72. | 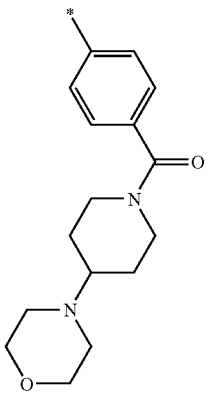 | H | 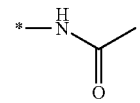 | 255-256 |
| 73. | 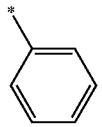 | 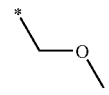 | 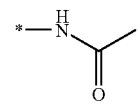 | |
| 74. | 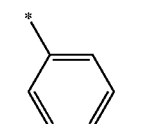 | H | 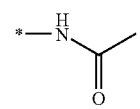 | |

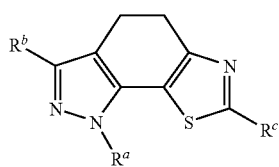
| | $R^a$ | $R^b$ | $R^c$ | $m_p$ |
|---|---|---|---|---|
| 75. | (4-(1,4-dioxaspiro[4.5]dec-8-ylcarbamoyl)phenyl) | H | *—NHC(O)CH₃ | |
| 76. | (2-trifluoromethylphenyl) | isopropyl | *—NHC(O)CH₃ | |
| 77. | (4-((4-piperidin-1-yl-cyclohexyl)carbamoyl)phenyl) | H | *—NHC(O)CH₃ | |
| 78. | (4-((4-(4-methylpiperazin-1-yl)cyclohexyl)carbamoyl)phenyl) | H | *—NHC(O)CH₃ | |

-continued
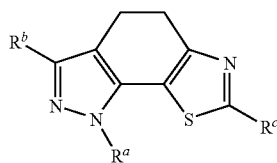
| | $R^a$ | $R^b$ | $R^c$ | $m_p$ |
|---|---|---|---|---|
| 79. | 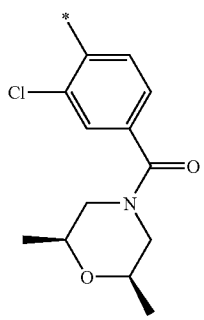 | H | 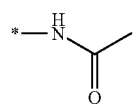 | |
| 80. | 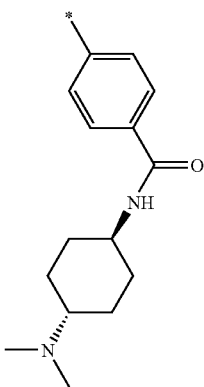 | H | 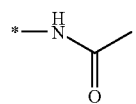 | |
| 81. | 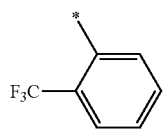 | 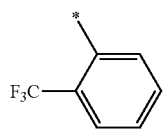 | 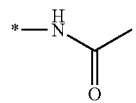 | |
| 82. | 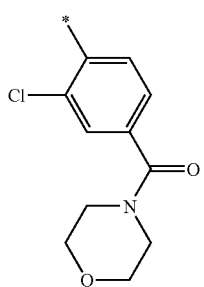 | H | 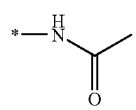 | |
| 83. | 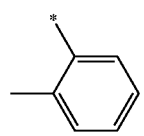 | 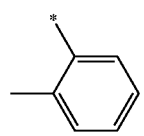 | 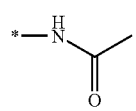 | |

-continued
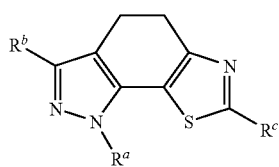
| | $R^a$ | $R^b$ | $R^c$ | $m_p$ |
|---|---|---|---|---|
| 84. | 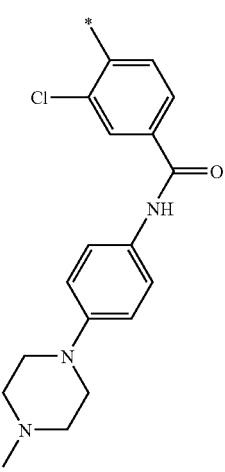 | H | 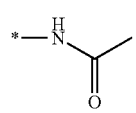 | |
| 85. | 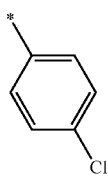 | —CH₃ | 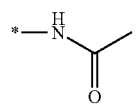 | |
| 86. | 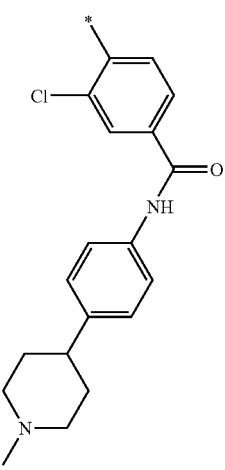 | H | 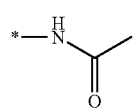 | |

-continued
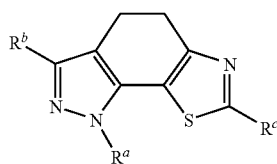
| | $R^a$ | $R^b$ | $R^c$ | $m_p$ |
|---|---|---|---|---|
87. 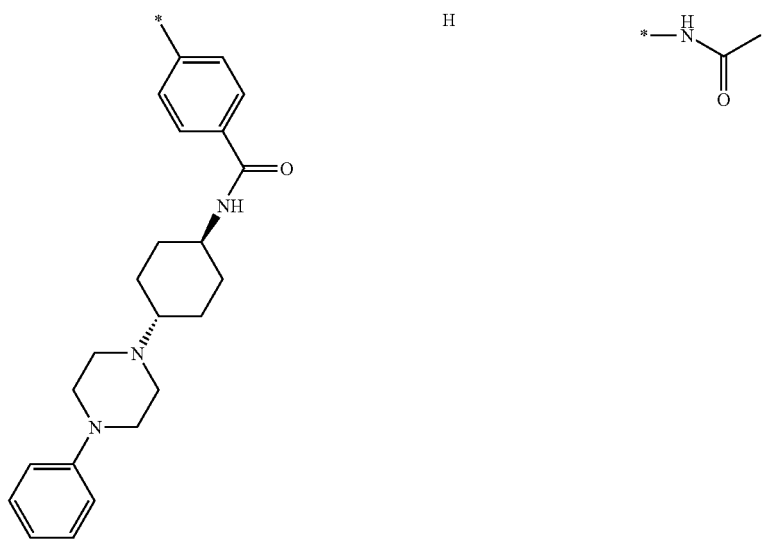 H *—NH—C(=O)CH₃
88. 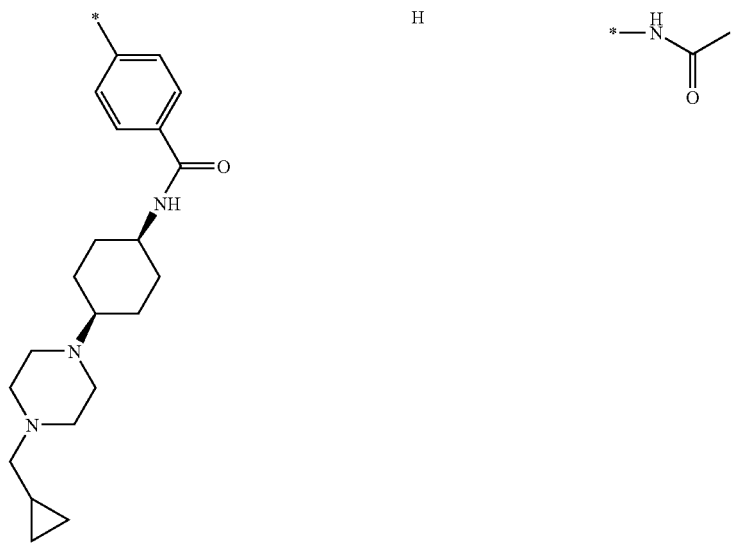 H *—NH—C(=O)CH₃

-continued
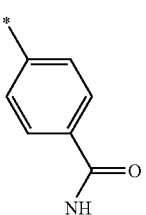
| | R<sup>a</sup> | R<sup>b</sup> | R<sup>c</sup> | m<sub>p</sub> |
|---|---|---|---|---|
| 89. | 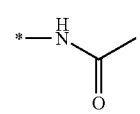 | H | 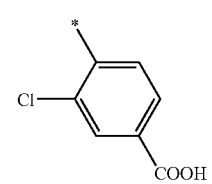 | 230 |
| 90. |  | 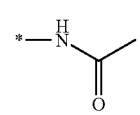 | 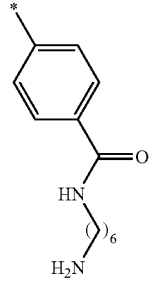 | |
| | 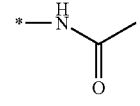 | H | 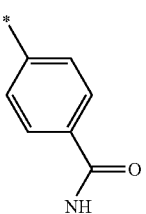 | 227.4 |
| 91. | 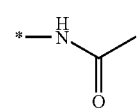 | H | | |

-continued
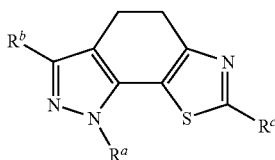
| | R$^a$ | R$^b$ | R$^c$ | m$_p$ |
|---|---|---|---|---|
| 92. | 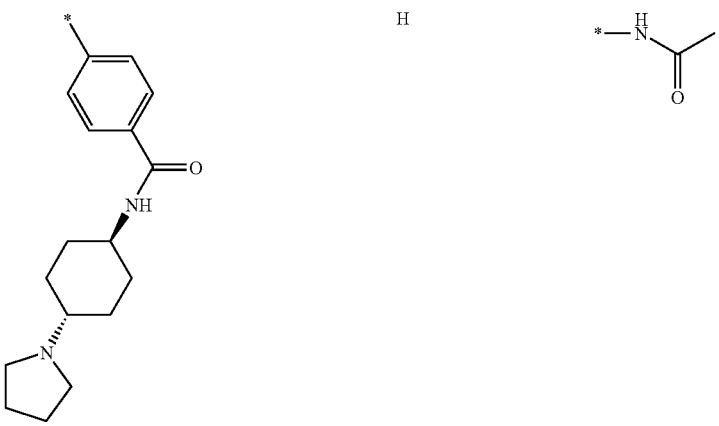 | H | 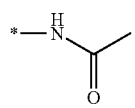 | |
| 93. | 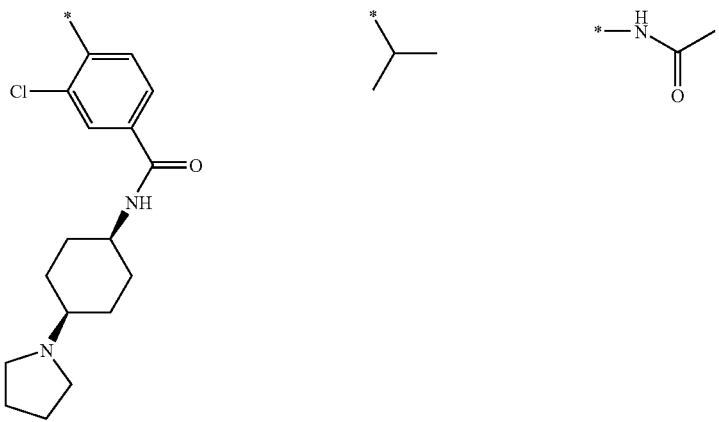 | 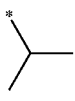 | 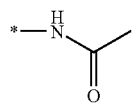 | |
| 94. | 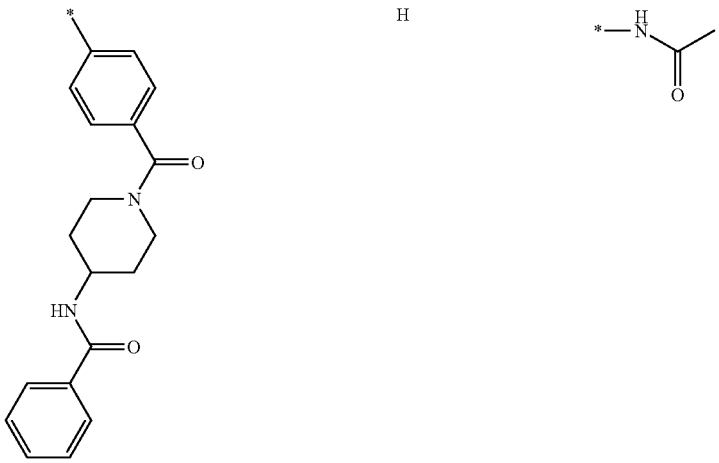 | H | 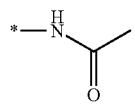 | |

-continued
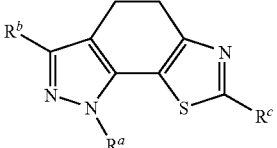
| | R<sup>a</sup> | R<sup>b</sup> | R<sup>c</sup> | m<sub>p</sub> |
|---|---|---|---|---|
| 95. | 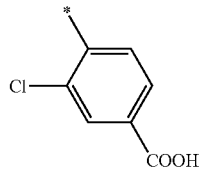 | H | 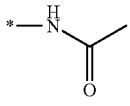 | >300 |
| 96. | 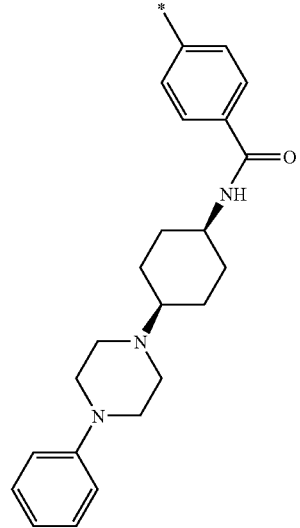 | H | 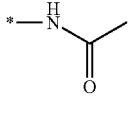 | |
| 97. | 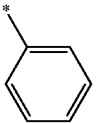 | 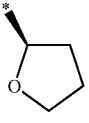 | 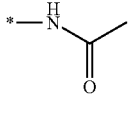 | |
| 98. | 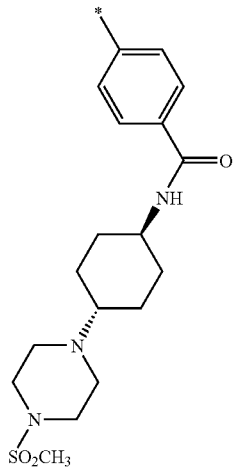 | H | 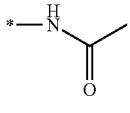 | |

-continued

| | $R^a$ | $R^b$ | $R^c$ | $m_p$ |
|---|---|---|---|---|
| 99. | 4-(morpholin-4-yl)cyclohexyl-NH-C(O)-C6H4-* | H | *-NHC(O)CH3 | |
| 100. | 2-bromophenyl-* | *-CH2OCH3 | *-NHC(O)CH3 | |
| 101. | 4-(4-aminocyclohexyl-NH-C(O))-C6H4-* | H | *-NHC(O)CH3 | |
| 102. | 4-((2,6-dimethylmorpholin-4-yl)cyclohexyl-NH-C(O))-C6H4-* | H | *-NHC(O)CH3 | |

-continued
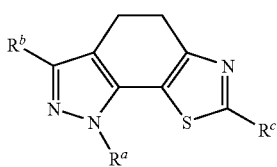
| | $R^a$ | $R^b$ | $R^c$ | $m_p$ |
|---|---|---|---|---|
| 103. | 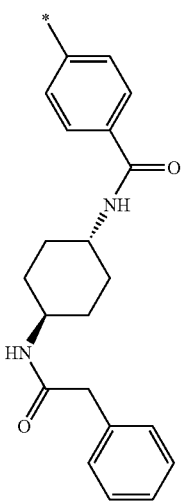 | H | 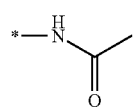 | |
| 104. | 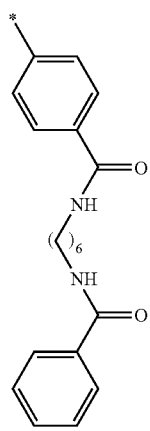 | H | 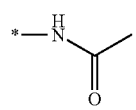 | |
| 105. | 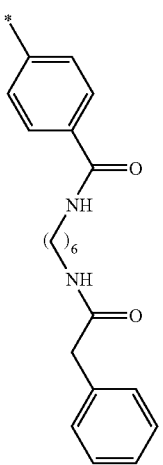 | H | 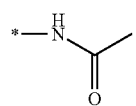 | |

-continued
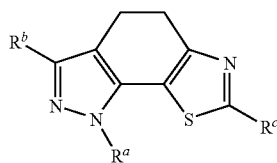
| | R$^a$ | R$^b$ | R$^c$ | m$_p$ |
|---|---|---|---|---|
| 106. | 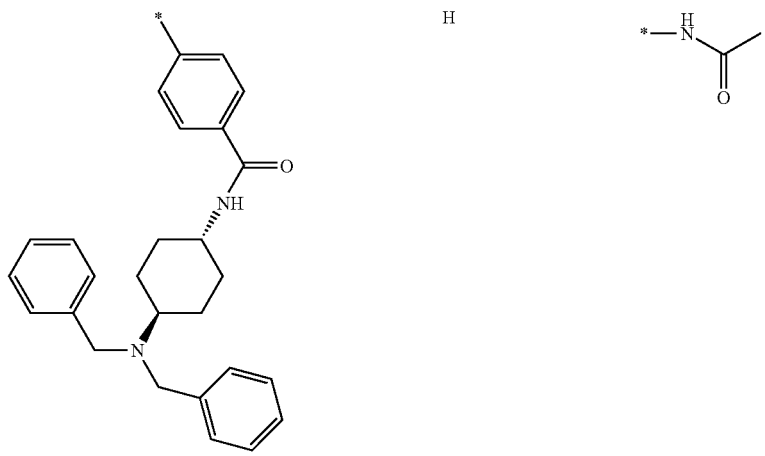 | H | 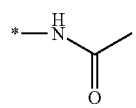 | |
| 107. | 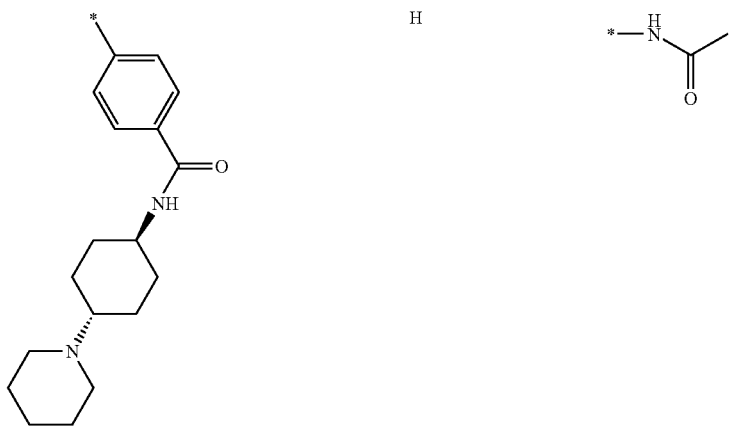 | H | 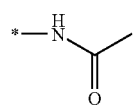 | |
| 108. | 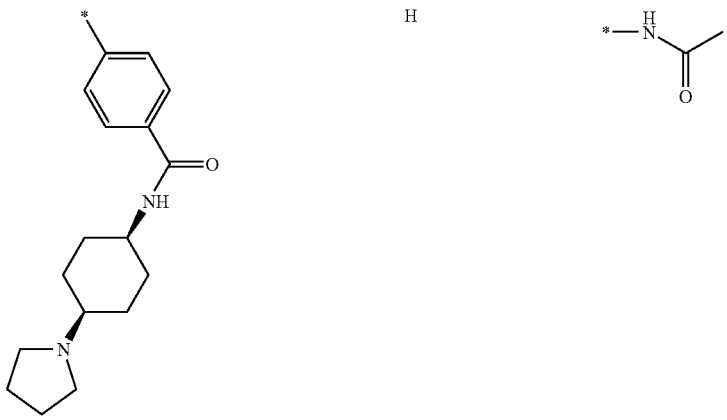 | H | 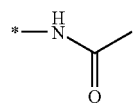 | |

-continued
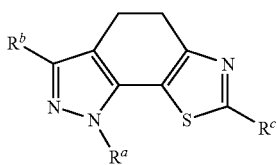
| | Rª | R♭ | Rᶜ | m_p |
|---|---|---|---|---|
| 109. | 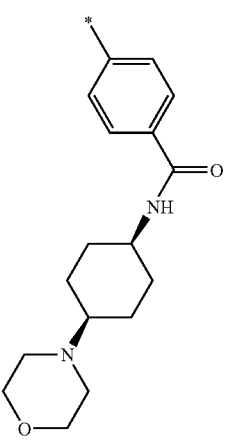 | H | 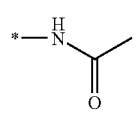 | |
| 110. | 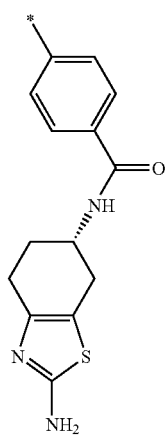 | H | 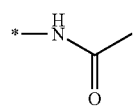 | |
| 111. | 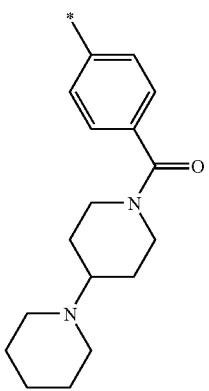 | H | 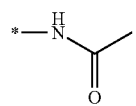 | |

-continued
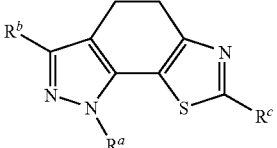
| | $R^a$ | $R^b$ | $R^c$ | $m_p$ |
|---|---|---|---|---|
| 112. | 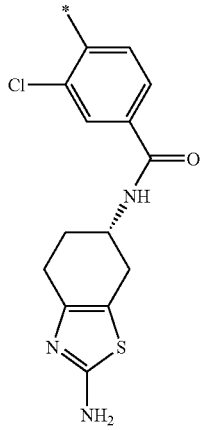 | H | 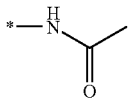 | |
| 113. | 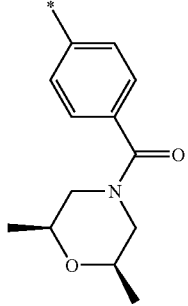 | H | 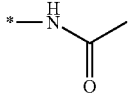 | |
| 114. | 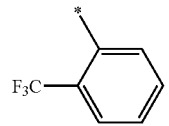 | —CH$_3$ | 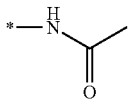 | |
| 115. | 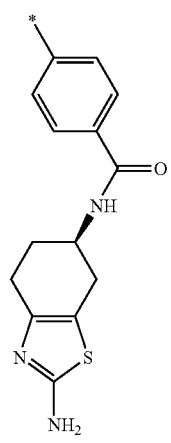 | H | 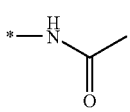 | |

-continued

| | R$^a$ | R$^b$ | R$^c$ | m$_p$ |
|---|---|---|---|---|
| 116. | 4-(naphthalene-1-carboxamido)cyclohexylcarbamoylphenyl | H | *—NHC(O)CH$_3$ | |
| 117. | phenyl | isopropyl | *—NHC(O)CH$_3$ | |
| 118. | 4-((2R,6S)-2,6-dimethylmorpholino)cyclohexylcarbamoylphenyl | H | *—NHC(O)CH$_3$ | |
| 119. | 2-methylphenyl | isopropyl | *—NHC(O)CH$_3$ | |
| 120. | 3-carboxyphenyl | H | *—NHC(O)CH$_3$ | |

-continued
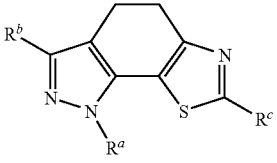
| | R<sup>a</sup> | R<sup>b</sup> | R<sup>c</sup> | m<sub>p</sub> |
|---|---|---|---|---|
| 121. | 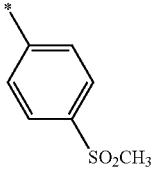 | H |  | |
| 122. | 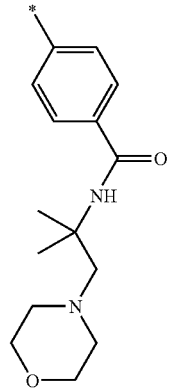 | H | 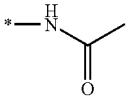 | 280-281 |
| 123. | 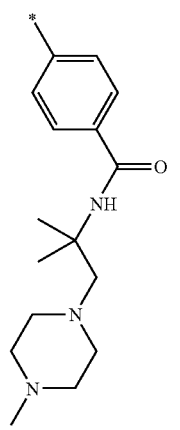 | H | 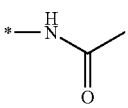 | 245 |
| 124. | 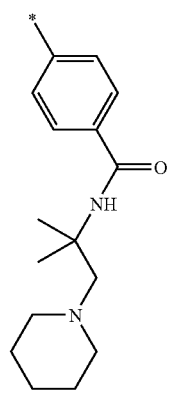 | H | 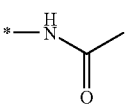 | 317-319 |

-continued
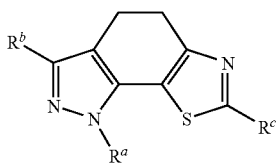
| | $R^a$ | $R^b$ | $R^c$ | $m_p$ |
|---|---|---|---|---|
| 125. | 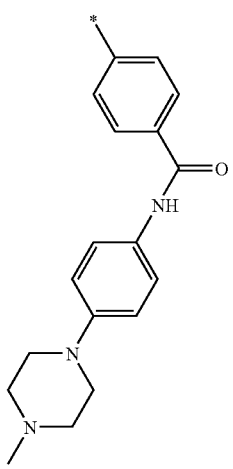 | H | 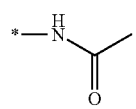 | 300-310 |
| 126. | 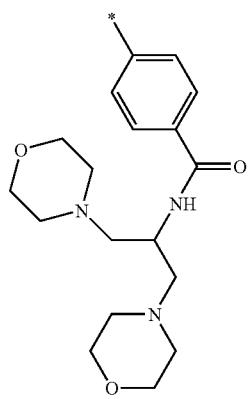 | H | 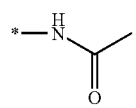 | 226-227 |
| 127. | 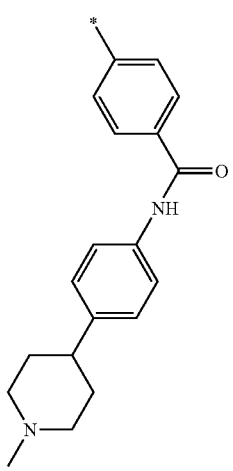 | H | 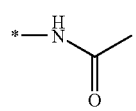 | 240-250 |

-continued
| | $R^a$ | $R^b$ | $R^c$ | $m_p$ |
|---|---|---|---|---|
| 128. | 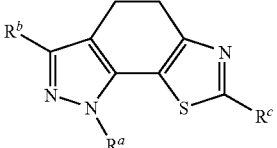 | H | 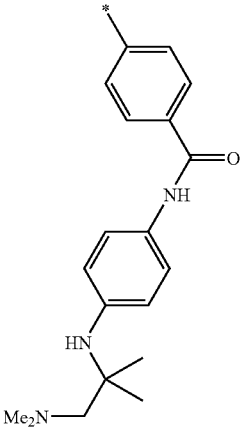 | 304-310 |
| 129. | 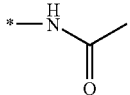 | H | 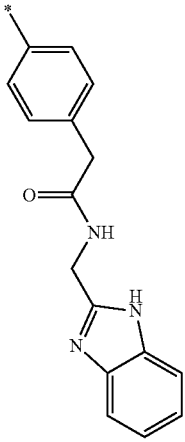 | |
| 130. | 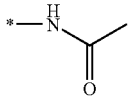 | H | 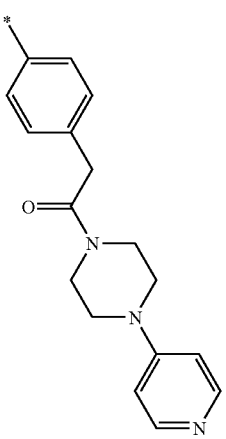 | |

-continued
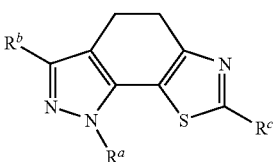
| | $R^a$ | $R^b$ | $R^c$ | $m_p$ |
|---|---|---|---|---|
| 131. | 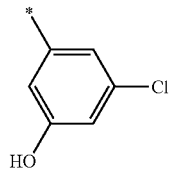 | H | 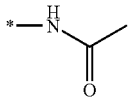 | |
| 132. | 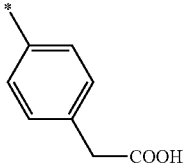 | H | 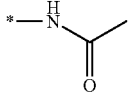 | |
| 133. | 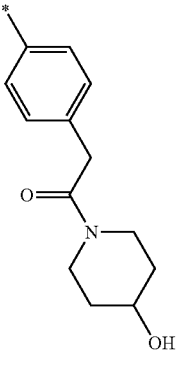 | H | 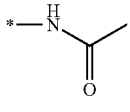 | |
| 134. | 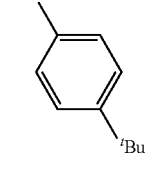 | H | 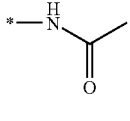 | |
| 135. | 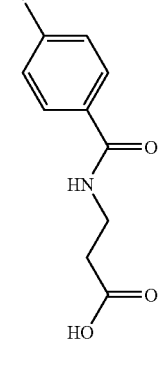 | H | 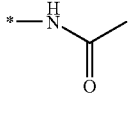 | |

-continued
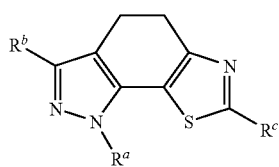
| | R<sup>a</sup> | R<sup>b</sup> | R<sup>c</sup> | m<sub>p</sub> |
|---|---|---|---|---|
| 136. | 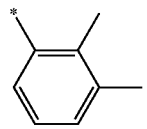 | H | 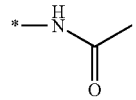 | |
| 137. | 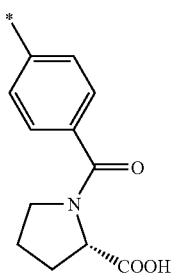 | H | 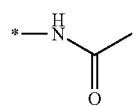 | |
| 138. | 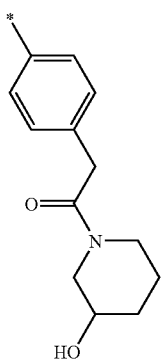 | H | 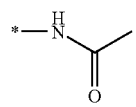 | |
| 139. | 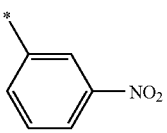 | H | 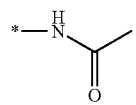 | |
| 140. | 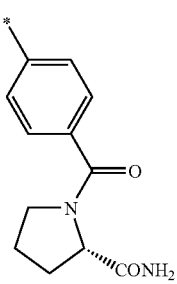 | H | 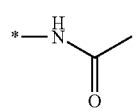 | |

-continued
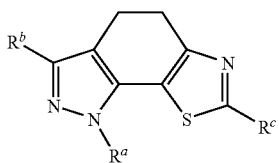
| | Rᵃ | Rᵇ | Rᶜ | mₚ |
|---|---|---|---|---|
| 141. | 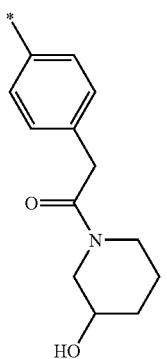 | H | 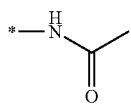 | |
| 142. | 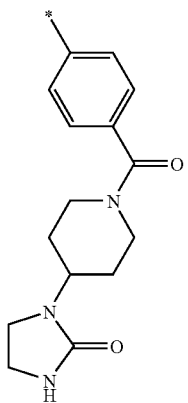 | H | 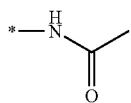 | |
| 143. | 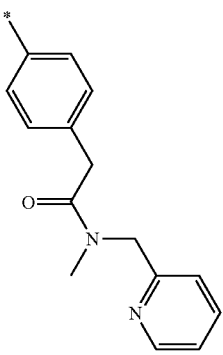 | H | 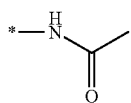 | |
| 144. | 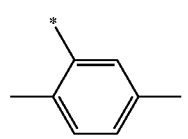 | H | 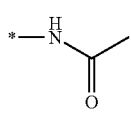 | |

-continued
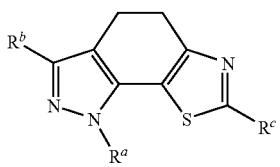
| | $R^a$ | $R^b$ | $R^c$ | $m_p$ |
|---|---|---|---|---|
| 145. | 2,4-dichlorophenyl* | H | *—NHC(O)CH₃ | |
| 146. | 4-(2-carbamoylpyrrolidine-1-carbonyl)phenyl* | H | *—NHC(O)CH₃ | |
| 147. | 1H-indazol-6-yl* | H | *—NHC(O)CH₃ | |
| 148. | 3-chloro-4-hydroxyphenyl* | H | *—NHC(O)CH₃ | |
| 149. | 4-cyanophenyl* | H | *—NHC(O)CH₃ | |
| 150. | 4-(2-(ethyl(propyl)amino)-2-oxoethyl)phenyl* | H | *—NHC(O)CH₃ | |

-continued

|     | Rᵃ | Rᵇ | Rᶜ | m_p |
|-----|----|----|----|-----|
| 151. | 4-(OCF₃)-phenyl | H | -NHC(O)CH₃ | |
| 152. | 4-(PhC(O)NHCH₂CH₂)-phenyl | H | -NHC(O)CH₃ | |
| 153. | 1H-benzimidazol-6-yl | H | -NHC(O)CH₃ | |
| 154. | 2,5-dichlorophenyl | H | -NHC(O)CH₃ | |
| 155. | benzothiazol-6-yl | H | -NHC(O)CH₃ | |
| 156. | 4-[[(S)-1-carbamoyl-2-(4-hydroxyphenyl)ethyl]carbamoyl]phenyl | H | -NHC(O)CH₃ | |

-continued
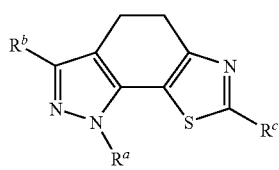
| | Rª | R^b | R^c | m_p |
|---|---|---|---|---|
| 157. | 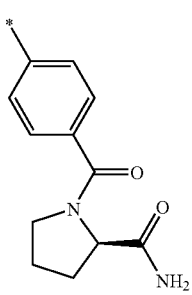 | H | 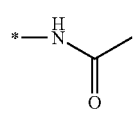 | |
| 158. | 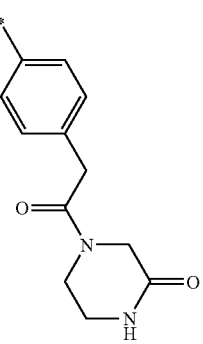 | H | 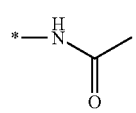 | |
| 159. | 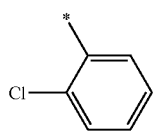 | 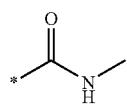 | 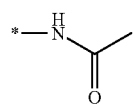 | 303.1 |
| 160. | 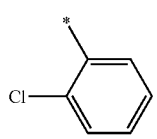 | 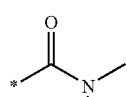 | 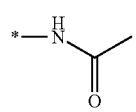 | 281.3 |
| 161. | 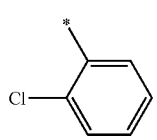 | 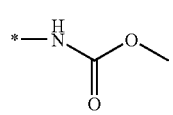 | 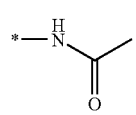 | 248.3 |
| 162. | 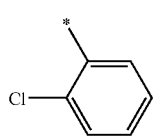 | 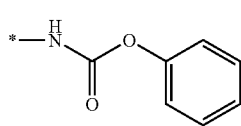 | 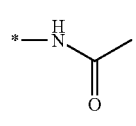 | |
| 163. | 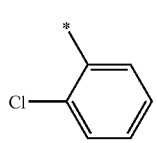 | 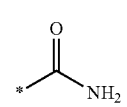 | 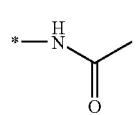 | |

-continued

| | $R^a$ | $R^b$ | $R^c$ | $m_p$ |
|---|---|---|---|---|
| 164. | *-C₆H₄-SO₃H | H | *-NH-C(O)-CH₃ | >300 |
| 165. | *-C₆H₄-SO₂NMe₂ | H | *-NH-C(O)-CH₃ | >280 |
| 166. | *-(2-methylphenyl) | *-(1-methylimidazol-4-yl) | *-NH-C(O)-CH₃ | >300 |
| 167. | *-(2-trifluoromethylphenyl) | *-(1-methylimidazol-4-yl) | *-NH-C(O)-CH₃ | >300 |
| 168. | *-C₆H₄-SO₂-(piperidin-1-yl) | H | *-NH-C(O)-CH₃ | 248-251 |
| 169. | *-C₆H₄-SO₂-N(Me)-CH₂CH₂-NMe₂ | H | *-NH-C(O)-CH₃ | 242-245 |

-continued
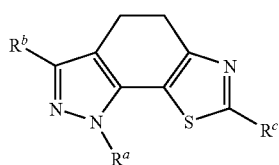
| | Rᵃ | Rᵇ | Rᶜ | m_p |
|---|---|---|---|---|
| 170. | 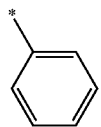 | 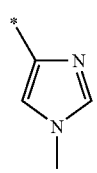 | 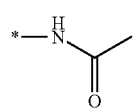 | >300 |
| 171. | 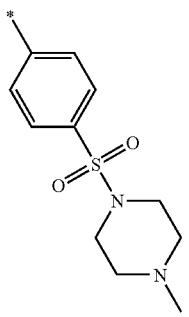 | H | 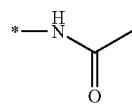 | 298->300 |
| 172. | 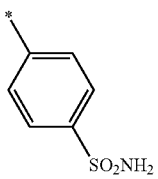 | H | 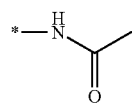 | >300 |
| 173. | 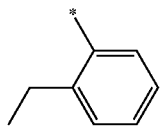 | H | 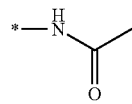 | 209-211 |
| 174. | 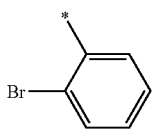 | 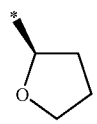 | 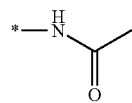 | |
| 175. | 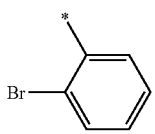 | 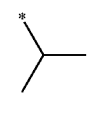 | 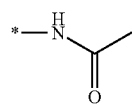 | |

-continued
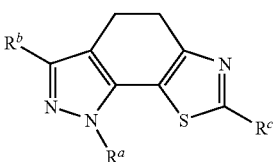
| | Rᵃ | Rᵇ | Rᶜ | m_p |
|---|---|---|---|---|
| 176. | 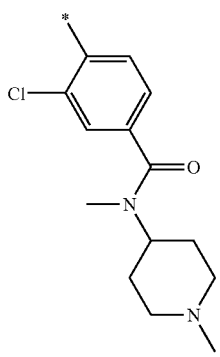 |  | 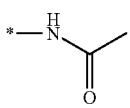 | |
| 177. | 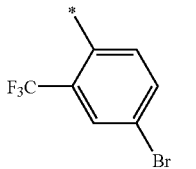 |  | 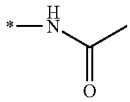 | |
| 178. | 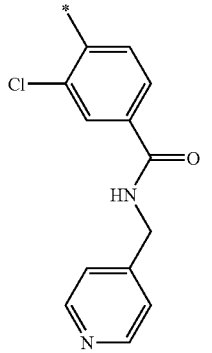 |  | 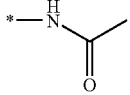 | |
| 179. | 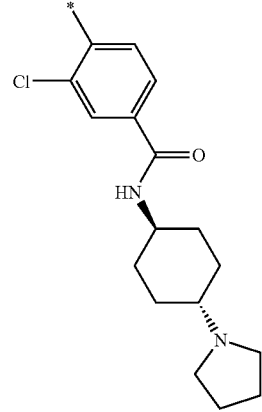 |  | 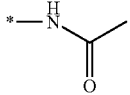 | |

-continued
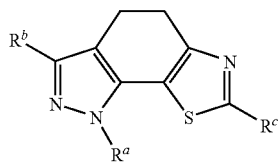
| | R<sup>a</sup> | R<sup>b</sup> | R<sup>c</sup> | m<sub>p</sub> |
|---|---|---|---|---|
| 180. | 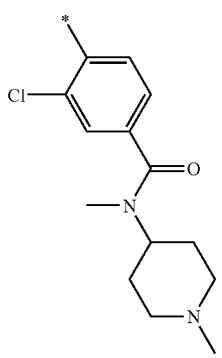 |  | 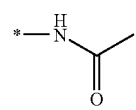 | |
| 181. | 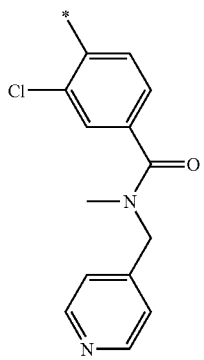 |  | 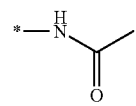 | |
| 182. | 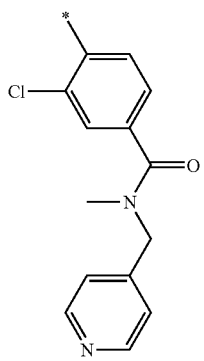 | 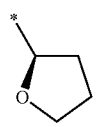 | 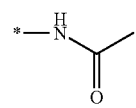 | |

-continued
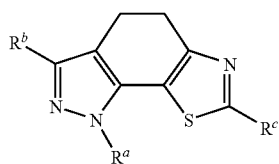
| | $R^a$ | $R^b$ | $R^c$ | $m_p$ |
|---|---|---|---|---|
| 183. | 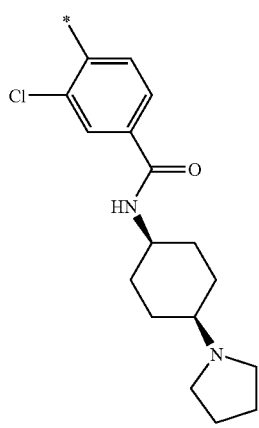 |  | 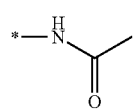 | |
| 184. | 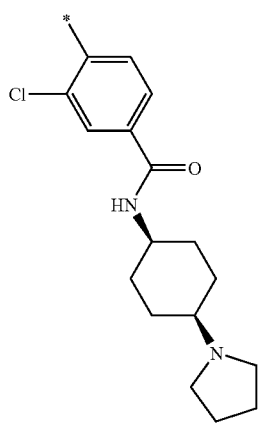 | 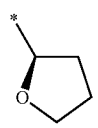 | 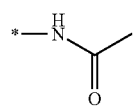 | |
| 185. | 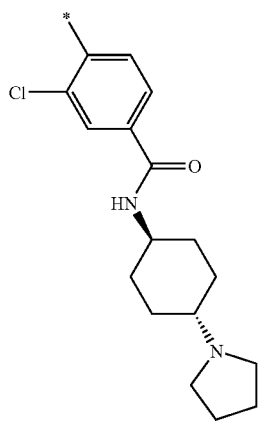 |  | 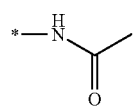 | |

-continued
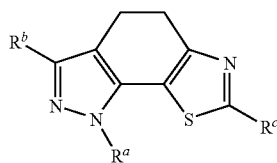
| Rᵃ | Rᵇ | Rᶜ | m_p |
|---|---|---|---|
186. 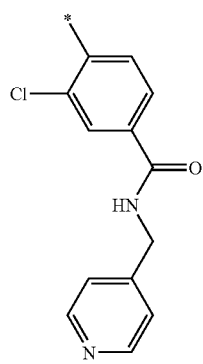  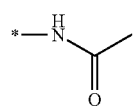
187. 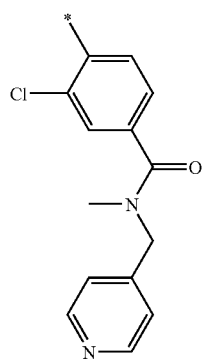  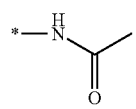
188. 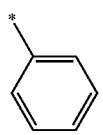 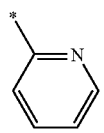 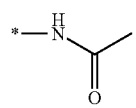
189. 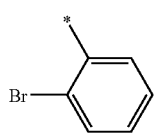 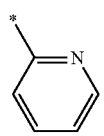 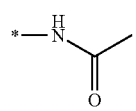
190. 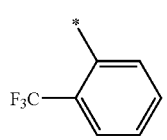 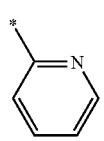 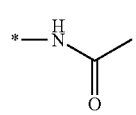
191. 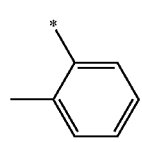 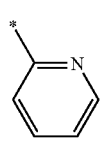 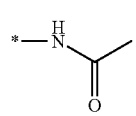

-continued
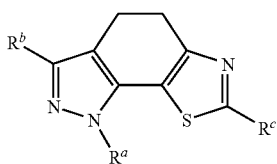
| | $R^a$ | $R^b$ | $R^c$ | $m_p$ |
|---|---|---|---|---|
| 192. | 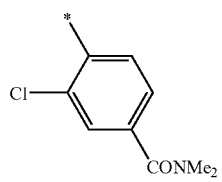 | 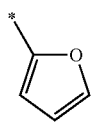 | 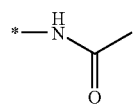 | |
| 193. | 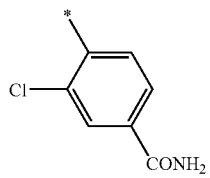 | 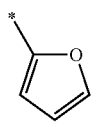 | 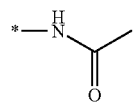 | |
| 194. | 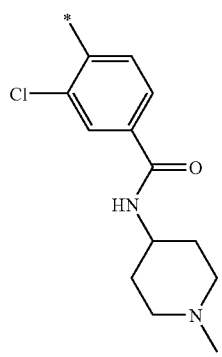 | 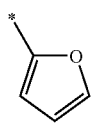 | 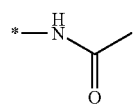 | |
| 195. | 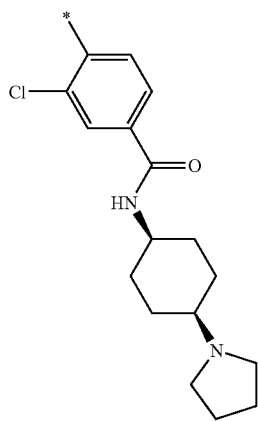 | 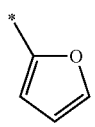 | 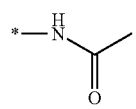 | |

-continued
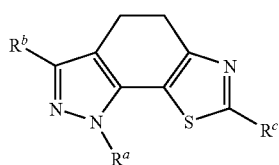
| | $R^a$ | $R^b$ | $R^c$ | $m_p$ |
|---|---|---|---|---|
| 196. | 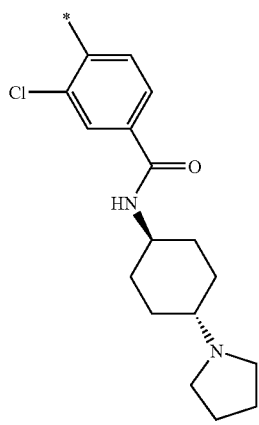 | 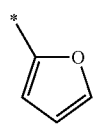 | 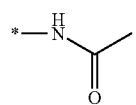 | |
| 197. | 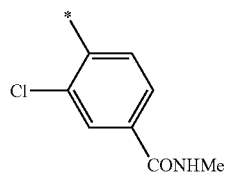 | 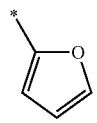 | 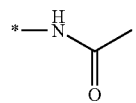 | |
| 198. | 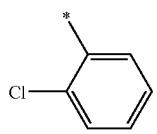 | 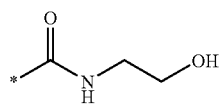 | 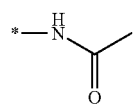 | |
| 199. | 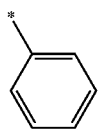 | H | 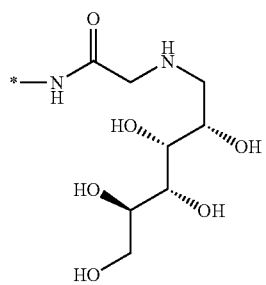 | |
| 200. | 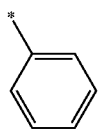 | H | 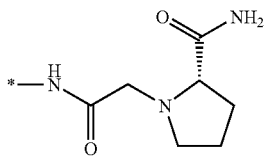 | |

-continued
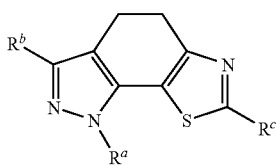
| | $R^a$ | $R^b$ | $R^c$ | $m_p$ |
|---|---|---|---|---|
| 201. | 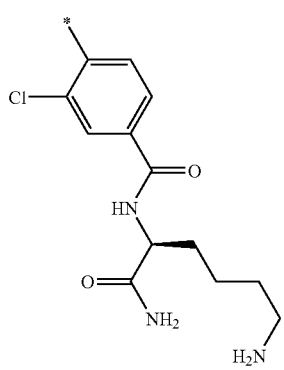 | H | 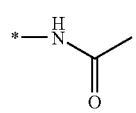 | |
| 202. | 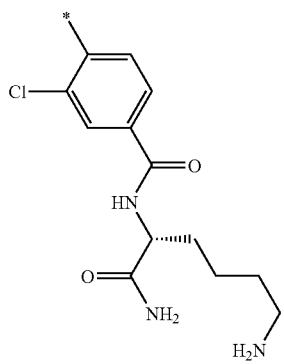 | H | 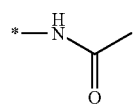 | |
| 203. | 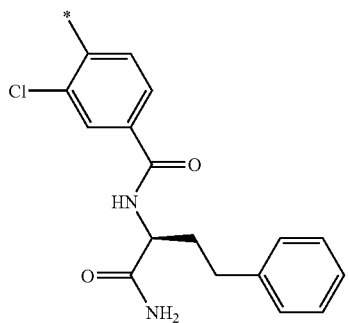 | H | 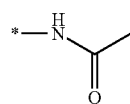 | |

-continued
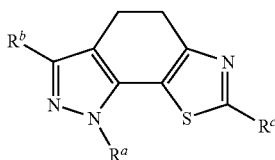
| | $R^a$ | $R^b$ | $R^c$ | $m_p$ |
|---|---|---|---|---|
| 204. | 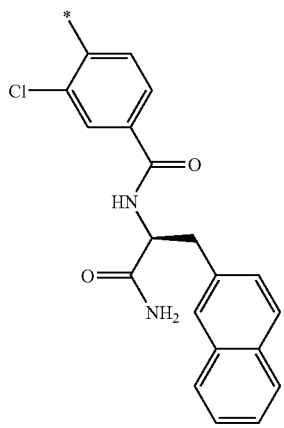 | H | 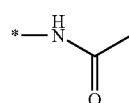 | |
| 205. | 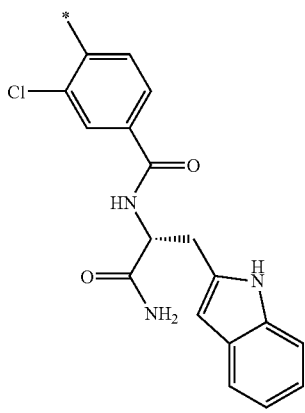 | H | 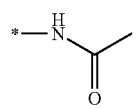 | |
| 206. | 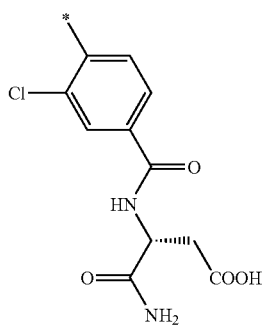 | H | 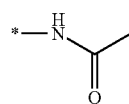 | |

-continued
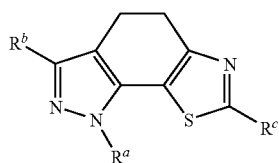
| | $R^a$ | $R^b$ | $R^c$ | $m_p$ |
|---|---|---|---|---|
| 207. | 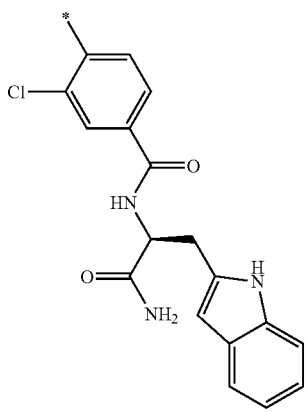 | H | 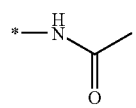 | |
| 208. | 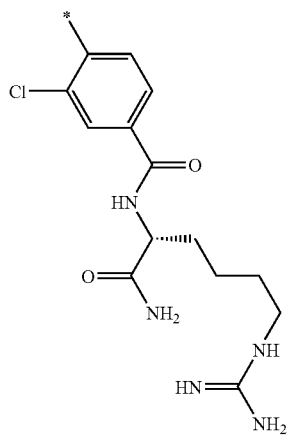 | H | 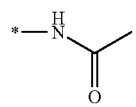 | |
| 209. | 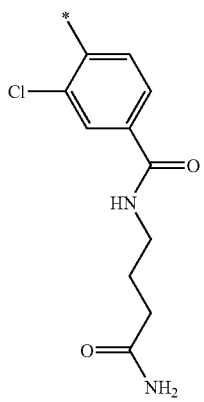 | H | 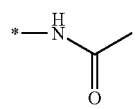 | |

-continued

| | $R^a$ | $R^b$ | $R^c$ | $m_p$ |
|---|---|---|---|---|
| 210. | 4-chloro-3-(...)phenyl with histidinamide benzamide linker | H | *—NHC(O)CH₃ | |
| 211. | 4-chloro-3-(...)phenyl with leucinamide benzamide linker | H | *—NHC(O)CH₃ | |
| 212. | 4-chloro-3-(...)phenyl with phenylglycinamide benzamide linker | H | *—NHC(O)CH₃ | |
| 213. | 4-chloro-3-(...)phenyl with 2-aminobutanamide benzamide linker | H | *—NHC(O)CH₃ | |

-continued
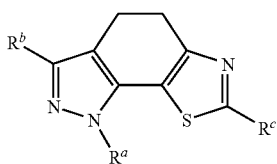
| | R$^a$ | R$^b$ | R$^c$ | m$_p$ |
|---|---|---|---|---|
| 214. | 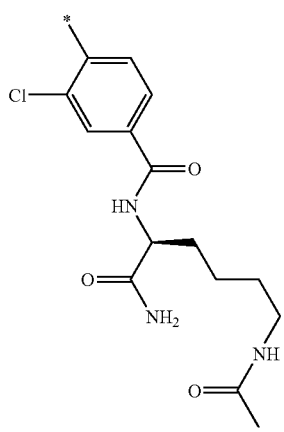 | H | 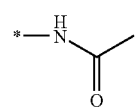 | |
| 215. | 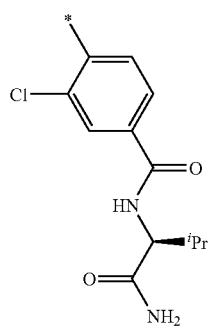 | H | 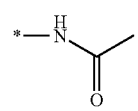 | |
| 216. | 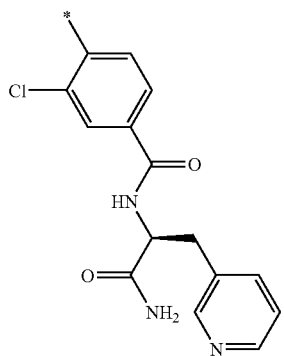 | H | 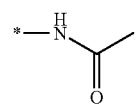 | |

-continued
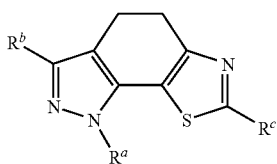
| | $R^a$ | $R^b$ | $R^c$ | $m_p$ |
|---|---|---|---|---|
| 217. | 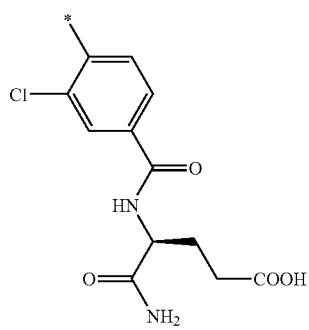 | H | 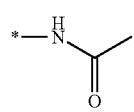 | |
| 218. | 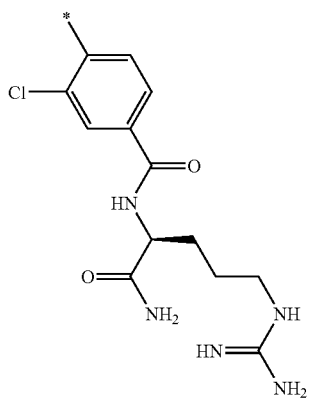 | H | 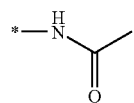 | |
| 219. | 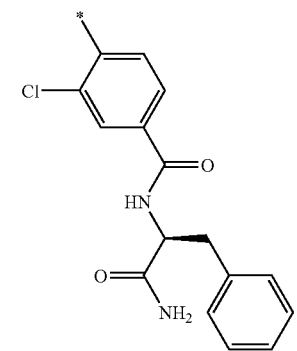 | H | 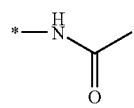 | |

-continued
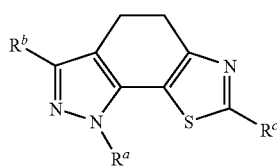
| | $R^a$ | $R^b$ | $R^c$ | $m_p$ |
|---|---|---|---|---|
| 220. | 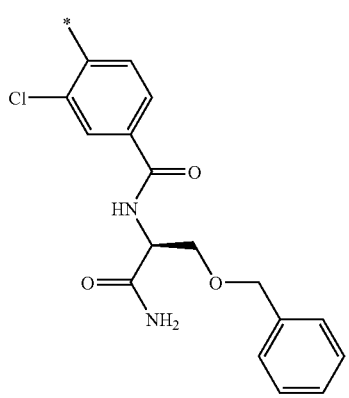 | H | 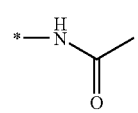 | |
| 221. | 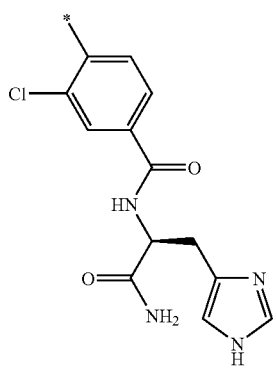 | H | 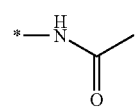 | |
| 222. | 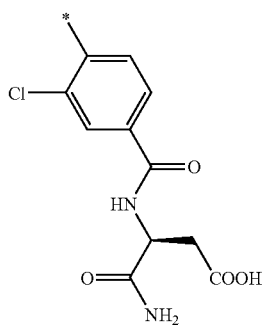 | H | 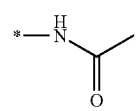 | |

-continued

| | $R^a$ | $R^b$ | $R^c$ | $m_p$ |
|---|---|---|---|---|
| 223. | 4-chloro-3-(benzamido) with tyrosine amide side chain | H | *—NHC(O)CH$_3$ | |
| 224. | 4-chloro-3-(benzamido) with threonine amide side chain | H | *—NHC(O)CH$_3$ | |
| 225. | 4-chloro-3-(benzamido) with threonine amide side chain (epimer) | H | *—NHC(O)CH$_3$ | |
| 226. | 4-chloro-3-(benzamido) with valine amide side chain ($^i$Pr) | H | *—NHC(O)CH$_3$ | |

-continued
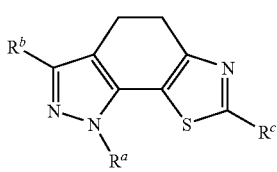
| | $R^a$ | $R^b$ | $R^c$ | $m_p$ |
|---|---|---|---|---|
| 227. | 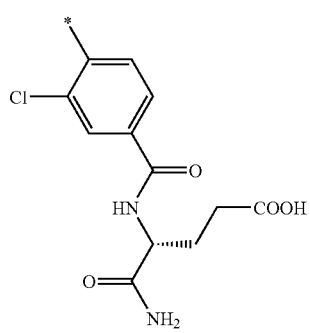 | H | 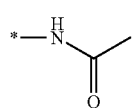 | |
| 228. | 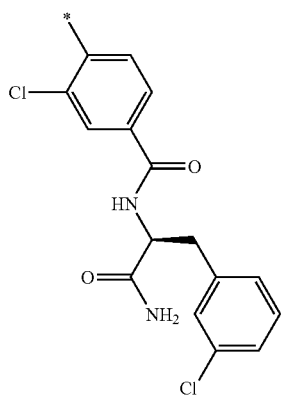 | H | 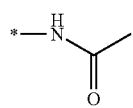 | |
| 229. | 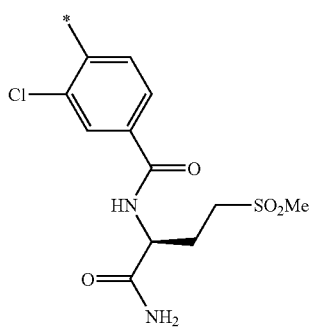 | H | 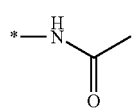 | |
| 230. | 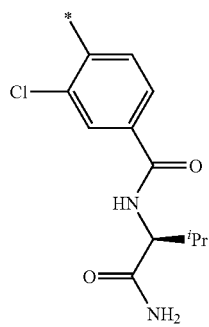 | H | 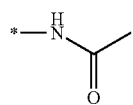 | |

-continued
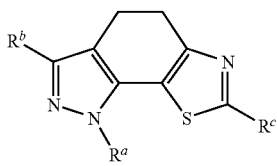
| | R$^a$ | R$^b$ | R$^c$ | m$_p$ |
|---|---|---|---|---|
| 231. | 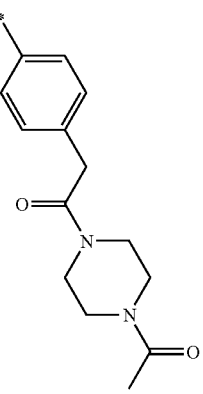 | H | 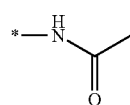 | |
| 232. | 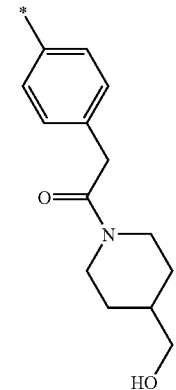 | H | 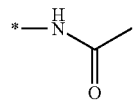 | |
| 233. | 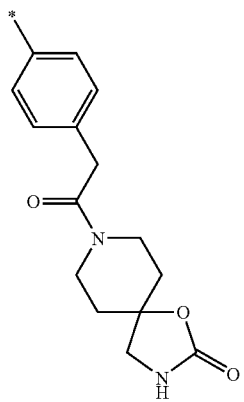 | H | 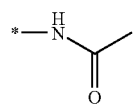 | |

-continued
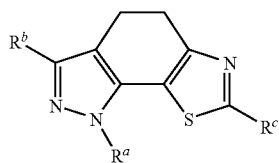
| | R<sup>a</sup> | R<sup>b</sup> | R<sup>c</sup> | m<sub>p</sub> |
|---|---|---|---|---|
| 234. | 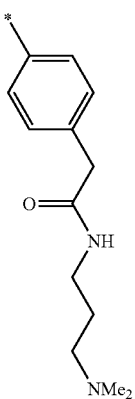 | H | 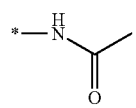 | |
| 235. | 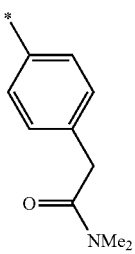 | H | 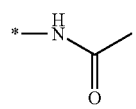 | |
| 236. | 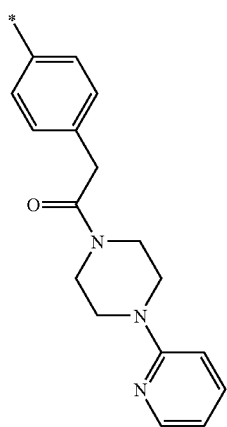 | H | 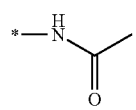 | |

-continued
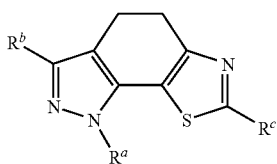
| | $R^a$ | $R^b$ | $R^c$ | $m_p$ |
|---|---|---|---|---|
| 237. | 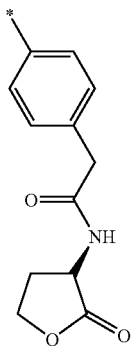 | H | 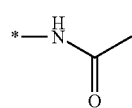 | |
| 238. | 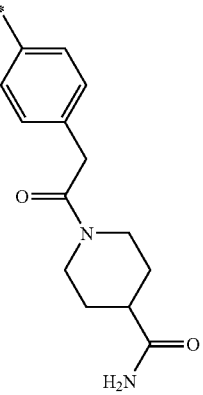 | H | 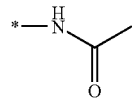 | |
| 239. | 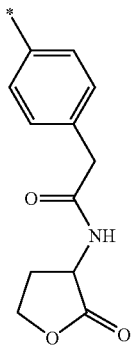 | H | 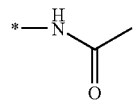 | |

-continued
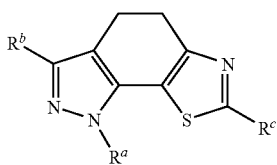
| | R$^a$ | R$^b$ | R$^c$ | m$_p$ |
|---|---|---|---|---|
| 240. | 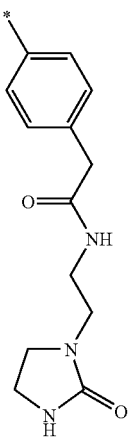 | H | 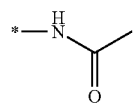 | |
| 241. | 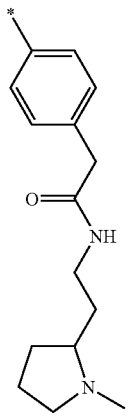 | H | 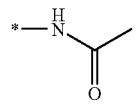 | |
| 242. | 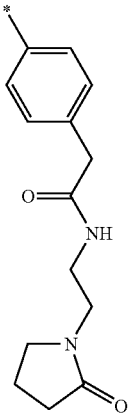 | H | 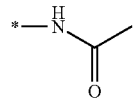 | |

-continued
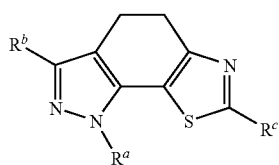
| | $R^a$ | $R^b$ | $R^c$ | $m_p$ |
|---|---|---|---|---|
| 243. | 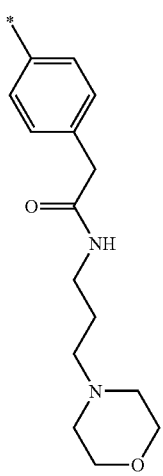 | H | 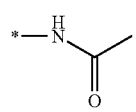 | |
| 244. | 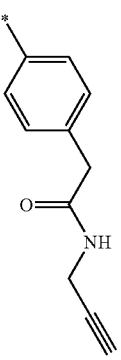 | H | 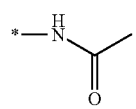 | |
| 245. | 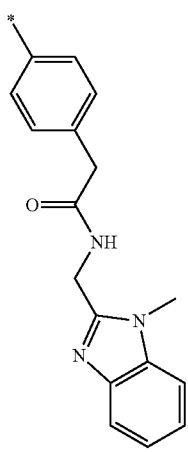 | H | 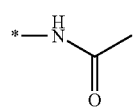 | |

-continued
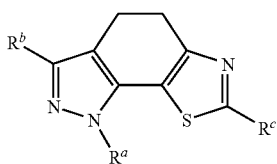
| | $R^a$ | $R^b$ | $R^c$ | $m_p$ |
|---|---|---|---|---|
| 246. | 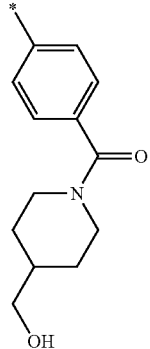 | H | 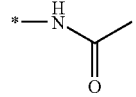 | |
| 247. | 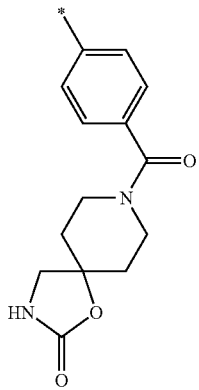 | H | 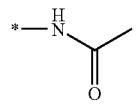 | |
| 248. | 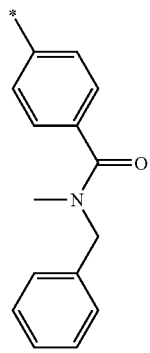 | H | 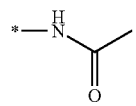 | |

-continued
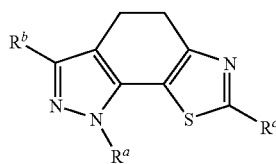
| | $R^a$ | $R^b$ | $R^c$ | $m_p$ |
|---|---|---|---|---|
| 249. | 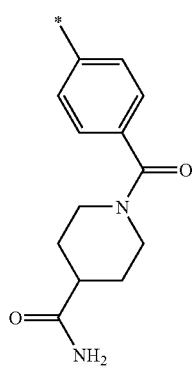 | H | 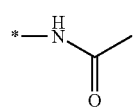 | |
| 250. | 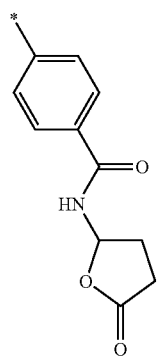 | H | 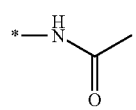 | |
| 251. | 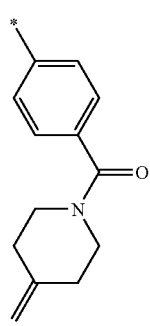 | H | 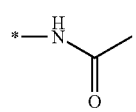 | |
| 252. | 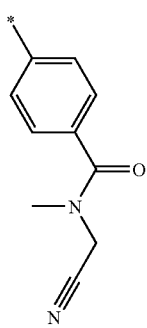 | H | 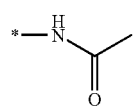 | |

-continued
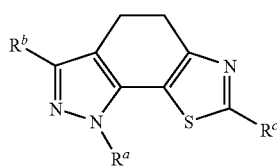
| | $R^a$ | $R^b$ | $R^c$ | $m_p$ |
|---|---|---|---|---|
| 253. | 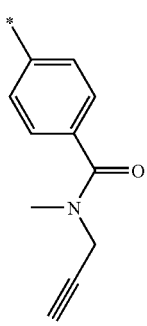 | H | 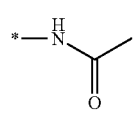 | |
| 254. | 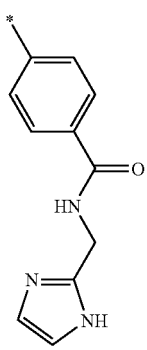 | H | 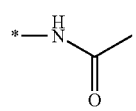 | |
| 255. | 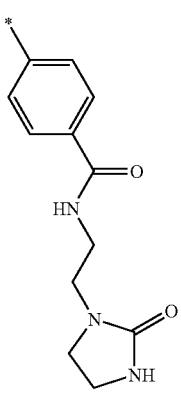 | H | 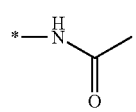 | |

-continued
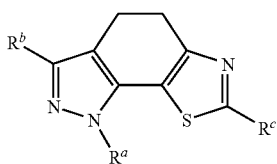
| | $R^a$ | $R^b$ | $R^c$ | $m_p$ |
|---|---|---|---|---|
| 256. | 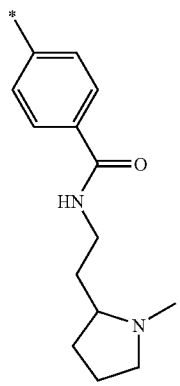 | H | 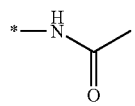 | |
| 257. | 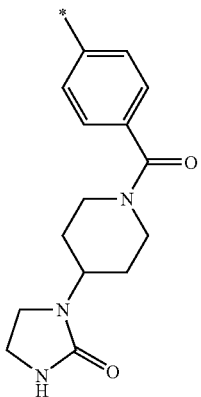 | H | 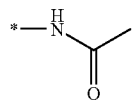 | |
| 258. | 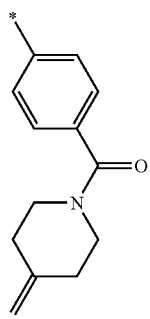 | H | 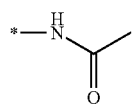 | |

-continued
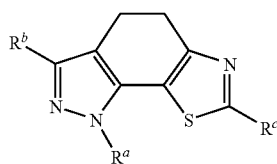
| | $R^a$ | $R^b$ | $R^c$ | $m_p$ |
|---|---|---|---|---|
| 259. | 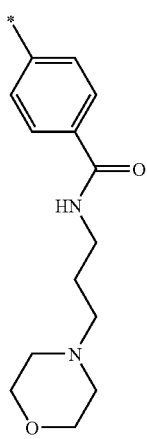 | H | 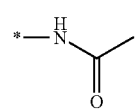 | |
| 260. | 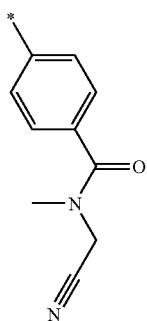 | H | 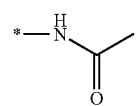 | |
| 261. | 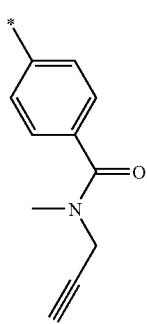 | H | 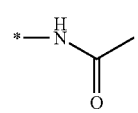 | |

-continued
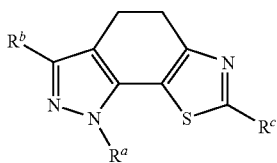
| | $R^a$ | $R^b$ | $R^c$ | $m_p$ |
|---|---|---|---|---|
| 262. | 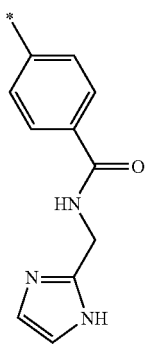 | H | 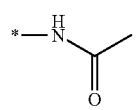 | |
| 263. | 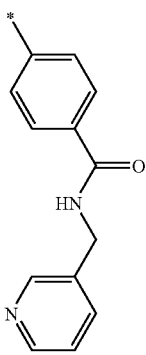 | H | 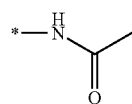 | |
| 264. | 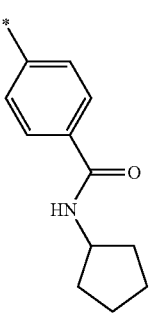 | H | 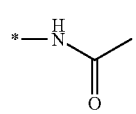 | |
| 265. | 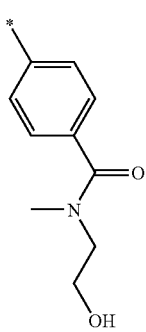 | H | 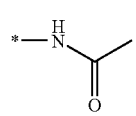 | |

-continued
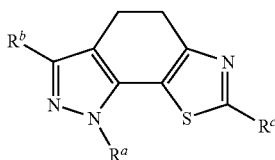
| | $R^a$ | $R^b$ | $R^c$ | $m_p$ |
|---|---|---|---|---|
| 266. | 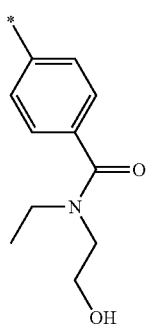 | H | 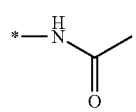 | |
| 267. | 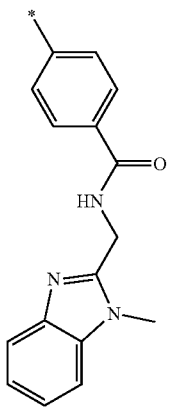 | H | 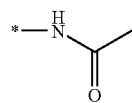 | |
| 268. | 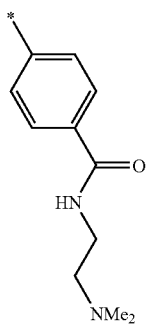 | H | 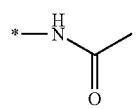 | |

-continued
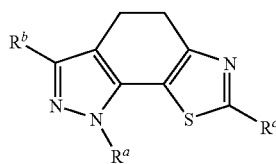
| | Rᵃ | Rᵇ | Rᶜ | m_p |
|---|---|---|---|---|
| 269. | 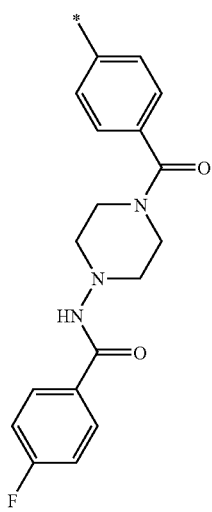 | H | 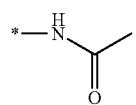 | |
| 270. | 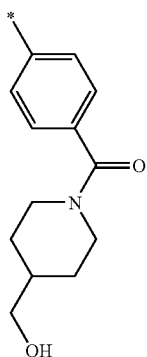 | H | 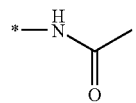 | |
| 271. | 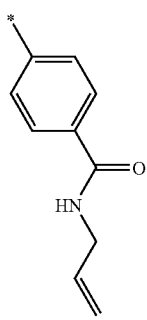 | H | 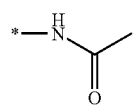 | |

-continued
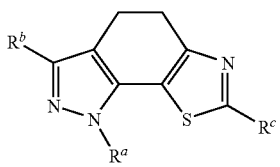
| | $R^a$ | $R^b$ | $R^c$ | $m_p$ |
|---|---|---|---|---|
| 272. | 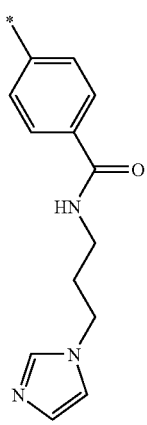 | H | 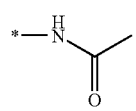 | |
| 273. | 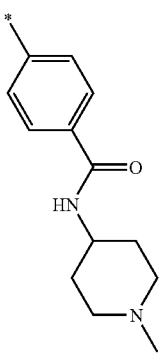 | H | 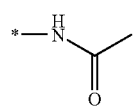 | |
| 274. | 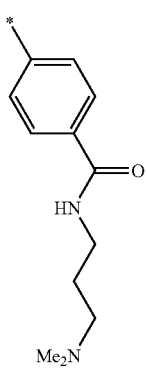 | H | 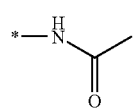 | |

-continued
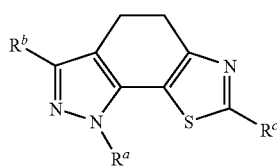
| | R$^a$ | R$^b$ | R$^c$ | m$_p$ |
|---|---|---|---|---|
| 275. | 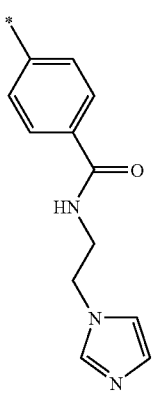 | H | 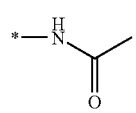 | |
| 276. | 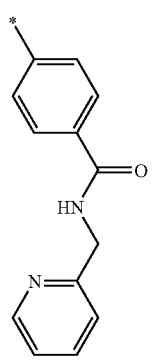 | H | 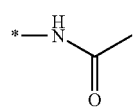 | |
| 277. | 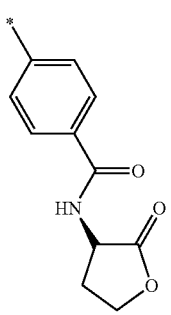 | H | 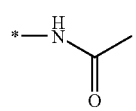 | |

-continued
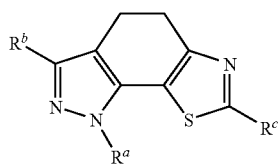
| | Rᵃ | Rᵇ | Rᶜ | m_p |
|---|---|---|---|---|
| 278. | 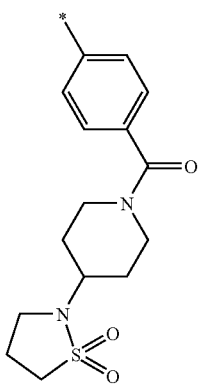 | H | 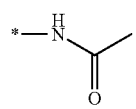 | |
| 279. | 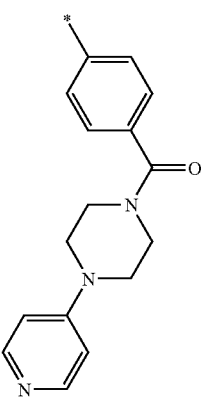 | H | 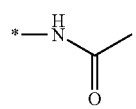 | |
| 280. | 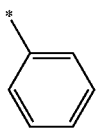 | 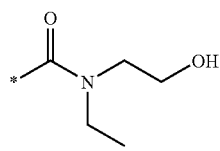 | 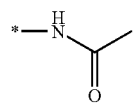 | |
| 281. | 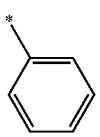 | 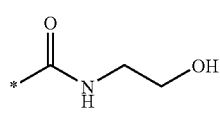 | 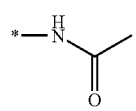 | |
| 282. | 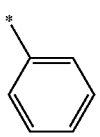 | 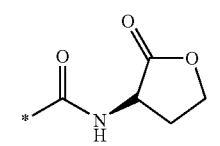 | 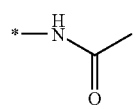 | |

-continued
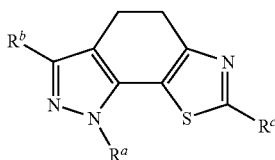
| | R$^a$ | R$^b$ | R$^c$ | m$_p$ |
|---|---|---|---|---|
| 283. | 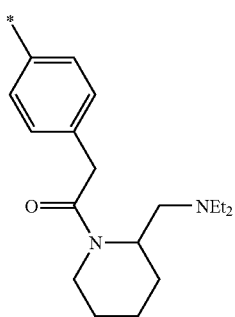 | H | 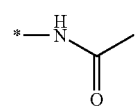 | |
| 284. | 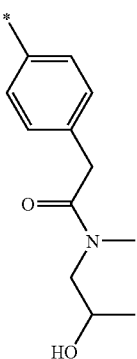 | H | 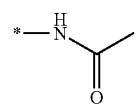 | |
| 285. | 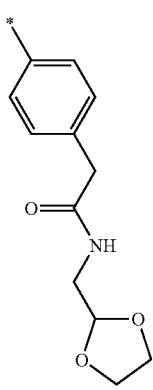 | H | 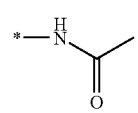 | |

-continued
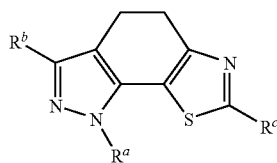
| | Rª | Rᵇ | Rᶜ | mₚ |
|---|---|---|---|---|
| 286. | 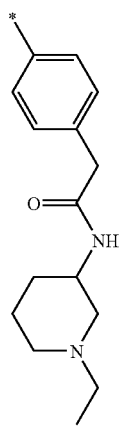 | H | 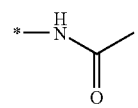 | |
| 287. | 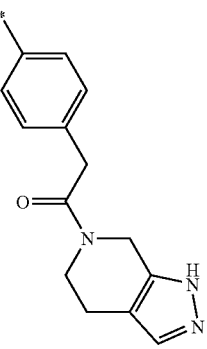 | H | 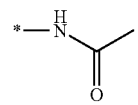 | |
| 288. | 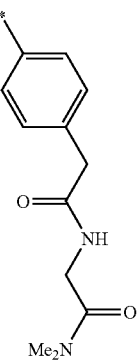 | H | 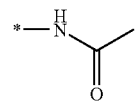 | |

-continued
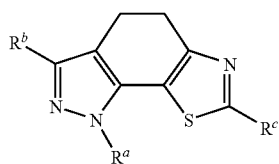
| | R$^a$ | R$^b$ | R$^c$ | m$_p$ |
|---|---|---|---|---|
| 289. | 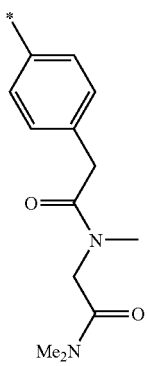 | H | 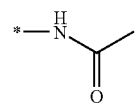 | |
| 290. | 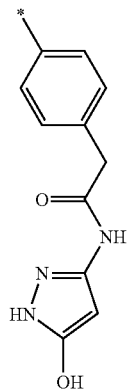 | H | 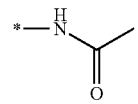 | |
| 291. | 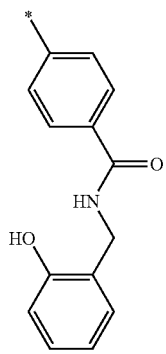 | H | 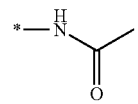 | |

-continued
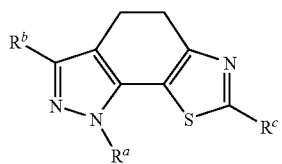
| | R$^a$ | R$^b$ | R$^c$ | m$_p$ |
|---|---|---|---|---|
| 292. | 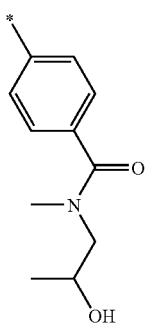 | H | 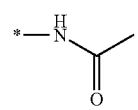 | |
| 293. | 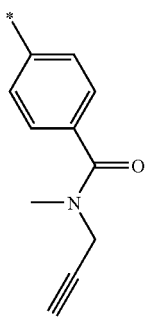 | H | 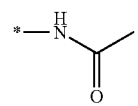 | |
| 294. | 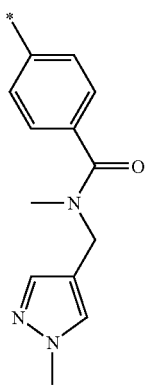 | H | 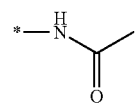 | |
| 295. | 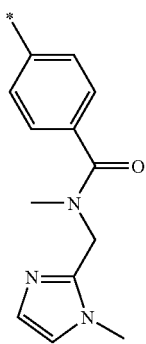 | H | 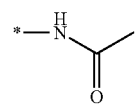 | |

-continued

| | R$^a$ | R$^b$ | R$^c$ | m$_p$ |
|---|---|---|---|---|
| 296. | [4-(tetrahydrothiophene-1,1-dioxide-3-ylaminocarbonylmethyl)phenyl] | H | *—NHC(O)CH$_3$ | |
| 297. | [4-(N-methyl-N-(morpholin-4-ylcarbonylmethyl)aminocarbonylmethyl)phenyl] | H | *—NHC(O)CH$_3$ | |
| 298. | [4-(prop-2-yn-1-ylaminocarbonylmethyl)phenyl] | H | *—NHC(O)CH$_3$ | |

-continued
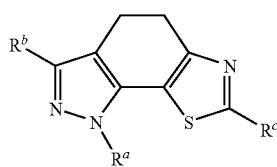
| | $R^a$ | $R^b$ | $R^c$ | $m_p$ |
|---|---|---|---|---|
| 299. | 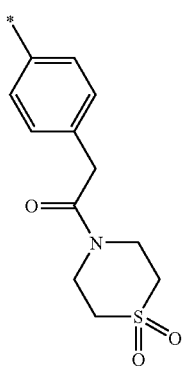 | H | 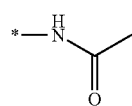 | |
| 300. | 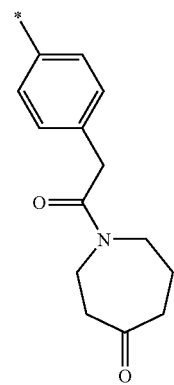 | H | 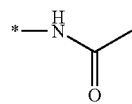 | |
| 301. | 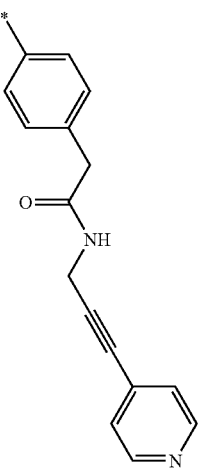 | H | 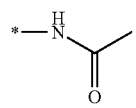 | |

-continued
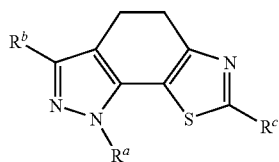
| | Rª | Rᵇ | Rᶜ | m_p |
|---|---|---|---|---|
| 302. | 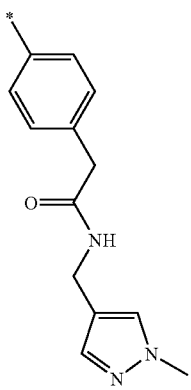 | H | 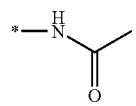 | |
| 303. | 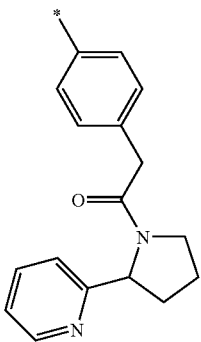 | H | 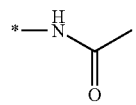 | |
| 304. | 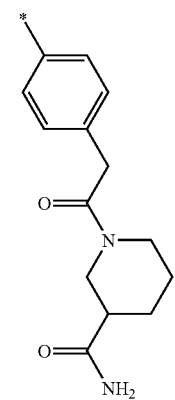 | H | 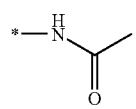 | |

-continued
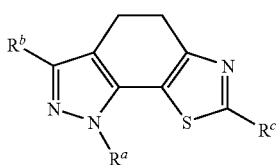
| | R<sup>a</sup> | R<sup>b</sup> | R<sup>c</sup> | m<sub>p</sub> |
|---|---|---|---|---|
| 305. | 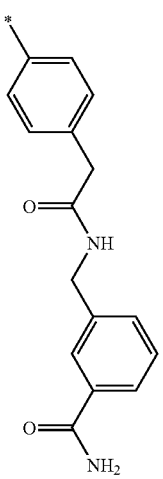 | H | 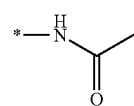 | |
| 306. | 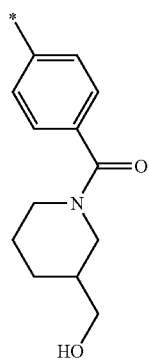 | H | 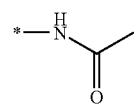 | |
| 307. | 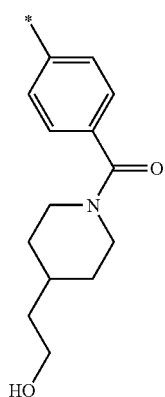 | H | 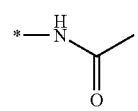 | |

-continued
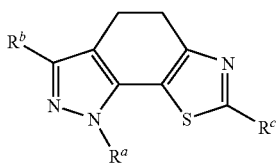
| | $R^a$ | $R^b$ | $R^c$ | $m_p$ |
|---|---|---|---|---|
| 308. | 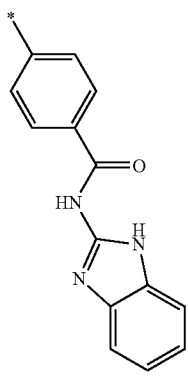 | H | 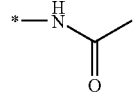 | |
| 309. | 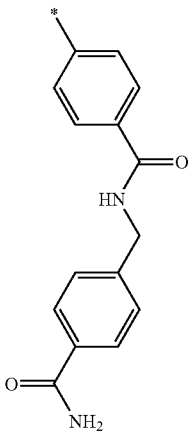 | H | 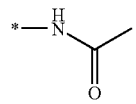 | |
| 310. | 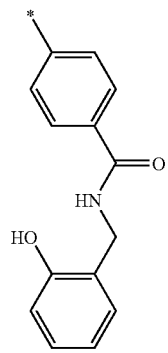 | H | 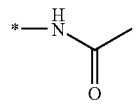 | |

-continued
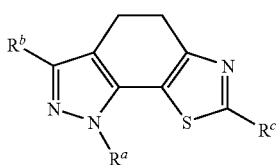
| | R$^a$ | R$^b$ | R$^c$ | m$_p$ |
|---|---|---|---|---|
| 311. | 4-(2-(hydroxymethyl)piperidine-1-carbonyl)phenyl* | H | *—NHC(O)CH$_3$ | |
| 312. | 4-(2-((diethylamino)methyl)piperidine-1-carbonyl)phenyl* | H | *—NHC(O)CH$_3$ | |
| 313. | 4-(((1,3-dioxolan-2-yl)methyl)carbamoyl)phenyl* | H | *—NHC(O)CH$_3$ | |
| 314. | 4-((3-(2-oxoimidazolidin-1-yl)benzyl)carbamoyl)phenyl* | H | *—NHC(O)CH$_3$ | |

-continued
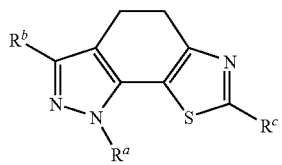
| $R^a$ | $R^b$ | $R^c$ | $m_p$ |
|---|---|---|---|
| 315. 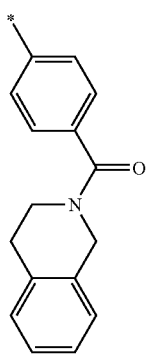 | H | 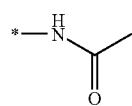 | |
| 316. 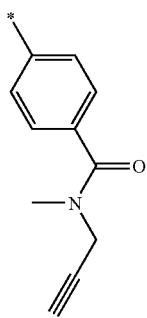 | H | 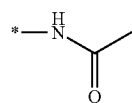 | |
| 317. 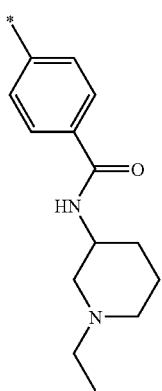 | H | 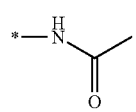 | |

| | $R^a$ | $R^b$ | $R^c$ | $m_p$ |
|---|---|---|---|---|
| 318. | *-C6H4-C(O)NH-CH(CH3)-CH2OH | H | *-NH-C(O)-CH3 | |
| 319. | *-C6H4-C(O)N(CH3)-CH2-(1-methylpyrazol-4-yl) | H | *-NH-C(O)-CH3 | |
| 320. | *-C6H4-C(O)-(2-methyl-2,7-diazaspiro[4.4]nonan-7-yl) | H | *-NH-C(O)-CH3 | |
| 321. | *-C6H4-C(O)N(CH3)-CH2-C(O)NMe2 | H | *-NH-C(O)-CH3 | |

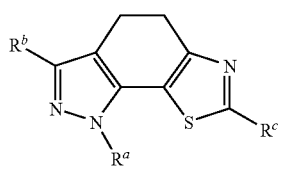
| | $R^a$ | $R^b$ | $R^c$ | $m_p$ |
|---|---|---|---|---|
| 322. | 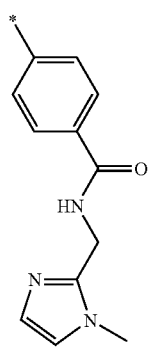 | H | 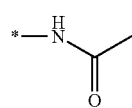 | |
| 323. | 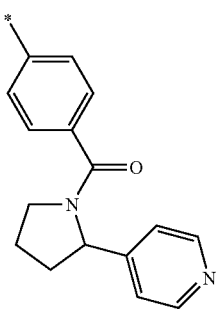 | H | 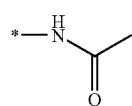 | |
| 324. | 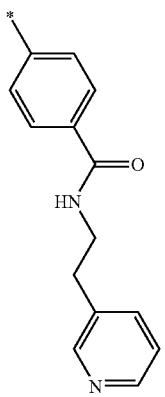 | H | 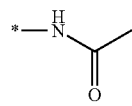 | |
| 325. | 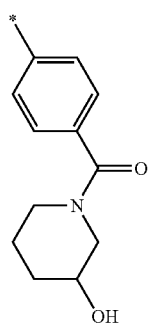 | H | 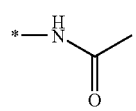 | |

-continued
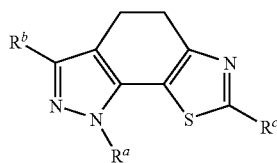
| | $R^a$ | $R^b$ | $R^c$ | $m_p$ |
|---|---|---|---|---|
| 326. | 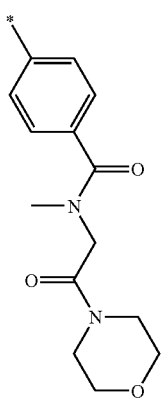 | H | 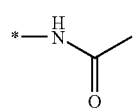 | |
| 327. | 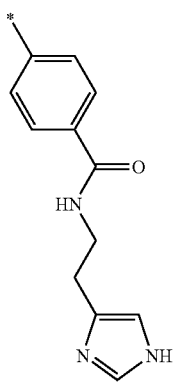 | H | 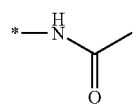 | |
| 328. | 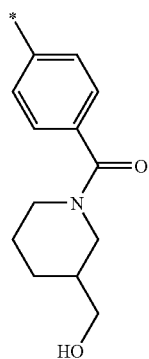 | H | 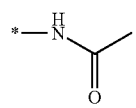 | |

-continued
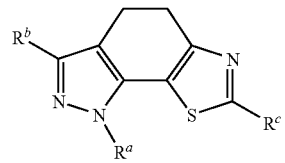
| | $R^a$ | $R^b$ | $R^c$ | $m_p$ |
|---|---|---|---|---|
| 329. | 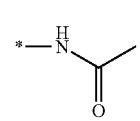 | H | 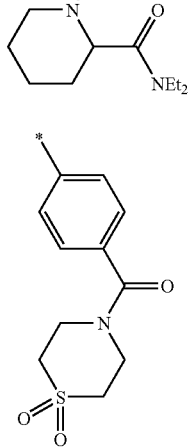 | |
| 330. | 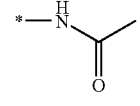 | H | 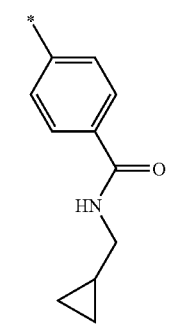 | |
| 331. | 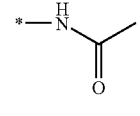 | H | 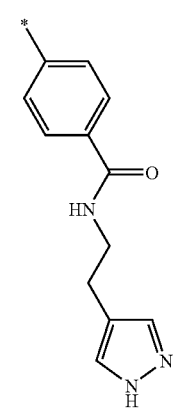 | |
| 332. | 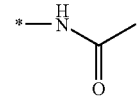 | H | 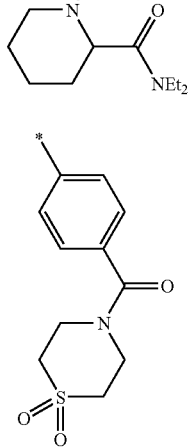 | |

-continued
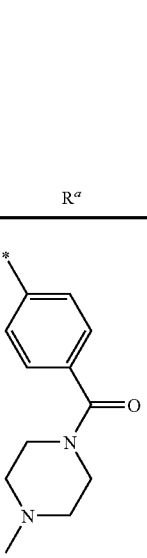
| | Rª | Rᵇ | Rᶜ | m_p |
|---|---|---|---|---|
| 333. | 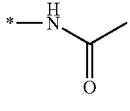 | H | 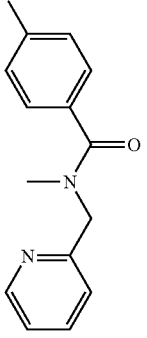 | |
| 334. | 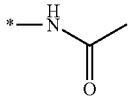 | H | 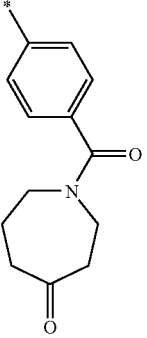 | |
| 335. | 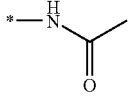 | H | 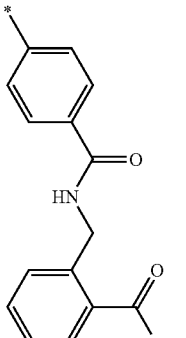 | |
| 336. | 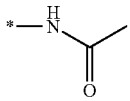 | H | | |

-continued
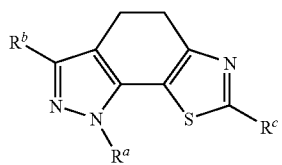
| | $R^a$ | $R^b$ | $R^c$ | $m_p$ |
|---|---|---|---|---|
| 337. | 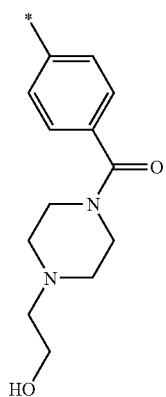 | H | 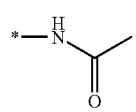 | |
| 338. | 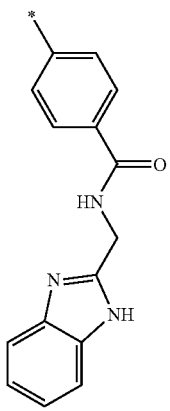 | H | 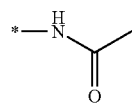 | |
| 339. | 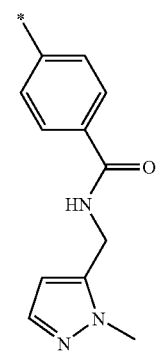 | H | 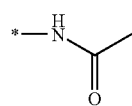 | |

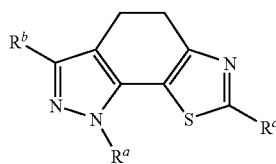
| | $R^a$ | $R^b$ | $R^c$ | $m_p$ |
|---|---|---|---|---|
| 340. | 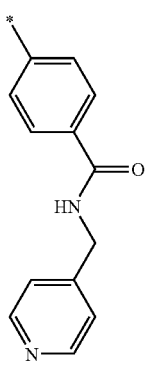 | H | 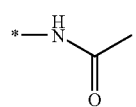 | |
| 341. | 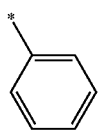 | 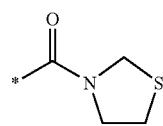 | 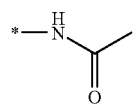 | |
| 342. | 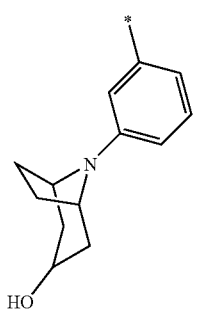 | H | 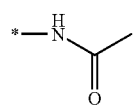 | |
| 343. | 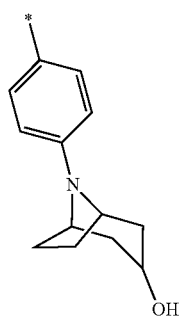 | H | 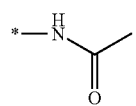 | |

EXAMPLES B

| | $R^a$ | $R^b$ | $R^c$ | $m_p$ |
|---|---|---|---|---|
| 344. | phenyl | H | *-NH-C(=O)-CH₃ | >300 |
| 345. | 3-chlorophenyl | H | *-NH-C(=O)-CH₃ | 298-305 |
| 346. | 2-chlorophenyl | H | *-NH-C(=O)-CH₃ | 255-260 |
| 347. | 2-methylphenyl | H | *-NH-C(=O)-CH₃ | 245-252 |
| 348. | 2-methoxyphenyl | H | *-NH-C(=O)-CH₃ | 288-295 |
| 349. | 2-fluorophenyl | H | *-NH-C(=O)-CH₃ | — |
| 350. | 4-methylphenyl | H | *-NH-C(=O)-CH₃ | >300 |
| 351. | 2-bromophenyl | H | *-NH-C(=O)-CH₃ | 296-300 |
| 352. | 3-methylphenyl | H | *-NH-C(=O)-CH₃ | 292-300 |
| 353. | 4-methoxyphenyl | H | *-NH-C(=O)-CH₃ | >280 |
| 354. | phenyl | H | *-NH-C(=O)-NMe₂ | 238-243 |
| 355. | phenyl | H | *-NH-C(=O)-NH₂ | >300 |
| 356. | phenyl | H | *-NH-C(=O)-NH-CH₂CH₂-NMe₂ | 205-210 |
| 357. | phenyl | H | *-NH-C(=O)-N(CH₃)-CH₂CH₂-NMe₂ | 200-204 |
| 358. | phenyl | H | *-NH-C(=O)-(4-methylpiperazin-1-yl) | 108-115 |
| 359. | 4-(SO₂CH₃)phenyl | H | *-NH-C(=O)-CH₃ | >300 |
| 360. | 2,6-dichlorophenyl | H | *-NH-C(=O)-CH₃ | 175-180 |
| 361. | 2-chlorophenyl | H | *-NH-C(=O)-NH-CH₂CH₂-NMe₂ | 172-175 |

297
-continued
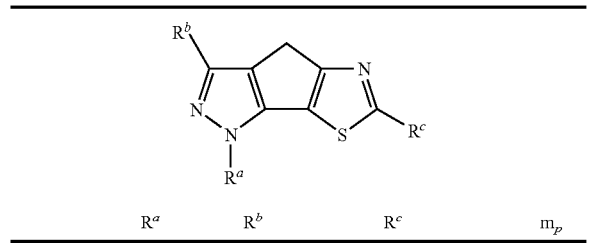
| | R$^a$ | R$^b$ | R$^c$ | m$_p$ |
|---|---|---|---|---|
| 362. | *-C$_6$H$_4$-Cl (o) | H | *-NH-C(O)-N(Me)-CH$_2$CH$_2$-NMe$_2$ | 220-222 |
| 363. | *-C$_6$H$_4$-Cl (o) | H | *-NH-C(O)-NH-Me | >250 |
| 364. | *-C$_6$H$_4$-Cl (o) | H | *-NH-C(O)-NH-CH$_2$CH$_2$-imidazolyl | 239-242 |
| 365. | *-C$_6$H$_4$-Cl (o) | H | *-NH-C(O)-NMe$_2$ | 216-219 |
298
-continued
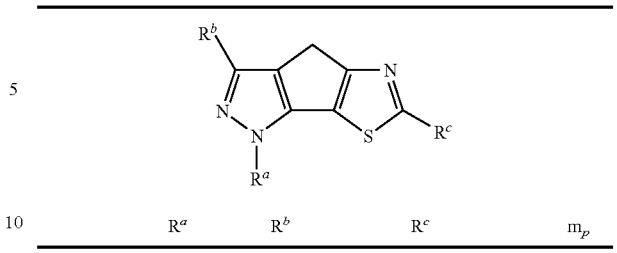
| | R$^a$ | R$^b$ | R$^c$ | m$_p$ |
|---|---|---|---|---|
| 366. | *-C$_6$H$_4$-Cl (o) | H | *-NH-C(O)-Me | >300 |
| 367. | *-C$_6$H$_4$-Et (o) | H | *-NH-C(O)-Me | 199-201 |
| 368. | *-C$_6$H$_4$-CF$_3$ (o) | H | *-NH-C(O)-Me | >300 |
| 369. | *-C$_6$H$_4$-Pr (o) | H | *-NH-C(O)-Me | 246-247 |
EXAMPLES C
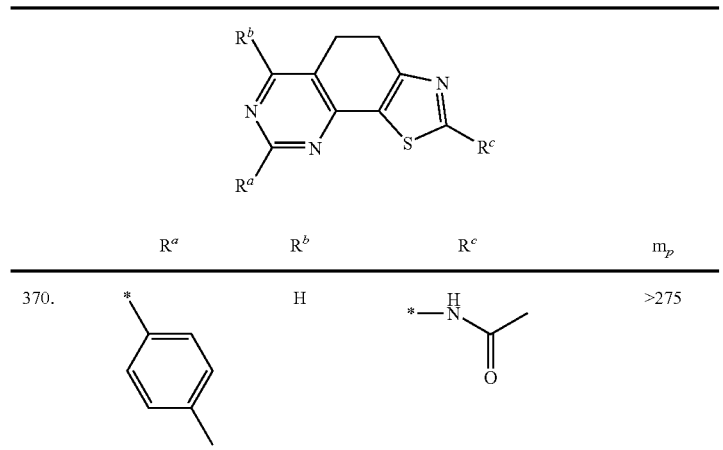
| | R$^a$ | R$^b$ | R$^c$ | m$_p$ |
|---|---|---|---|---|
| 370. | *-C$_6$H$_4$-Me (p) | H | *-NH-C(O)-Me | >275 |
| 371. | *-C$_6$H$_4$-Me (m) | H | *-NH-C(O)-Me | 267-268 |
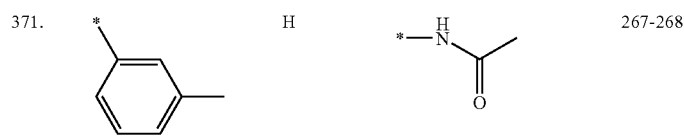

-continued
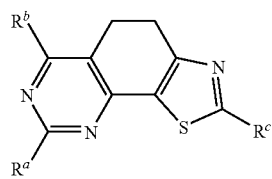
| | $R^a$ | $R^b$ | $R^c$ | $m_p$ |
|---|---|---|---|---|
| 372. | 2-pyridyl | H | *—NHC(O)CH₃ | 267-268 |
| 373. | phenyl | H | *—NHC(O)CH₃ | >295 |
| 374. | phenyl | H | *—NHC(O)NH₂ | >300 |
| 375. | phenyl | H | *—NHC(O)NHMe | >300 |
| 376. | phenyl | H | *—NHC(O)NMe₂ | 208-209 |
| 377. | phenyl | H | *—NHC(O)NHCH₂CH₂NMe | 132-133 |
| 378. | 1-pyrazolyl | H | *—NHC(O)CH₃ | >300 |
| 379. | phenyl | H | *—NHC(O)-(4-methylpiperazin-1-yl) | 147.4-150 |
| 380. | phenyl | H | *—NHC(O)-(piperidin-1-yl) | 147-149.3 |

-continued
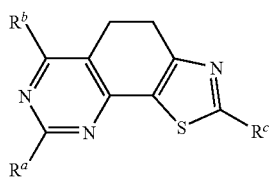
| | $R^a$ | $R^b$ | $R^c$ | $m_p$ |
|---|---|---|---|---|
| 381. | phenyl | H | *—NH-C(O)-pyrrolidine | 263.4-264.5 |
| 382. | 2-Cl-phenyl | H | *—NH-C(O)-CH₃ | 237.9-239.4 |
| 383. | 3-Cl-phenyl | H | *—NH-C(O)-CH₃ | 272-273 |
| 384. | 3-OMe-phenyl | H | *—NH-C(O)-CH₃ | 242-243 |
| 385. | 4-(H₂N-C(O))-phenyl | H | *—NH-C(O)-CH₃ | >300 |
| 386. | 2-methylphenyl | H | *—NH-C(O)-CH₃ | 196-199 |
| 387. | phenyl | H | *—NH-C(O)-NH-CH₃ | 221-222 |
| 388. | phenyl | H | *—NH-C(O)-NH₂ | >300 |
| 389. | 2-methylphenyl | H | *—NH-C(O)-N(CH₃)₂ | 231-232 |

-continued
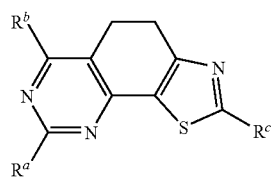
| | Rᵃ | Rᵇ | Rᶜ | m_p |
|---|---|---|---|---|
| 390. | 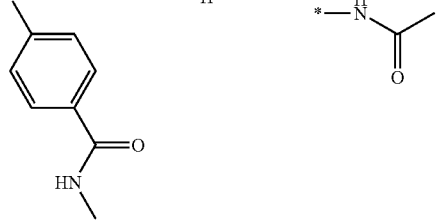 | H | *—NH-C(O)-CH₃ | >300 |
| 391. | 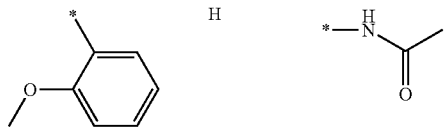 | H | *—NH-C(O)-CH₃ | 234-234.5 |
| 392. | 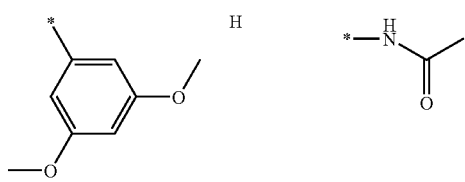 | H | *—NH-C(O)-CH₃ | 273-274 |
| 393. | 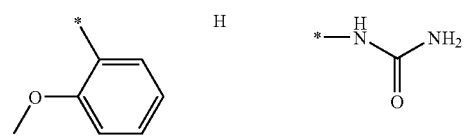 | H | *—NH-C(O)-NH₂ | 194-196 |
| 394. | 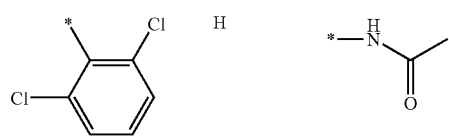 | H | *—NH-C(O)-CH₃ | 287.7-289 |
| 395. | 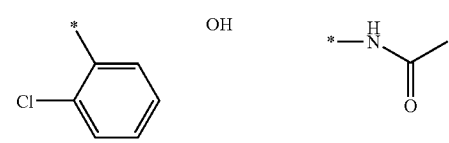 | OH | *—NH-C(O)-CH₃ | |

EXAMPLES D
| | R$^a$ | R$^b$ | R$^c$ | m$_p$ |
|---|---|---|---|---|
| 396. | 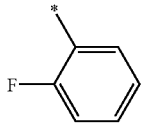 | 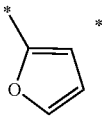 | 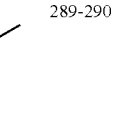 | 289-290 |
| 397. | 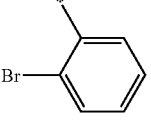 | 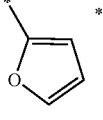 |  | >300 |
| 398. | 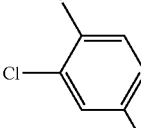 | 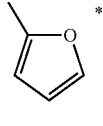 |  | |
| 399. | 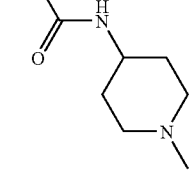 | 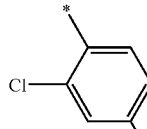 | 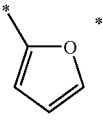 | |
| 400. |  | 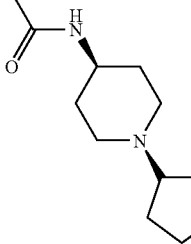 | 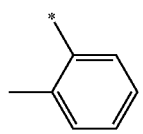 | >300 |
| 401. | 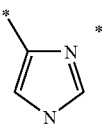 |  | 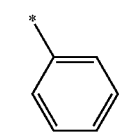 | >300 |

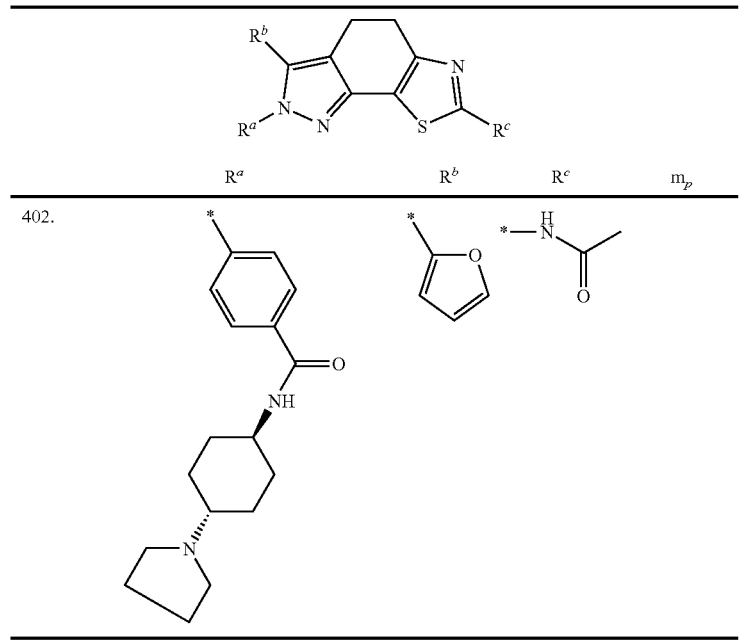
| | $R^a$ | $R^b$ | $R^c$ | $m_p$ |
|---|---|---|---|---|
| 402. | 4-(trans-4-pyrrolidin-1-yl-cyclohexylaminocarbonyl)phenyl | 2-furyl | *—NHC(O)CH₃ | |
| 403. | —CH₃ | H | *—NHC(O)CH₃ | |
| 404. | *-n-butyl | H | *—NHC(O)CH₃ | |
| 405. | *-CH₂CH₂-phenyl | H | *—NHC(O)CH₃ | |
| 406. | *-isopropyl | H | *—NHC(O)CH₃ | |
| 407. | *-ethyl | H | *—NHC(O)CH₃ | |
| 408. | *-(1-trifluoroacetyl-piperidin-4-yl) | H | *—NHC(O)CH₃ | |
| 409. | *-n-propyl | H | *—NHC(O)CH₃ | 246-247 |
| 410. | *-(2-chlorobenzoyl) | H | *—NHC(O)CH₃ | |
| 411. | *-CH₂CH=CHCH₃ | H | *—NHC(O)CH₃ | |
| 412. | *-CH₂CH=CHCH₃ | H | *—NHC(O)CH₃ | |
EXAMPLES E

309
-continued

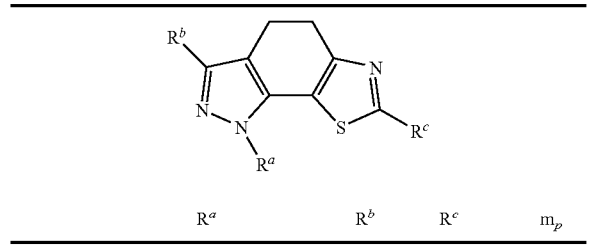

| | $R^a$ | $R^b$ | $R^c$ | $m_p$ |
|---|---|---|---|---|
| 413. | *isopentyl | H | *-NHC(O)CH3 | 191 |
| 414. | *butanoyl | H | *-NHC(O)CH3 | |
| 415. | *cyclopropanecarbonyl | H | *-NHC(O)CH3 | |
| 416. | *isobutanoyl | H | *-NHC(O)CH3 | |

EXAMPLES F

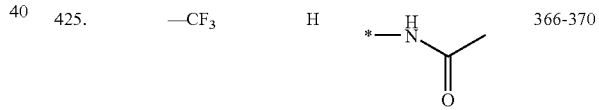

| | $R^a$ | $R^b$ | $R^c$ | $m_p$ |
|---|---|---|---|---|
| 417. | *cyclohexyl | H | *-NHC(O)CH3 | |
| 418. | *cyclopropyl | H | *-NHC(O)CH3 | |
| 419. | *tert-butyl | H | *-NHC(O)CH3 | |

310
-continued

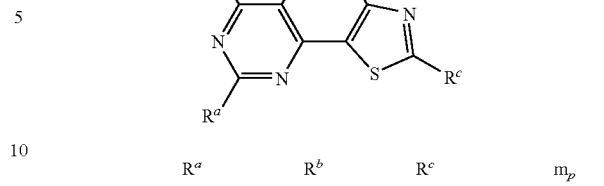

| | $R^a$ | $R^b$ | $R^c$ | $m_p$ |
|---|---|---|---|---|
| 420. | *2,6-dichlorobenzyl | H | *-NHC(O)CH3 | |
| 421. | *(2-chlorophenoxy)methyl | H | *-NHC(O)CH3 | |
| 422. | *morpholino | H | *-NHC(O)CH3 | |
| 423. | *NHCH3 | H | *-NHC(O)CH3 | 235-238 |
| 424. | *N(CH3)2 | H | *-NHC(O)CH3 | 281-282 |
| 425. | —CF3 | H | *-NHC(O)CH3 | 366-370 |
| 426. | *isopropyl | H | *-NHC(O)CH3 | 248.4-250.6 |
| 427. | *phenethyl | H | *-NHC(O)CH3 | 198-199 |
| 428. | —CH3 | H | *-NHC(O)CH3 | 224-225 |
| 429. | *benzyl | H | *-NHC(O)CH3 | 94-103 |

311
-continued
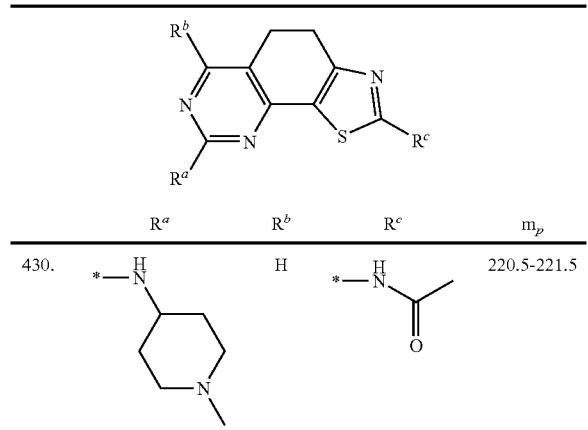
| | R^a | R^b | R^c | m_p |
|---|---|---|---|---|
| 430. | 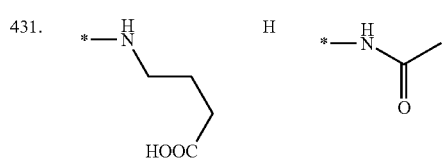 | H | 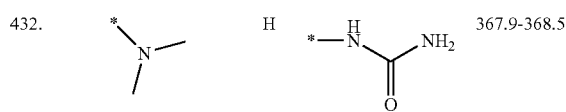 | 220.5-221.5 |
| 431. | 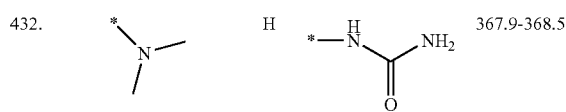 | H | 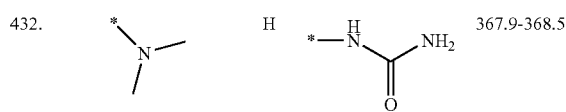 | |
| 432. | 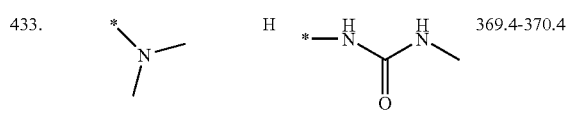 | H | 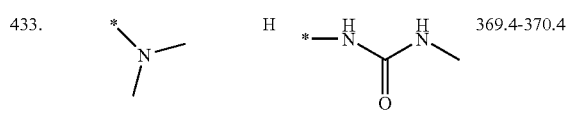 | 367.9-368.5 |
| 433. | 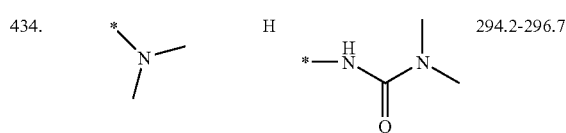 | H | 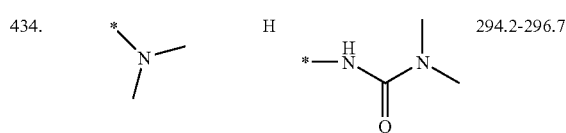 | 369.4-370.4 |
| 434. | 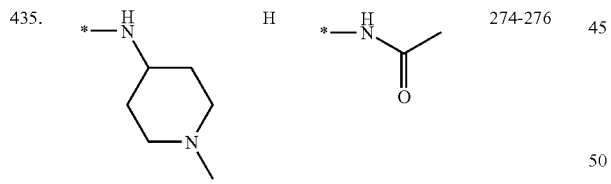 | H | 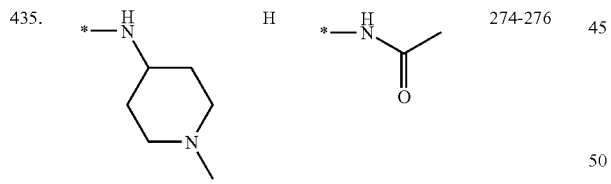 | 294.2-296.7 |
| 435. | 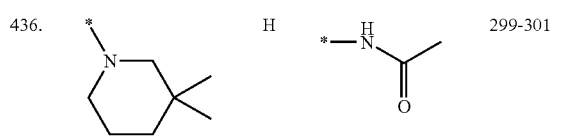 | H | 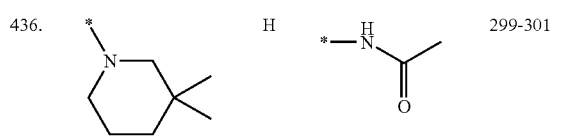 | 274-276 |
| 436. | 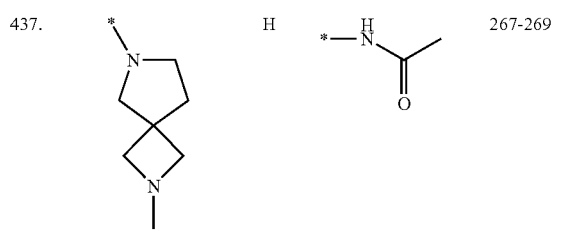 | H | | 299-301 |
| 437. | 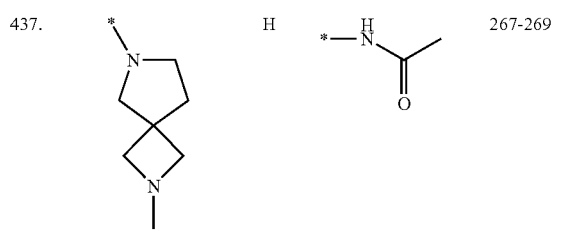 | H | | 267-269 |
312
-continued
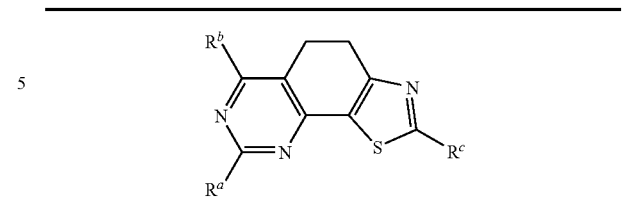
| | R^a | R^b | R^c | m_p |
|---|---|---|---|---|
| 438. | 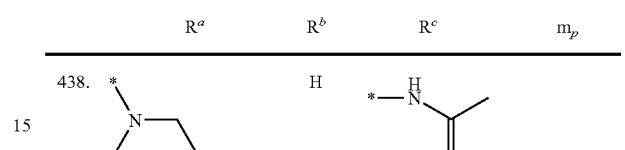 | H | 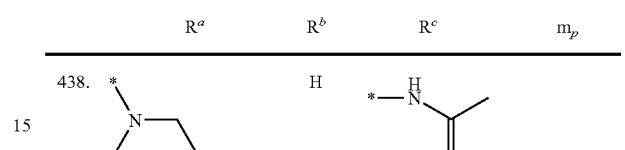 | |
| 439. | 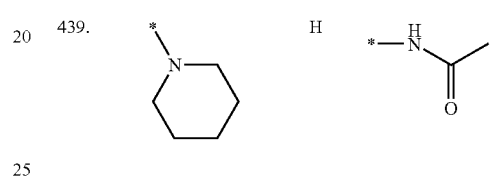 | H | 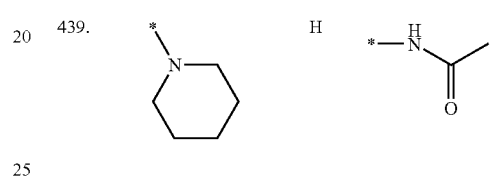 | |
| 440. | 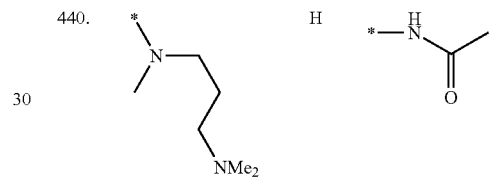 | H | 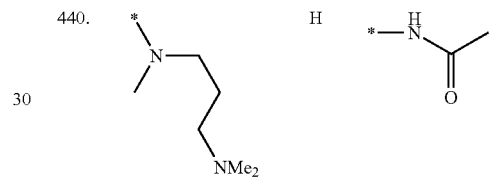 | |
| 441. | 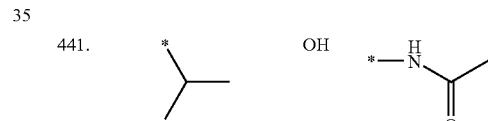 | OH | 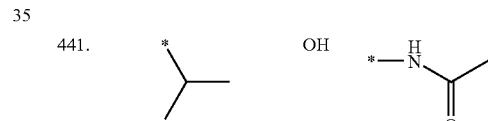 | |
| 442. | 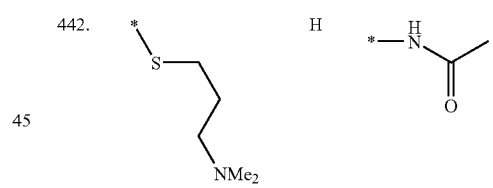 | H | 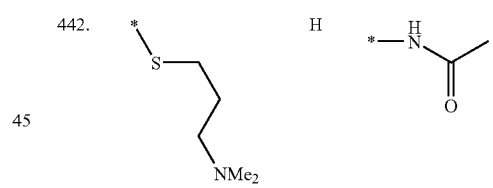 | |
| 443. | 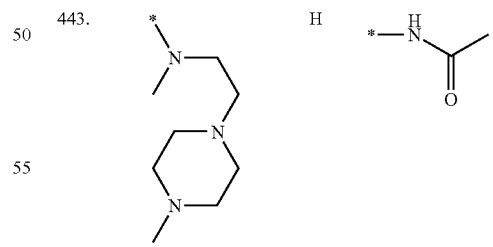 | H | 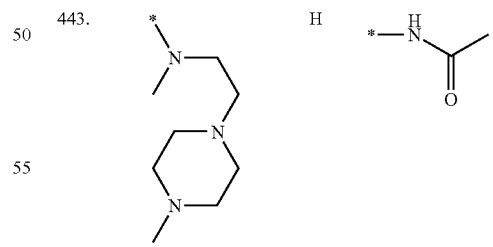 | |
| 444. | 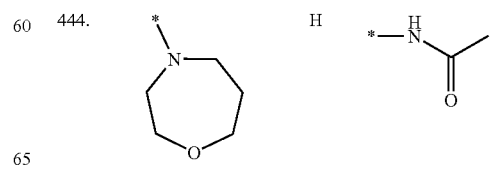 | H | 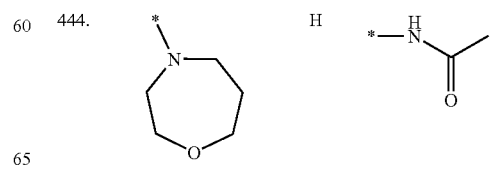 | |

EXAMPLES G

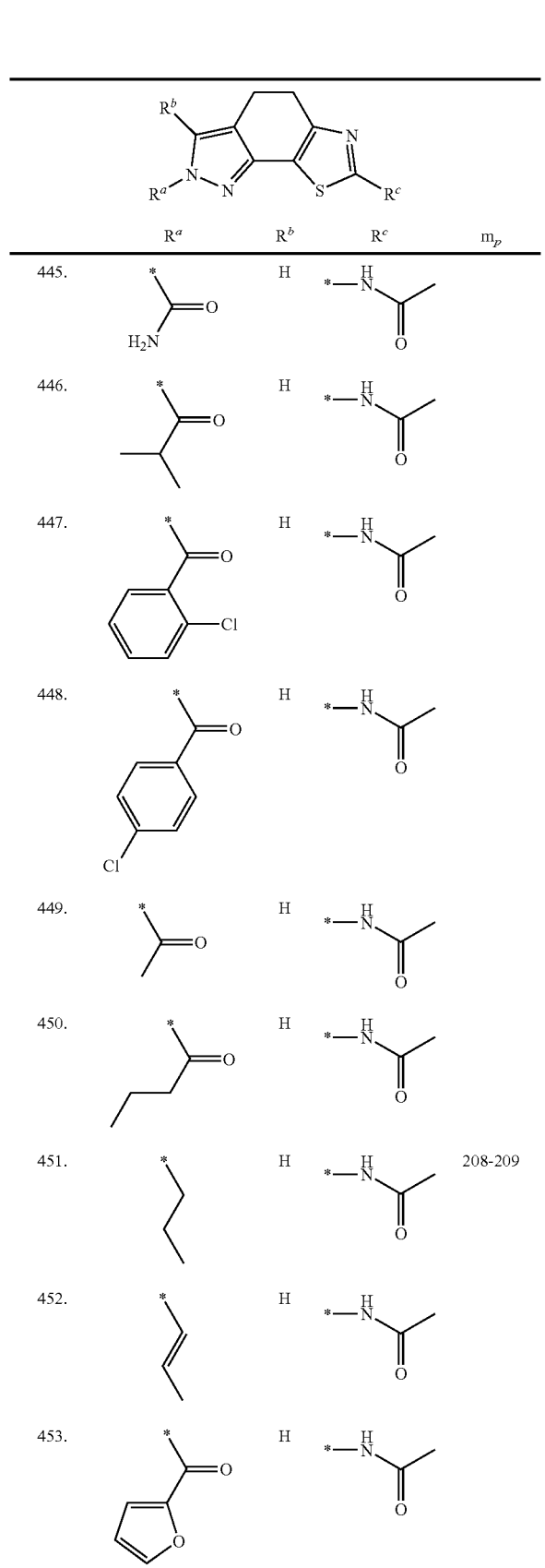

EXAMPLES H

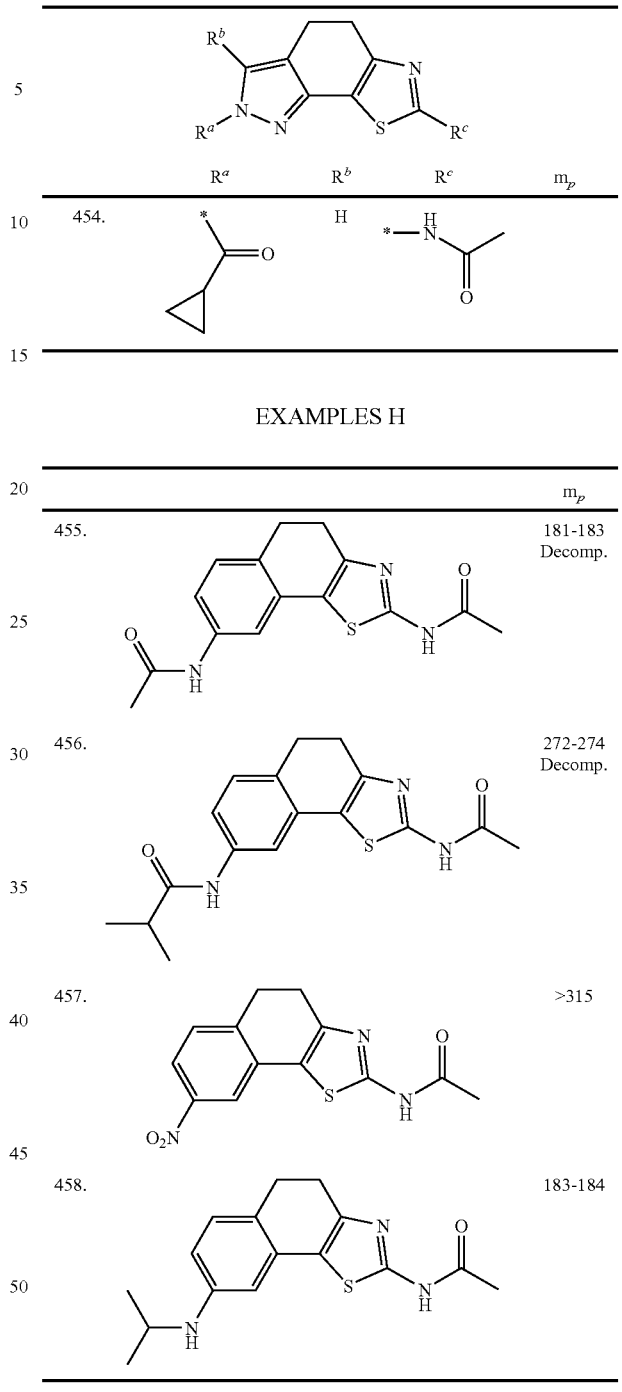

Ranges of Indications

It has been found that the compounds of formula 1 are characterised by a variety of possible applications in the therapeutic field. Particular mention should be made of those applications for which the compounds of formula 1 according to the invention are preferably used by virtue of their pharmaceutical activity as PI3-kinase modulators.

Generally speaking, these are diseases in whose pathology PI3-kinases are implicated, particularly inflammatory and allergic diseases. Particular mention should be made of inflammatory and allergic respiratory complaints, inflammatory diseases of the gastrointestinal tract, inflammatory diseases of the motor apparatus, inflammatory and allergic skin diseases, inflammatory eye diseases, diseases of the nasal mucosa, inflammatory or allergic ailments which involve autoimmune reactions or inflammation of the kidneys. The treatment may be symptomatic, adaptive, curative or preventative.

Respiratory complaints deserving special mention would be chronic and/or obstructive respiratory complaints. The compounds of formula 1 according to the invention may, by virtue of their pharmacological properties, bring about a reduction in Tissue Damage
Inflammation of the airways
bronchial hyperreactivity
the process of reconstruction of the lung as a result of inflammation
worsening of the disease (progression).

The compounds according to the invention are particularly preferred for preparing a medicament for the treatment of chronic bronchitis, acute bronchitis, bronchitis caused by bacterial or viral infection or fungi or helminths, allergic bronchitis, toxic bronchitis, chronic obstructive bronchitis (COPD), asthma (intrinsic or allergic), pediatric asthma, bronchiectasis, allergic alveolitis, allergic or non-allergic rhinitis, chronic sinusitis, cystic fibrosis or mucoviscidosis, alpha-1-antitrypsin deficiency, cough, pulmonary emphysema, interstitial lung diseases such as e.g. pulmonary fibrosis, asbestosis and silicosis and alveolitis; hyperreactive airways, nasal polyps, pulmonary oedema such as e.g. toxic pulmonary oedema and ARDS/IRDS, pneumonitis of different origins, e.g. radiation-induced or by caused by aspiration or infectious pneumonitis, collagenoses such as lupus eryth, systemic sclerodermy, sarcoidosis or Boeck's disease.

The compounds of formula 1 are also suitable for the treatment of diseases of the skin, such as e.g. psoriasis, contact dermatitis, atopic dermatitis, alopecia areata (circular hair loss), erythema exsudativum multiforme (Stevens-Johnson Syndrome), dermatitis herpetiformis, sclerodermy, vitiligo, nettle rash (urticaria), lupus erythematodes, follicular and surface pyodermy, endogenous and exogenous acne, acne rosacea and other inflammatory or allergic or proliferative skin diseases.

Moreover, the compounds of formula 1 are suitable for therapeutic use in cases of inflammatory or allergic complaints which involve autoimmune reactions, such as e.g. inflammatory bowel diseases, e.g. Crohn's disease or ulcerative colitis; diseases of the arthritis type, such as e.g. rheumatoid or psoriatic arthritis, osteoarthritis, rheumatoid spondylitis and other arthritic conditions or multiple sclerosis.

The following general inflammatory or allergic diseases may also be mentioned, which can be treated with medicaments containing compounds of formula 1:

inflammation of the eye, such as e.g. conjunctivitis of various kinds, e.g. caused by infections with fungi or bacteria, allergic conjunctivitis, irritable conjunctivitis, drug-induced conjunctivitis, keratitis, uveitis diseases of the nasal mucosa, such as e.g. allergic rhinitis/sinusitis or nasal polyps inflammatory or allergic conditions, such as e.g. systemic lupus erythematodes, chronic hepatitis, kidney inflammations such as glomerulonephritis, interstitial nephritis or idiopathic nephrotic syndrome.

Other diseases which may be treated with a drug containing compounds of formula 1 on the basis of their pharmacological activity include toxic or septic shock syndrome, atherosclerosis, middle ear infections (otitis media), hypertrophy of the heart, cardiac insufficiency, stroke, ischaemic reperfusion injury or neurodegenerative diseases such as Parkinson's disease or Alzheimer's.

Combinations

The compounds of formula 1 may be used on their own or in conjunction with other active substances of formula 1 according to the invention. If desired the compounds of general formula 1 may also be used in conjunction with other pharmacologically active substances.

Preferably active substances are used which are selected, for example, from among the betamimetics, anticholinergics, corticosteroids, PDE4-inhibitors, LTD4-antagonists, EGFR-inhibitors, dopamine-agonists, H1-antihistamines, PAF-antagonists and PI3-kinase inhibitors or double or triple combinations thereof, such as for example combinations of Betamimetics with corticosteroids, PDE4-inhibitors, EGFR-inhibitors or LTD4-antagonists,
Anticholinergics with betamimetics, corticosteroids, PDE4-inhibitors, EGFR-inhibitors or LTD4-antagonists,
corticosteroids with PDE4-inhibitors, EGFR-inhibitors or LTD4-antagonists
PDE4-inhibitors with EGFR-inhibitors or LTD4-antagonists
EGFR-inhibitors with LTD4-antagonists.

The invention also encompasses combinations of three active substances, each selected from one of the above-mentioned categories of compounds.

Suitable betamimetics used are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, sulphsoterenol, sulphonterol, terbutaline, tiaramide, tolubuterol, zinterol, CHF-1035, HOKU-81, KUL-1248 and
3-(4-{6-[2-hydroxy-2-(4-hydroxy-3-hydroxymethyl-phenyl)-ethylamino]-hexyloxy}-butyl)-benzyl-sulphonamide
5-[2-(5,6-diethyl-indan-2-ylamino)-1-hydroxy-ethyl]-8-hydroxy-1H-quinolin-2-one
4-hydroxy-7-[2-{[2-{[3-(2-phenylethoxy)propyl]sulphonyl}ethyl]-amino}ethyl]-2(3H)-benzothiazolone
1-(2-fluoro-4-hydroxyphenyl)-2-[4-(1-benzimidazolyl)-2-methyl-2-butylamino]ethanol
1-[3-(4-methoxybenzyl-amino)-4-hydroxyphenyl]-2-[4-(1-benzimidazolyl)-2-methyl-2-butylamino]ethanol
1-[2H-5-hydroxy-3-oxo-4H-1,4-benzoxazin-8-yl]-2-[3-(4-N,N-dimethylaminophenyl)-2-methyl-2-propylamino]ethanol
1-[2H-5-hydroxy-3-oxo-4H-1,4-benzoxazin-8-yl]-2-[3-(4-methoxyphenyl)-2-methyl-2-propylamino]ethanol
1-[2H-5-hydroxy-3-oxo-4H-1,4-benzoxazin-8-yl]-2-[3-(4-n-butyloxyphenyl)-2-methyl-2-propylamino]ethanol
1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2,4,6-trimethyl phenyl)-ethylamino]-1-hydroxy-ethyl}6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1,1dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3,4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol optionally in the form of the racemates, enantiomers, diastereomers and optionally in the form of the pharmacologically acceptable acid addition salts, solvates or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active ingredients. As anions the above-mentioned salts may preferably contain chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chloride, bromide, iodide and methanesulphonate are particularly preferred. Other named compounds are:
tropenol 2,2-diphenylpropionate-methobromide
scopine 2,2-diphenylpropionate-methobromide
scopine 2-fluoro-2,2-diphenylacetate-methobromide
tropenol 2-fluoro-2,2-diphenylacetate-methobromide
tropenol 3,3',4,4'-tetrafluorobenzilate-methobromide
scopine 3,3',4,4'-tetrafluorobenzilate-methobromide
tropenol 4,4'-difluorobenzylate-methobromide
scopine 4,4'-difluorobenzylate-methobromide
tropenol 3,3'-difluorobenzylate-methobromide
scopine 3,3'-difluorobenzylate-methobromide
tropenol 9-hydroxy-fluorene-9-carboxylate-methobromide
tropenol 9-fluoro-fluorene-9-carboxylate-methobromide
scopine 9-hydroxy-fluorene-9-carboxylate-methobromide
scopine 9-fluoro-fluorene-9-carboxylate-methobromide
tropenol 9-methyl-fluorene-9-carboxylate-methobromide
scopine 9-methyl-fluorene-9-carboxylate-methobromide
cyclopropyltropine benzylate-methobromide
cyclopropyltropine 2,2-diphenylpropionat-methobromide
cyclopropyltropine 9-hydroxy-xanthene-9-carboxylate-methobromide
cyclotropine 9-methyl-fluorene-9-carboxylate-methobromide
cyclotropine 9-methyl-xanthene-9-carboxylate-methobromide
cyclotropine 9-hydroxy-fluorene-9-carboxylate-methobromide
methyl cyclopropyltropine 4,4'-difluorobenzylate-methobromide
tropenol 9-hydroxy-xanthene-9-carboxylate-methobromide
scopine 9-hydroxy-xanthene-9-carboxylate-methobromide
tropenol 9-methyl-xanthene-9-carboxylate-methobromide
scopine 9-methyl-xanthene-9-carboxylate methobromide
tropenol 9-ethyl-xanthene-9-carboxylate-methobromide
tropenol 9-difluormethyl-xanthene-9-carboxylate-methobromide
scopine 9-hydroxymethyl-xanthene-9-carboxylate-methobromide Corticosteroids used here are preferably compounds selected from among prednisolone, prednisone, butixocortpropionate, flunisolide, beclomethasone, triamcinolone, budesonide, fluticasone, mometasone, ciclesonide, rofleponide, dexamethasone, betamethasone, deflazacort, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3S-yl) 6,9-difluoro-11-hydroxy-16-methyl-3-oxo-17-propionyloxy-androsta-1,4-diene-17-carbothionate,
etiprednol-dichloroacetate optionally in the form of the racemates, enantiomers or diastereomers thereof and optionally in the form of the salts and derivatives, solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulfobenzoates, phosphates, isonicotinates, acetates, propionates, dihydrogenphosphates, palmitates, pivalates or furoates thereof.

PDE4 inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, CI-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)$_p$-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N$^2$-cyano-5-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of the racemates, enantiomers, diastereomers and optionally in the form of the pharmacologically acceptable acid addition salts, solvates or hydrates thereof. Preferably, according to the invention, the acid addition salts of the PDE4 inhibitors are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

LTD4-antagonists which may be used are preferably compounds selected from among montelukast, pranlukast, zafirlukast, MCC-847 (ZD-3523), MN-001, MEN-91507 (LM-1507), VUF-5078, VUF-K-8707, L-733321 and
1-(((R)-(3-(2-(6,7-difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropane-acetic acid
[2-[[2-(4-tert-butyl-2-thiazolyl)-5-benzofuranyl]oxymethyl]phenyl]acetic acid
optionally in the form of the racemates, enantiomers, diastereomers and optionally in the form of the pharmacologically acceptable acid addition salts, solvates or hydrates thereof. Preferably, according to the invention, the acid addition salts of the LTD4-antagonists are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate und hydro-p-toluenesulphonate. By salts or derivatives which the LTD4-antagonists may be capable of forming are meant, for example: alkali metal salts, such as for example sodium or potassium salts, alkaline earth metal salts, sulphobenzoates, phosphates, isonicotinates, acetates, propionates, dihydrogenphosphates, palmitates, pivalates or furoates.

EGFR-inhibitors which may be used are preferably compounds selected from among cetuximab, trastuzumab, ABX-EGF, Mab ICR-62 and
4-[(3-chloro-4-fluorophenyl)amino]-6-{[4-(morpholin-4-yl)-1-oxo-2-buten-1-yl]amino}-7-cyclopropylmethoxy-quinazoline
4-[(3-chloro-4-fluorophenyl)amino]-6-{[4-(N,N-diethylamino)-1-oxo-2-buten-1-yl]amino}-7-cyclopropylmethoxy-quinazoline
4-[(3-chloro-4-fluorophenyl)amino]-6-{[4-(N,N-dimethylamino)-1-oxo-2-buten-1-yl]amino}-7-cyclopropylmethoxy-quinazoline
4-[(R)-(1-phenyl-ethyl)amino]-6-{[4-(morpholin-4-yl)-1-oxo-2-buten-1-yl]-amino}-7-cyclopentyloxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline
4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline
4-[(3-chloro-4-fluoro-phenyl)amino]-6-[2-((S)-6-methyl-2-oxo-morpholin-4-yl)-ethoxy]-7-methoxy-quinazoline
4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethylamino)-1-oxo-2-buten-1-yl]amino}-7-cyclopentyloxy-quinazoline
4-[(R)-(1-phenyl-ethyl)amino]-6-{[4-(N,N-bis-(2-methoxy-ethyl)-amino]-1-oxo-2-buten-1-yl}amino}-7-cyclopropylmethoxy-quinazoline
4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline
4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline
4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline
4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline
4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline
4-[(3-chloro-4-fluorophenyl)amino]-6-{[4-(N-cyclopropyl-N-methyl-amino)-1-oxo-2-buten-1-yl]amino}-7-cyclopentyloxy-quinazoline
4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline
4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline
4-[(3-ethynyl-phenyl)amino]-6,7-bis-(2-methoxy-ethoxy)-quinazoline
4-[(3-chloro-4-fluorophenyl)amino]-7-[3-(morpholin-4-yl)-propyloxy]-6-[(vinylcarbonyl)amino]-quinazoline
4-[(R)-(1-phenyl-ethyl)amino]-6-(4-hydroxy-phenyl)-7H-pyrrolo[2,3-d]pyrimidine
3-cyano-4-[(3-chloro-4-fluorophenyl)amino]-6-{[4-(N,N-dimethylamino)-1-oxo-2-buten-1-yl]amino}-7-ethoxy-quinoline
4-{[3-chloro-4-(3-fluoro-benzyloxy)-phenyl]amino}-6-(5-{[(2-methanesulphonyl-ethyl)amino]methyl}-furan-2-yl)quinazoline
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline
4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline
4-[(3-chloro-4-fluorophenyl)amino]-6-({4-[N,N-bis-(2-methoxy-ethyl)-amino]-1-oxo-2-buten-1-yl}amino)-7-[(tetrahydrofuran-2-yl)methoxy]-quinazoline
4-[(3-ethynyl-phenyl)amino]-6-{[4-(5,5-dimethyl-2-oxo-morpholin-4-yl)-1-oxo-2-buten-1-yl]amino}-quinazoline
4-[(3-chloro-4-fluoro-phenyl)amino]-6-[2-(2,2-dimethyl-6-oxo-morpholin-4-yl)-ethoxy]-7-methoxy-quinazoline
4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(methoxymethyl)carbonyl]-piperidin-4-yloxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylaminoethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7-(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2.2.1]hept-5-yl)carbonyl]-piperidin-4-yloxy}-7-methoxy-quinazoline 4-[(3-chloro-4-fluoro-phenyl)amino]-6-{1-[(N-methyl-$N^2$-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methane-sulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers and optionally in the form of the pharmacologically acceptable acid addition salts, solvates or hydrates thereof. Preferably, according to the invention, the acid addition salts of the EGFR-inhibitors are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

Dopamine agonists which may be used are preferably compounds selected from among bromocriptin, cabergolin, alpha-dihydroergocryptin, lisuride, pergolide, pramipexol, roxindol, ropinirol, talipexol, terguride and viozan, optionally in the form of the racemates, enantiomers, diastereomers and optionally in the form of the pharmacologically acceptable acid addition salts, solvates or hydrates thereof.

Preferably, according to the invention, the acid addition salts of the Dopamine agonists are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastin, cetirizin, azelastin, fexofenadin, levocabastin, loratadin, mizolastin, ketotifen, emedastin, dimetinden, clemastin, bamipin, cexchlorpheniramine, pheniramine, doxylamine, chlorphenoxamine, dimenhydrinate, diphenhydramine, promethazine, ebastin, desloratidine and meclozine, optionally in the form of the racemates, enantiomers, diastereomers and optionally in the form of the pharmacologically acceptable acid addition salts, solvates or hydrates thereof. Preferably, according to the invention, the acid addition salts of the H1-Antihistamines are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

PAF-Antagonists which may be used are preferably compounds selected from among 4-(2-chlorophenyl)-9-methyl-2-[3(4-morpholinyl)-3-propanon-1-yl]-6H-thieno-[3,2-f]-[1,2,4]triazolo[4,3-a][1,4]diazepine 6-(2-chlorophenyl)-8,9-dihydro-1-methyl-8-[(4-morpholinyl)carbonyl]-4H,7H-cyclo-penta-[4,5]thieno-[3,2-f][1,2,4]triazolo[4,3-a][1,4]diazepine optionally in the form of the racemates, enantiomers, diastereomers and optionally in the form of the pharmacologically acceptable acid addition salts, solvates or hydrates thereof. Preferably, according to the invention, the acid addition salts of the PAF-Antagonists are selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

Formulations

The compounds according to the invention may be administered by oral, transdermal, inhalative, parenteral or sublingual route. The compounds according to the invention are present as active ingredients in conventional preparations, for example in compositions consisting essentially of an inert pharmaceutical carrier and an effective dose of the active substance, such as for example tablets, coated tablets, capsules, lozenges, powders, solutions, suspensions, emulsions, syrups, suppositories, transdermal systems etc. An effective dose of the compounds according to the invention is between 0.1 and 5000, preferably between 1 and 500, more preferably between 5-300 mg/dose for oral administration, and between 0.001 and 50, preferably between 0.1 and 10 mg/dose for intravenous. subcutaneous or intramuscular administration. For inhalation, according to the invention, solutions containing 0.01 to 1.0, preferably 0.1 to 0.5% active substance are suitable. For administration by inhalation the use of powders, ethanolic or aqueous solutions is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable formulations include, for example, tablets, capsules, suppositories, solutions, syrups, emulsions or dispersible powders. Corresponding tablets may be obtained for example by mixing the active substance(s) with known excipients, for example inert diluents, such as calcium carbonate, calcium phosphate or lactose, disintegrants such as maize starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g. with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules. Suitable suppositories may be made for example by mixing with carriers provided for this purpose, such as neutral fats or polyethyleneglycol or the derivatives thereof.

A therapeutically effective daily dose is between 1 and 2000 mg, preferably 10-500 mg per adult.

The Examples which follow illustrate the present invention without restricting its scope:

Examples of Pharmaceutical Formulations

| A) Tablets | per tablet |
|---|---|
| active substance | 100 mg |
| lactose | 140 mg |
| maize starch | 240 mg |
| polyvinylpyrrolidone | 15 mg |
| magnesium stearate | 5 mg |
| | 500 mg |

The finely ground active substance, lactose and some of the corn starch are mixed together. The mixture is screened, then moistened with a solution of polyvinylpyrrolidone in water, kneaded, granulated while wet and dried. The granulate, the rest of the corn starch and the magnesium stearate are screened and mixed together. The mixture is compressed to form tablets of a suitable shape and size.

| B) Tablets | per tablet |
|---|---|
| active substance | 80 mg |
| corn starch | 190 mg |
| lactose | 55 mg |
| microcrystalline cellulose | 35 mg |
| polyvinylpyrrolidone | 15 mg |
| sodium-carboxymethyl starch | 23 mg |
| magnesium stearate | 2 mg |
| | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C) Coated tablets | per coated tablet |
|---|---|
| Active substance | 5 mg |
| Corn starch | 41.5 mg |
| Lactose | 30 mg |
| Polyvinylpyrrolidone | 3 mg |
| Magnesium stearate | 0.5 mg |
| | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in a known manner with a covering consisting essentially of sugar and talc. The finished coated tablets are polished with wax

| D) Capsules | per capsule |
|---|---|
| Active substance | 50 mg |
| Corn starch | 268.5 mg |
| Magnesium stearate | 1.5 mg |
| | 320 mg |

The substance and corn starch are mixed and moistened with water. The moist mass is screened and dried. The dry granules are screened and mixed with magnesium stearate. The finished mixture is packed into size 1 hard gelatine capsules.

| E) Ampoule solution | |
|---|---|
| active substance | 50 mg |
| sodium chloride | 50 mg |
| water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

| F) Suppositories | |
|---|---|
| Active substance | 50 mg |
| Solid fat | 1650 mg |
| | 1700 mg |

The hard fat is melted. At 40° C. the ground active substance is homogeneously dispersed. It is cooled to 38° C. and poured into slightly chilled suppository moulds.

|   |   |   |
|---|---|---|
| G) | Oral suspension | |
| | active substance | 50 mg |
| | hydroxyethylcellulose | 50 mg |
| | sorbic acid | 5 mg |
| | sorbitol (70%) | 600 mg |
| | glycerol | 200 mg |
| | flavouring | 15 mg |
| | water ad | 5 ml |

Distilled water is heated to 70° C. Hydroxyethyl-cellulose is dissolved therein with stirring. After the addition of sorbitol solution and glycerol the mixture is cooled to ambient temperature. At ambient temperature, sorbic acid, flavouring and substance are added. To eliminate air from the suspension it is evacuated with stirring.

What is claimed is:

1. A compound of formula 1;

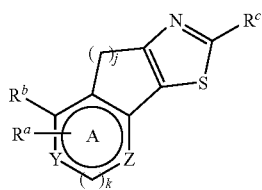

1 with the proviso that the circular line designated A denotes an aromatic system;
wherein
Y denotes nitrogen;
Z denotes nitrogen;
j denotes 3;
k denotes 0;
$R^a$ denotes H, $COR^8$, $NR^9R^{10}$, $NO_2$, $OR^8$, $SR^{11}$, $SOR^{11}$, $SO_2R^{11}$, $NHCO$—$C_{1-6}$-alkyl-$NH_2$, or a group selected from among $C_{1-6}$-alkyl, $C_{2-6}$-alkenyl, $C_{3-8}$-cycloalkyl, $C_{3-8}$-cycloalkenyl, $C_{1-6}$-haloalkyl, aryl, $C_{7-11}$-aralkyl, spiro, het, hetaryl and $CH_2$—O-aryl, which may optionally be substituted;
$R^8$ denotes $C_{1-6}$-alkyl, $C_{3-6}$-cycloalkyl, $NH_2$, hetaryl or aryl, optionally substituted by one or more halogens or $C_{1-4}$-alkyl;
$R^9$ denotes H, $COOR^{12}$, $CONHR^{12}$ or $C_{1-6}$-alkyl, optionally substituted by one or more COOH, $N(C_{1-6}$-alkyl$)_2$ or het, optionally substituted by one or more $C_{1-6}$-alkyl; or $R^9$ denotes het, optionally substituted by one or more $C_{1-4}$-alkyl;
$R^{10}$ denotes H, $C_{1-6}$-alkyl, CO—$C_{1-6}$-alkyl or $C_{2-6}$-alkynyl;
$R^{11}$ denotes $C_{1-6}$-alkyl, optionally substituted by one or more $N(C_{1-4}$-alkyl$)_2$;
$R^{12}$ denotes $C_{1-6}$alkyl;
$R^b$ denotes $R^4$, $OR^4$, —$CH_2OR^4$, $COR^4$, $COOR^4$, $CONR^4R^5$, $NR^4R^5$, $NR^5COR^4$, $NR^5COOR^4$, $NR^5CONR^4R^5$, $NR^5SOR^4$ or $NR^5SO_2R^4$;
$R^4$ and $R^5$ are independently selected from H, $C_{1-6}$-alkyl, $C_{1-6}$-haloalkyl, $C_{1-6}$-alkylene-OH, $C_{2-6}$-alkenyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $C_{2-6}$-alkynyl, optionally substituted by Si($C_{1-4}$-alkyl$)_3$, or $R^4$ denotes a group selected from among aryl, het or hetaryl and optionally substituted by $C_{1-4}$-alkyl;

or $R^4$ and $R^5$ together form a five-, six- or seven-membered ring consisting of carbon atoms and optionally a heteroatom selected from among oxygen, nitrogen and sulphur;
$R^c$ denotes $NHR^6$ or a group selected from among

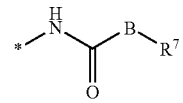

wherein
B denotes a bond, $C_{1-6}$-alkyl, $C_{2-6}$-alkenyl or $C_{2-6}$-alkynyl;
$R^6$ denotes H or a group selected from among $C_{1-4}$-alkyl, $C_{2-4}$-alkenyl, $C_{2-4}$-alkynyl, $C_{3-6}$-cycloalkyl, $C_{3-6}$-cycloalkenyl, het, aryl, hetaryl optionally substituted by one or more groups $R^{6.1}$;
$R^{6.1}$ denotes halogen, $CF_3$, OH, CN, OMe or $SO_2(C_{1-4}$-alkyl);
$R^7$ denotes H, $C_{1-4}$-alkyl, $C_{2-4}$-alkenyl, $C_{2-4}$-alkynyl, $C_{3-6}$-cycloalkyl, $NR^{7.1}R^{7.2}$, $OR^{7.2}$, $SR^{7.2}$, hetaryl or het, optionally substituted by $C_{1-4}$-alkyl or $CONH_2$;
$R^{7.1}$ denotes H, $C_{1-6}$-alkyl, $(CH_2)_{1-4}R^{7.1.1}$ or COObutyl;
$R^{7.2}$ denotes H, $C_{1-6}$-alkyl, optionally substituted by one or more OH;
$R^{7.1.1}$ denotes $NR^{7.1.1.1}R^{7.1.1.2}$, het or 1-imidazolyl, 2-(N-ethylpyrrolidine);
$R^{7.1.1.1}$ denotes H or $C_{1-6}$-alkyl;
$R^{7.1.1.2}$ denotes H or $C_{1-6}$-alkyl;
or a pharmacologically acceptable salt thereof.

2. The compound of formula 1 according to claim 1; wherein
$R^a$ denotes a group selected from among aryl, $C_{7-11}$-aralkyl and hetaryl, which may optionally be substituted by one or more groups selected from among $R^1$, $R^2$ and $R^3$;
$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$, $SR^{1.1}$, $SOR^{1.1}$, $SO_2R^{1.1}$, het or hetaryl,
$R^{1.1}$ denotes OH, $C_{1-6}$-alkyl, $C_{2-6}$alkenyl $C_{2-6}$-alkynyl or $NR^{1.1.1}R^{1.1.2}$;
$R^{1.1.1}$ denotes H or $C_{1-6}$-alkyl, optionally substituted by a group selected from among $NH_2$, NHMe and $NMe_2$;
$R^{1.1.2}$ denotes H or $C_{1-6}$-alkyl;
or $R^{1.1.1}$ and $R^{1.1.2}$ together form a five- or six-membered heterocyclic ring, which may optionally be substituted by a group selected from among methyl, ethyl and propyl;
$R^3$ denotes a group selected from among

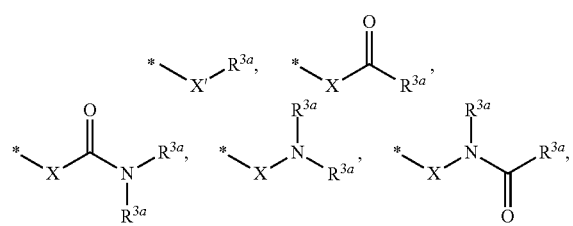

-continued

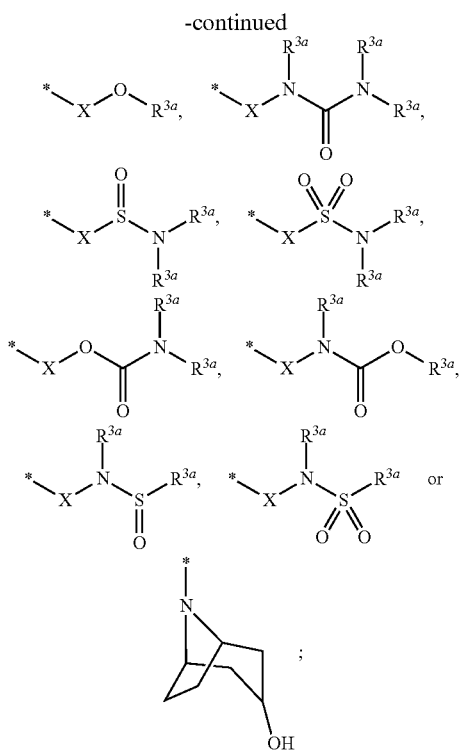

wherein

X denotes a bond or $C_{1-4}$-alkylene;

X' denotes $C_{1-4}$-alkylene, $C_{2-4}$-alkenylene or $C_{1-4}$-alkynylene;

$R^{3a}$ denotes a group, which may be identical or different, selected from among $R^{3.1}$, $R^{3.2}$ and $R^{3.3}$;

$R^{3.1}$ denotes spiro or het, while het may optionally be substituted by one or more $R^{3.1.1}$;

$R^{3.1.1}$ denotes $C_{1-6}$-alkyl, $C_{2-6}$-alkenyl, OH, $C_{1-4}$-alkylene-OH, $C_{1-4}$-alkylene-$NR^{3.1.1.1}R^{3.1.1.2}$, $COR^{3.1.1.1}$, $COOR^{3.1.1.1}$, $CONR^{3.1.1.1}R^{3.1.1.2}$, $NR^{3.1.1.1}R^{3.1.1.2}$, het, hetaryl, or $NHCOR^{3.1.1.1}$ $R^{3.1.1.1}$ denotes a group selected from among H, $C_{1-4}$-alkyl, aryl and $C_{7-11}$-aralkyl;

optionally substituted by a group selected from among halogen, OH and CN;

$R^{3.1.1.2}$ denotes H or $C_{1-4}$-alkyl;

$R^{3.2}$ denotes a group selected from among $C_{3-6}$-cycloalkyl, het, hetaryl and spiro which is optionally substituted by one or more $R^{3.2.1}$;

$R^{3.2.1}$ denotes $C_{1-6}$-alkyl, $C_{3-6}$-cycloalkyl, OH, $NR^{3.2.1.1}R^{3.2.1.2}$, $NHCOR^{3.2.1.3}$ or het, optionally substituted by one or more groups selected from among $C_{1-4}$-alkyl, $SO_2R^{3.2.1.1}$ $CH_2$—$C_{3-6}$-cycloalkyl and aryl;

$R^{3.2.1.1}$ denotes H, $C_{1-4}$-alkyl or $C_{7-11}$-aralkyl;

$R^{3.2.1.2}$ denotes H, $C_{1-4}$-alkyl or $C_{7-11}$-aralkyl;

$R^{3.2.1.3}$ denotes aryl, $C_{7-11}$-aralkyl; or $C_{1-6}$-alkyl, which is optionally substituted by one or two $R^{3.2.2}$;

$R^{3.2.2}$ denotes $C_{1-6}$-alkyl, $C_{2-6}$-alkenyl, $C_{2-6}$-alkynyl, $COOR^{3.2.2.1}$, $CONR^{3.2.2.1}R^{3.2.2.2}$ $NR^{3.2.2.1}R^{3.2.2.2}$, $NHCOR^{3.2.2.1}$, $C_{1-6}$-haloalkyl, CN, $OR^{3.2.2.1}$, $SO_2R^{3.2.2.1}$, $C_{3-6}$-cycloalkyl, CO-het, $C_{2-4}$-alkynyl-hetaryl, guanidine or a group selected from among het, hetaryl and aryl, which is optionally substituted by one or more groups selected from among halogen, $C_{1-6}$-alkyl, $CONR^{3.2.2.1}R^{3.2.2.2}$, OH and imidazolidinone;

$R^{3.2.2.1}$ denotes H or $C_{1-6}$-alkyl, aryl or $C_{7-11}$-aralkyl $R^{3.2.2.2}$ denotes H or $C_{1-6}$-alkyl; or aryl, which is optionally substituted by one or two $R^{3.2.3}$ $R^{3.2.3}$ denotes a group selected from among NH—$C_{1-6}$-alkyl-N($C_{1-6}$-alkyl)$_2$ or het, while het may optionally be substituted by a $C_{1-6}$-alkyl group;

$R^{3.3}$ denotes H or a group selected from among $C_{1-6}$-alkyl, $C_{2-6}$-alkenyl, $C_{2-6}$-alkynyl, $C_{1-6}$-haloalkyl and aryl, which may optionally be substituted by one or more groups $R^{3.3.1}$;

$R^{3.3.1}$ denotes $C_{3-6}$-cycloalkyl, $C_{3-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C=(NR^{3.3.1.3})NR^{3.3.1.1}R^{3.3.1.2}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2 R^{3.2.1.1}$, $SO_2C_{1-4}$-alkyl, $SO_2C_{7-11}$-aralkyl, $CH_2$—$C_{3-6}$-cycloalkyl and aryl;

$R^{3.3.1.1}$, $R^{3.3.1.2}$ and $R^{3.3.1.3}$ denote a group selected from among $C_{1-6}$-alkyl, $C_{2-6}$-alkenyl, $C_{2-6}$-alkynyl, $C_{7-11}$-aralkyl, $C_{2-4}$-alkenyl-aryl, $C_{2-4}$-alkynyl-aryl, $C_{1-4}$-alkyl-hetaryl, $C_{2-4}$-alkenyl-hetaryl, $C_{2-4}$-alkynyl-hetaryl, $COC_{1-4}$-alkyl-hetaryl, $COC_{2-4}$-alkenyl-hetaryl and $COC_{2-4}$-alkynyl-hetaryl; or two of the groups $R^{3.3.1.1}$, $R^{3.3.1.2}$ and $R^{3.3.1.3}$ together form a ring, consisting of carbon atoms and optionally a heteroatom selected from among oxygen, nitrogen or sulphur;

or $R^a$ denotes H, $C_{1-6}$-alkyl, $C_{2-6}$-alkenyl, $C_{3-8}$-cycloalkyl, $C_{3-8}$-cycloalkenyl, $C_{1-6}$-haloalkyl, $COR^8$, $NR^9R^{10}$, $NO_2$, $OR^8$, $SR^{11}$, $SOR^{11}$, $SO_2R^{11}$, NHCO—$C_{1-6}$-alkyl-$NH_2$, spiro or a group selected from among $C_{7-11}$-aralkyl, $CH_2$—O-aryl and het which may optionally be substituted by one or more halogens, $C_{1-6}$-alkyl, CO—$C_{1-4}$-haloalkyl, $C_{1-4}$-alkyl-$NH_2$ or $CH_2NHCOOR^{12}$;

$R^8$ denotes $C_{1-6}$-alkyl, $C_{3-6}$-cycloalkyl, $NH_2$, hetaryl or aryl, optionally substituted by one or more halogens or $C_{1-4}$-alkyl;

$R^9$ denotes H, $COOR^{12}$, $CONHR^{12}$ or $C_{1-6}$-alkyl, optionally substituted by one or more COOH, N($C_{1-6}$-alkyl)$_2$ or het, optionally substituted by one or more $C_{1-6}$-alkyl; or $R^9$ denotes het, optionally substituted by one or more $C_{1-4}$-alkyl;

$R^{10}$ denotes H, $C_{1-6}$-alkyl, CO—$C_{1-6}$-alkyl or $C_{2-6}$-alkynyl;

$R^{11}$ denotes $C_{1-6}$-alkyl, optionally substituted by one or more N($C_{1-4}$-alkyl)$_2$;

$R^{12}$ denotes H or $C_{1-6}$-alkyl;

or a pharmacologically acceptable salt thereof.

3. The compound of formula 1 according to claim 1; wherein $R^a$ denotes a group selected from among aryl, $C_{7-11}$-aralkyl and hetaryl, which may optionally be substituted by one or more groups selected from among $R^1$, $R^2$ and $R^3$;

$R^1$ and $R^2$ independently of one another denote $C_{1-6}$-alkyl, $C_{2-6}$-alkenyl $C_{2-6}$-alkynyl, $C_{3-6}$-cycloalkyl, $C_{3-6}$-cycloalkenyl, $C_{1-6}$-haloalkyl, $C_{1-6}$-alkylene-COOH, $C_{1-6}$-alkoxy, halogen, OH, CN, $COR^{1.1}$, O—$C_{1-4}$-haloalkyl, $NO_2$ or $SR^{1.1}$, $SOR^{1.1}$, $SO_2R^{1.1}$, het or hetaryl, $R^{1.1}$ denotes OH, $C_{1-6}$-alkyl, $C_{2-6}$-alkenyl $C_{2-6}$-alkynyl or $NR^{1.1.1}R^{1.1.2}$;

$R^{1.1.1}$ denotes H, $C_{1-6}$-alkyl, optionally substituted by a group selected from among $NH_2$, NHMe and $NMe_2$;

$R^1$ denotes H, $C_{1-6}$-alkyl;

or R$^{1.1.1}$ and R$^{1.1.2}$ together form a five- or six-membered heterocyclic ring, which may optionally be substituted by a group selected from among methyl, ethyl and propyl;

R$^3$ denotes a group selected from among

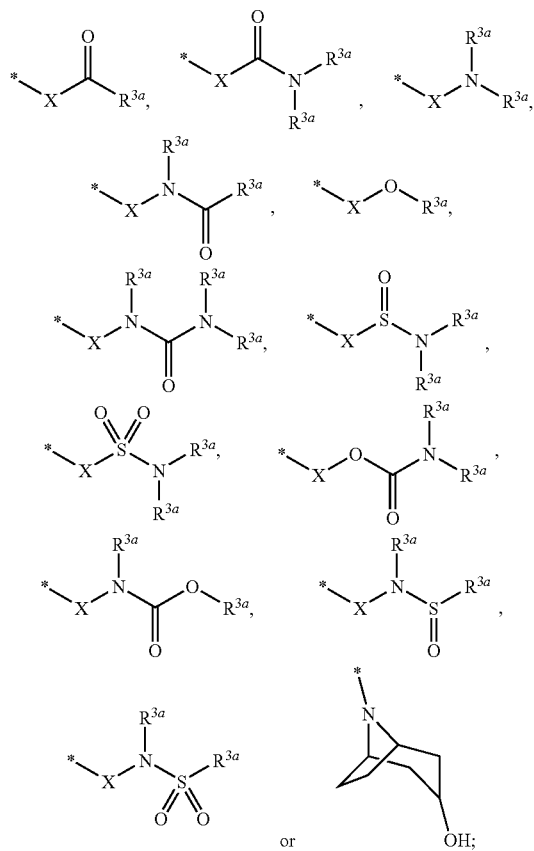

wherein

X denotes a bond or C$_{1-4}$-alkylene;

R$^{3a}$ denotes a group, which may be identical or different, selected from among R$^{3.1}$, R$^{3.2}$ and R$^{3.3}$;

R$^{3.1}$ denotes spiro or het, while het may optionally be substituted by one or more R$^{1.1.1}$;

R$^{3.1.1}$ denotes C$_{1-6}$-alkyl, C$_{2-6}$-alkenyl, OH, C$_{1-4}$-alkylene-OH, C$_{1-4}$-alkylene-NR$^{3.1.1.1}$R$^{3.1.1.2}$, COR$^{3.1.1.1}$, COOR$^{3.1.1.1}$, CONR$^{3.1.1.1}$R$^{3.1.1.2}$, NR$^{3.1.1.1}$R$^{3.1.1.2}$, het, hetaryl or NHCOR$^{3.1.1.1}$;

R$^{3.1.1.1}$ denotes a group selected from among H, C$_{1-4}$-alkyl, aryl and C$_{7-11}$-aralkyl;

optionally substituted by a group selected from among halogen, OH and CN;

R$^{3.1.1.2}$ denotes H, C$_{1-4}$-alkyl;

R$^{3.2}$ denotes a group selected from among C$_{3-6}$-cycloalkyl, het, hetaryl and spiro which is optionally substituted by one or more R$^{3.2.1}$;

R$^{3.2.1}$ denotes C$_{1-6}$-alkyl, C$_{3-6}$-cycloalkyl, OH, —NR$^{3.2.1.1}$R$^{3.2.1.2}$, NHCOR$^{3.2.1.3}$ or het, optionally substituted by one or more groups selected from among C$_{1-4}$-alkyl, SO$_2$R$^{3.2.1.1}$, CH$_2$—C$_{3-6}$-cycloalkyl and aryl;

R$^{3.2.1.1}$ denotes H, C$_{1-4}$-alkyl or C$_{7-11}$-aralkyl;

R$^{3.2.1.2}$ denotes H, C$_{1-4}$-alkyl or C$_{7-11}$-aralkyl;

R$^{3.2.1.3}$ denotes aryl, C$_{7-11}$-aralkyl; or

—C$_{1-6}$-alkyl, which is optionally substituted by one or two R$^{3.2.2}$;

R$^{3.2.2}$ denotes C$_{1-6}$-alkyl, C$_{2-6}$-alkenyl, C$_{2-6}$-alkynyl, COOR$^{3.2.2.1}$, CONR$^{3.2.2.1}$R$^{3.2.2.2}$, NR$^{3.2.2.1}$R$^{3.2.2.2}$, NHCOR$^{3.2.2.1}$, C$_{1-6}$-haloalkyl, CN, OR$^{3.2.2.1}$, SO$_2$R$^{3.2.2.1}$, C$_{3-6}$-cycloalkyl, CO-het, C$_{2-4}$-alkynyl-hetaryl, guanidine or a group selected from among het, hetaryl and aryl, which is optionally substituted by one or more groups selected from among halogen, C$_{1-6}$ alkyl, CONR$^{3.2.2.1}$R$^{3.2.2.2}$, OH and imidazolidinone;

R$^{3.2.2.1}$ denotes H or C$_{1-6}$-alkyl, aryl or C$_{7-11}$-aralkyl;

R$^{3.2.2.2}$ denotes H or C$_{1-6}$-alkyl; or aryl, which is optionally substituted by one or two R$^{3.2.3}$;

R$^{3.2.3}$ denotes a group selected from among NH—C$_{1-6}$-alkyl-N(C$_{1-6}$-alkyl)$_2$ or het, while het may optionally be substituted by a C$_{1-6}$-alkyl group;

R$^{3.3}$ denotes H or a group selected from among C$_{1-6}$-alkyl, C$_{2-4}$-alkenyl, C$_{2-4}$-alkynyl, C$_{1-4}$-haloalkyl and aryl, which may optionally be substituted by one or more groups R$^{3.3.1}$;

R$^{3.3.1}$ denotes C$_{5-6}$-cycloalkyl, C$_{5-6}$-cycloalkenyl, OR$^{3.3.1.1}$, NR$^{3.3.1.1}$R$^{3.3.1.2}$, CONR$^{3.3.1.1}$R$^{3.3.1.2}$, COOR$^{3.3.1.1}$, NR$^{3.3.1.1}$COR$^{3.3.1.2}$, SOR$^{3.3.1.1}$, SO$_2$R$^{3.3.1.1}$, C=(NR$^{3.3.1.3}$)NR$^{3.3.1.1}$R$^{3.3.1.2}$, NR$^{3.3.1.1}$CONR$^{3.3.1.2}$R$^{3.3.1.3}$, OH, CN, halogen or het, optionally substituted by one or more groups selected from among C$_{1-4}$-alkyl, SO$_3$R$^{3.2.1.1}$, SO$_2$C$_{1-4}$-alkyl, SO$_2$C$_{7-11}$-aralkyl, CH$_2$—C$_{3-6}$-cycloalkyl and aryl;

R$^{3.3.1.1}$, R$^{3.3.1.2}$ and R$^{3.3.1.3}$ denote a group selected from among C$_{1-4}$-alkyl, C$_{2-4}$-alkenyl, C$_{2-4}$-alkynyl, C$_{7-11}$-aralkyl, C$_{2-4}$-alkenyl-aryl, C$_{2-4}$-alkynyl-aryl, C$_{1-4}$-alkyl-hetaryl, C$_{2-4}$-alkenyl-hetaryl, C$_{2-4}$-alkynyl-hetaryl, COC$_{1-4}$-alkyl-hetaryl, COC$_{2-4}$-alkenyl-hetaryl and COC$_{2-4}$-alkynyl-hetaryl; or two of the groups R$^{3.3.1.1}$, R$^{3.3.1.2}$ and R$^{3.3.1.3}$ together form a five-, six- or seven-membered ring, consisting of carbon atoms and optionally a heteroatom selected from among oxygen, nitrogen and sulphur;

or

R$^a$ denotes H, C$_{1-6}$-alkyl, C$_{2-6}$-alkenyl, C$_{3-8}$-cycloalkyl, C$_{3-8}$-cycloalkenyl, C$_{1-6}$-haloalkyl, COR$^8$, NR$^9$R$^{10}$, NO$_2$, OR$^8$, SR$^{11}$, SOR$^{11}$, SO$_2$R$^{11}$, NHCO—C$_{1-6}$—NH$_2$, spiro or a group selected from among C$_{7-11}$-aralkyl, CH$_2$—O-aryl and het which may optionally be substituted by one or more halogens, C$_{1-6}$-alkyl, CO—C$_{1-4}$-haloalkyl, C$_{1-4}$-alkyl-NH$_2$ or CH$_2$NHCOOR$^{12}$;

R$^8$ denotes C$_{1-6}$-alkyl, C$_{3-6}$-cycloalkyl, NH$_2$, hetaryl or aryl, optionally substituted by one or more halogens or C$_{1-4}$-alkyl;

R$^9$ denotes H, COOR$^{12}$ or C$_{1-4}$-alkyl, optionally substituted by one or more COOH, N(C$_{1-4}$-alkyl)$_2$ or het, optionally substituted by one or more C$_{1-4}$-alkyl; or R$^9$ denotes het, optionally substituted by one or more C$_{1-4}$-alkyl;

R$^{10}$ denotes H, C$_{1-6}$-alkyl, CO—C$_{1-4}$-alkyl or C$_{2-6}$-alkynyl;

R$^{11}$ denotes C$_{1-6}$-alkyl, optionally substituted by one or more N(C$_{1-4}$-alkyl)$_2$;

R$^{12}$ denotes C$_{1-6}$-alkyl;

R$^b$ denotes R$^4$, OR$^4$, —CH$_2$OR$^4$, COR$^4$, COOR$^4$, CONR$^4$R$^5$, NR$^4$R$^5$, NR$^5$COR$^4$, NR$^5$COOR$^4$, NR$^5$CONR$^4$R$^5$, NR$^5$SOR$^4$ or NR$^5$SO$_2$R$^4$;

R$^4$ denotes H, C$_{1-6}$-alkyl, C$_{1-6}$-haloalkyl, C$_{1-6}$-alkylene-OH, C$_{2-6}$-alkenyl, C$_{7-11}$-aralkyl, C$_{2-4}$-alkenyl-aryl, C$_{2-4}$-alkynyl-aryl, C$_{1-4}$-alkyl-hetaryl, C$_{2-4}$-alkenyl-hetaryl, C$_{2-4}$-alkynyl-hetaryl, C$_{2-6}$-alkynyl, optionally substituted by Si(C$_{1-4}$-alkyl)$_3$, or R$^4$ denotes a group selected from among aryl, het and hetaryl, optionally substituted by C$_{1-4}$-alkyl;

R$^5$ denotes H or C$_{1-6}$-alkyl;

or R$^4$ and R$^5$ together form a five-, six- or seven-membered ring consisting of carbon atoms and optionally a heteroatom selected from among oxygen, nitrogen and sulphur;

R$^c$ denotes NHR$^6$ or a group selected from among

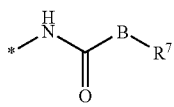

wherein

B denotes a bond, C$_{1-4}$-alkyl or C$_{2-4}$-alkynyl;

R$^6$ denotes H or a group selected from among C$_{1-4}$-alkyl, C$_{2-4}$-alkenyl, C$_{2-4}$-alkynyl, C$_{3-6}$-cycloalkyl, C$_{3-6}$-cycloalkenyl, het, aryl and hetaryl optionally substituted by one or more groups R$^{6.1}$;

R$^{6.1}$ denotes halogen, CF$_3$, OH, CN, OMe or SO$_2$(C$_{1-4}$-alkyl);

R$^7$ denotes H, C$_{1-4}$-alkyl, C$_{2-4}$-alkenyl, C$_{2-4}$-alkynyl, C$_{3-6}$-cycloalkyl, NR$^{7.1}$R$^{7.2}$, OR$^{7.2}$, SR$^{7.2}$, hetaryl or het, optionally substituted by C$_{1-4}$-alkyl or CONH$_2$;

R$^{7.3.1}$ denotes H, C$_{1-4}$-alkyl, (CH$_2$)$_{2-4}$R$^{7.1.1}$ or COObutyl;

R$^{7.2}$ denotes H, C$_{1-6}$-alkyl, optionally substituted by one or more OH;

R$^{7.1.1}$ denotes NR$^{7.1.1.1}$R$^{7.1.1.2}$, het or 1-imidazolyl, 2-(N-ethylpyrrolidine);

R$^{7.1.1.1}$ denotes H or C$_{1-6}$-alkyl;

R$^{7.1.1.2}$ denotes H or C$_{1-6}$-alkyl;

or the pharmacologically acceptable salt thereof.

4. The compound of formula 1 according to claim 1; wherein

R$^a$ denotes a group selected from among aryl and C$_{7-11}$-aralkyl, which may optionally be substituted by one or more groups selected from among R$^1$, R$^2$ and R$^3$; or hetaryl optionally substituted by one or more C$_{1-4}$-alkyl;

R$^1$ denotes C$_{1-4}$-alkyl, C$_{1-4}$-haloalkyl, C$_{1-4}$-alkylene-COOH, C$_{1-4}$-alkoxy, halogen, OH, CN, COR$^{1.1}$, O—C$_{1-4}$-haloalkyl, NO$_2$ or SO$_2$R$^{1.1}$;

R$^{1.1}$ denotes OH, methyl, NH$_2$, NHMe, NMe$_2$,

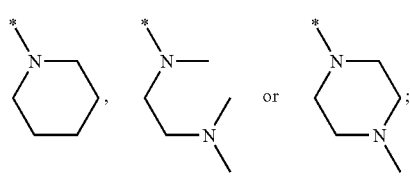

R$^2$ denotes C$_{1-4}$-alkyl, C$_{1-4}$-alkoxy or halogen;

R$^3$ denotes a group selected from among

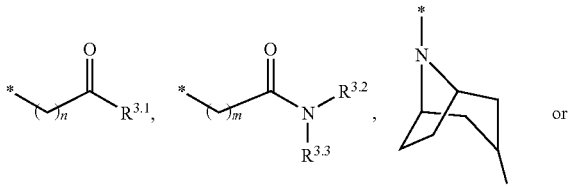

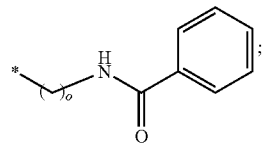

wherein
n denotes 0 or 1;
m denotes 0 or 1;
o denotes 2;
R$^{3.1}$ denotes spiro or het, while het may optionally be substituted by one or more R$^{3.1.1}$;
R$^{3.1.1}$ denotes C$_{1-4}$-alkyl, C$_{2-4}$-alkenyl, OH, C$_{1-4}$-alkylene-OH, CH$_2$NEt$_2$, COMe, COOH, CONH$_2$, NH$_2$, het, hetaryl,

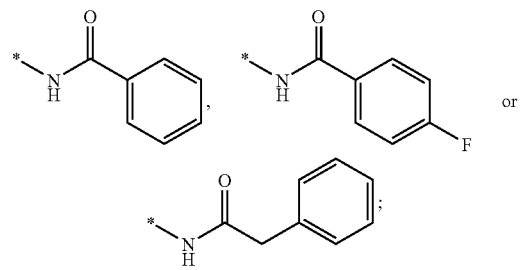

R$^{3.2}$ denotes a group selected from among C$_{3-6}$-cycloalkyl, het, hetaryl and spiro which is optionally substituted by one or two R$^{3.2.1}$;
R$^{3.2.1}$ denotes C$_{1-4}$-alkyl, cyclopentyl, OH, —NR$^{3.2.1.1}$R$^{3.2.1.2}$,

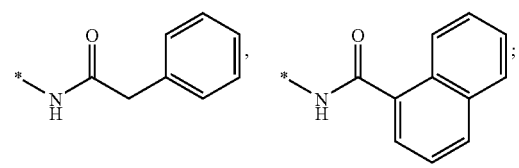

or het, is optionally substituted by one or more groups selected from among methyl, SO$_2$R$^{3.2.1.1}$,

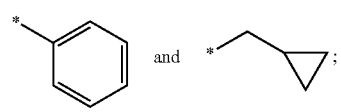

R$^{3.2.1.1}$ denotes H, methyl or benzyl;
R$^{3.2.1.2}$ denotes H, methyl or benzyl; or
—C$_{1-6}$-alkyl, which is optionally substituted by one or two R$^{3.2.2}$;

$R^{3.2.2}$ denotes $C_{2-4}$-alkenyl, $C_{2-4}$-alkynyl, $COOR^{3.2.2.1}$, $CONR^{3.2.2.1}R^{3.2.2.2}$, $NR^{3.2.2.1}R^{3.2.2.2}$, $NHCOR^{3.2.2.1}$, $C_{1-4}$-haloalkyl, CN, OH, $SO_2R^{3.2.2.1}$, $C_{3-6}$-cycloalkyl or a group selected from among

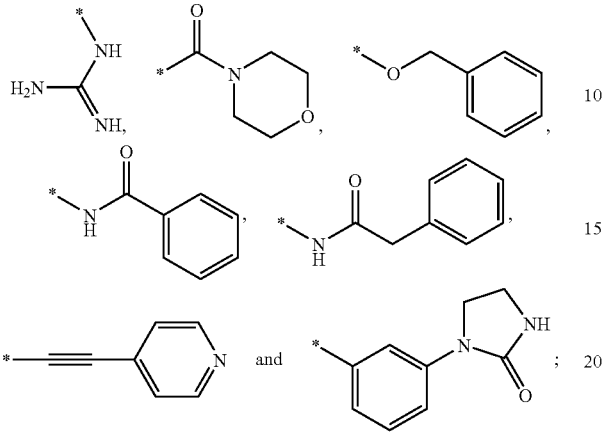

or a group selected from among het, hetaryl and aryl, which is optionally substituted by one or more groups selected from among Cl, methyl, $CONR^{3.2.2.1}R^{3.2.2.2}$ and OH;

$R^{3.2.2.1}$ denotes H or methyl;

$R^{3.2.2.2}$ denotes H or methyl; or aryl, which is optionally substituted by one or two $R^{3.2.3}$;

$R^{3.2.3}$ denotes a group selected from among

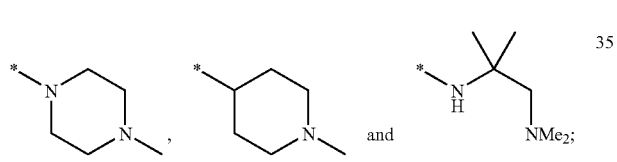

$R^{3.3}$ denotes H or a group selected from among $C_{1-6}$-alkyl and aryl, which may optionally be substituted by one or more groups $R^{3.3.1}$;

$R^{3.3.1}$ denotes $C_{5-6}$-cycloalkyl, $C_{5-6}$-cycloalkenyl, $OR^{3.3.1.1}$, $NR^{3.3.1.1}R^{3.3.1.2}$, $CONR^{3.3.1.1}R^{3.3.1.2}$, $COOR^{3.3.1.1}$, $NR^{3.3.1.1}COR^{3.3.1.2}$, $SOR^{3.3.1.1}$, $SO_2R^{3.3.1.1}$, $C=(NR^{3.3.1.3})NR^{3.3.1.1}R^{3.3.1.2}$, $NR^{3.3.1.1}CONR^{3.3.1.2}R^{3.3.1.3}$, OH, CN, halogen or het, optionally substituted by one or more groups selected from among $C_{1-4}$-alkyl, $SO_2R^{3.2.1.1}$, $SO_2C_{1-4}$-alkyl, $SO_2C_{7-11}$-aralkyl,

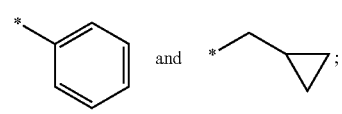

$R^{3.3.1.1}$, $R^{3.3.1.2}$ and $R^{3.3.1.3}$ denote a group selected from among $C_{1-4}$-alkyl, $C_{7-11}$-aralkyl, $C_{1-4}$-alkyl-hetaryl or $COC_{1-4}$-alkyl-hetaryl;

or $R^a$ denotes H, $C_{1-6}$-alklyl, $C_{2-6}$-alkenyl, $C_{3-6}$-cycloalkyl, $CF_3$, $COR^8$, $NR^9R^{10}$, $NO_2$, $SR^{11}$, $SOR^{11}$, $SO_2R^{11}$, or a group selected from among

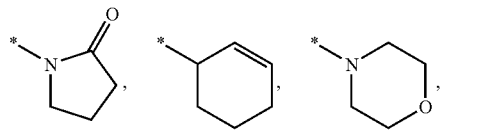

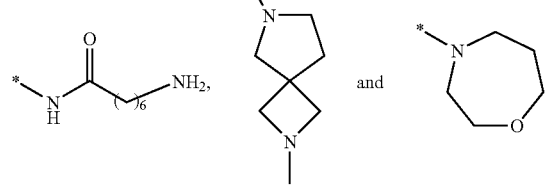

or a group selected from among

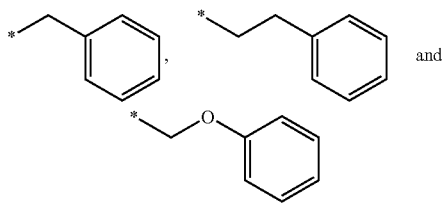

which may optionally be substituted by one or more Cl;

or a group selected from among

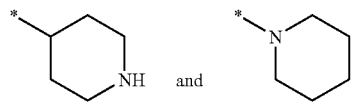

which may optionally be substituted by one or more $CH_3$, $COCF_3$, $CH_2NH_2$ or $CH_2NHCOOR^{12}$;

$R^8$ denotes $C_{1-4}$-alkyl, $C_{3-6}$-cycloalkyl, $NH_2$, furanyl or phenyl, optionally substituted by one or more chlorine;

$R^9$ denotes H, $COOR^{12}$ or piperidino, optionally substituted by one or more $CH_3$, or a group selected from among $C_{1-4}$-alkyl, which may optionally be substituted by one or more COOH, $NMe_2$ or 4-methylpiperazine;

$R^{10}$ denotes H, $C_{1-4}$-alkyl, $C_{2-4}$-alkynyl or $COCH_3$;

$R^{11}$ denotes $C_{1-4}$-alkyl, optionally substituted by one or more $NMe_2$, $R^{12}$ denotes $C_{1-4}$-alkyl;

$R^b$ denotes $R^4$, $CH_2OR^4$, $COR^4$, $COOR^4$, $CONR^4R^5$, $NH_2$, $NHCOOR^4$, $NHCONR^4R^5$ or OH;

$R^4$ denotes H, $C_{1-4}$-alkyl, $C_{1-4}$-alkylene-OH, $C_{2-4}$-alkynyl, $C_{1-6}$-haloalkyl, aryl, het, hetaryl,

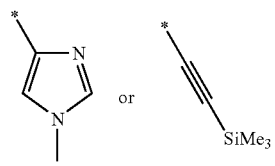

$R^5$ denotes H or $C_{1-4}$-alkyl;

$R^c$ denotes $NHR^6$ or a group selected from among

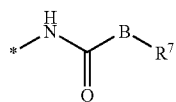

wherein
B denotes a bond, $C_{1-4}$-alkyl or $C_{2-4}$-alkynyl;
$R^6$ denotes H, $C_{3-6}$-cycloalkyl or aryl, optionally substituted by $SO_2CH_3$;
$R^7$ denotes H, $NR^{7.1}R^{7.2}$, $OR^{7.2}$, $SR^{7.2}$, hetaryl, het, optionally substituted by $C_{1-4}$-alkyl or $CONH_2$, or a group selected from among

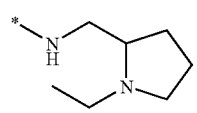 and 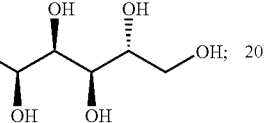

$R^{7.1}$ denotes H, $(CH_2)_2R^{7.1.1}$ or COObutyl;
$R^{7.2}$ denotes H or $C_{1-4}$-alkyl;
$R^{7.1.1}$ denotes $NR^{7.1.1.1}R^{7.1.1.2}$, het or 1-imidazolyl, 2-(N-ethylpyrrolidine);
$R^{7.1.1.1}$ denotes H or $C_{1-6}$-alkyl;
$R^{7.1.1.2}$ denotes H or $C_{1-6}$-alkyl;
or the pharmacologically acceptable salt thereof.

5. The compound of formula 1 according to claim 1; wherein
$R^a$ denotes phenyl or benzyl, in each case optionally substituted by one or more groups selected from among $R^1$, $R^2$ and $R^3$; or

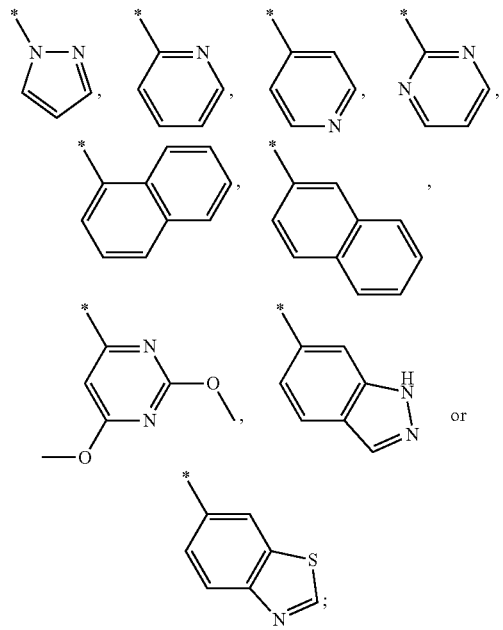

$R^1$ denotes methyl, ethyl, propyl, butyl, $CF_3$, $CH_2COOH$, methoxy, F, Cl, Br, OH, CN, $COR^{1.1}$, $OCF_3$, $NO_2$ or $SO_2R^{1.1}$;
$R^{1.1}$ denotes OH, methyl, $NH_2$, NHMe, $NMe_2$,

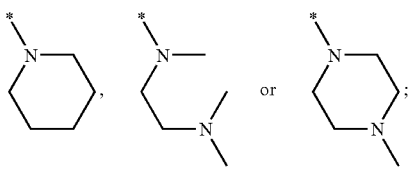

$R^2$ denotes methyl, methoxy, F, Cl or Br;
$R^3$ denotes a group selected from among

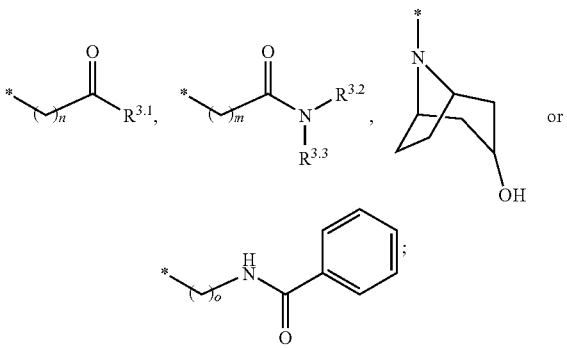

wherein
n denotes 0 or 1;
m denotes 0 or 1;
o denotes 2;
$R^{3.1}$ denotes a group selected from among

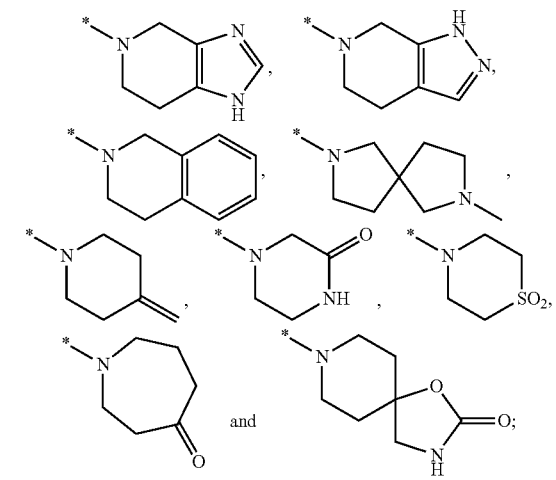

or a group selected from among

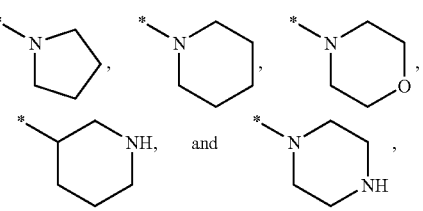

which may optionally be substituted by one or more $R^{3.1.1}$;

$R^{3.1.1}$ denotes methyl, ethyl, OH, $CH_2OH$, $CH_2CH_2OH$, $CH_2NEt_2$, COMe, COOH, $CONH_2$, $NH_2$,

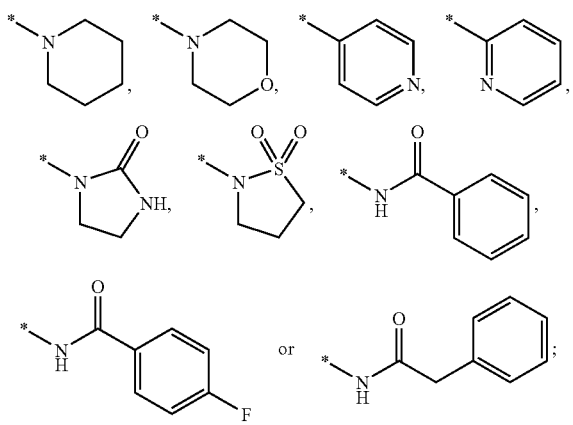

$R^{3.2}$ denotes a group selected from among

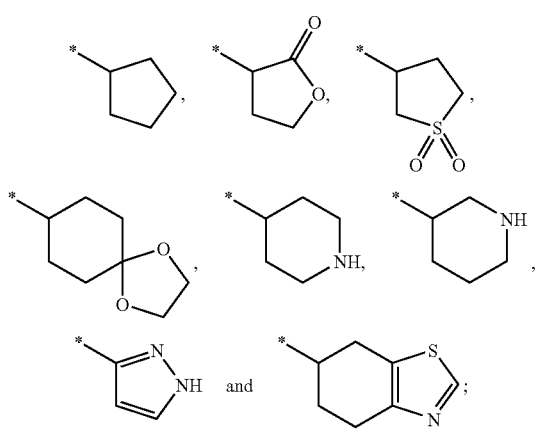

which is optionally substituted by one or more groups selected from among methyl, ethyl, cyclopentyl, OH, $NH_2$; or cyclohexyl, which is optionally substituted by one or two $R^{3.2.1}$;

$R^{3.2.1}$ denotes $—NR^{3.2.1.1}R^{3.2.1.2}$ or a group selected from among

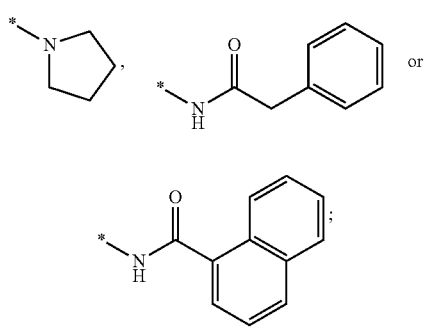

or a group selected from among

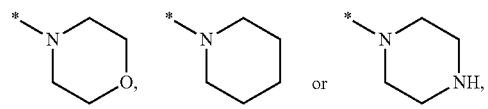

which is optionally substituted by one or more groups selected from among methyl, $SO_2R^{3.2.1.1}$,

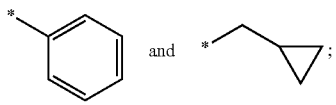

$R^{3.2.1.1}$ denotes H, methyl or benzyl;
$R^{3.2.1.2}$ denotes H, methyl or benzyl; or
—$C_{1-6}$-alkyl, straight-chain or branched, which is optionally substituted by one or two $R^{3.2.2}$;
$R^{3.2.2}$ denotes $C=CH_2$, $C\equiv CH$, $COOR^{3.2.2.1}$, $CONR^{3.2.2.1}R^{3.2.2.2}$, $NR^{3.2.2.1}R^{3.2.2.2}$, $NHCOR^{3.2.2.1}$, $CF_3$, CN, OH, $SO_2R^{3.2.2.1}$ or a group selected from among

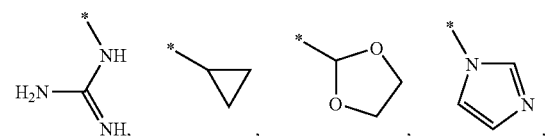

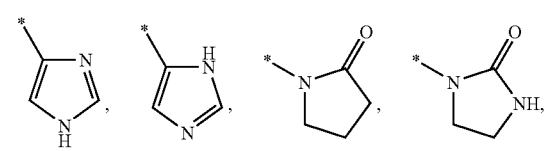

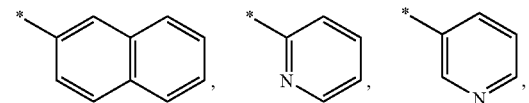

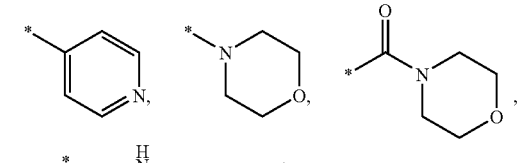

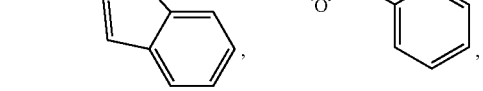

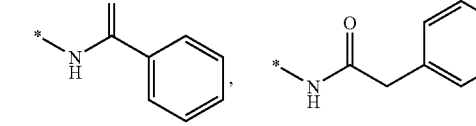

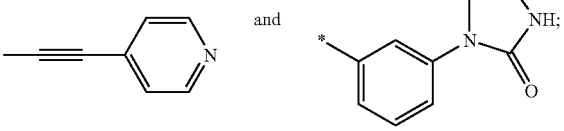

or a group selected from among

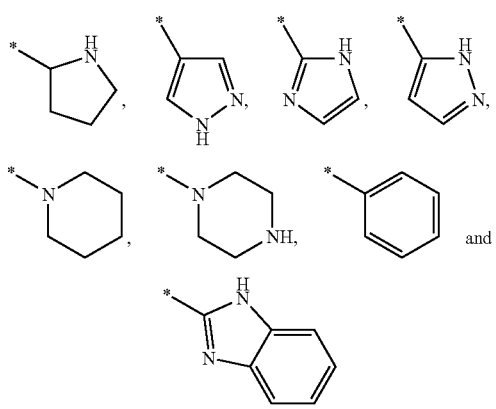

which is optionally substituted by one or more groups selected from among Cl, methyl, CONR$^{3.2.2.1}$R$^{3.2.2.2}$ and OH;

R$^{3.2.2.1}$ denotes H or methyl;

R$^{3.2.2.2}$ denotes H or methyl; or phenyl, which is optionally substituted by one or two R$^{3.2.3}$;

R$^{3.2.3}$ denotes a group selected from among

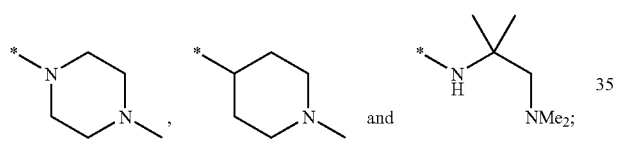

R$^{3.3.3}$ denotes H or C$_{1-6}$-alkyl, optionally substituted by one or more R$^{3.3.1}$;

R$^{3.3.1}$ denotes C$_{5-6}$-cycloalkyl, C$_{5-6}$-cycloalkenyl, OR$^{3.3.1.1}$, NR$^{3.3.1.1}$R$^{3.3.1.2}$, CONR$^{3.3.1.1}$R$^{3.3.1.2}$, COOR$^{3.3.1.1}$, NR$^{3.3.1.1}$COR$^{3.3.1.2}$, SOR$^{3.3.1.1}$, SO$_2$R$^{3.3.1.1}$, C=(NR$^{3.3.1.3}$)NR$^{3.3.1.1}$R$^{3.3.1.2}$, NR$^{3.3.1.1}$CONR$^{3.3.1.2}$R$^{3.3.1.3}$, OH, CN, halogen or het which is optionally substituted by one or more groups selected from among methyl, SO$_2$H, SO$_2$CH$_3$, SO$_2$CH$_2$-phenyl,

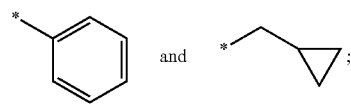

R$^{3.3.1.1}$, R$^{3.3.1.2}$ and R$^{3.3.1.3}$ denote a group selected from among C$_{1-4}$-alkyl, C$_{7-11}$-aralkyl, C$_{1-4}$-alkyl-hetaryl or COC$_{1-4}$-alkyl-hetaryl;

or

R$^a$ denotes H, methyl, ethyl, propyl, butyl, 3-methyl-butyl, propenyl, cyclopropyl, cyclohexyl, CF$_3$, COR$^8$, NR$^9$R$^{10}$, NO$_2$, OR$^8$, SR$^{11}$, SOR$^{11}$, SO$_2$R$^{11}$ or a selected group from among

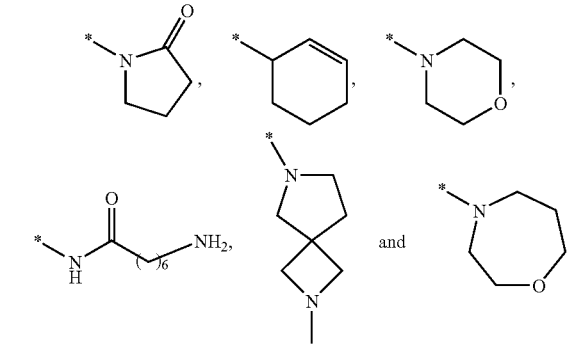

or a group selected from among

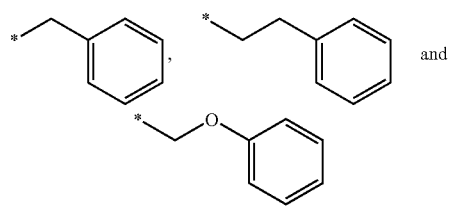

which may optionally be substituted by one or more Cl, or a group selected from among

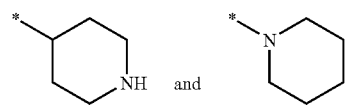

which may optionally be substituted by one or more CH$_3$, COCF$_3$, CH$_2$NH$_2$ or CH$_2$NHCOOR$^{12}$;

R$^8$ denotes methyl, propyl, cyclopropyl, NH$_2$, furanyl or phenyl, optionally substituted by one or more chlorine;

R$^9$ denotes H, COOR$^{12}$ or piperidino, optionally substituted by one or more CH$_3$, or a group selected from among methyl, ethyl and propyl, which may optionally be substituted by one or more COOH, NMe$_2$ or 4-methylpiperazine;

R$^{10}$ denotes H, methyl, COCH$_3$, C≡CH or CH$_2$C≡CH;

R$^{11}$ denotes ethyl or propyl, optionally substituted by one or more NMe$_2$;

R$^{12}$ denotes butyl;

R$^b$ denotes R$^4$, CH$_2$OR$^4$, COR$^4$, COOR$^4$, CONR$^4$R$^5$, NH$_2$, NHCOOR$^4$, NHCONR$^4$R$^5$ or OH;

R$^4$ denotes H, methyl, ethyl, 2-hydroxyethyl, propyl, C≡CH, CF$_3$, phenyl,

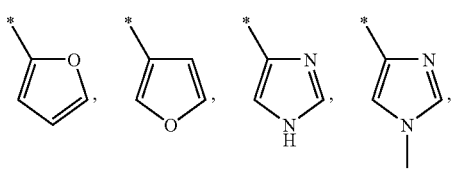

-continued

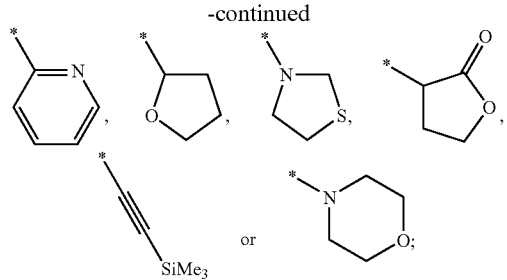

$R^5$ denotes H, methyl or ethyl;
denotes $NHR^6$ or a group selected from among

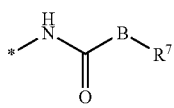

wherein
B denotes a bond, methylene, ethylene, propylene or butynylene;
$R^6$ denotes H, $C_{1-4}$-alkyl or aryl, optionally substituted by $SO_2CH_3$;
$R^7$ denotes H, $NR^{7.1}R^{7.2}$, $OR^{7.2}$, $SR^{7.2}$ or a group selected from among

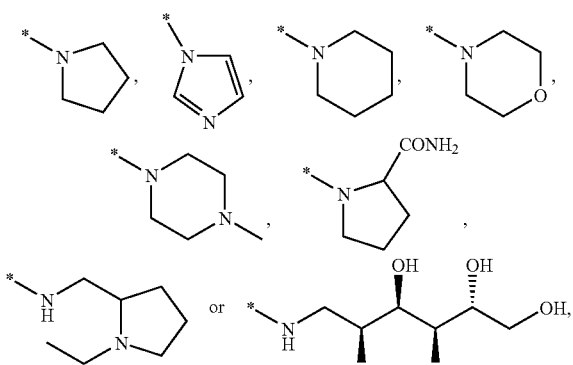

$R^{7.1}$ denotes H, methyl, ethyl, $(CH_2)_2R^{7.1.1}$ or COObutyl;
$R^{7.2}$ denotes H, methyl or ethyl;
$R^{7.1.1}$ denotes $NR^{7.1.1.1}R^{7.1.1.2}$, het or 1-imidazolyl, 2-(N-ethylpyrrolidine);
$R^{7.1.1.1}$ denotes H or $C_{1-6}$-alkyl;
$R^{7.1.1.2}$ denotes H or $C_{1-6}$-alkyl;
or the pharmacologically acceptable salt thereof.

6. The compound of formula I according to claim 1; wherein
$R^a$ denotes phenyl or benzyl, in each case optionally substituted by one or more groups selected from among $R^1$, $R^2$ and $R^3$; or

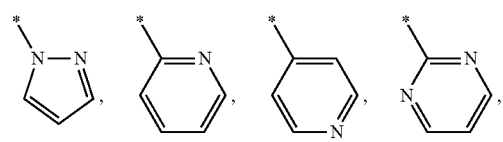

-continued

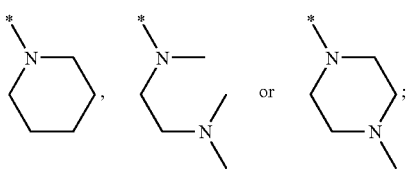

$R^1$ denotes methyl, ethyl, propyl, butyl, $CF_3$, $CH_2COOH$, methoxy, F, Cl, Br, OH, CN, $COR^{1.1}$, $OCF_3$, $NO_2$ or $SO_2R^{1.1}$;
$R^{1.1}$ denotes OH, methyl, $NH_2$, NHMe, $NMe_2$,

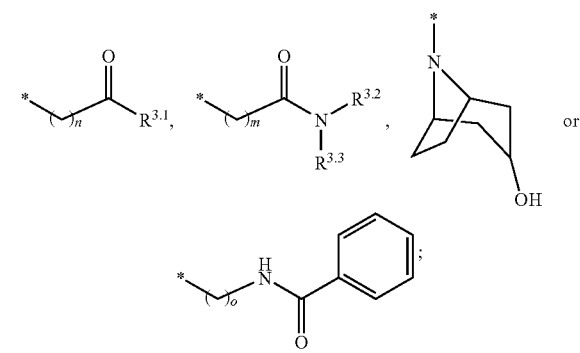

$R^2$ denotes methyl, methoxy, F, Cl or Br;
$R^3$ denotes a group selected from among wherein
n denotes 0 or 1;
m denotes 0 or 1;
o denotes 2;
$R^{3.1}$ denotes a group selected from among

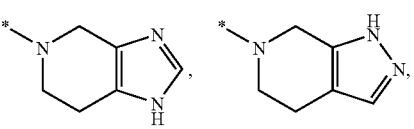

-continued

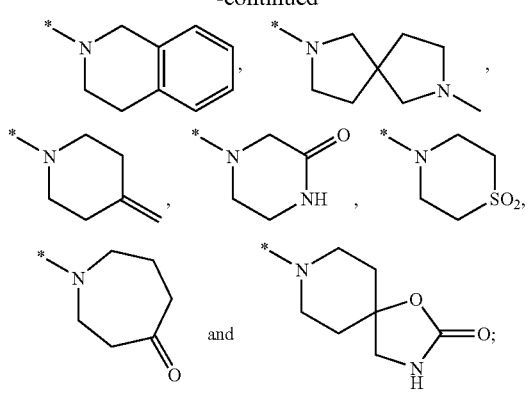

or a group selected from among

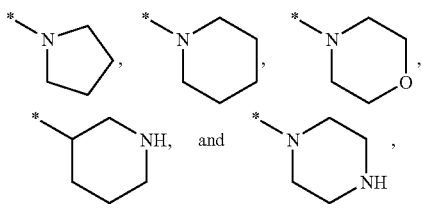

which may optionally be substituted by one or more $R^{3.1.1}$;

$R^{3.1.1}$ denotes methyl, ethyl, OH, $CH_2OH$, $CH_2CH_2OH$, $CH_2NEt_2$, COMe, COOH, $CONH_2$, $NH_2$,

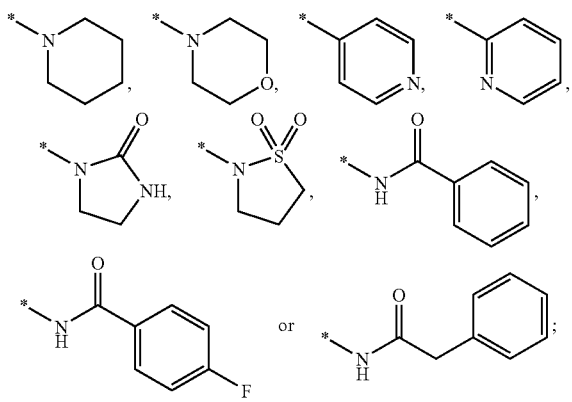

$R^{3.2}$ denotes a group selected from among

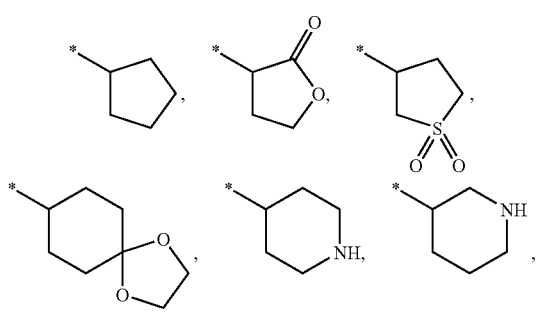

-continued

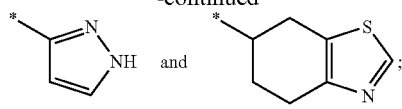

which is optionally substituted by one or more groups selected from among methyl, ethyl, cyclopentyl, OH, $NH_2$; or cyclohexyl, which is optionally substituted by one or two $R^{3.2.1}$;

$R^{3.2.1}$ denotes —$NR^{3.2.1.1}R^{3.2.1.2}$ or a group selected from among

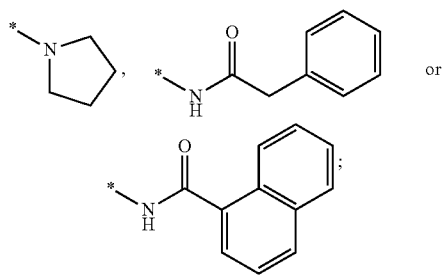

or a group selected from among

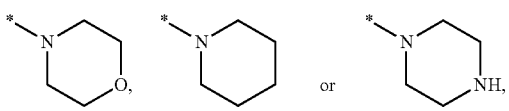

which is optionally substituted by one or more groups selected from among methyl, $SO_2R^{3.2.1.1}$,

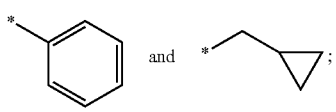

$R^{3.2.1.1}$ denotes H, methyl or benzyl;

$R^{3.2.1.2}$ denotes H, methyl or benzyl; or

—$C_{1-6}$-alkyl, straight-chain or branched, which is optionally substituted by one or two $R^{3.2.2}$;

$R^{3.2.2}$ denotes $C=CH_2$, $C\equiv CH$, $COOR^{3.2.2.1}$, $CONR^{3.2.2.1}R^{3.2.2.2}$, $NR^{3.2.2.1}R^{3.2.2.2}$, $NHCOR^{3.2.2.1}$, $CF_3$, CN, OH, $SO_2R^{3.2.2.1}$ or a group selected from among

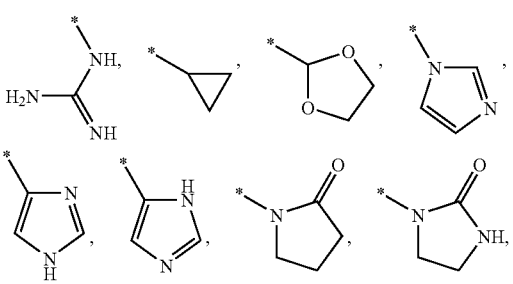

-continued

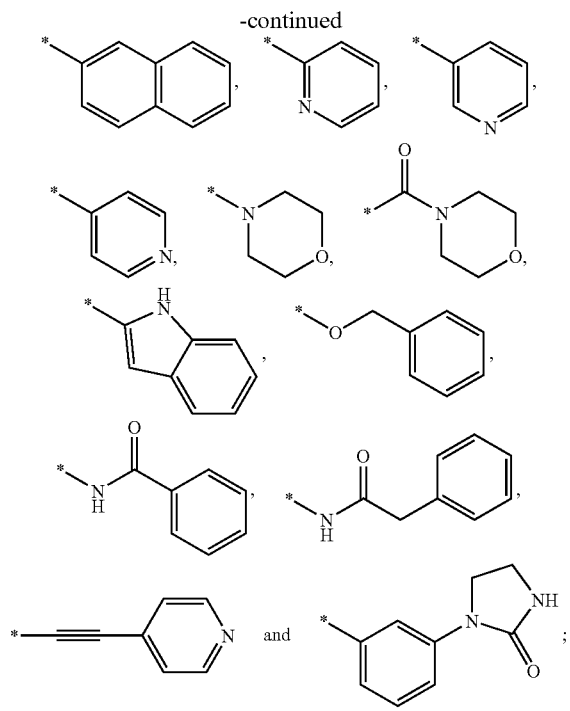

or a group selected from among

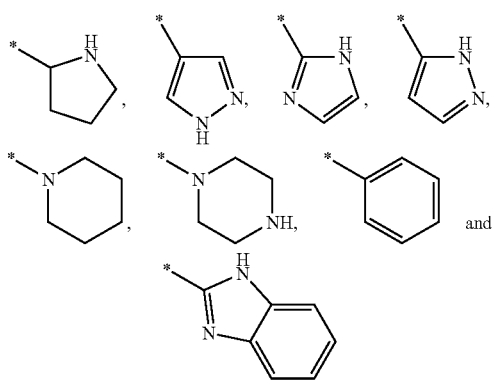

which is optionally substituted by one or more groups selected from among Cl, methyl, CONR$^{3.2.2.1}$R$^{3.2.2.2}$, OH;
R$^{3.2.2.1}$ denotes H or methyl;
R$^{3.2.2.2}$ denotes H or methyl; or
phenyl, which is optionally substituted by one or two R$^{3.2.3}$;
R$^{3.2.3}$ denotes a group selected from among

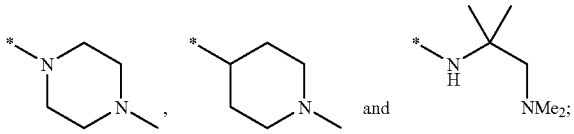

R$^{3.3}$ denotes H, methyl or ethyl;
R$^b$ denotes R$^4$, CH$_2$OR$^4$, COR$^4$, COOR$^4$, CONR$^4$R$^5$, NH$_2$, NHCOOR$^4$, NHCONR$^4$R$^5$ or OH;

R$^4$ denotes H, methyl, ethyl, 2-hydroxyethyl, propyl, C≡CH, CF$_3$, phenyl,

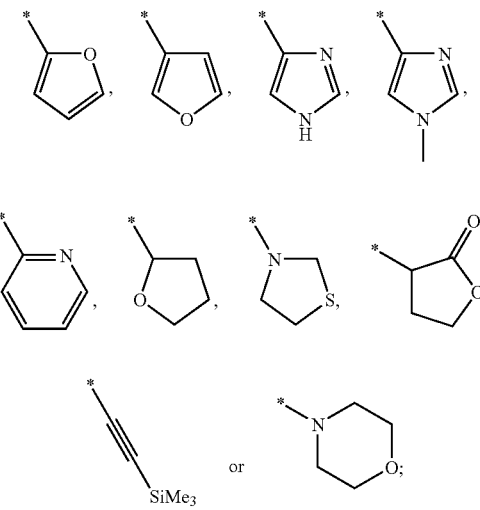

R$^5$ denotes H, methyl or ethyl;
denotes NHR$^6$ or a group selected from among

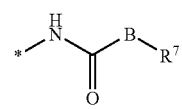

wherein
B denotes a bond, methylene, ethylene, propylene or butynylene;
R$^6$ denotes H or phenyl, optionally substituted by SO$_2$CH$_3$;
R$^7$ denotes H, NR$^{7.1}$R$^{7.2}$, OR$^{7.2}$, SR$^{7.2}$ or a group selected from among

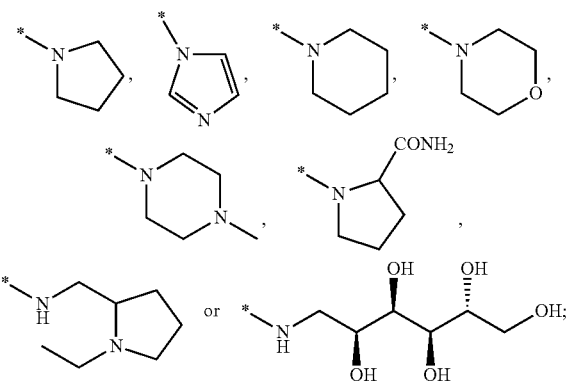

R$^{7.1}$ denotes H, methyl, ethyl, (CH$_2$)$_2$R$^{7.1.1}$ or COObutyl;
R$^{7.2}$ denotes H, methyl or ethyl;
R$^{7.1.1}$ denotes NMe$_2$ or 1-imidazolyl;
or the pharmacologically acceptable salt thereof.

7. The compound of formula 1 according to claim 1; wherein
$R^c$ denotes a group $$*-\underset{H}{N}-\underset{\underset{O}{\parallel}}{C}-B-R^7;$$

wherein
B denotes methylene or propylene;
$R^7$ denotes H, $NR^{7.1}R^{7.2}$ or 1-imidazolyl;
$R^{7.1}$ denotes H or methyl;
$R^{7.2}$ denotes H or methyl;
or the pharmacologically acceptable salt thereof.

8. The compound of formula 1 according to claim 1; wherein
$R^a$ denotes phenyl;
or the pharmacologically acceptable salt thereof.

9. The compound of formula 1 according to claim 2; wherein
$R^a$ denotes phenyl, optionally substituted by one or more groups selected from among methyl, ethyl, propyl, $CF_3$, methoxy, F, Cl, Br or $$*-(\phantom{x})_{0-1}-\underset{\underset{O}{\parallel}}{C}-R^{3.1};$$

or the pharmacologically acceptable salt thereof.

10. The compound of formula 1 according to claim 2; wherein
$R^a$ denotes phenyl, optionally substituted by one or more groups selected from among methyl, ethyl, propyl, $CF_3$, methoxy, F, Cl, Br or $$*-(\phantom{x})_{0-1}-\underset{\underset{O}{\parallel}}{C}-N\underset{R^{3.3}}{\overset{R^{3.2}}{\diagup}};$$

or the pharmacologically acceptable salt thereof.

11. The compound of formula 1 according to claim 1; wherein
$R^a$ denotes H, $C_{1-6}$-alklyl, $C_{2-6}$-alkenyl, $C_{3-6}$-cycloalkyl, $C_{3-6}$-cycloalkenyl, $CF_3$, $COR^8$, $NR^9R^{10}$, $NO_2$, $S(O)_nR^{11}$, spiro, $NHCO-C_{1-6}$-alkyl-$NH_2$ or a group selected from among $C_{7-11}$-aralkyl and $CH_2O$-aryl, which may optionally be substituted by one or more Cl; or a group selected from among het, which may optionally be substituted by one or more $C_{1-4}$-alkyl, $COCF_3$, $CH_2NH_2$ or $CH_2NHCOOR^{12}$;
$R^8$ denotes $C_{1-4}$-alkyl, $C_{3-6}$-cycloalkyl, $NH_2$, hetaryl or aryl, optionally substituted by one or more chlorine;
$R^9$ denotes H, $COOR^{12}$ or het, optionally substituted by one or more $C_{1-4}$-alkyl, or a group selected from among $C_{1-4}$-alkyl, which may optionally be substituted by one or more COOH, $N(C_{1-4}$-alkyl$)_2$ or 4-methylpiperazine;
$R^{10}$ denotes H, $C_{1-4}$-alkyl, $C_{2-4}$-alkynyl or $COCH_3$;
$R^{11}$ denotes $C_{1-4}$-alkyl, optionally substituted by one or more $N(C_{1-4}$-alkyl$)_2$,
$R^{12}$ denotes $C_{1-4}$-alkyl;
n denotes 0 or 2;
$R^b$ denotes H, OH or COOEt;
$R^c$ denotes $NH_2$ or $NHCOR^{13}$;
$R^{13}$ denotes $C_{1-4}$-alkyl, or $NR^{13.1}R^{13.2}$,
$R^{13.1}$ denotes H or $C_{1-4}$-alkyl;
$R^{13.2}$ denotes H or $C_{1-4}$-alkyl;
or the pharmacologically acceptable salt thereof.

12. The compound of formula 1 according to claim 11; wherein
$R^a$ denotes H, methyl, ethyl, propyl, butyl, 3-methyl-butyl, propenyl, cyclopropyl, cyclohexyl, $CF_3$, $COR^8$, $NR^9R^{10}$, $NO_2$, $S(O)_nR^{11}$, or a group selected from among

[structures: N-pyrrolidinone, cyclohexenyl, morpholinyl, NHCO-(CH2)6-NH2, 2,6-diazaspiro[3.4]octane, 1,4-oxazepane]

or a group selected from among

[structures: benzyl, phenethyl, phenoxymethyl]

which may optionally be substituted by one or more Cl;
or a group selected from among

[structures: 4-aminopiperidinyl, piperidinyl]

which may optionally be substituted by one or more $CH_3$, $COCF_3$, $CH_2NH_2$ or $CH_2NHCOOR^{12}$;
$R^8$ denotes methyl, propyl, cyclopropyl, $NH_2$, furanyl or phenyl, optionally substituted by one or more chlorine;
$R^9$ denotes H, $COOR^{12}$ or piperidino, optionally substituted by one or more $CH_3$, or a group selected from among methyl, ethyl and propyl, which may optionally be substituted by one or more COOH, $NMe_2$ or 4-methylpiperazine;
$R^{10}$ denotes H, methyl, $COCH_3$, $C\equiv CH$ or $CH_2C\equiv CH$;
$R^{11}$ denotes ethyl or propyl, optionally substituted by one or more $NMe_2$;
$R^{12}$ denotes butyl;
$R^b$ denotes H, OH or COOEt;
$R^c$ denotes $NH_2$ or $NHCOR^{13}$;

$R^{13}$ denotes methyl or $NR^{13.1}R^{13.2}$,
$R^{13.1}$ denotes H or methyl;
$R^{13.2}$ denotes H or methyl;
or the pharmacologically acceptable salt thereof.

13. A pharmaceutical composition comprising a compound according to claim 1 and one or more pharmaceutically acceptable excipients or carriers.

* * * * *